(12) United States Patent
Ha et al.

(10) Patent No.: US 10,738,034 B2
(45) Date of Patent: Aug. 11, 2020

(54) SPIRO COMPOUND AND ORGANIC LIGHT-EMITTING DEVICE COMPRISING SAME

(71) Applicant: LG Chem, Ltd., Seoul (KR)

(72) Inventors: Jae Seung Ha, Daejeon (KR); Dong Uk Heo, Daejeon (KR); Jiwon Kwak, Daejeon (KR)

(73) Assignee: LG Chem, Ltd. (KR)

( * ) Notice: Subject to any disclaimer, the term of this patent is extended or adjusted under 35 U.S.C. 154(b) by 245 days.

(21) Appl. No.: 15/574,984

(22) PCT Filed: Oct. 6, 2016

(86) PCT No.: PCT/KR2016/011182
§ 371 (c)(1),
(2) Date: Nov. 17, 2017

(87) PCT Pub. No.: WO2017/061786
PCT Pub. Date: Apr. 13, 2017

(65) Prior Publication Data
US 2018/0141933 A1    May 24, 2018

(30) Foreign Application Priority Data

Oct. 6, 2015   (KR) .................. 10-2015-0140433
Jun. 8, 2016   (KR) .................. 10-2016-0071259

(51) Int. Cl.
*H01L 51/50* (2006.01)
*C07D 405/10* (2006.01)
(Continued)

(52) U.S. Cl.
CPC ......... *C07D 405/10* (2013.01); *C07D 405/04* (2013.01); *C07D 405/14* (2013.01); *C07D 409/04* (2013.01); *C07D 409/10* (2013.01); *C07D 409/14* (2013.01); *C09K 11/06* (2013.01); *H01L 51/0067* (2013.01); *H01L 51/0072* (2013.01); *H01L 51/0073* (2013.01); *H01L 51/0074* (2013.01); *H01L 51/5012* (2013.01);
(Continued)

(58) Field of Classification Search
None
See application file for complete search history.

(56) References Cited

U.S. PATENT DOCUMENTS

2004/0023060 A1   2/2004 Kim et al.
2004/0067387 A1   4/2004 Kim et al.
(Continued)

FOREIGN PATENT DOCUMENTS

JP   2004529937 A   9/2004
JP   2005531552 A   10/2005
(Continued)

OTHER PUBLICATIONS

Search report from International Application No. PCT/KR2016/011182, dated Jan. 16, 2017.
(Continued)

*Primary Examiner* — Gregory D Clark
(74) *Attorney, Agent, or Firm* — Lerner, David, Littenberg, Krumholz & Mentlik, LLP

(57) ABSTRACT

The present specification relates to a spiro structure compound and an organic light emitting device including the same.

15 Claims, 1 Drawing Sheet

(51) Int. Cl.
  *C07D 405/04* (2006.01)
  *C07D 405/14* (2006.01)
  *C07D 409/04* (2006.01)
  *C07D 409/10* (2006.01)
  *C07D 409/14* (2006.01)
  *H01L 51/00* (2006.01)
  *C09K 11/06* (2006.01)

(52) U.S. Cl.
  CPC .............. *C09K 2211/1029* (2013.01); *C09K 2211/1059* (2013.01); *C09K 2211/1088* (2013.01); *C09K 2211/1092* (2013.01); *H01L 51/0054* (2013.01); *H01L 51/0059* (2013.01); *H01L 51/0094* (2013.01); *H01L 51/5076* (2013.01)

(56) References Cited

U.S. PATENT DOCUMENTS

2004/0251816 A1  12/2004  Leo et al.
2009/0146554 A1  6/2009  Lee et al.

FOREIGN PATENT DOCUMENTS

| KR | 20090059842 A | | 6/2009 | |
| KR | 2010-082676 | * | 7/2010 | ........... C07D 333/50 |
| KR | 20100082676 A | | 7/2010 | |
| KR | 10-2013-096666 | * | 8/2013 | ........... C07D 333/78 |
| KR | 20130096666 A | | 8/2013 | |
| KR | 20150010016 A | | 1/2015 | |
| WO | 2003012890 A2 | | 2/2003 | |
| WO | 2012141229 A1 | | 10/2012 | |
| WO | 2013120577 A1 | | 8/2013 | |
| WO | 2015012618 A1 | | 1/2015 | |

OTHER PUBLICATIONS

Search report from International Application No. PCT/KR2016/011184, dated Jan. 16, 2017.
Search report from International Application No. PCT/KR2016/011181, dated Jan. 19, 2017.
U.S. Appl. No. 15/575,098 (Ha, et al), filed Nov. 17, 2017.
U.S. Appl. No. 15/575,148 (Ha, et al.), filed Nov. 17, 2017.

* cited by examiner

[Figure 1]
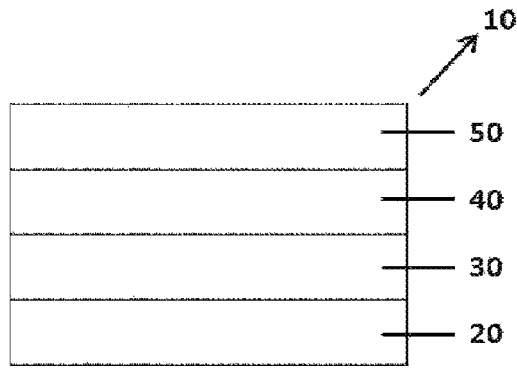
[Figure 2]
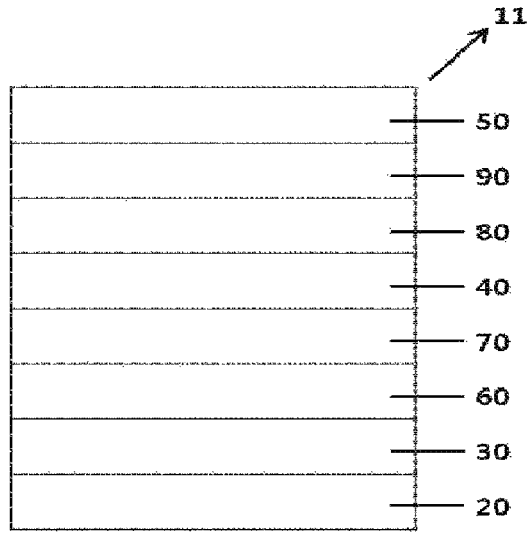

SPIRO COMPOUND AND ORGANIC LIGHT-EMITTING DEVICE COMPRISING SAME

TECHNICAL FIELD

This application claims priority to and the benefit of Korean Patent Application Nos. 10-2015-0140433 and 10-2016-0071259 filed in the Korean Intellectual Property Office on Oct. 6, 2015 and Jun. 8, 2016, respectively, the entire contents of which are incorporated herein by reference.

The present specification relates to a spiro structure compound and an organic light emitting device including the same.

BACKGROUND ART

In general, an organic light emitting phenomenon refers to a phenomenon in which electric energy is converted into light energy by using an organic material. An organic light emitting device using the organic light emitting phenomenon usually has a structure including a positive electrode, a negative electrode, and an organic material layer interposed therebetween. Here, the organic material layer may have a multi-layered structure composed of different materials in order to improve the efficiency and stability of an organic light emitting device in many cases, and for example, may be composed of a hole injection layer, a hole transport layer, a light emitting layer, an electron transport layer, an electron injection layer, and the like. In the structure of the organic light emitting device, if a voltage is applied between two electrodes, holes are injected from a positive electrode into the organic material layer and electrons are injected from a negative electrode into the organic material layer, and when the injected holes and electrons meet each other, an exciton is formed, and light is emitted when the exciton falls down again to a ground state.

There is a continuous need for developing a new material for the aforementioned organic light emitting device.

CITATION LIST

Patent Document

US Patent Application Publication No. 2004-0251816

DISCLOSURE

Technical Problem

The present specification provides a spiro structure compound and an organic light emitting device including the same.

Technical Solution

The present specification provides a spiro structure compound and an organic light emitting device including the same.

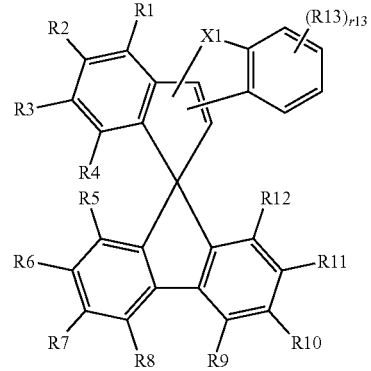

[Chemical Formula 1]

In Chemical Formula 1,

X1 is O or S, at least one of R1 to R12 is -L1-Ar1, and the others and R13 are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, r13 is an integer of 1 to 4, when r13 is 2 or more, two or more R13's are the same as or different from each other, L1 is a direct bond; a substituted or unsubstituted arylene group; or a substituted or unsubstituted heteroarylene group, Ar1 is a substituted or unsubstituted phosphine oxide group; or is represented by any one of the following Chemical Formulae 2 to 6,

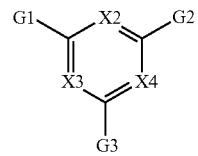

[Chemical Formula 2]

in Chemical Formula 2,

X2 is N or CR14, X3 is N or CR15, and X4 is N or CR16, at least one of X2 to X4 is N, any one of G1 to G3 and R14 to R16 is a moiety bonded to L1 of Chemical Formula 1, and the others are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group,

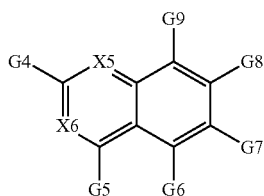

[Chemical Formula 3]

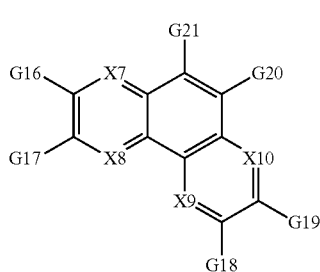

[Chemical Formula 5]

in Chemical Formula 3, $X5$ is N or $CR17$, and $X6$ is N or $CR18$, at least one of $X5$ and $X6$ is N, any one of $G4$ to $G9$, $R17$, and $R18$ is a moiety bonded to $L1$ of Chemical Formula 1, and the others are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, or adjacent groups combine with each other to form a substituted or unsubstituted ring, in Chemical Formula 5, $X7$ is N or $CR19$, $X8$ is N or $CR20$, $X9$ is N or $CR21$, and $X10$ is N or $CR22$, at least one of $X7$ to $X10$ is N, any one of $G16$ to $G21$ and $R19$ to $R22$ is a moiety bonded to $L1$ of Chemical Formula 1, and the others are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group,

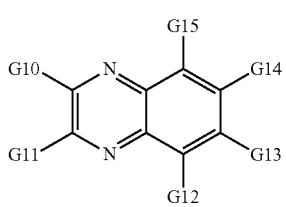

[Chemical Formula 4]

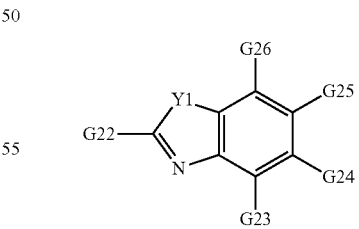

[Chemical Formula 6]

in Chemical Formula 4, any one of $G10$ to $G15$ is a moiety bonded to $L1$ of Chemical Formula 1, and the others are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy in Chemical Formula 6, $Y1$ is O, S, $NQ1$, or $CQ2Q3$, and any one of $G22$ to $G26$ is a moiety bonded to $L1$ of Chemical Formula 1, and the others and $Q1$ to $Q3$ are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group.

Further, an exemplary embodiment of the present specification provides an organic light emitting device including: a first electrode; a second electrode provided to face the first electrode; and one or more organic material layers provided between the first electrode and the second electrode, in which one or more layers of the organic material layers include the spiro structure compound represented by Chemical Formula 1.

Advantageous Effects

A spiro structure compound according to an exemplary embodiment of the present specification may be used as a material for an organic material layer of an organic light emitting device, and it is possible to improve efficiency, achieve low driving voltage, and/or improve lifetime characteristics in the organic light emitting device by using the same.

DESCRIPTION OF DRAWINGS

FIG. 1 illustrates an organic light emitting device 10 according to an exemplary embodiment of the present specification.

FIG. 2 illustrates an organic light emitting device 11 according to another exemplary embodiment of the present specification.

MODE FOR INVENTION

Hereinafter, the present specification will be described in more detail.

The present specification provides the spiro structure compound represented by Chemical Formula 1.

When one part "includes" one constituent element in the present specification, unless otherwise specifically described, this does not mean that another constituent element is excluded, but means that another constituent element may be further included.

When one member is disposed "on" another member in the present specification, this includes not only a case where the one member is brought into contact with the another member, but also a case where still another member is present between the two members.

In the present specification, examples of the substituents will be described below, but the present specification is not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the term "substituted or unsubstituted" means being substituted with one or two or more substituents selected from the group consisting of deuterium; a halogen group; a nitrile group; a nitro group; an imide group; an amide group; a carbonyl group; an ether group; an ester group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; and a substituted or unsubstituted heterocyclic group or being substituted with a substituent to which two or more substituents are linked among the substituents exemplified above, or having no substituent. For example, "the substituent to which two or more substituents are linked" may be a biphenyl group. That is, the biphenyl group may also be an aryl group, and may be interpreted as a substituent to which two phenyl groups are linked.

In the present specification,

means a moiety bonded to another substituent or a binding portion.

In the present specification, the halogen group may be fluorine, chlorine, bromine, or iodine.

In the present specification, the number of carbon atoms of an imide group is not particularly limited, but is preferably 1 to 30. Specifically, the imide group may be a compound having the following structures, but is not limited thereto.

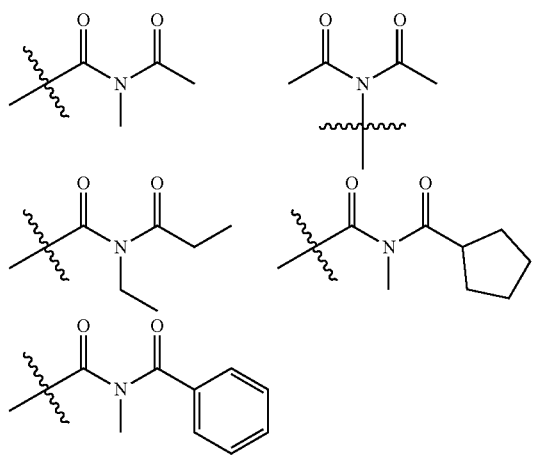

In the present specification, for an amide group, the nitrogen of the amide group may be substituted with hydrogen, a straight-chained, branch-chained, or cyclic alkyl group having 1 to 30 carbon atoms, or an aryl group having 6 to 30 carbon atoms. Specifically, the amide group may be a compound having the following structural formulae, but is not limited thereto.

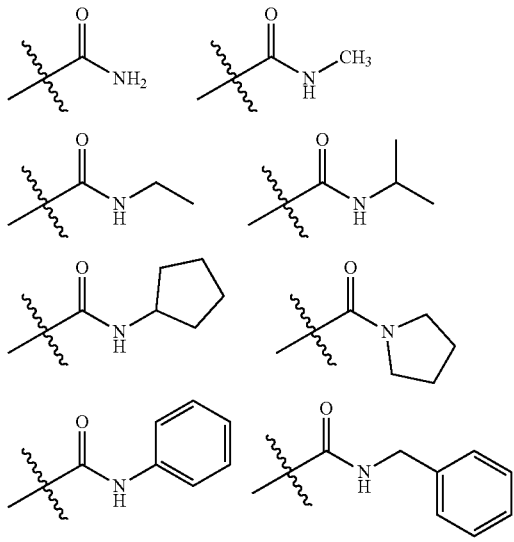

In the present specification, the number of carbon atoms of a carbonyl group is not particularly limited, but is preferably 1 to 30. Specifically, the carbonyl group may be a compound having the following structures, but is not limited thereto.

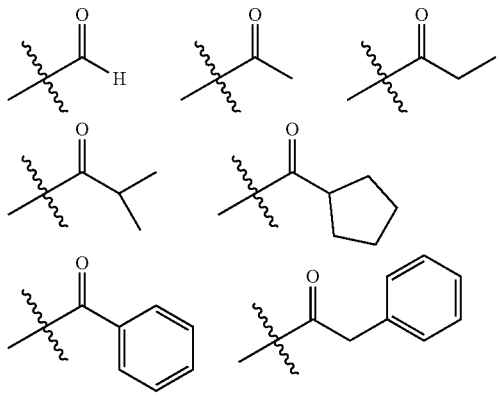

In the present specification, for an ester group, the oxygen of the ester group may be substituted with a straight-chained, branch-chained, or cyclic alkyl group having 1 to 25 carbon atoms, or an aryl group having 6 to 30 carbon atoms. Specifically, the ester group may be a compound having the following structural formulae, but is not limited thereto.

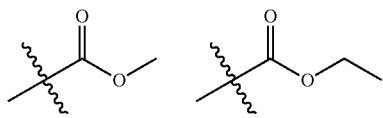

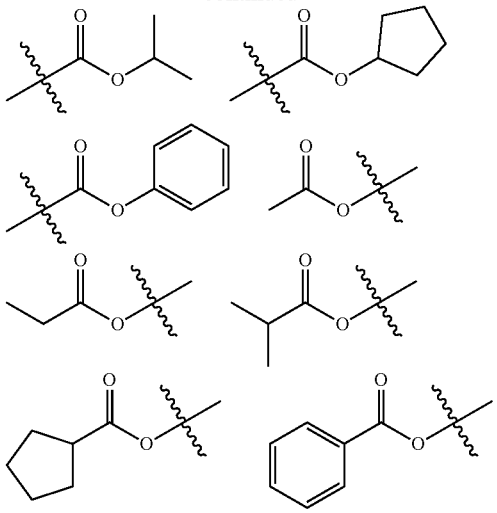

In the present specification, for an ether group, the oxygen of the ether group may be substituted with a straight-chained, branch-chained, or cyclic alkyl group having 1 to 25 carbon atoms, or an aryl group having 6 to 30 carbon atoms. Specifically, the ether group may be a compound having the following structural formulae, but is not limited thereto.

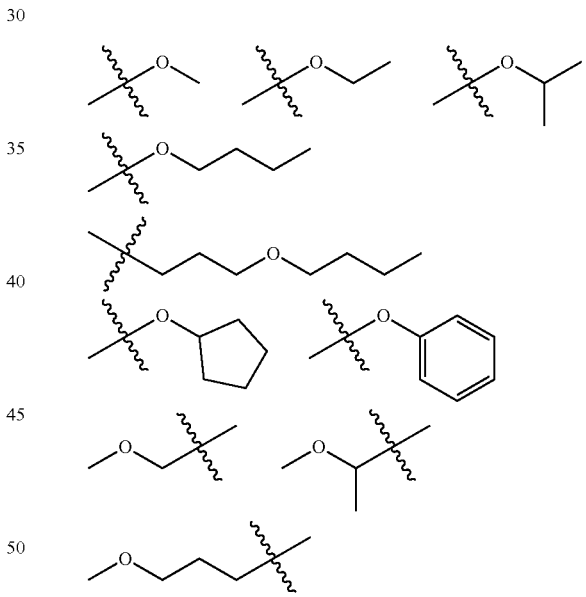

In the present specification, the alkyl group may be straight-chained or branch-chained, and the number of carbon atoms thereof is not particularly limited, but is preferably 1 to 30. Specific examples thereof include methyl, ethyl, propyl, n-propyl, isopropyl, butyl, n-butyl, isobutyl, tert-butyl, sec-butyl, 1-methyl-butyl, 1-ethylbutyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, a cycloalkyl group is not particularly limited, but has preferably 3 to 30 carbon atoms, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto. In the present specification, the alkoxy group may be straight-chained, branch-chained, or cyclic. The number of carbon atoms of the alkoxy group is not particularly limited, but is preferably 1 to 30. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, an amine group may be selected from the group consisting of —NH$_2$; a monoalkylamine group; a dialkylamine group; an N-alkylarylamine group; a monoarylamine group; a diarylamine group; an N-arylheteroarylamine group; an N-alkylheteroarylamine group, a monoheteroarylamine group, and a diheteroarylamine group, and the number of carbon atoms thereof is not particularly limited, but is preferably 1 to 30. Specific examples of the amine group include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a ditolylamine group, an N-phenyltolylamine group, a triphenylamine group, an N-phenylbiphenylamine group; an N-phenylnaphthylamine group; an N-biphenylnaphthylamine group; an N-naphthylfluorenylamine group; an N-phenylphenanthrenylamine group; an N-biphenylphenanthrenylamine group; an N-phenylfluorenylamine group; an N-phenyl terphenylamine group; an N-phenanthrenylfluorenylamine group; an N-biphenylfluorenylamine group, and the like, but are not limited thereto.

In the present specification, the N-alkylarylamine group means an amine group in which an alkyl group and an aryl group are substituted with N of the amine group.

In the present specification, the N-arylheteroarylamine group means an amine group in which an aryl group and a heteroaryl group are substituted with N of the amine group.

In the present specification, the N-alkylheteroarylamine group means an amine group in which an alkyl group and a heteroarylamine group are substituted with N of the amine group.

In the present specification, the alkyl group in the alkylamine group, the N-alkylarylamine group, the alkylthioxy group, the alkylsulfoxy group, and the N-alkylheteroarylamine group is the same as the above-described examples of the alkyl group. Specifically, examples of the alkylthioxy group include a methylthioxy group, an ethylthioxy group, a tert-butylthioxy group, a hexylthioxy group, an octylthioxy group, and the like, and examples of the alkylsulfoxy group include mesyl, an ethylsulfoxy group, a propylsulfoxy group, a butylsulfoxy group, and the like, but are not limited thereto.

In the present specification, the alkenyl group may be straight-chained or branch-chained, and the number of carbon atoms thereof is not particularly limited, but is preferably 2 to 30. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, specific examples of a silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, the boron group may be —BR$_{100}$R$_{101}$, and R$_{100}$ and R$_{101}$ are the same as or different from each other, and may be each independently selected from the group consisting of hydrogen; deuterium; halogen; a nitrile group; a substituted or unsubstituted monocyclic or polycyclic cycloalkyl group having 3 to 30 carbon atoms; a substituted or unsubstituted straight-chained or branch-chained alkyl group having 1 to 30 carbon atoms; a substituted or unsubstituted monocyclic or polycyclic aryl group having 6 to 30 carbon atoms; and a substituted or unsubstituted monocyclic or polycyclic heteroaryl group having 2 to 30 carbon atoms.

In the present specification, specific examples of the phosphine oxide group include a diphenylphosphine oxide group, dinaphthylphosphine oxide, and the like, but are not limited thereto.

In the present specification, an aryl group is not particularly limited, but has preferably 6 to 30 carbon atoms, and the aryl group may be monocyclic or polycyclic.

When the aryl group is a monocyclic aryl group, the number of carbon atoms thereof is not particularly limited, but is preferably 6 to 30. Specific examples of the monocyclic aryl group include a phenyl group, a biphenyl group, a terphenyl group, and the like, but are not limited thereto.

When the aryl group is a polycyclic aryl group, the number of carbon atoms thereof is not particularly limited, but is preferably 10 to 30. Specific examples of the polycyclic aryl group include a naphthyl group, an anthracenyl group, a phenanthryl group, a triphenyl group, a pyrenyl group, a phenalenyl group, a perylenyl group, a chrysenyl group, a fluorenyl group, and the like, but are not limited thereto.

In the present specification, the fluorenyl group may be substituted, and adjacent substituents may combine with each other to form a ring.

When the fluorenyl group is substituted, the fluorenyl group may be

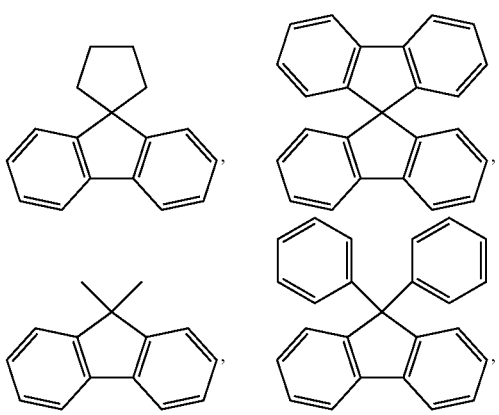

-continued

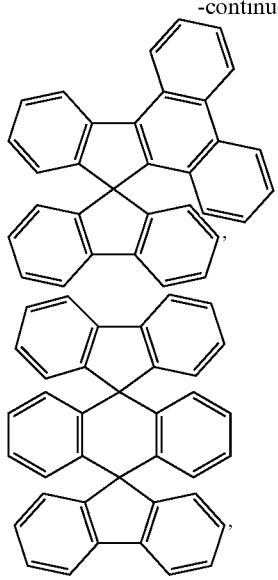

and the like. However, the fluorenyl group is not limited thereto.

In the present specification, the "adjacent" group may mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as groups which are "adjacent" to each other.

In the present specification, the aryl group in the aryloxy group, the arylthioxy group, the arylsulfoxy group, the N-arylalkylamine group, the N-arylheteroarylamine group, and the arylphosphine group is the same as the above-described examples of the aryl group. Specifically, examples of the aryloxy group include a phenoxy group, a p-tolyloxy group, an m-tolyloxy group, a 3,5-dimethyl-phenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthryloxy group, a 2-anthryloxy group, a 9-anthryloxy group, a 1-phenanthryloxy group, a 3-phenanthryloxy group, a 9-phenanthryloxy group, and the like, examples of the arylthioxy group include a phenylthioxy group, a 2-methylphenylthioxy group, a 4-tert-butylphenylthioxy group, and the like, and examples of the arylsulfoxy group include a benzenesulfoxy group, a p-toluenesulfoxy group, and the like, but the examples are not limited thereto.

In the present specification, examples of an arylamine group include a substituted or unsubstituted monoarylamine group, a substituted or unsubstituted diarylamine group, or a substituted or unsubstituted triarylamine group. The aryl group in the arylamine group may be a monocyclic aryl group or a polycyclic aryl group. The arylamine group including two or more aryl groups may include a monocyclic aryl group, a polycyclic aryl group, or both a monocyclic aryl group and a polycyclic aryl group. For example, the aryl group in the arylamine group may be selected from the above-described examples of the aryl group.

In the present specification, a heteroaryl group includes one or more of an atom other than carbon, that is, a heteroatom, and specifically, the heteroatom may include one or more atoms selected from the group consisting of O, N, Se, and S, and the like. The number of carbon atoms thereof is not particularly limited, but is preferably 2 to 30, and the heteroaryl group may be monocyclic or polycyclic. Examples of the heterocyclic group include a thiophene group, a furanyl group, a pyrrole group, an imidazolyl group, a thiazolyl group, an oxazolyl group, an oxadiazolyl group, a pyridyl group, a bipyridyl group, a pyrimidyl group, a triazinyl group, a triazolyl group, an acridyl group, a pyridazinyl group, a pyrazinyl group, a qinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophene group, a dibenzothiophene group, a benzofuranyl group, a phenanthrolinyl group (phenanthroline), a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, examples of a heteroarylamine group include a substituted or unsubstituted monoheteroarylamine group, a substituted or unsubstituted diheteroarylamine group, or a substituted or unsubstituted triheteroarylamine group. The heteroarylamine group including two or more heteroaryl groups may include a monocyclic heteroaryl group, a polycyclic heteroaryl group, or both a monocyclic heteroaryl group and a polycyclic heteroaryl group. For example, the heteroaryl group in the heteroarylamine group may be selected from the above-described examples of the heteroaryl group.

In the present specification, examples of the heteroaryl group in the N-arylheteroarylamine group and the N-alkylheteroarylamine group are the same as the above-described examples of the heteroaryl group.

In the present specification, the heterocyclic group may be monocyclic or polycyclic, may be an aromatic ring, an aliphatic ring, or a fused ring of the aromatic ring and the aliphatic ring, and may be selected from the examples of the heteroaryl group. In addition, examples of the heterocyclic group include a heterocyclic structure including a hydroacridyl group (for example,

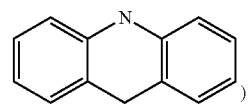 [SMILES: c1ccc2c(c1)Cc1ccccc1N2])

and a sulfonyl group, for example,

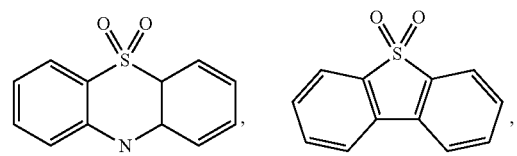 [SMILES: O=S1(=O)c2ccccc2NC2C=CC=CC21 ; O=S1(=O)c2ccccc2-c2ccccc21]

and the like, a fused structure of the heteroaryl group, and the like, but are not limited thereto.

In the present specification, the fused structure may be a structure in which an aromatic ring is fused with the corresponding substituent. Examples of a fused ring of benzimidazole include

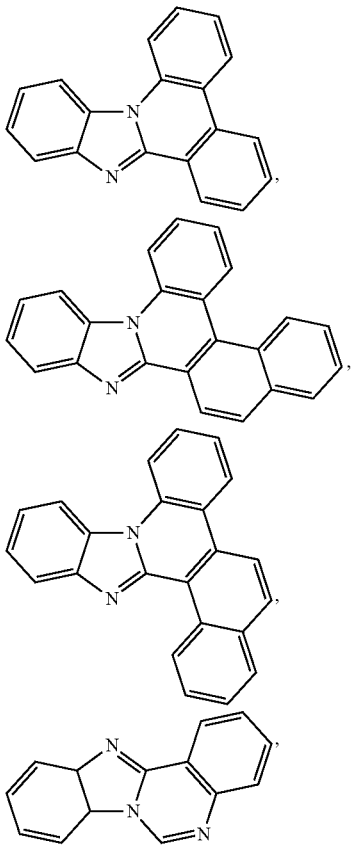

and the like, but are not limited thereto.

In the present specification, an aromatic ring group may be monocyclic or polycyclic, and may be selected from the examples of the aryl group.

In the present specification, in a substituted or unsubstituted ring formed by combining adjacent groups, the "ring" means a substituted or unsubstituted hydrocarbon ring; or a substituted or unsubstituted hetero ring.

In the present specification, a hydrocarbon ring may be an aromatic ring, an aliphatic ring, or a fused ring of the aromatic ring and the aliphatic ring, and may be selected from the examples of the cycloalkyl group or the aryl group, except for the hydrocarbon ring which is not monovalent.

In the present specification, an aromatic ring may be monocyclic or polycyclic, and may be selected from the examples of the aryl group, except for the aromatic ring which is not monovalent.

In the present specification, a hetero ring includes one or more of an atom other than carbon, that is, a heteroatom, and specifically, the heteroatom may include one or more atoms selected from the group consisting of O, N, Se, and S, and the like. The hetero ring may be monocyclic or polycyclic, may be an aromatic ring, an aliphatic ring, or a fused ring of the aromatic ring and the aliphatic ring, and may be selected from the examples of the heteroaryl group or the heterocyclic group, except for the hetero ring which is not monovalent.

In the present specification, the arylene group means that there are two bonding positions in an aryl group, that is, a divalent group. The above-described description on the aryl group may be applied, except that the arylene groups are each a divalent group.

In the present specification, the heteroarylene group means that there are two bonding positions in a heteroaryl group, that is, a divalent group. The above-described description on the heteroaryl group may be applied, except that these are each a divalent group.

According to an exemplary embodiment of the present specification, Chemical Formula 1 is represented by any one of the following Chemical Formulae 1-1 to 1-3.

[Chemical Formula 1-1]

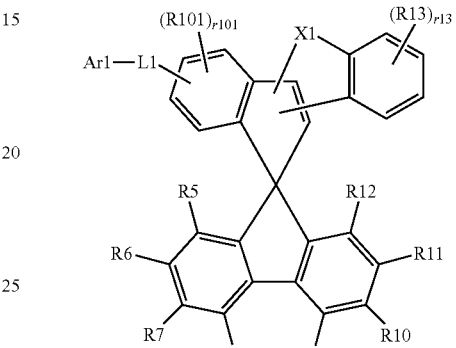

[Chemical Formula 1-2]

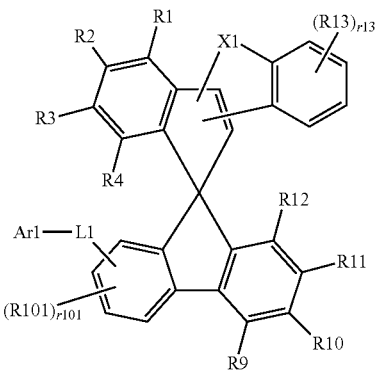

[Chemical Formula 1-3]

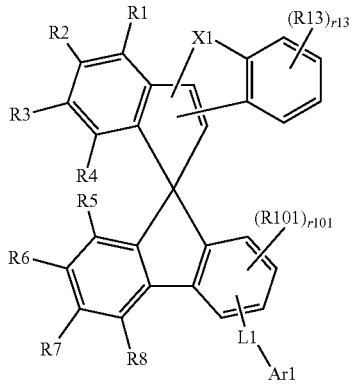

In Chemical Formulae 1-1 to 1-3,
the definitions of X1, R1 to R13, L1, Ar1, and r13 are the same as those in Chemical Formula 1,
R101 is hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group;

a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, r101 is 1 to 3, and when r101 is 2 or more, two or more R101's are the same as or different from each other.

According to an exemplary embodiment of the present specification, Chemical Formula 1 is represented by any one of the following Chemical Formulae 1-4 to 1-15.

[Chemical Formula 1-4]

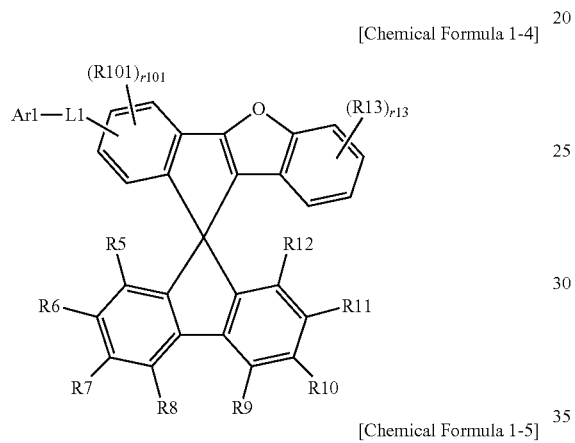

[Chemical Formula 1-5]

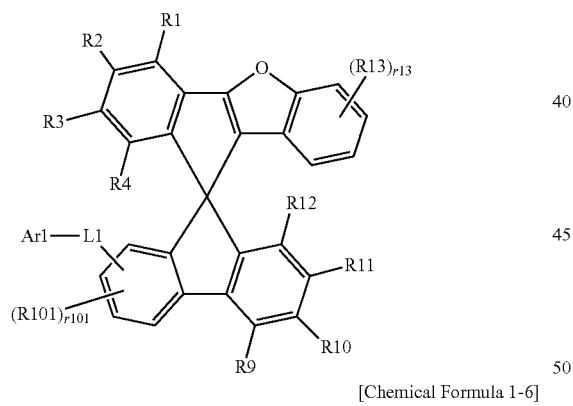

[Chemical Formula 1-6]

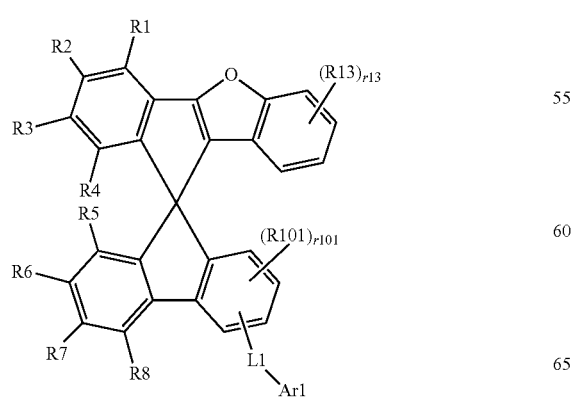

[Chemical Formula 1-7]

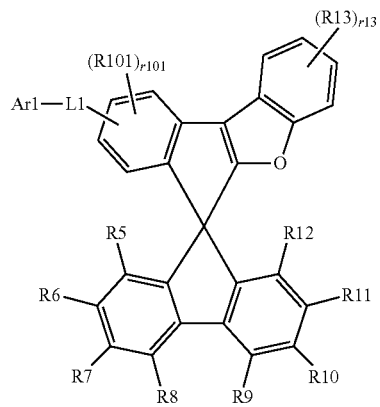

[Chemical Formula 1-8]

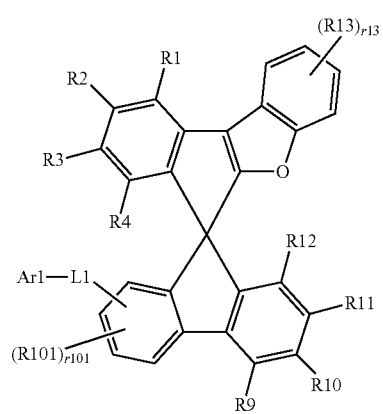

[Chemical Formula 1-9]

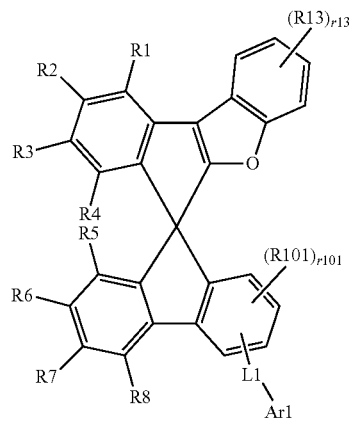

[Chemical Formula 1-10]

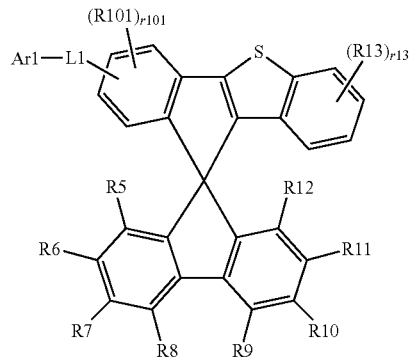

[Chemical Formula 1-11]

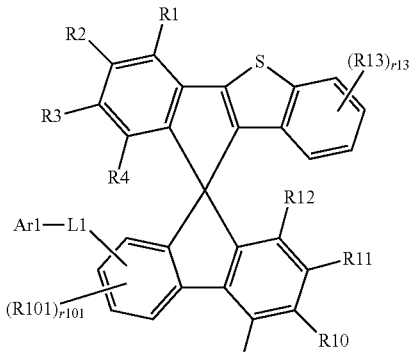

[Chemical Formula 1-12]

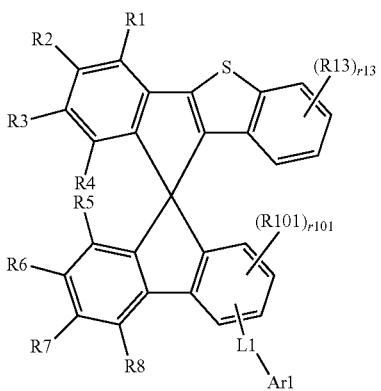

[Chemical Formula 1-13]

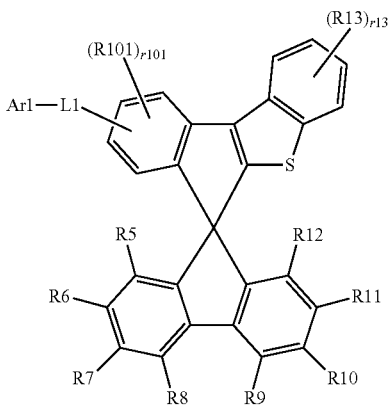

[Chemical Formula 1-14]

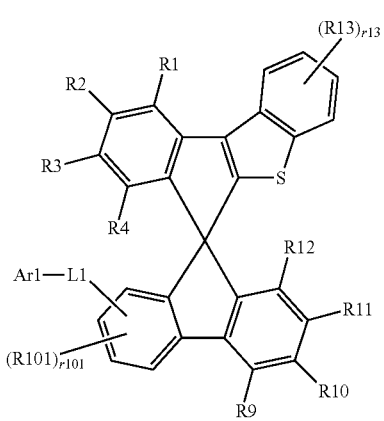

[Chemical Formula 1-15]

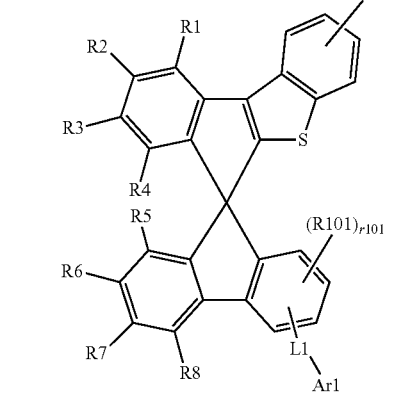

In Chemical Formulae 1-4 to 1-15, the definitions of R1 to R13, L1, Ar1, and r13 are the same as those in Chemical Formula 1, R101 is hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, r101 is 1 to 3, and when r101 is 2 or more, two or more R101's are the same as or different from each other.

According to an exemplary embodiment of the present specification, in Chemical Formula 1, L1 is a direct bond; or a substituted or unsubstituted arylene group.

According to an exemplary embodiment of the present specification, in Chemical Formula 1, L1 is a direct bond; or a substituted or unsubstituted phenylene group.

According to an exemplary embodiment of the present specification, in Chemical Formula 1, L1 is a direct bond; or a phenylene group.

According to an exemplary embodiment of the present specification, in Chemical Formula 1, Ar1 is a substituted or unsubstituted phosphine oxide group.

According to an exemplary embodiment of the present specification, in Chemical Formula 1, Ar1 is a phosphine oxide group which is unsubstituted or substituted with an aryl group.

According to an exemplary embodiment of the present specification, in Chemical Formula 1, Ar1 is a phosphine oxide group which is unsubstituted or substituted with a phenyl group or a naphthyl group.

According to an exemplary embodiment of the present specification, in Chemical Formula 1, Ar1 is a phosphine oxide group which is substituted with a phenyl group or a naphthyl group.

According to an exemplary embodiment of the present specification, in Chemical Formula 1, Ar1 is represented by Chemical Formula 2.

According to another exemplary embodiment of the present specification, Chemical Formula 2 is represented by any one of the following Chemical Formulae 2-1 to 2-3.

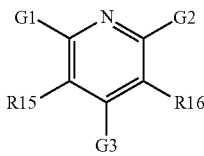
[Chemical Formula 2-1]

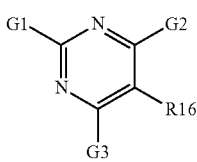
[Chemical Formula 2-2]

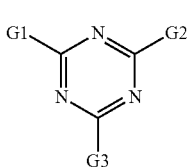
[Chemical Formula 2-3]

In Chemical Formulae 2-1 to 2-3, any one of G1 to G3, R15, and R16, any one of G1 to G3 and R16, or any one of G1 to G3 is a moiety bonded to L1 of Chemical Formula 1, and the others are hydrogen; an aryl group which is unsubstituted or substituted with an alkyl group; or a substituted or unsubstituted heteroaryl group.

According to another exemplary embodiment of the present specification, in Chemical Formula 2-1, any one of G1 to G3, R15, and R16 is a moiety bonded to L1 of Chemical Formula 1, and the others are hydrogen; or an aryl group.

According to still another exemplary embodiment of the present specification, in Chemical Formula 2-1, any one of G1 to G3, R15, and R16 is a moiety bonded to L1 of Chemical Formula 1, and the others are hydrogen; a phenyl group; a naphthyl group; or a biphenyl group.

According to yet another exemplary embodiment of the present specification, in Chemical Formula 2-2, any one of G1 to G3 and R16 is a moiety bonded to L1 of Chemical Formula 1, and the others are hydrogen; or an aryl group.

According to still yet another exemplary embodiment of the present specification, in Chemical Formula 2-2, any one of G1 to G3 and R16 is a moiety bonded to L1 of Chemical Formula 1, and the others are hydrogen; a phenyl group; a naphthyl group; or a biphenyl group.

According to a further exemplary embodiment of the present specification, in Chemical Formula 2-3, any one of G1 to G3 is a moiety bonded to L1 of Chemical Formula 1, and the others are hydrogen; an aryl group which is unsubstituted or substituted with an alkyl group; or a heteroaryl group.

According to another further exemplary embodiment of the present specification, in Chemical Formula 2-3, any one of G1 to G3 is a moiety bonded to L1 of Chemical Formula 1, and the others are hydrogen; a phenyl group; a naphthyl group; a biphenyl group; a fluorenyl group substituted with a methyl group; or a pyridyl group.

According to an exemplary embodiment of the present specification, in Chemical Formula 1, Ar1 is represented by Chemical Formula 3.

According to another exemplary embodiment of the present specification, Chemical Formula 3 is represented by any one of the following Chemical Formulae 3-1 to 3-3.

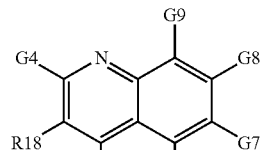
[Chemical Formula 3-1]

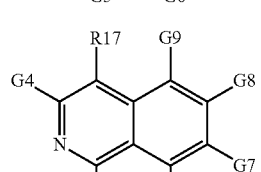
[Chemical Formula 3-2]

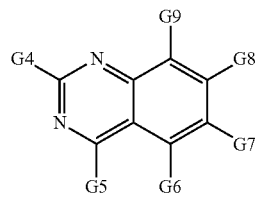
[Chemical Formula 3-3]

In Chemical Formulae 3-1 to 3-3,
any one of G4 to G9 and R18, any one of G4 to G9 and R17, or any one of G4 to G9 is a moiety bonded to L1 of Chemical Formula 1, and the others are hydrogen; or a substituted or unsubstituted aryl group, or adjacent groups combine with each other to form a substituted or unsubstituted ring.

According to another exemplary embodiment of the present specification, in Chemical Formula 3-1, any one of G4 to G9 and R18 is a moiety bonded to L1 of Chemical Formula 1, and the others are hydrogen; or an aryl group.

According to still another exemplary embodiment of the present specification, in Chemical Formula 3-1, any one of G4 to G9 and R18 is a moiety bonded to L1 of Chemical Formula 1, and the others are hydrogen; a phenyl group; a biphenyl group; or a naphthyl group.

According to yet another exemplary embodiment of the present specification, in Chemical Formula 3-3, any one of G4 to G9 is a moiety bonded to L1 of Chemical Formula 1, and the others are hydrogen; or an aryl group.

According to still yet another exemplary embodiment of the present specification, in Chemical Formula 3-3, any one of G4 to G9 is a moiety bonded to L1 of Chemical Formula 1, and the others are hydrogen; a phenyl group; a biphenyl group; or a naphthyl group.

According to a further exemplary embodiment of the present specification, in Chemical Formula 3-3, any one of G4 to G9 is a moiety bonded to L1 of Chemical Formula 1, and adjacent groups in the others combine with each other to form a substituted or unsubstituted hetero ring.

According to another further exemplary embodiment of the present specification, in Chemical Formula 3-3, any one of G4 to G9 is a moiety bonded to L1 of Chemical Formula 1, and adjacent groups in the others combine with each other to form a hetero ring.

According to still another further exemplary embodiment of the present specification, in Chemical Formula 3-3, any one of G4 to G9 is a moiety bonded to L1 of Chemical Formula 1, and adjacent groups in the others combine with each other to form a benzimidazole ring.

According to an exemplary embodiment of the present specification, in Chemical Formula 1, Ar1 is represented by Chemical Formula 4.

According to another exemplary embodiment of the present specification, in Chemical Formula 4, any one of G10 to G15 is a moiety bonded to L1 of Chemical Formula 1, and the others are hydrogen.

According to an exemplary embodiment of the present specification, in Chemical Formula 1, Ar1 is represented by Chemical Formula 5.

According to another exemplary embodiment of the present specification, Chemical Formula 5 is represented by any one of the following Chemical Formulae 5-1 to 5-8.

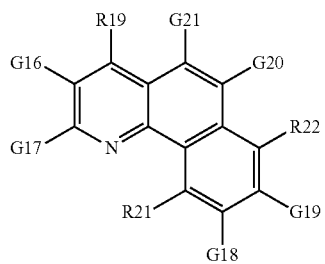

[Chemical Formula 5-1]

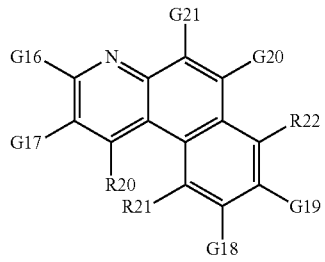

[Chemical Formula 5-2]

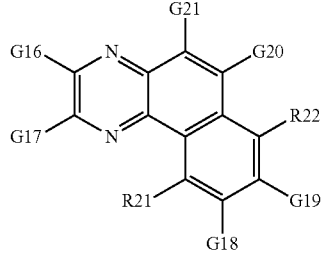

[Chemical Formula 5-3]

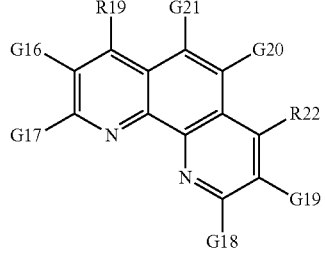

[Chemical Formula 5-4]

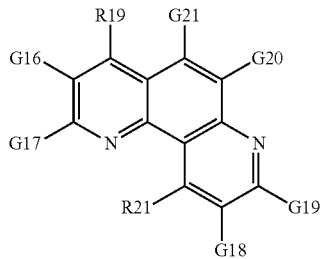

[Chemical Formula 5-5]

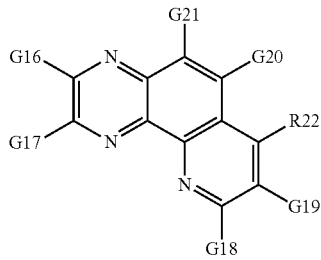

[Chemical Formula 5-6]

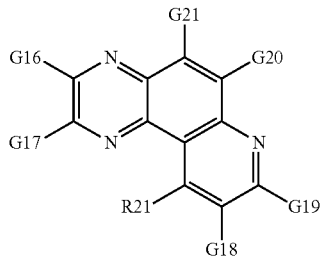

[Chemical Formula 5-7]

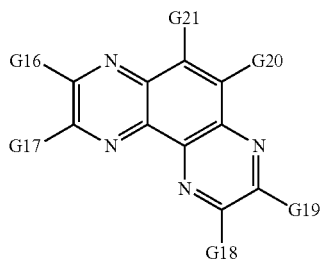

[Chemical Formula 5-8]

In Chemical Formulae 5-1 to 5-8, any one of G16 to G21, R18, R21, and R22, any one of G16 to G21 and R20 to R22, any one of G16 to G21, R21, and R22, any one of G16 to G21, R19, and R22, any one of G16 to G21, R19, and R21, any one of G16 to G21 and R22, any one of G16 to G21 and R21, or any one of G16 to G21 is a moiety bonded to L1 of Chemical Formula 1, and the others are hydrogen.

According to an exemplary embodiment of the present specification, in Chemical Formula 1, Ar1 is represented by Chemical Formula 6.

According to another exemplary embodiment of the present specification, Chemical Formula 6 is represented by following Chemical Formulae 6-1 to 6-4.

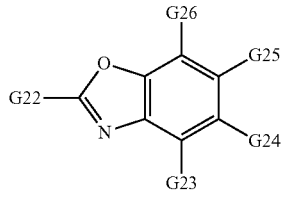

[Chemical Formula 6-1]

-continued

[Chemical Formula 6-2]

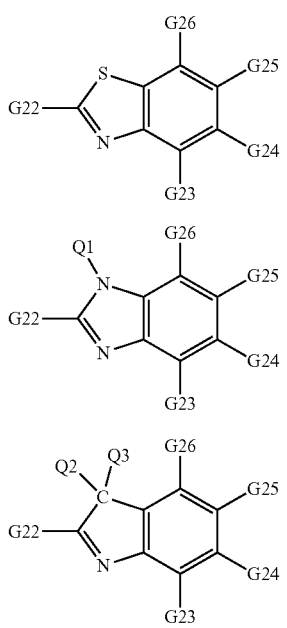

[Chemical Formula 6-3]

[Chemical Formula 6-4]

In Chemical Formulae 6-1 to 6-4, the definitions of G22 to G26 and Q1 to Q3 are the same as those in Chemical Formula 6.

According to another exemplary embodiment of the present specification, in Chemical Formula 6-3, any one of G22 to G26 is a moiety bonded to L1 of Chemical Formula 1, and the others are hydrogen; or an aryl group.

According to still another exemplary embodiment of the present specification, in Chemical Formula 6-3, any one of G22 to G26 is a moiety bonded to L1 of Chemical Formula 1, and the others are hydrogen; a phenyl group; or a biphenyl group.

According to an exemplary embodiment of the present specification, in Chemical Formula 1, -L1-Ar1 is selected from the following structures.

B-1

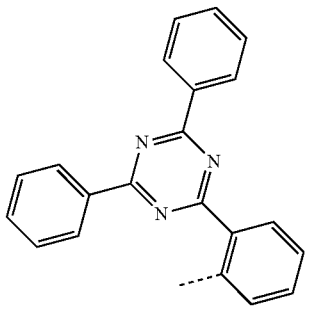

B-2

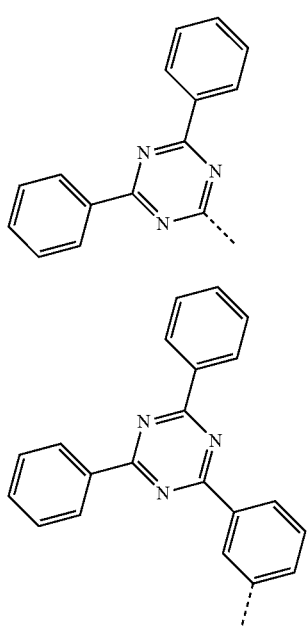

B-3

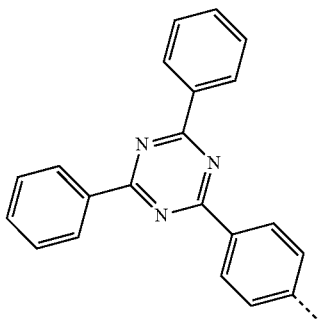

B-4

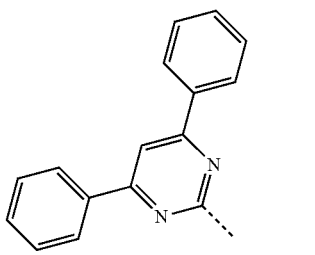

B-5

B-6

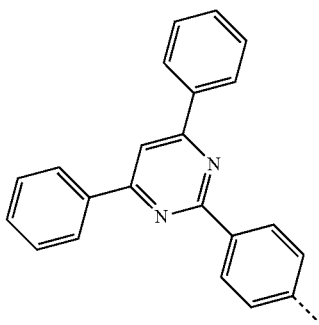

B-7

-continued
B-8
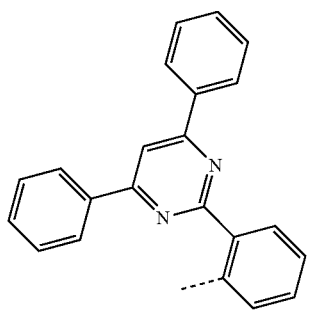
B-9
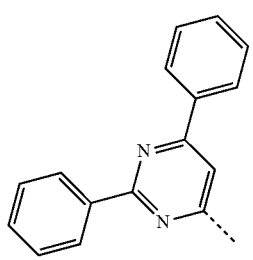
B-10
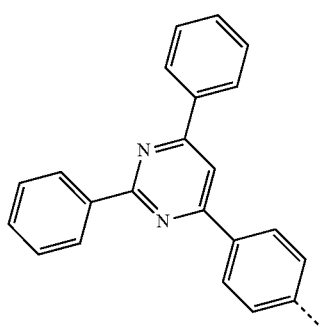
B-11
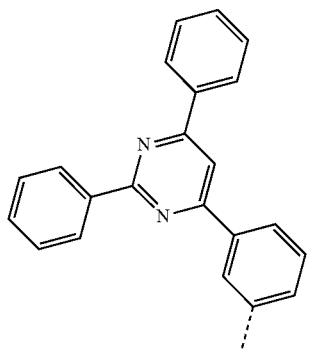
B-12
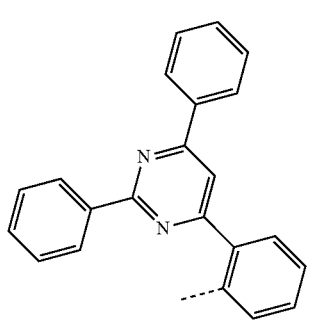
B-13
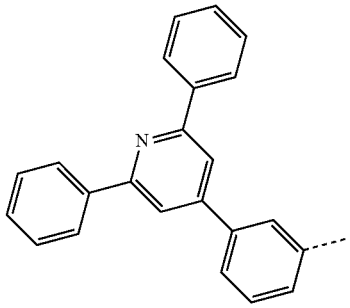
B-14
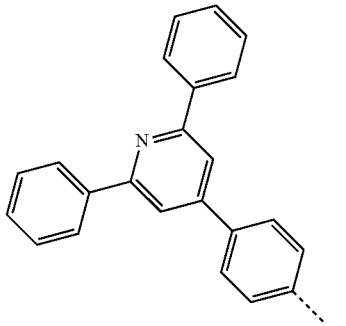
B-15
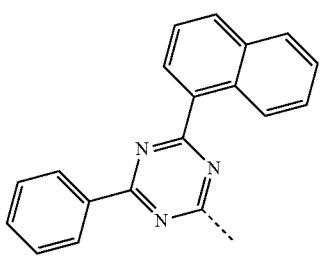
B-16
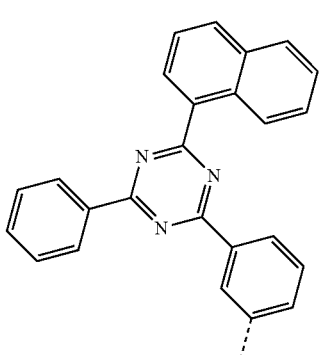
B-17
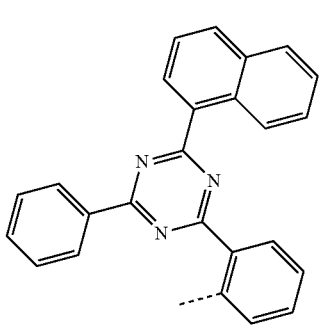

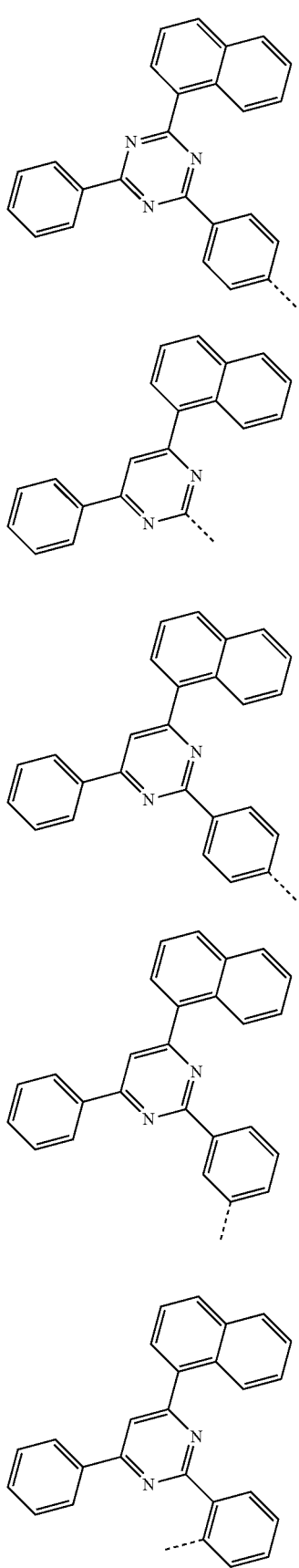
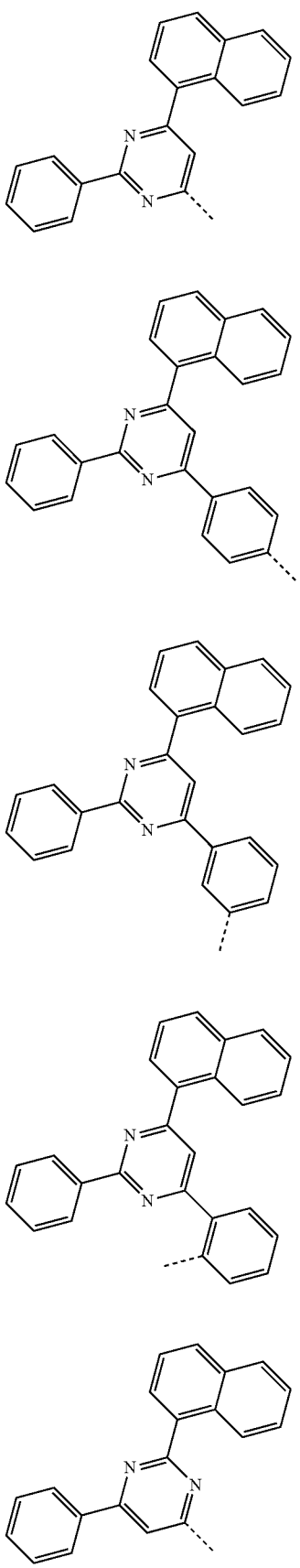

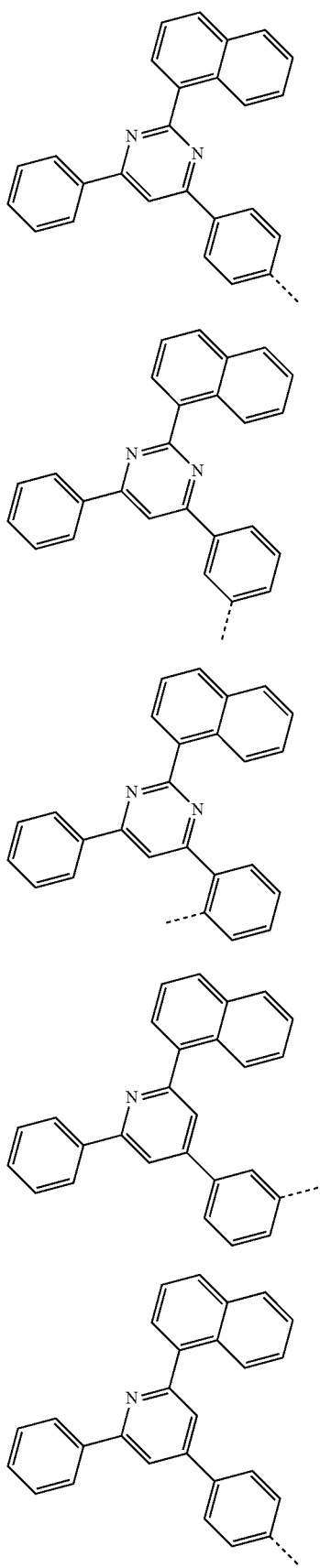
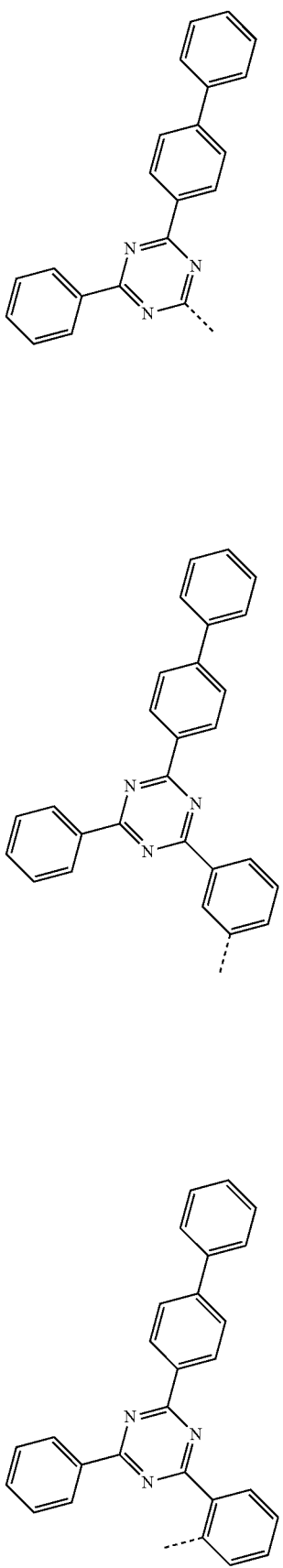

B-36
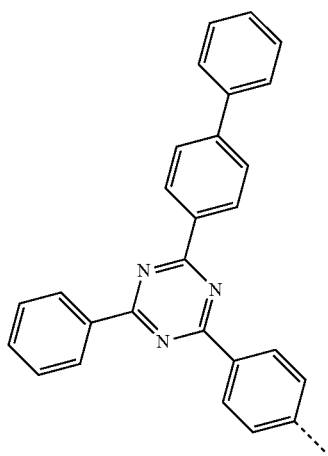
B-37
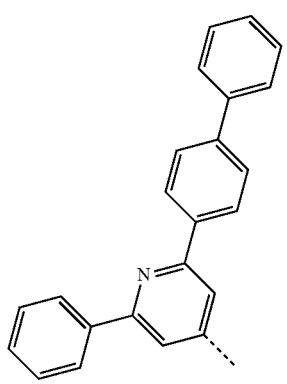
B-38
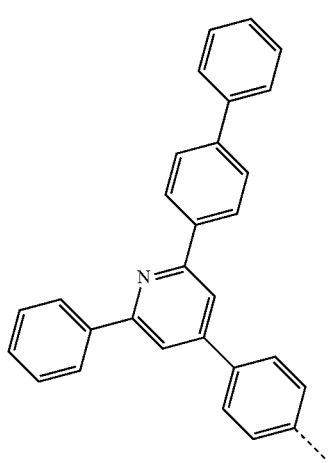
B-39
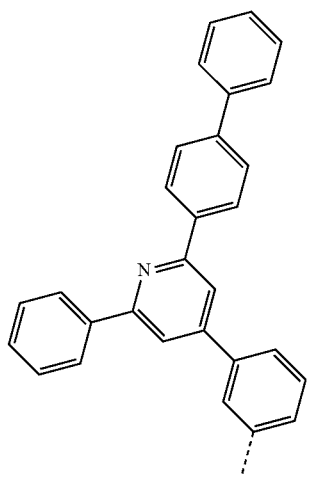
B-40
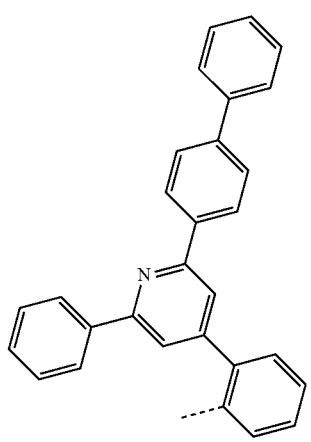
B-41
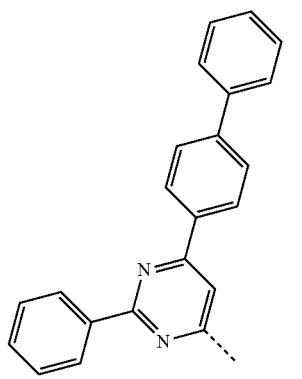

B-42 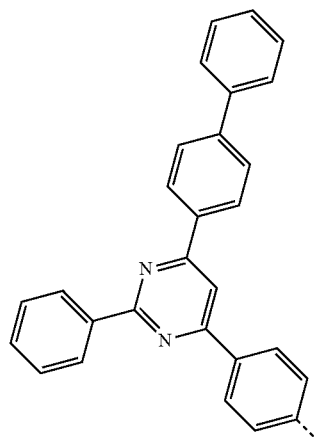
B-43 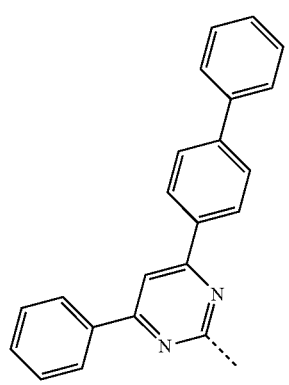
B-44 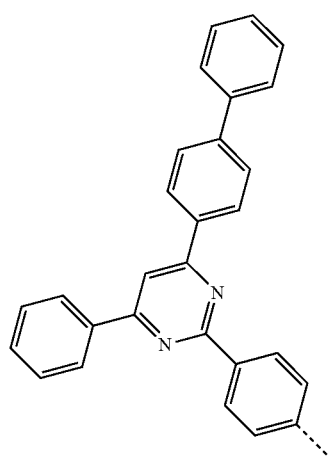
B-45 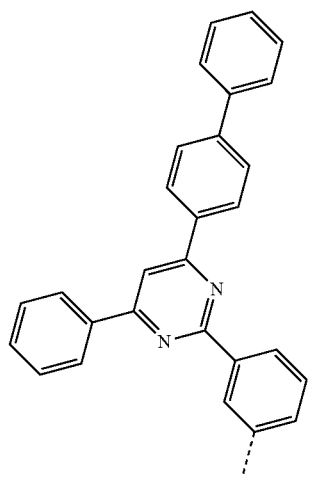
B-46 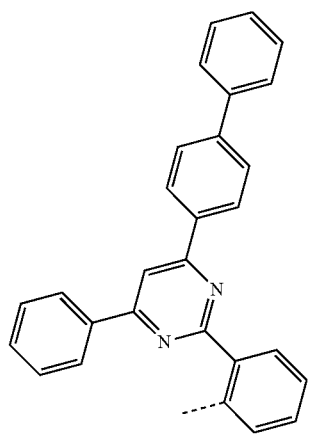
B-47 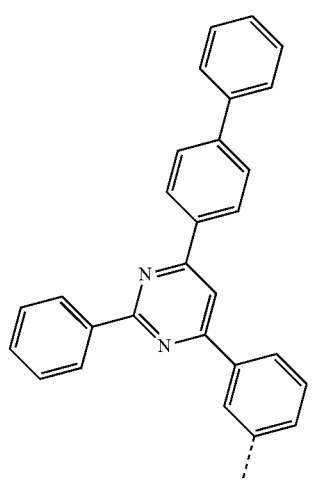

B-48
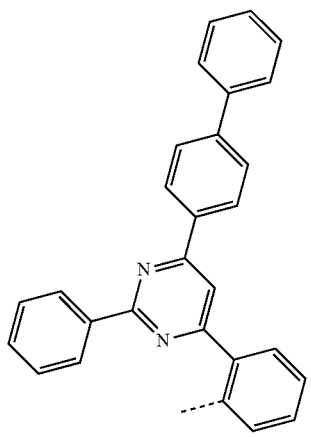
B-49
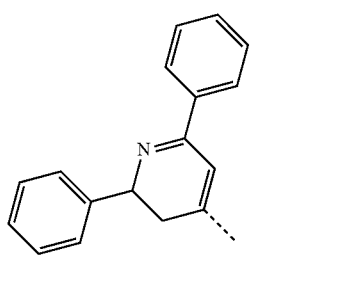
B-50
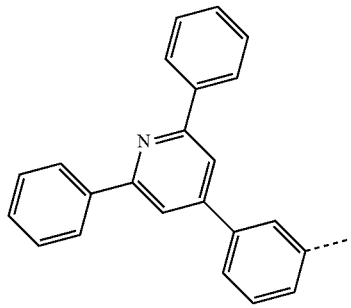
B-51
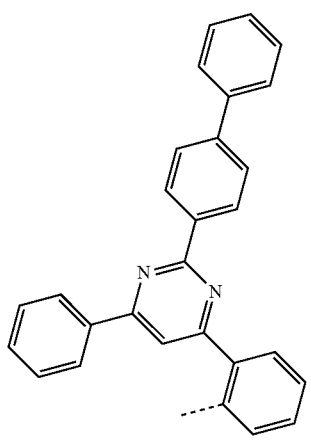
B-52
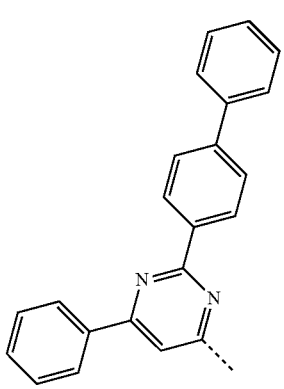
B-53
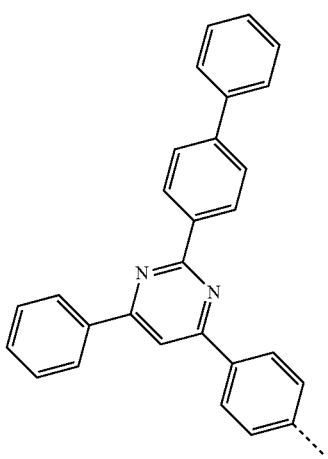
B-54
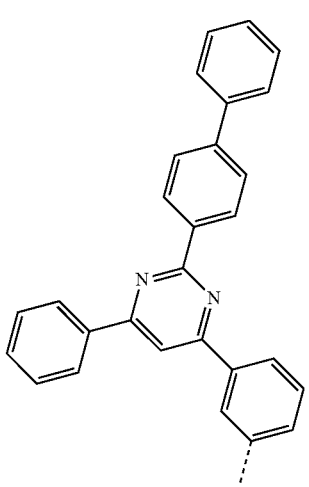
B-55
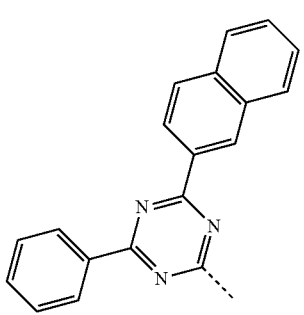

B-56 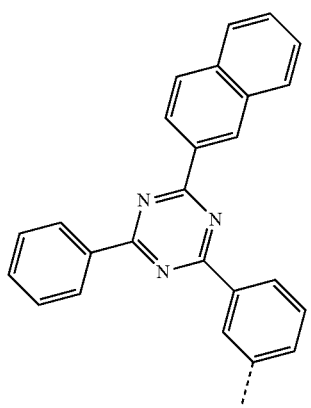
B-60 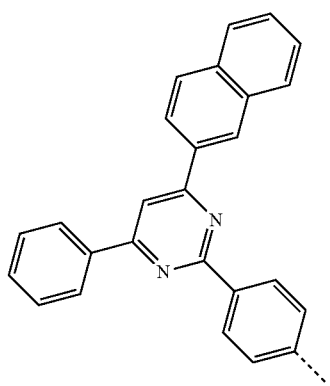
B-57 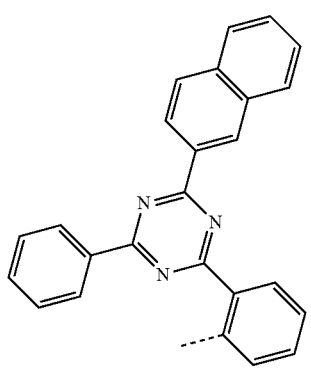
B-61 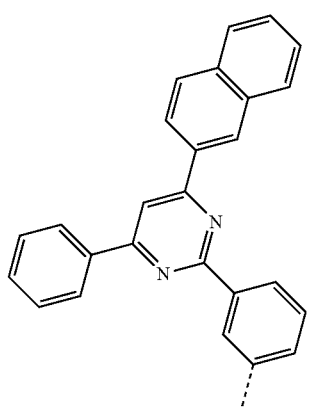
B-58 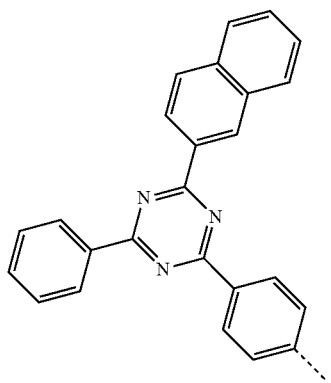
B-62 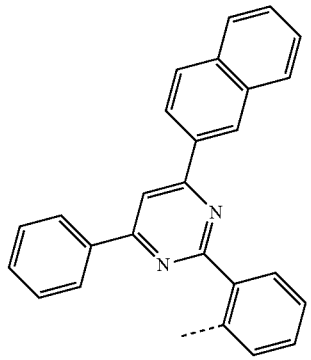
B-59 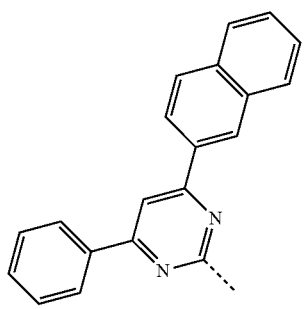
B-63 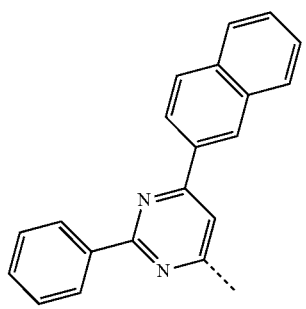

B-64
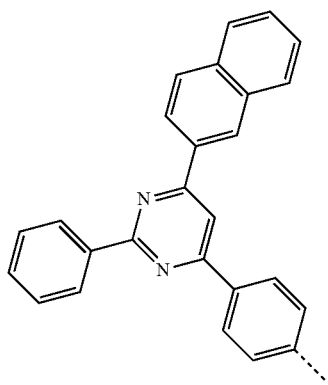
B-65
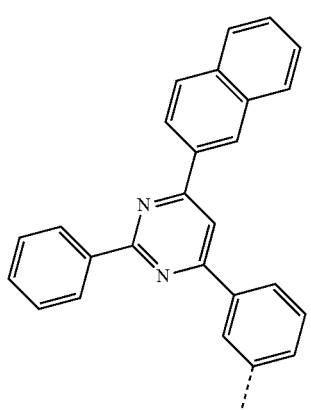
B-66
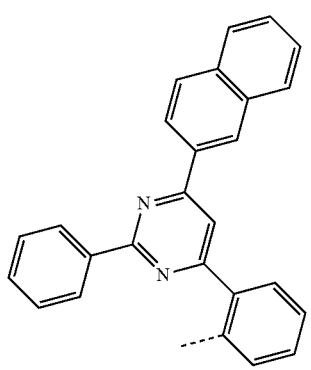
B-67
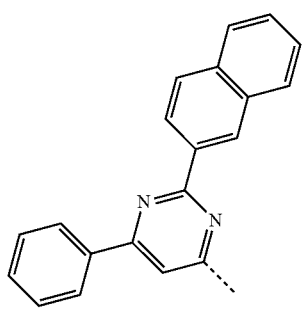
B-68
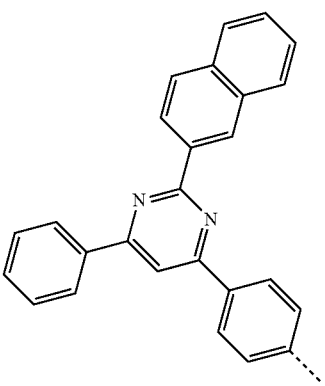
B-69
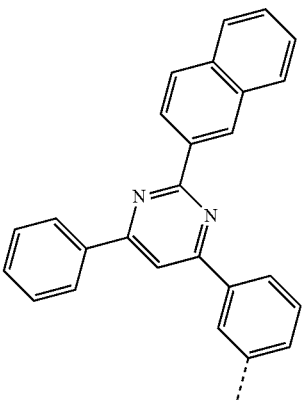
B-70
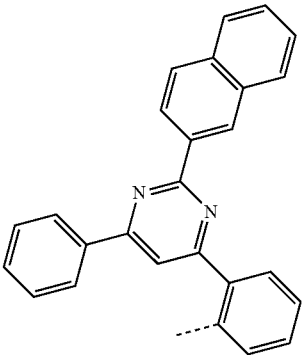
B-71
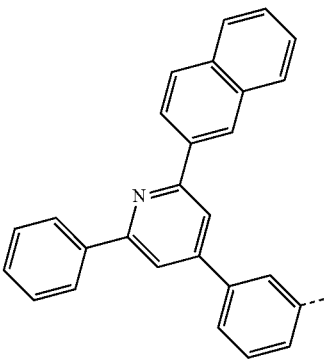

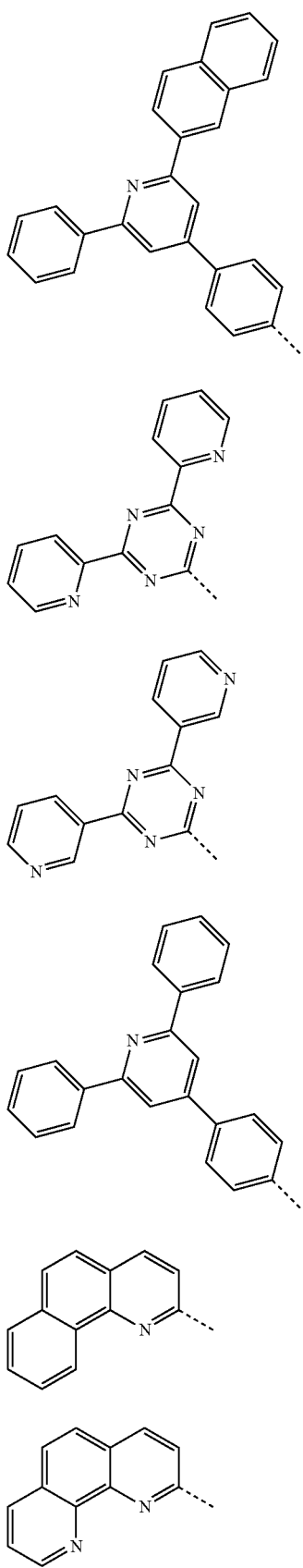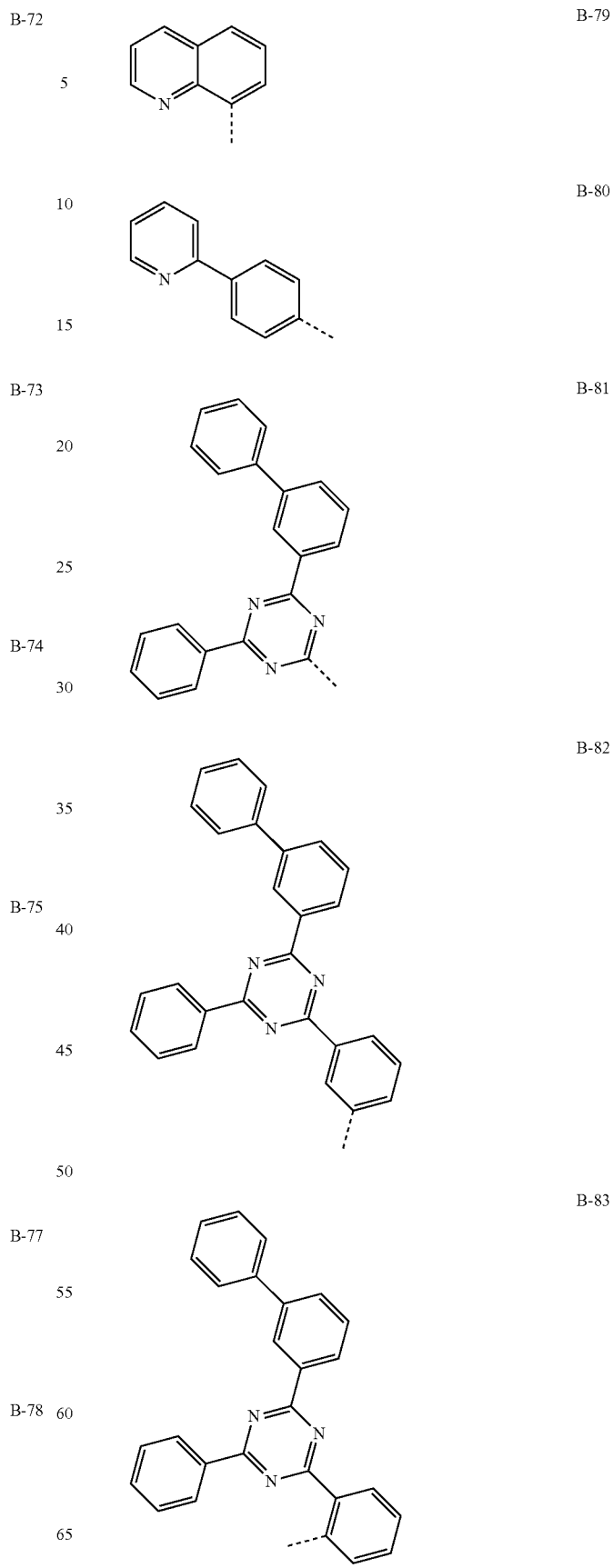

-continued
B-84
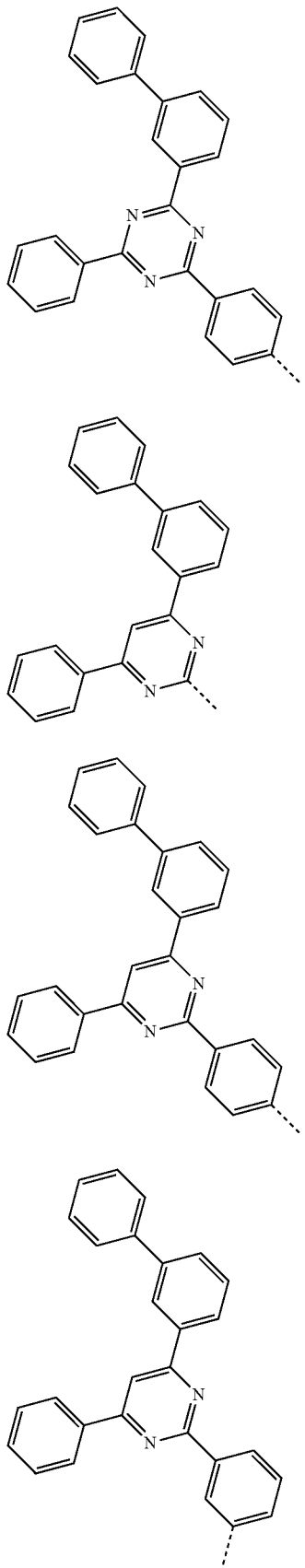
B-85
B-86
B-87
-continued
B-88
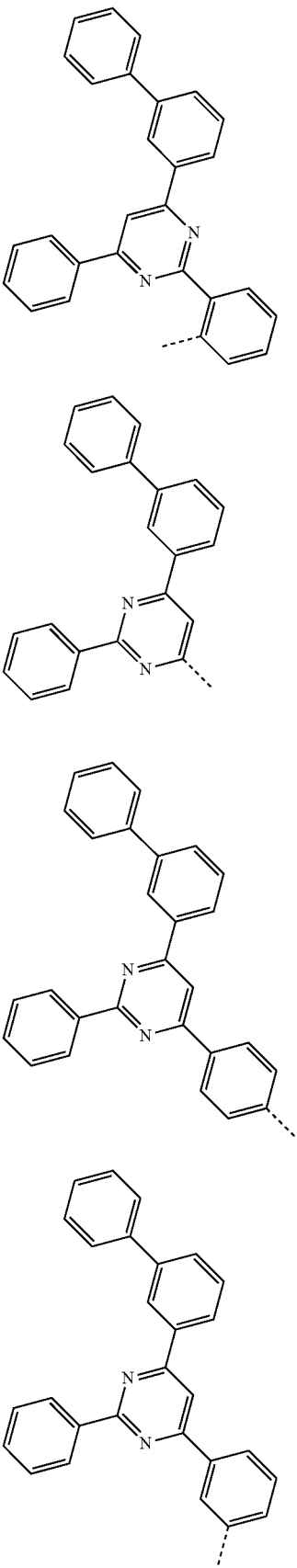
B-89
B-90
B-91

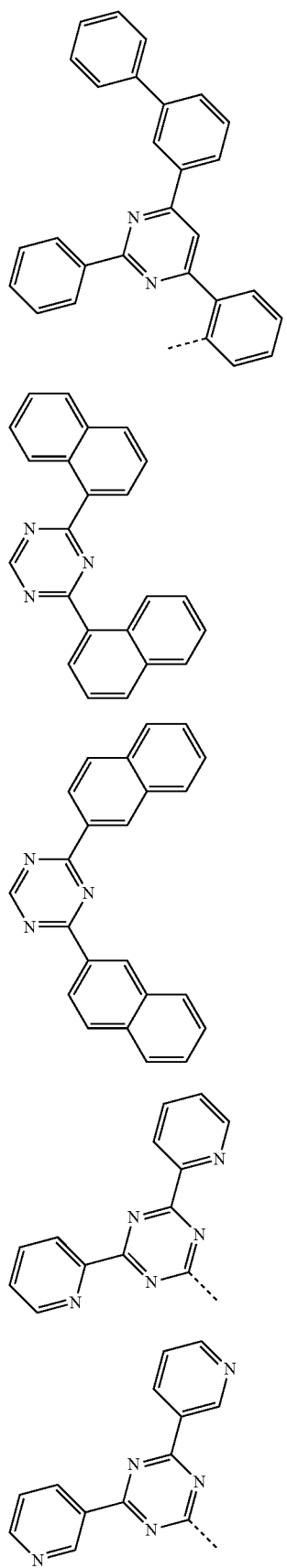
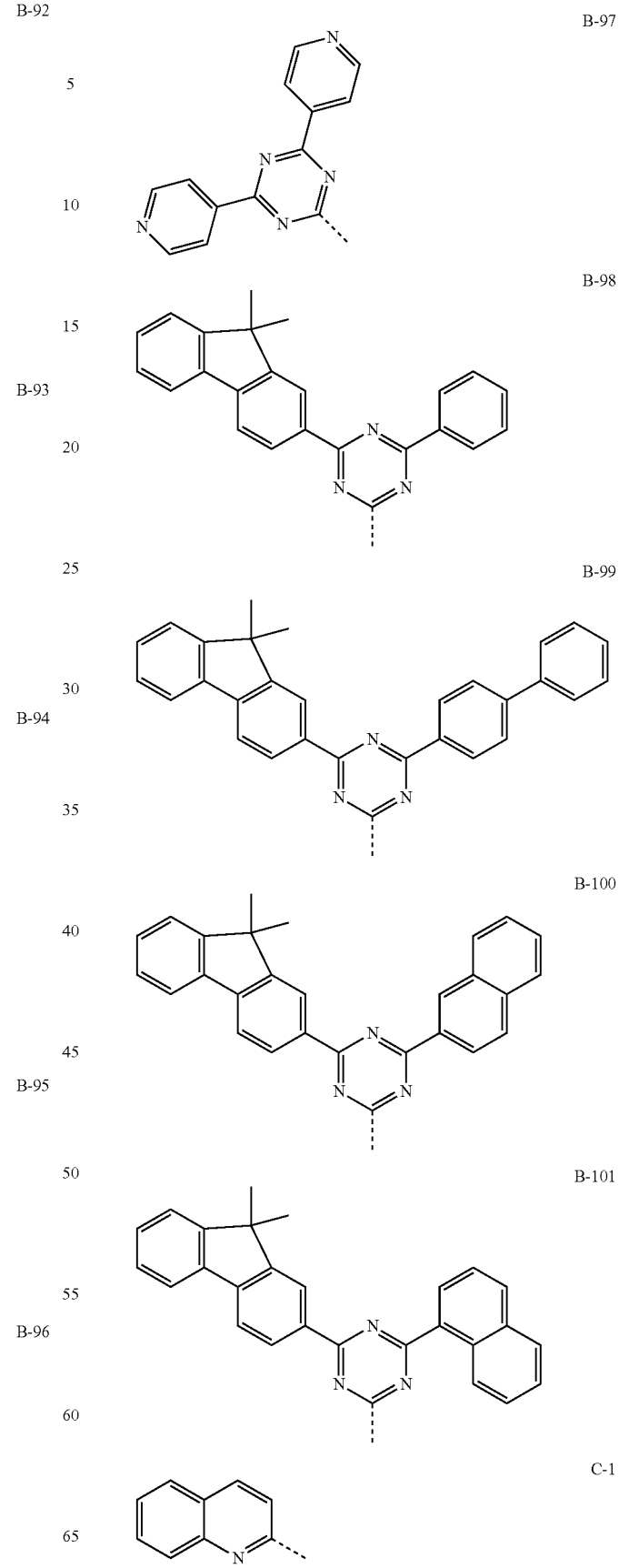

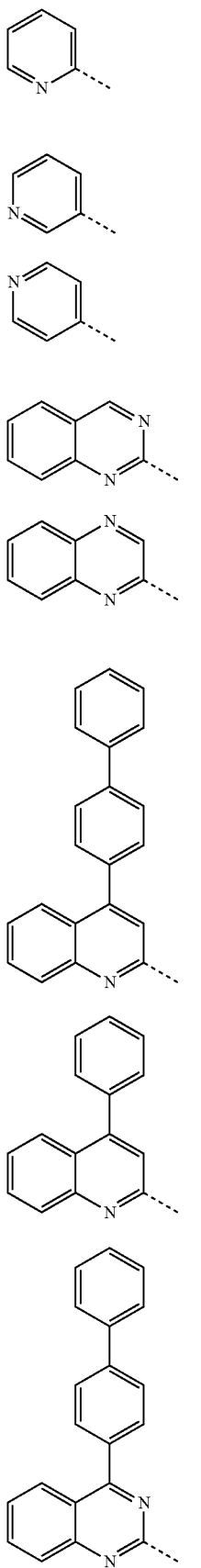
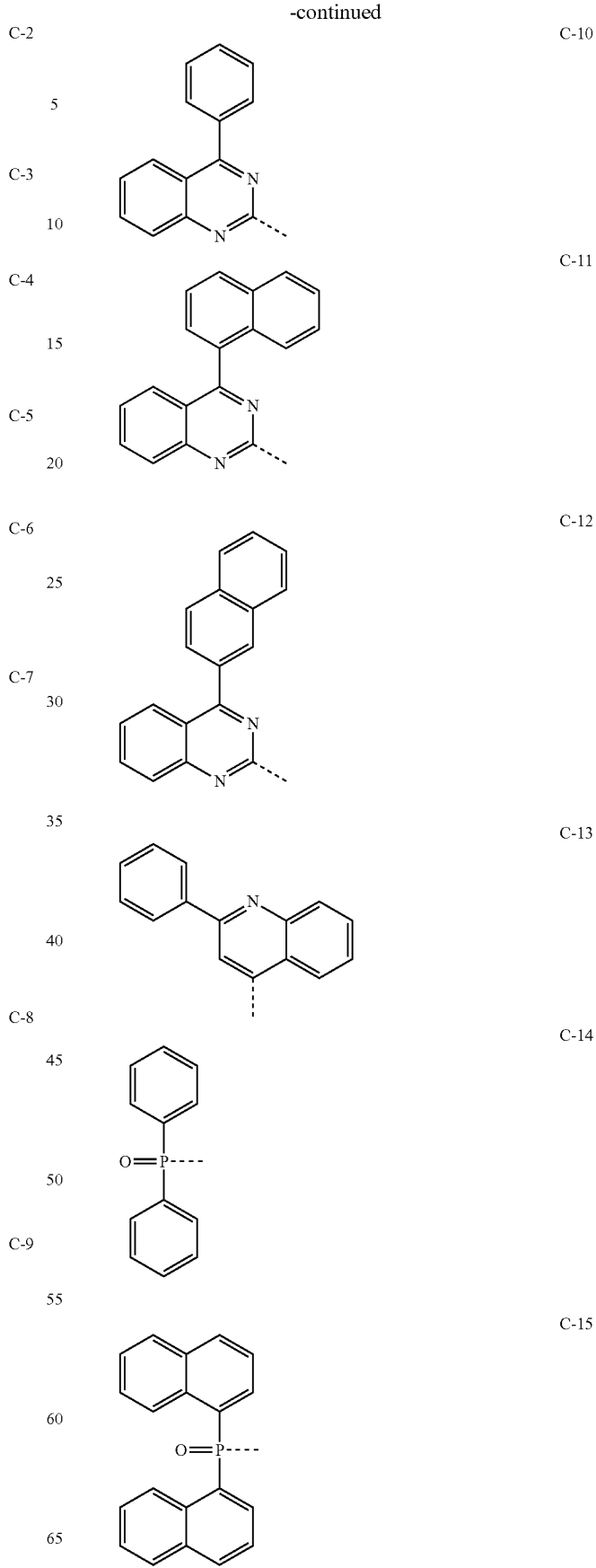

C-16
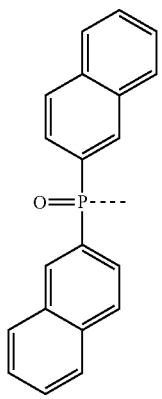
C-17
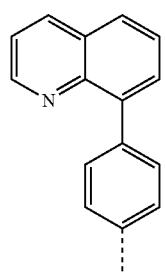
C-18
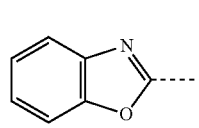
C-20
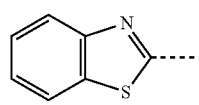
C-21
C-22
C-23
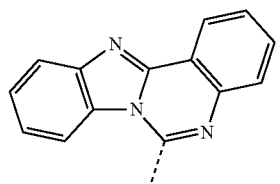
In the structures, - - - is a moiety linked to Chemical Formula 1.
According to an exemplary embodiment of the present specification, Chemical Formula 1 is selected from the following compounds.
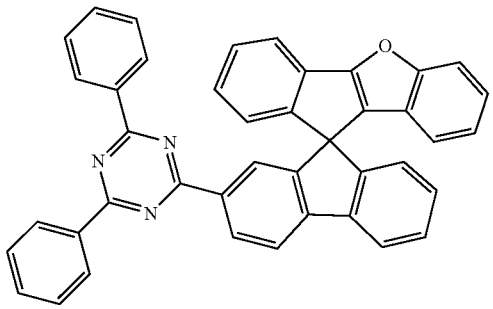
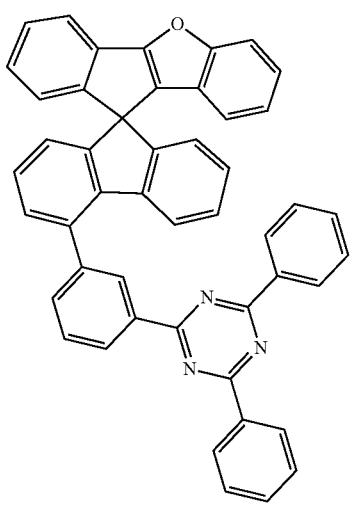
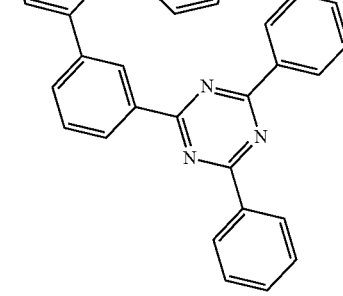
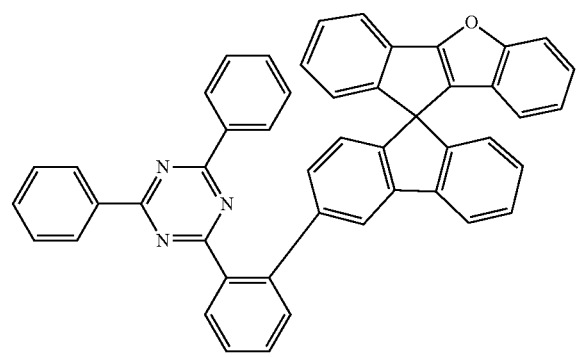

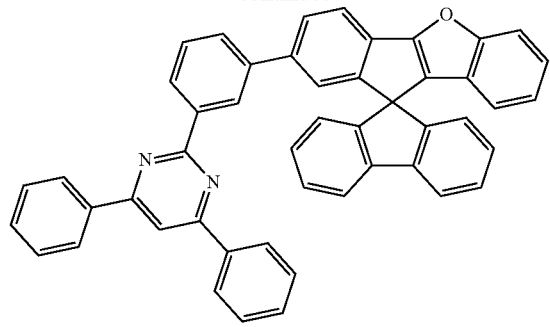
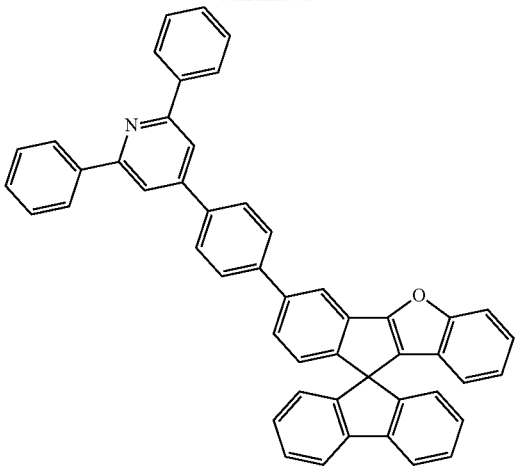
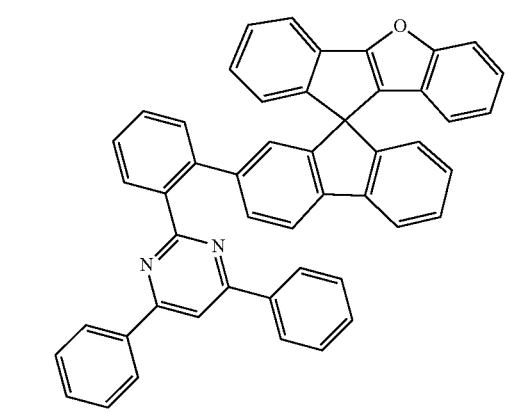
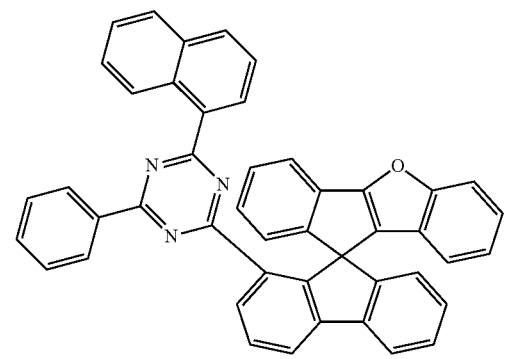
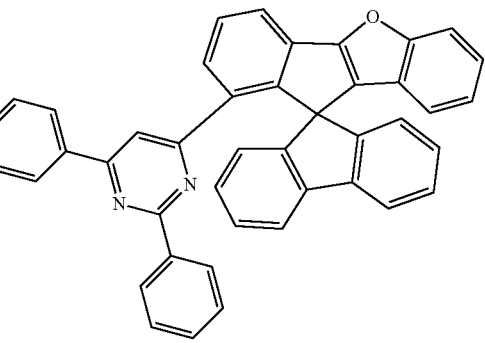
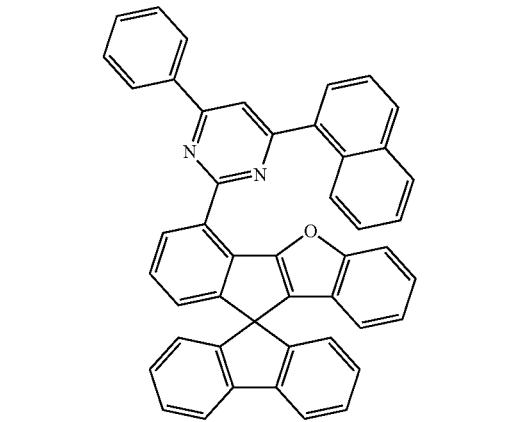
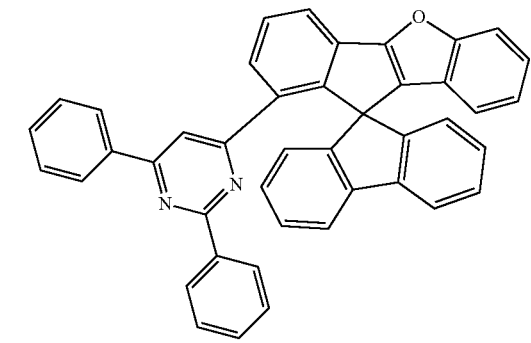
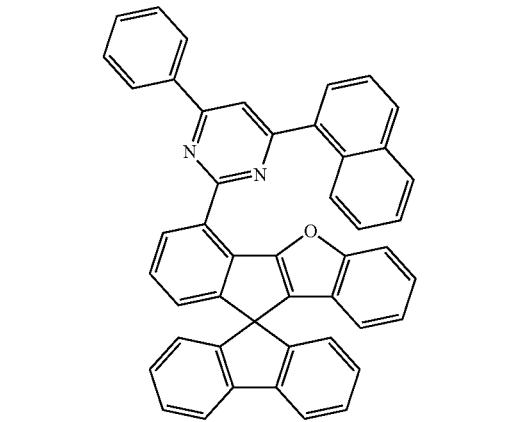

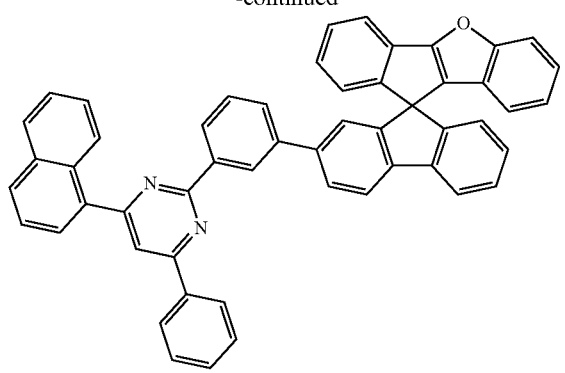
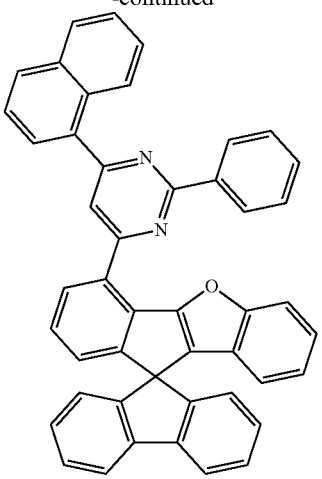
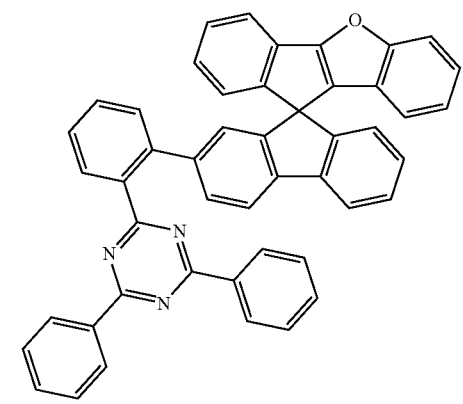
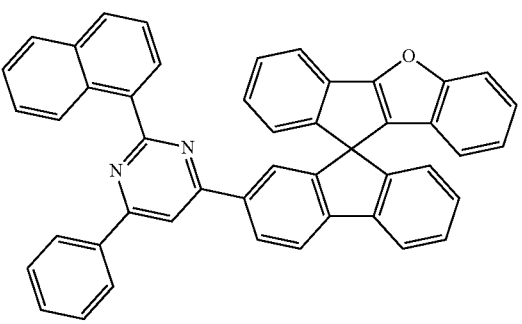
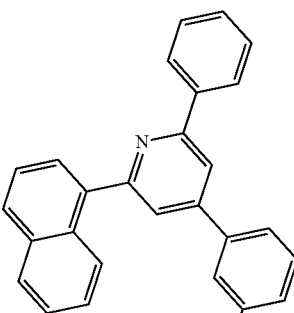
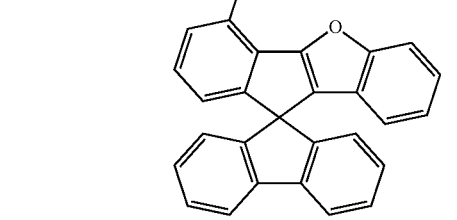
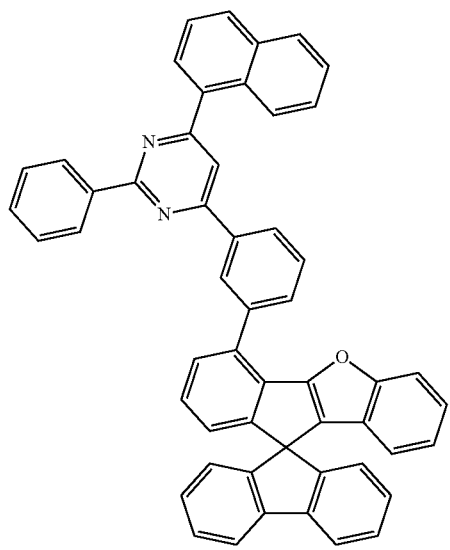
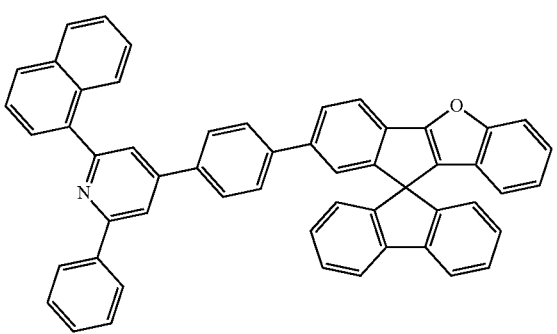

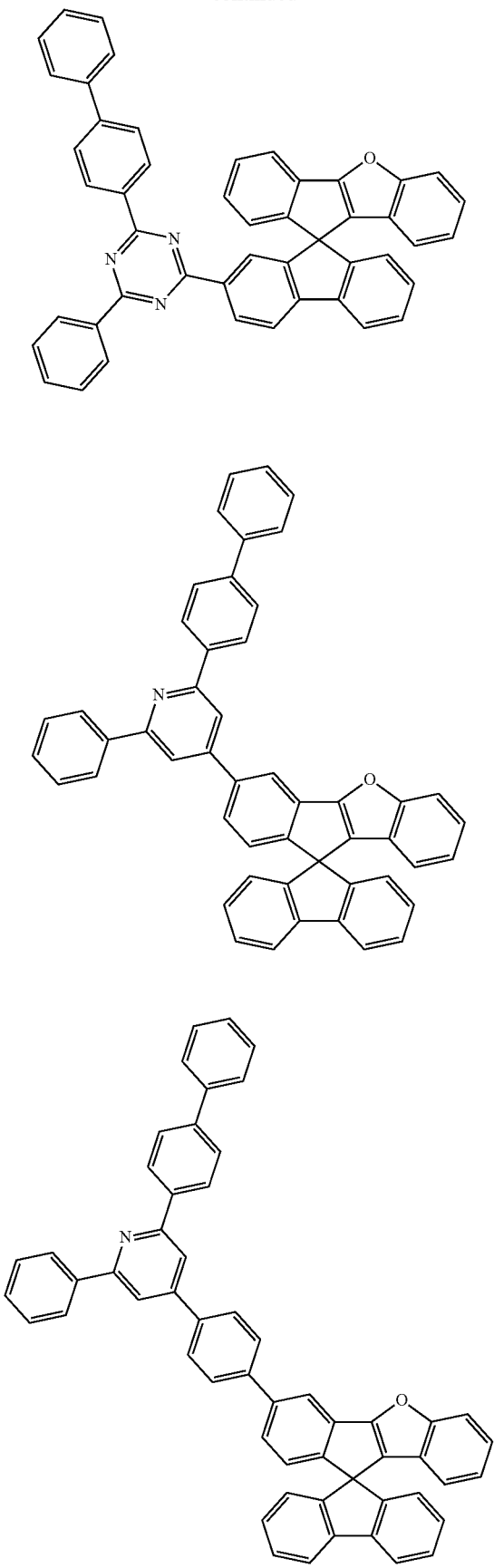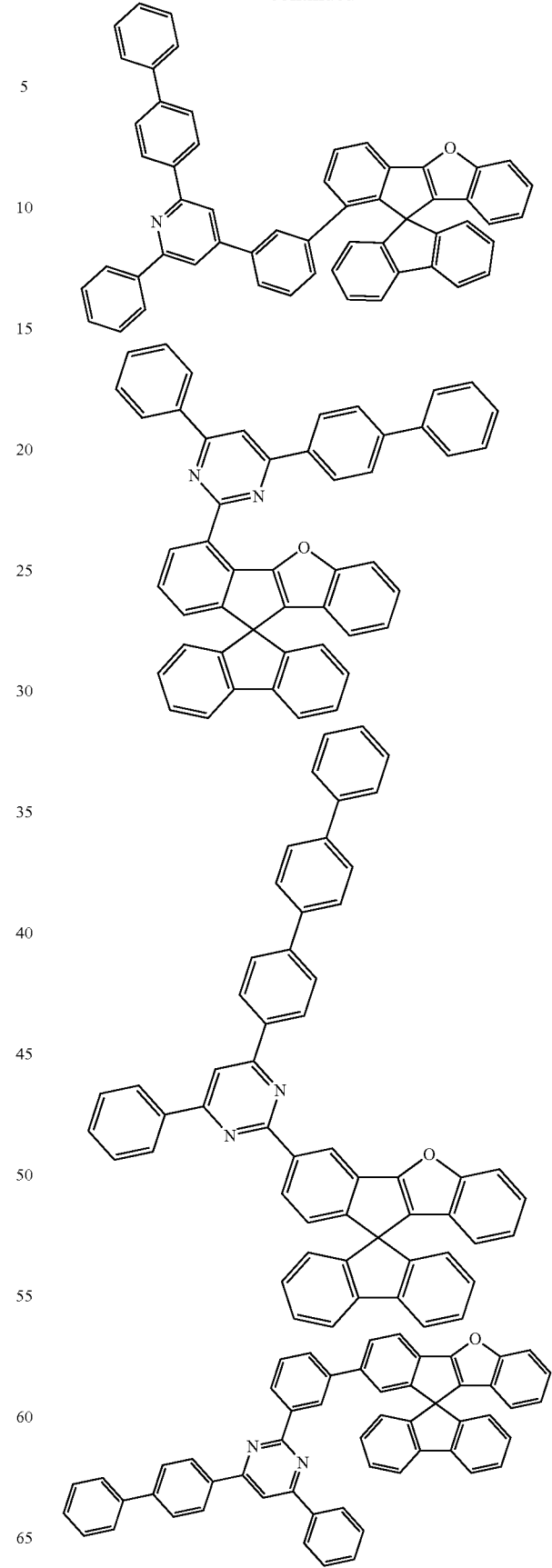

-continued
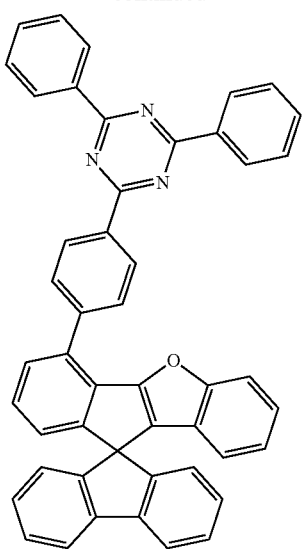
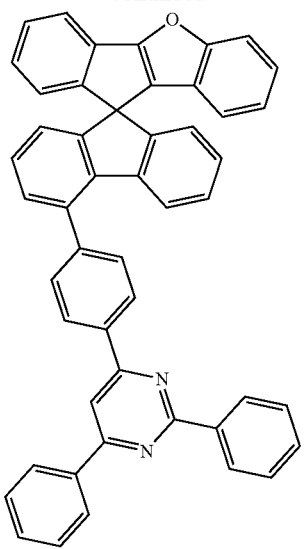
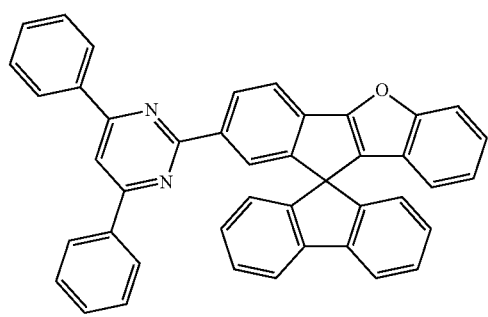
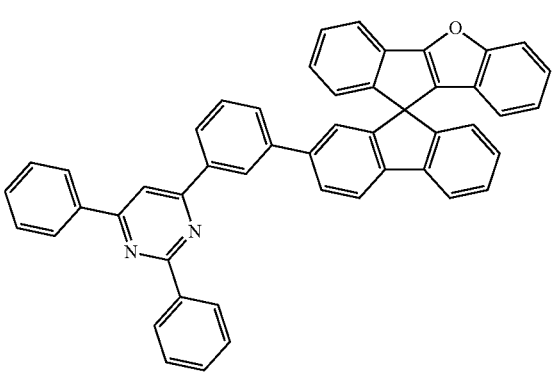
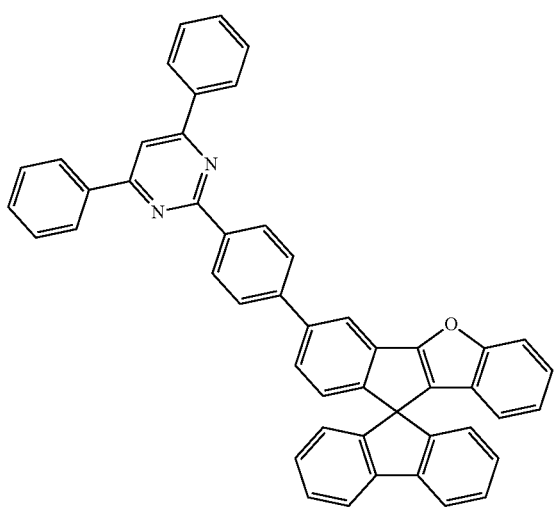
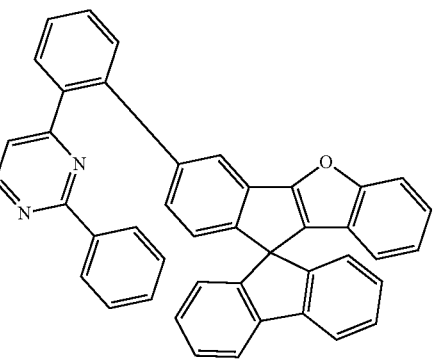

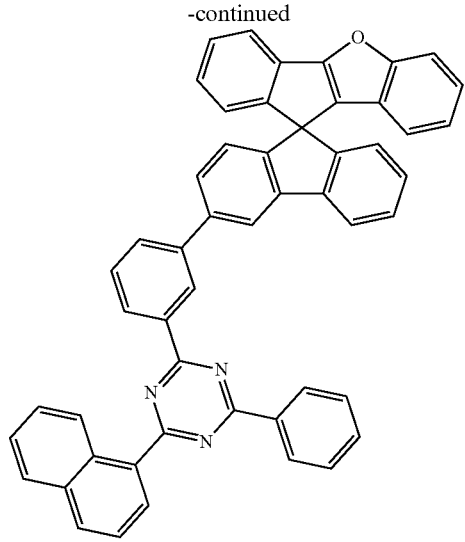
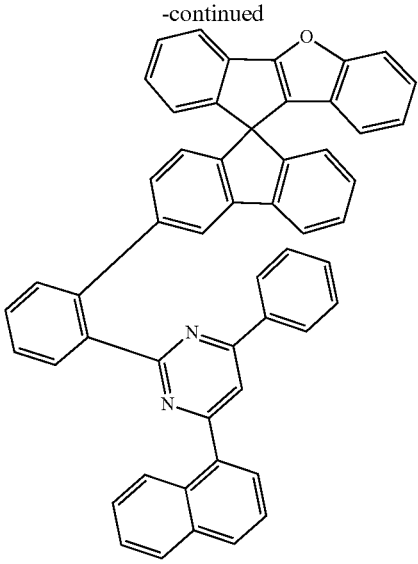
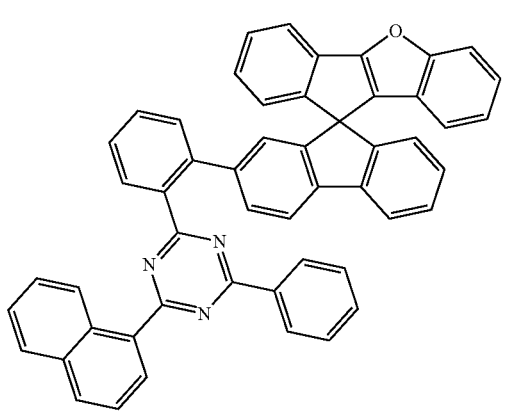
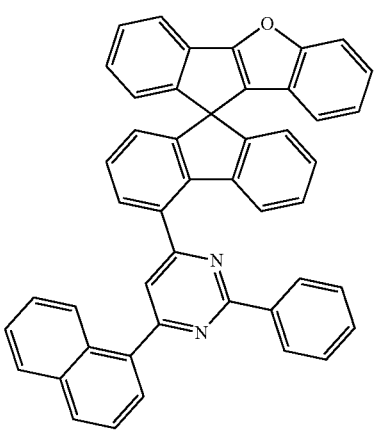
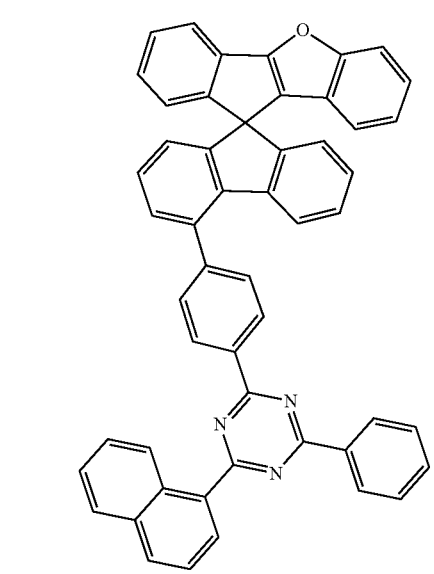
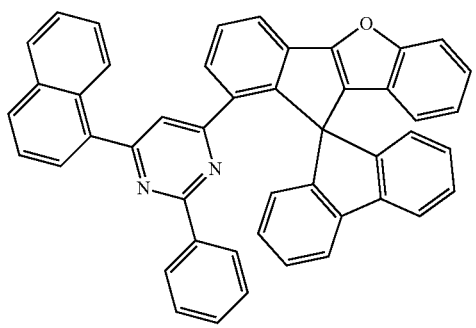

61
-continued
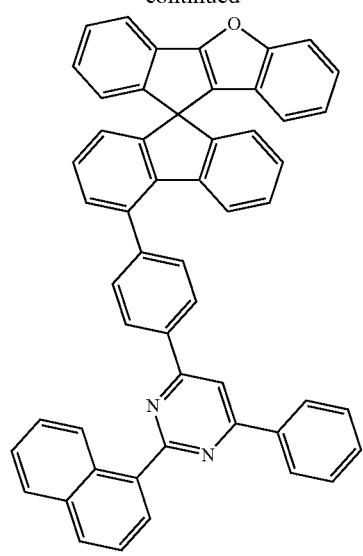
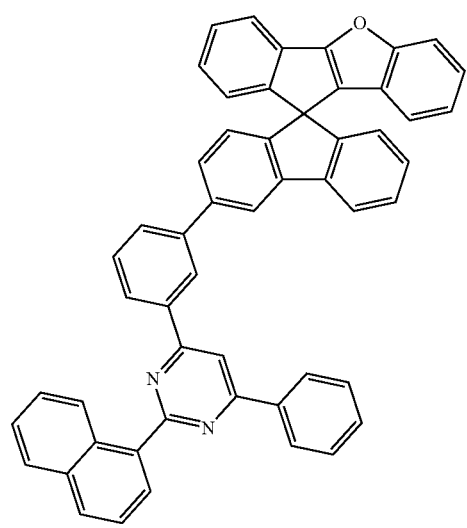
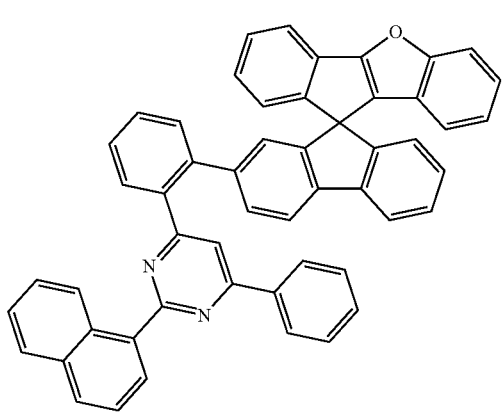
62
-continued
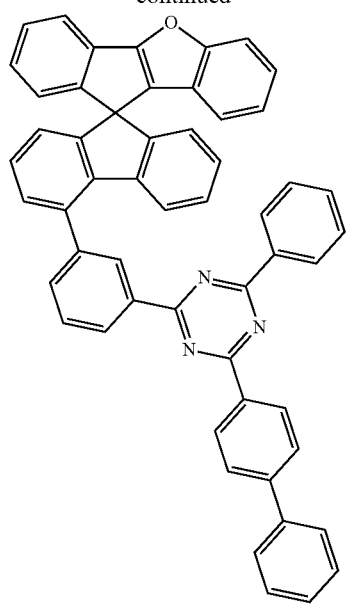
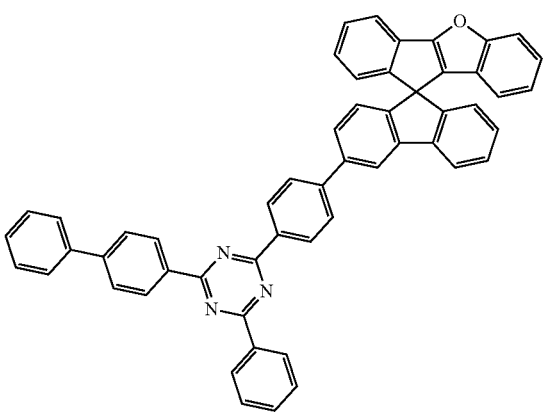

63
-continued
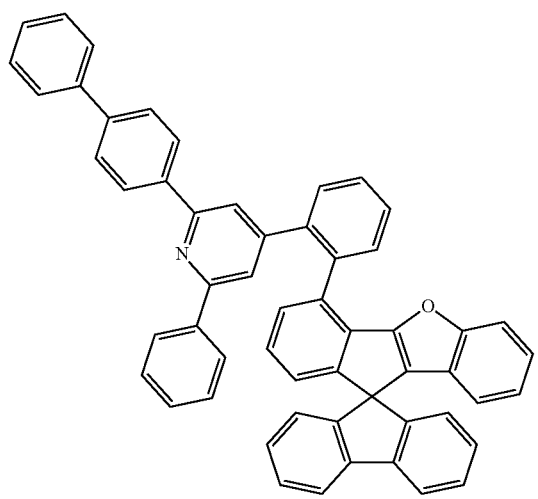
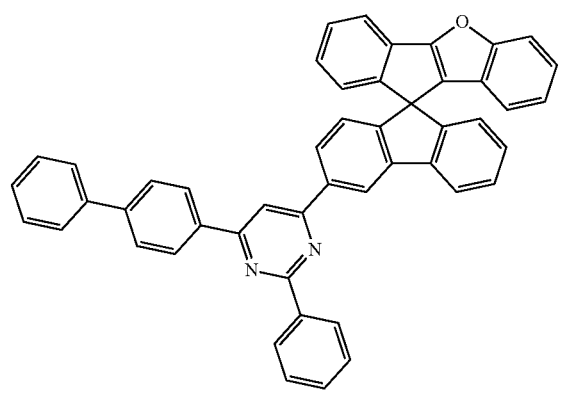
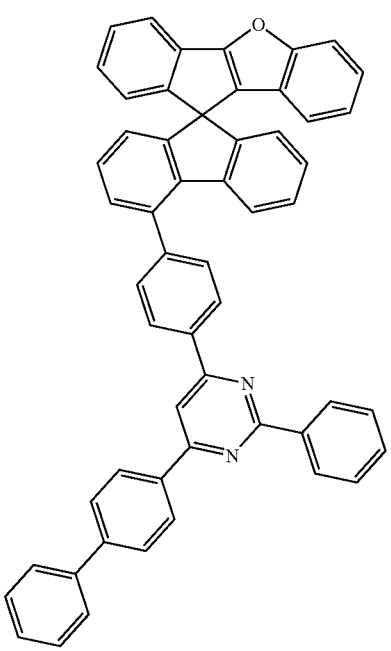
64
-continued
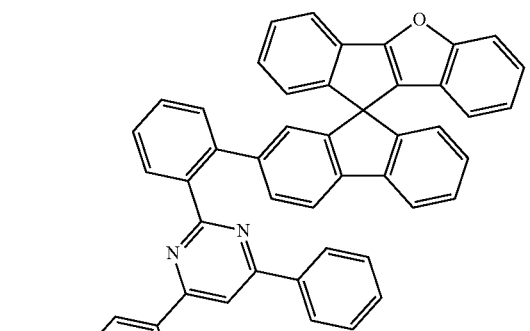
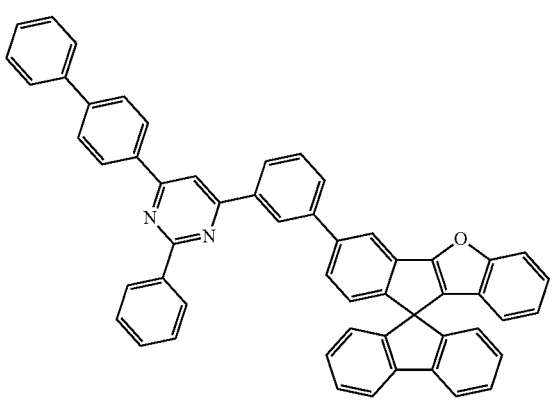
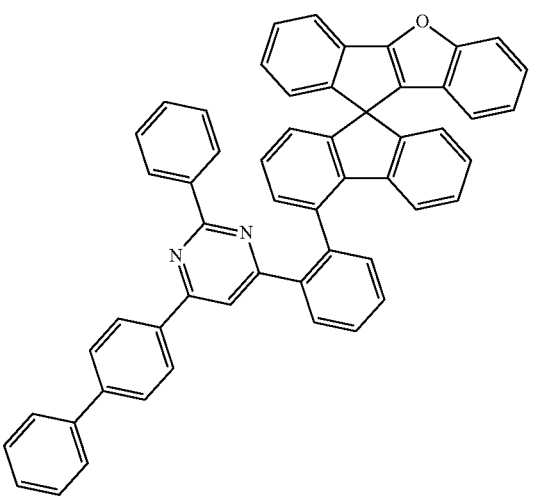

-continued
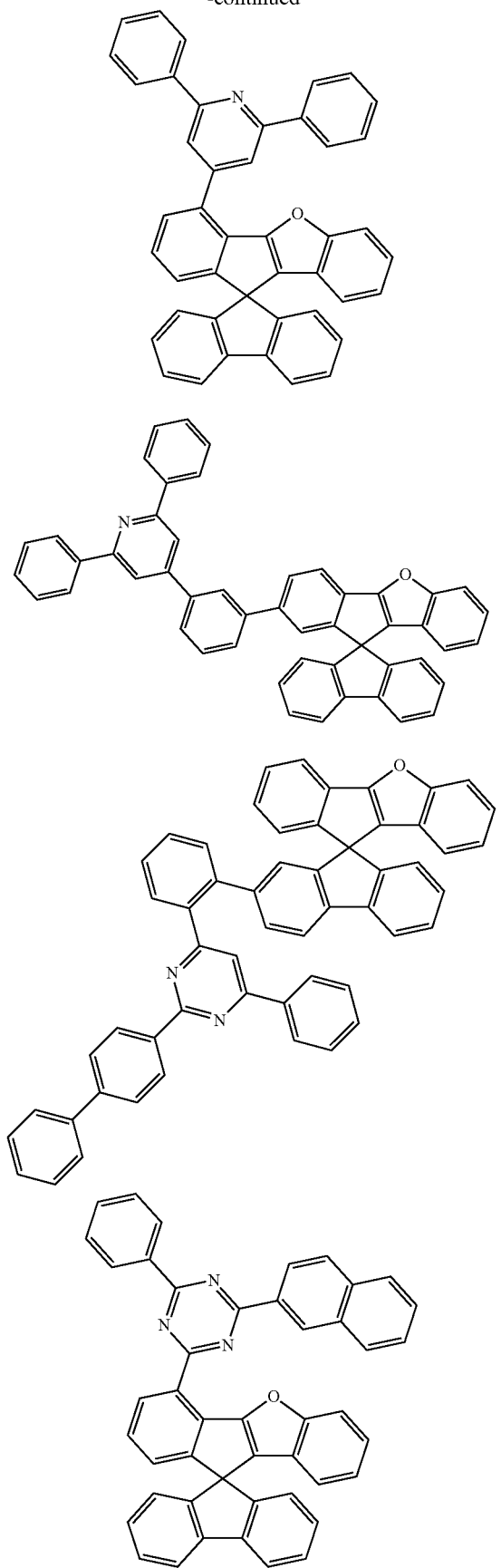
-continued
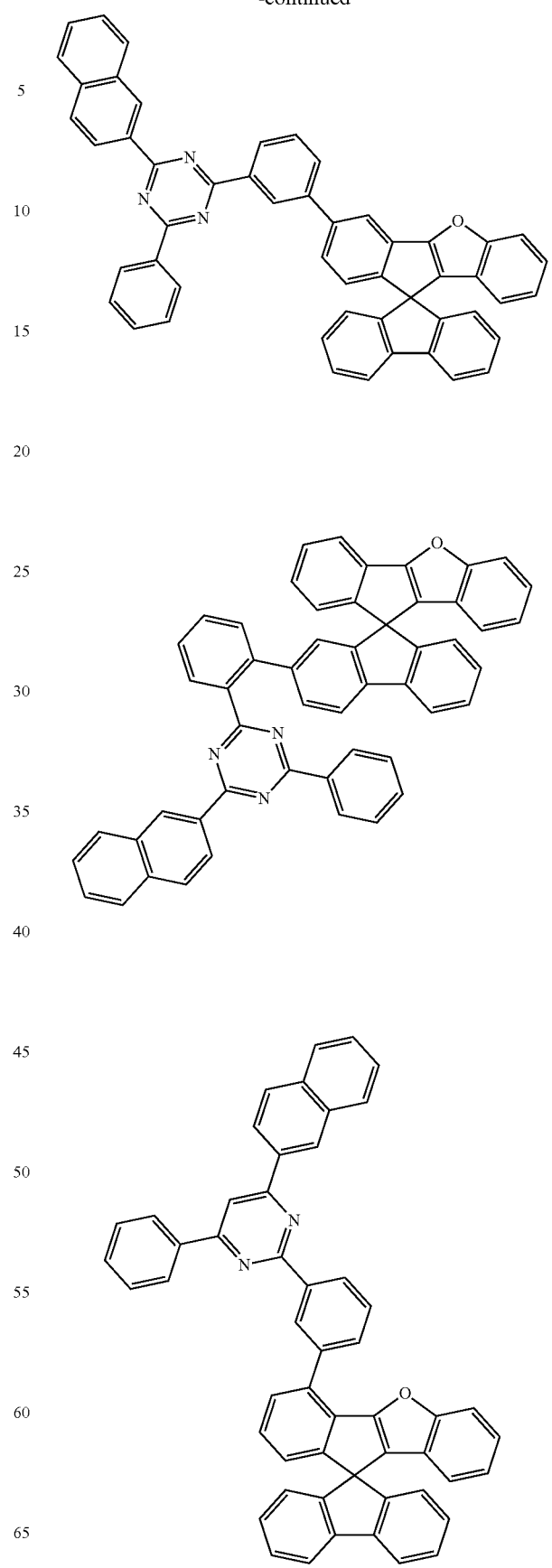

-continued
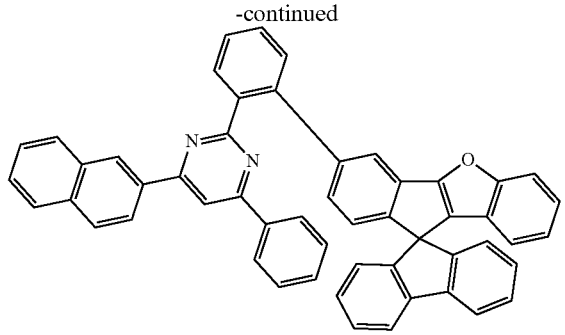
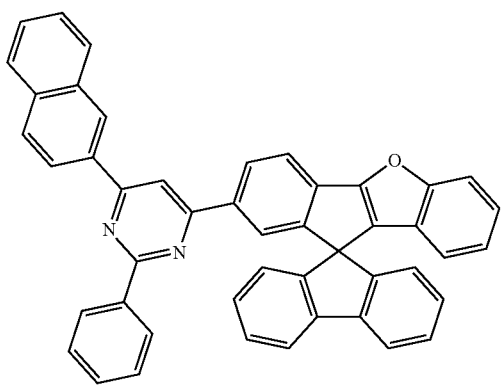
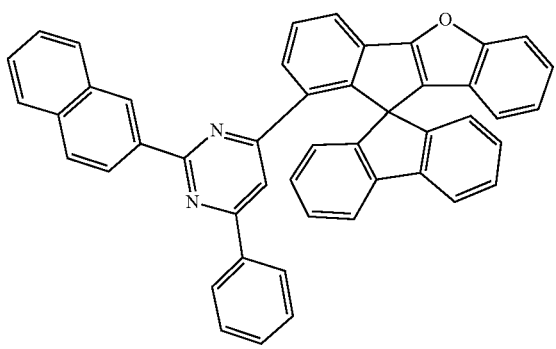
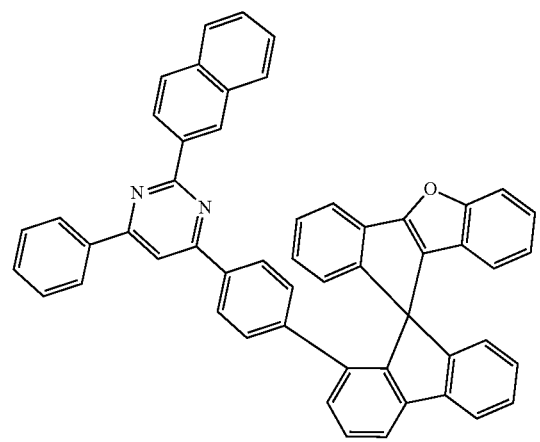
-continued
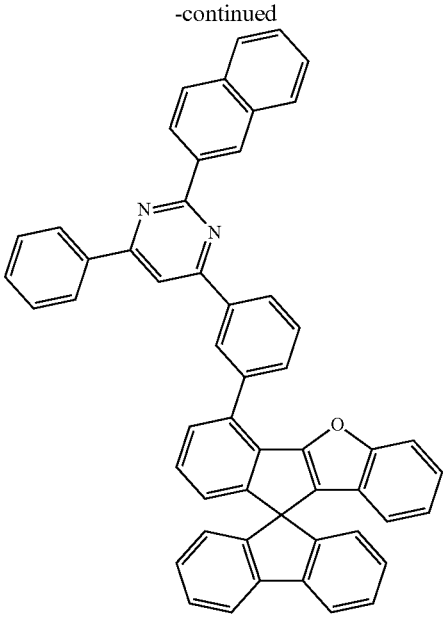
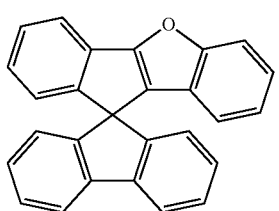
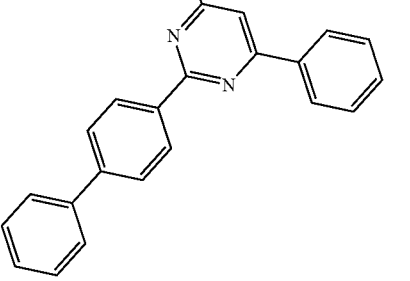
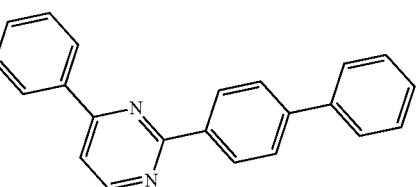
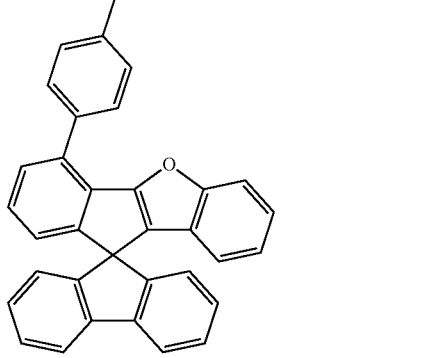

69
-continued
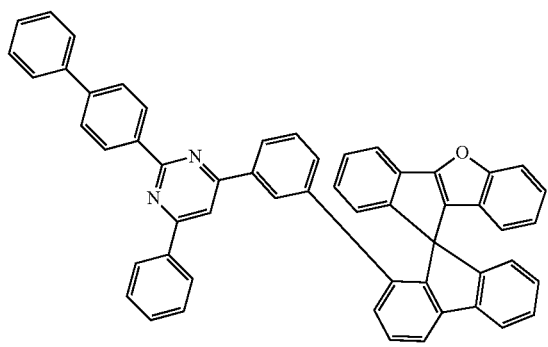
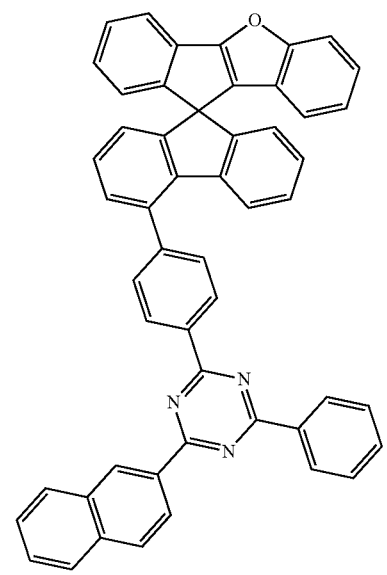
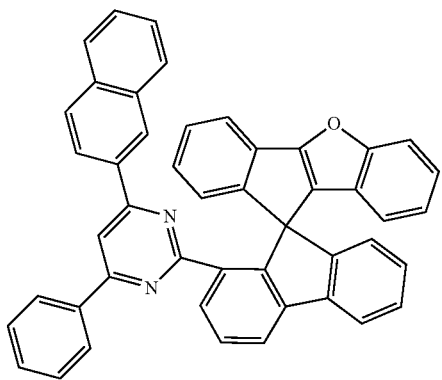
70
-continued
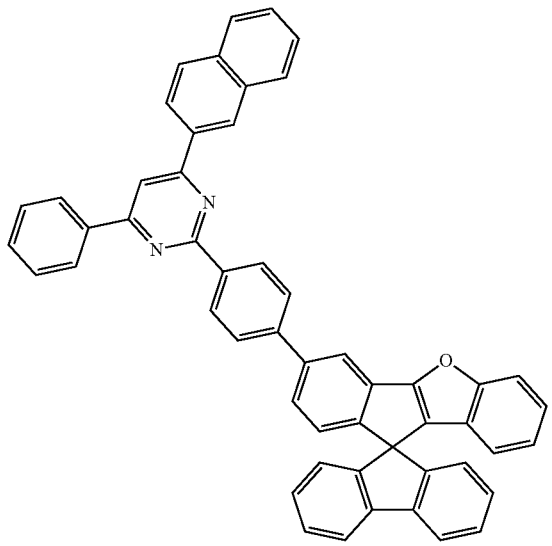
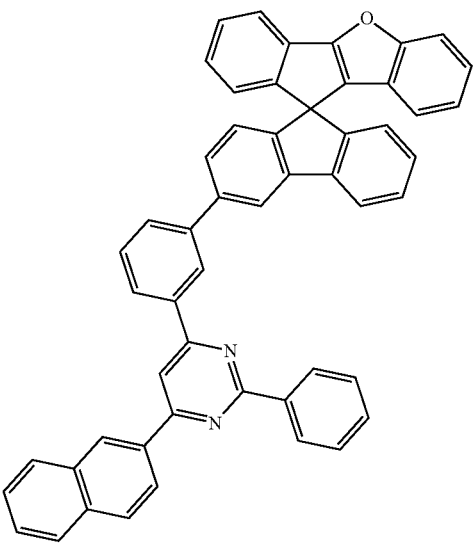

-continued
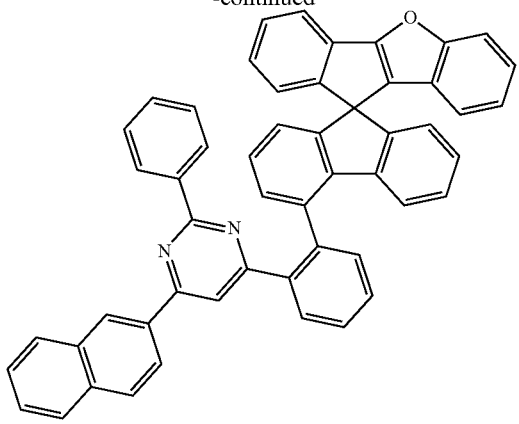
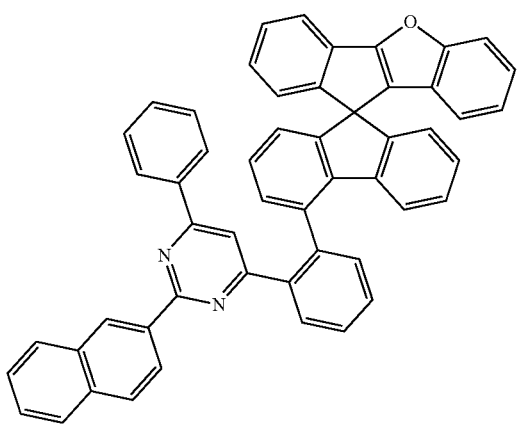
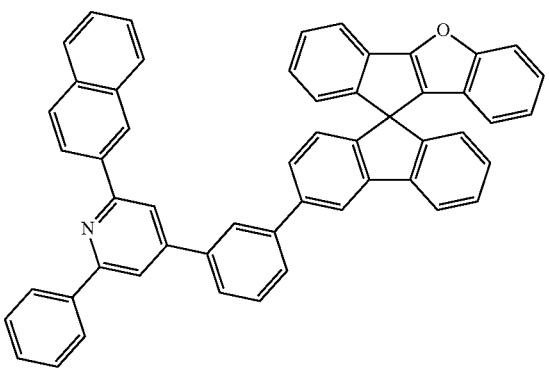
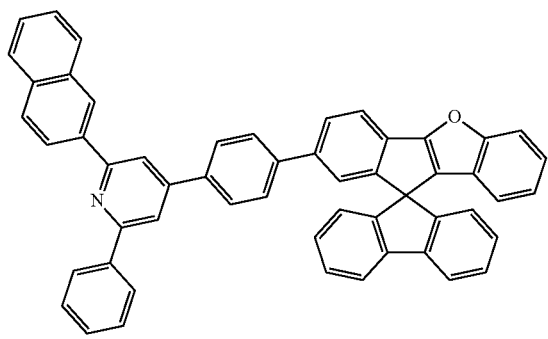
-continued
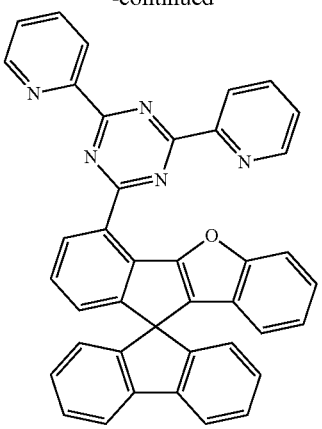
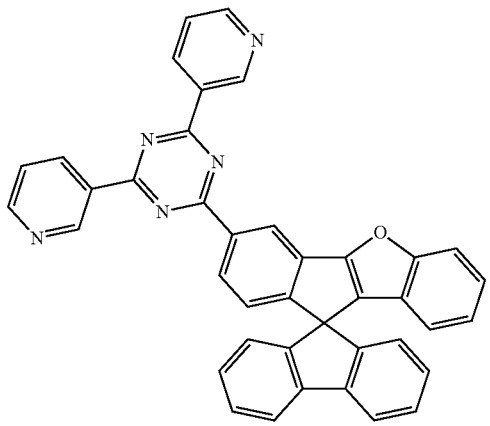
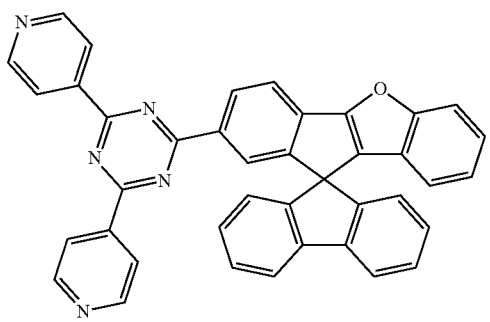
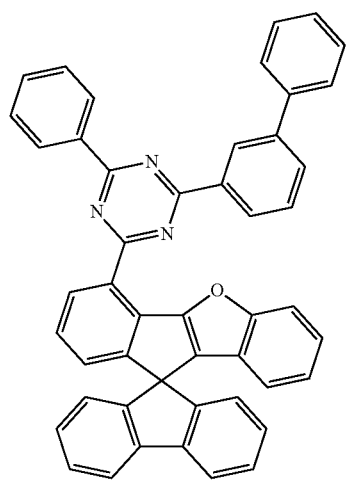

-continued
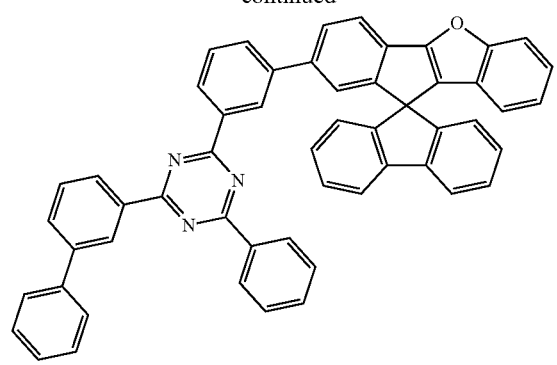
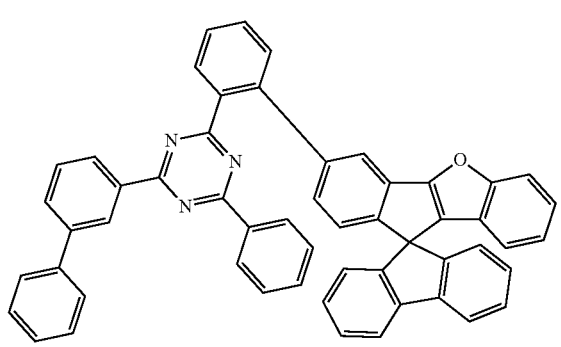
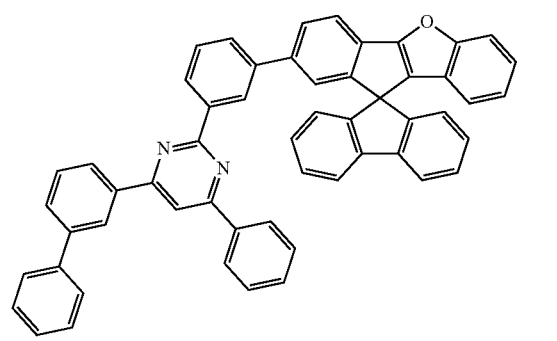
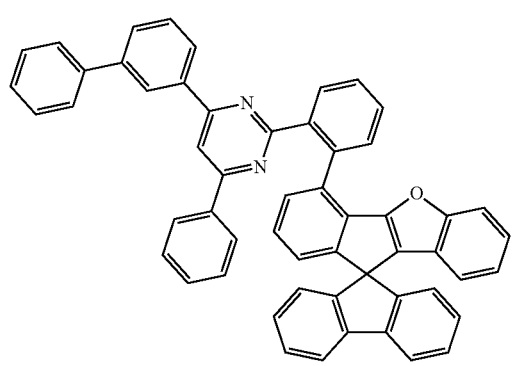
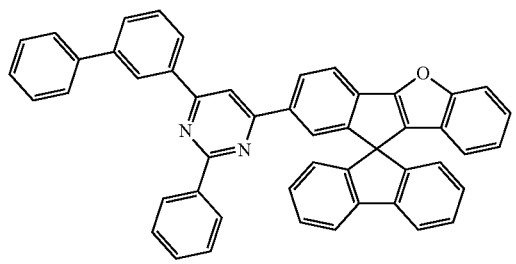
-continued
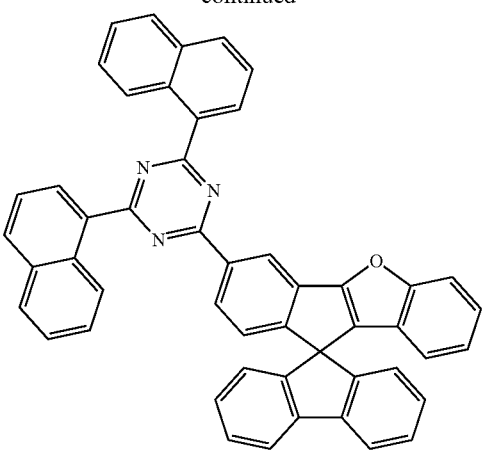
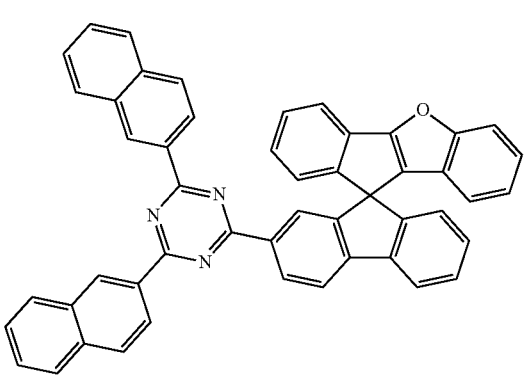
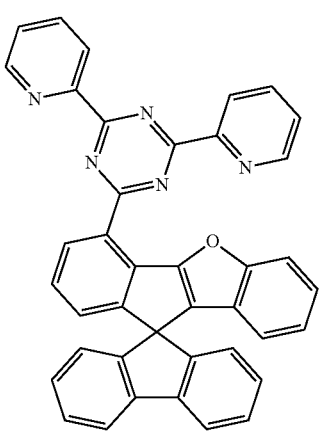
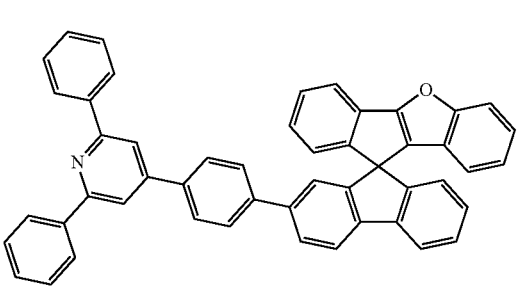

75
-continued
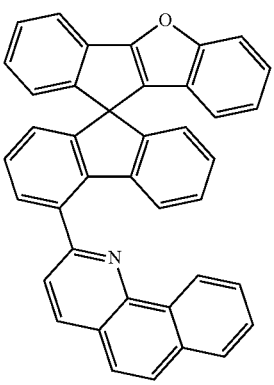
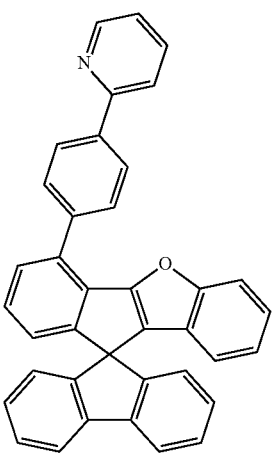
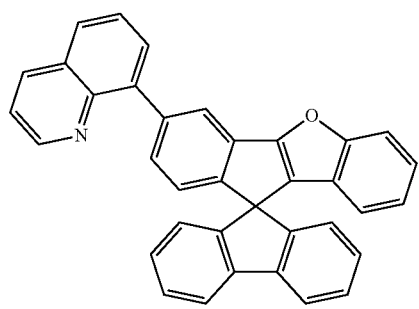
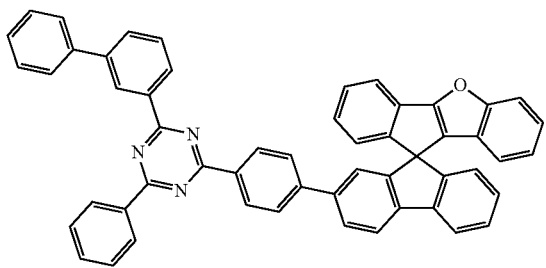
76
-continued
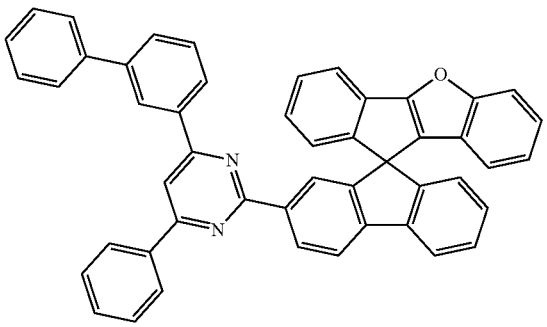
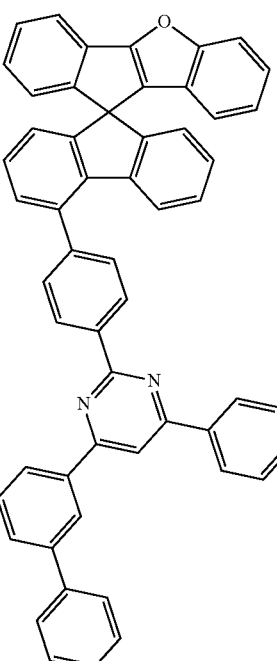
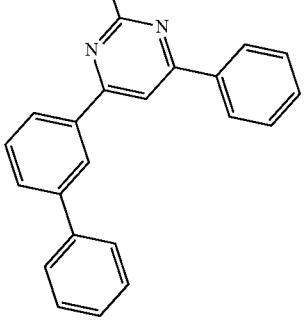
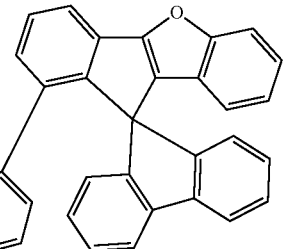

-continued
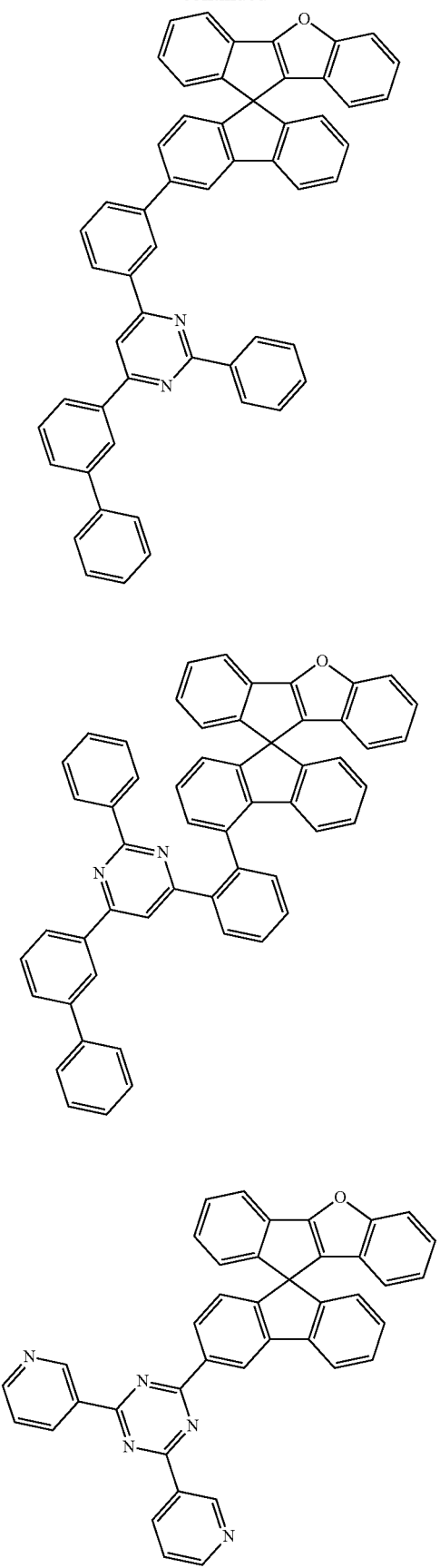
-continued
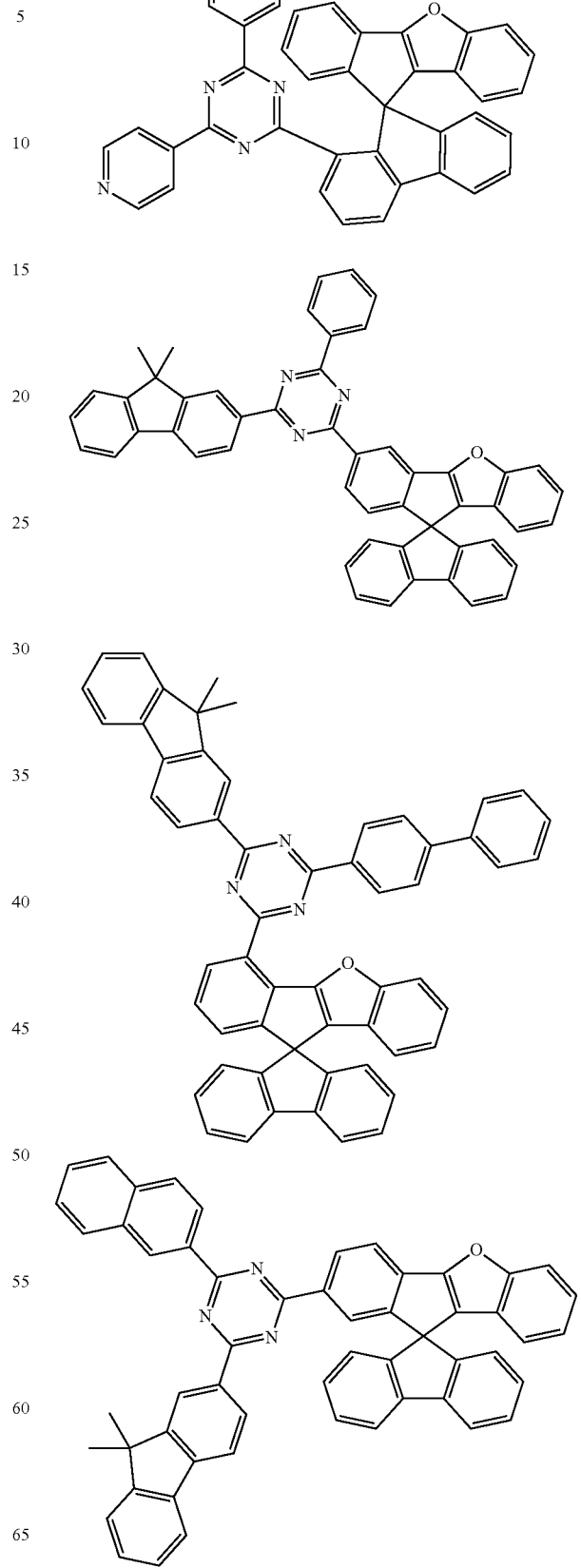

-continued
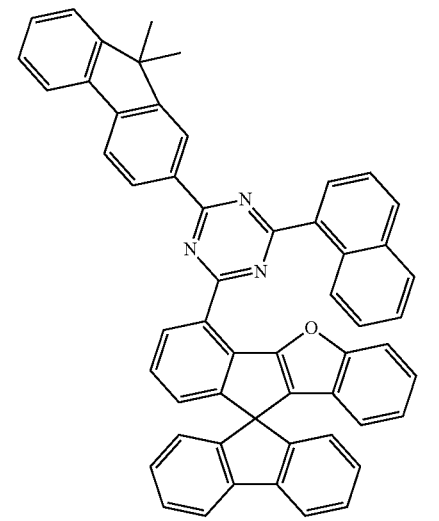
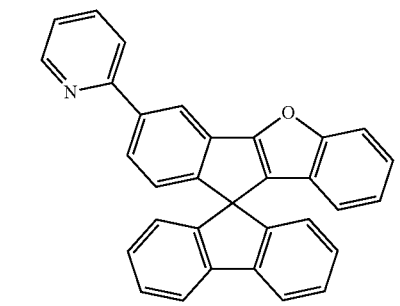
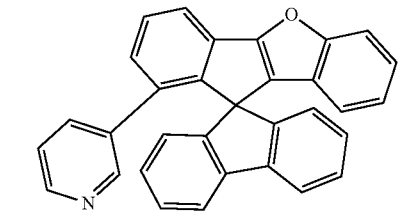
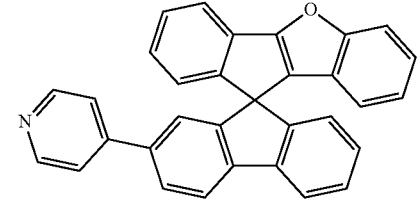
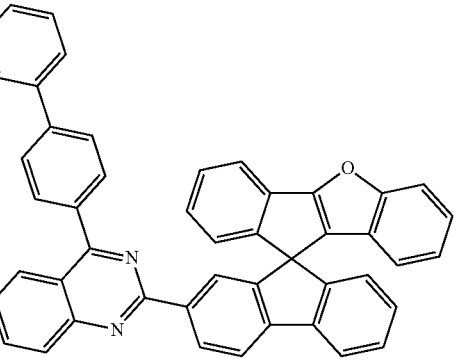
-continued
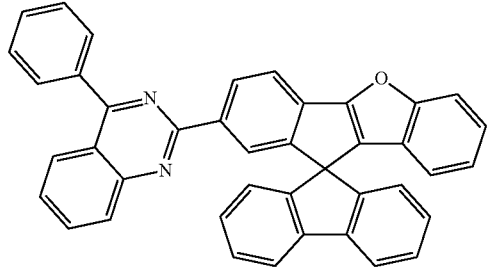
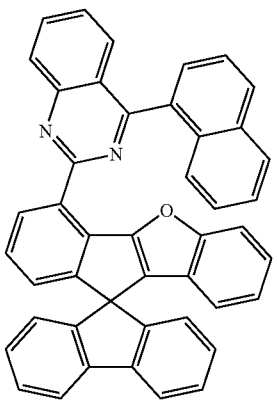
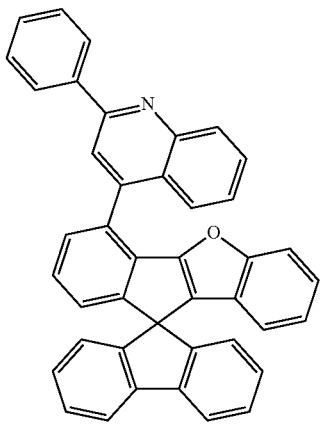
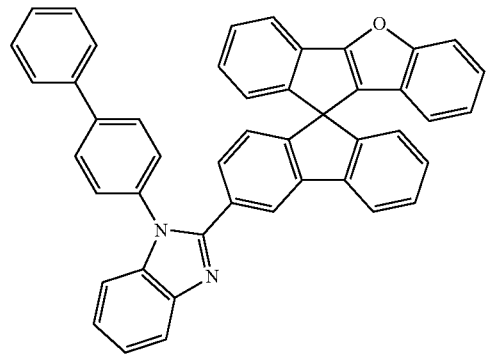

81
-continued
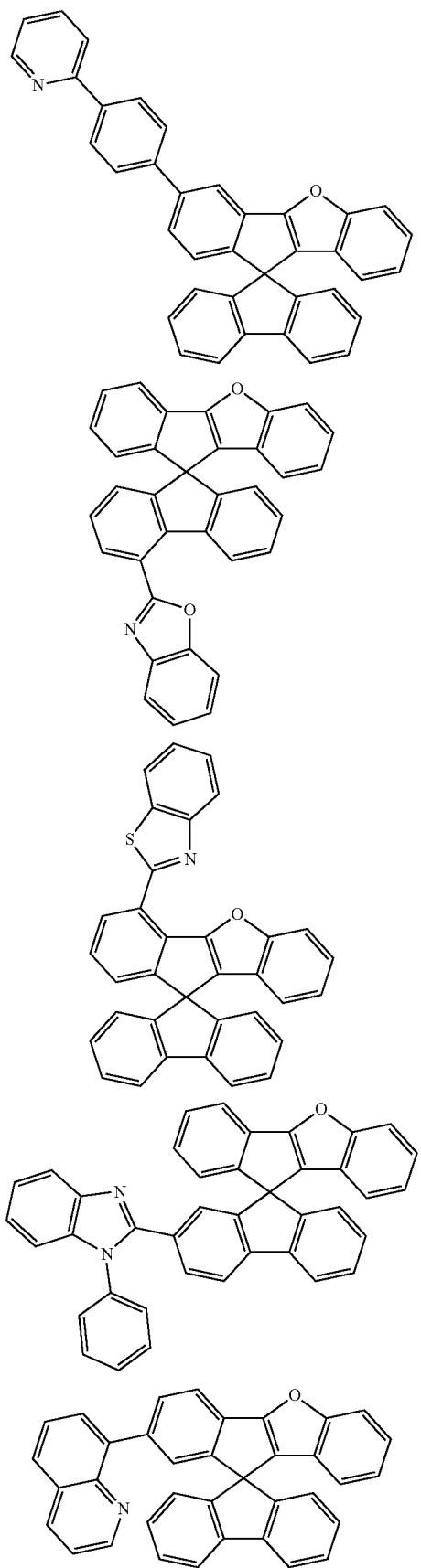
82
-continued
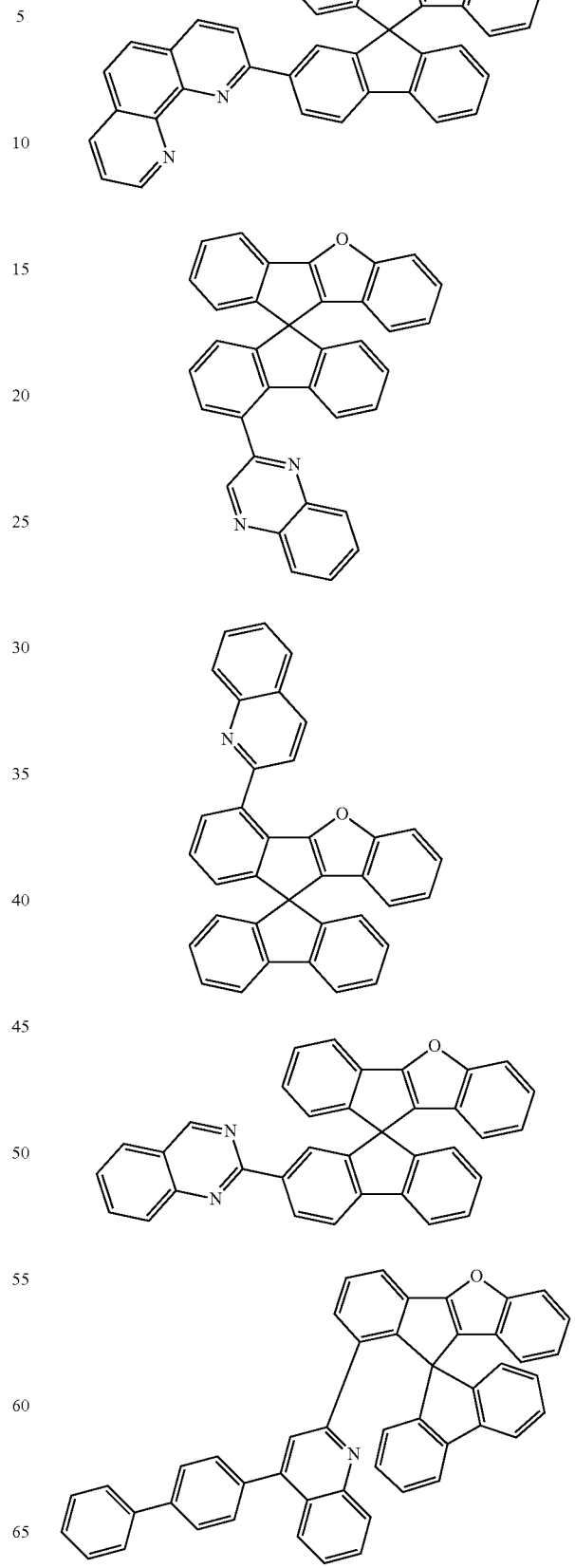

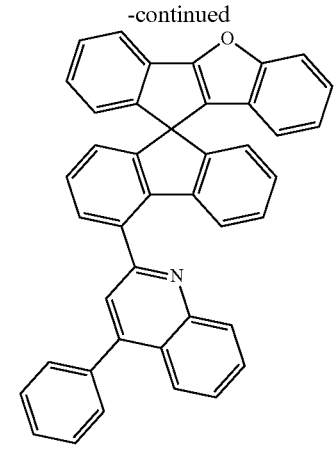
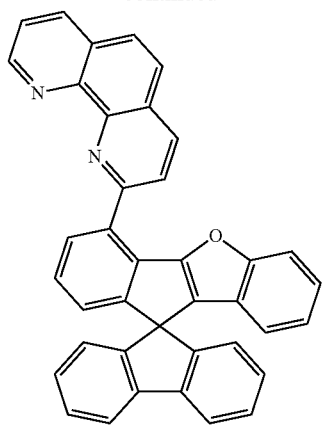
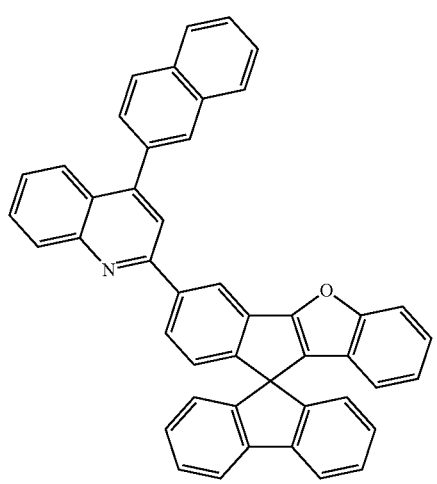
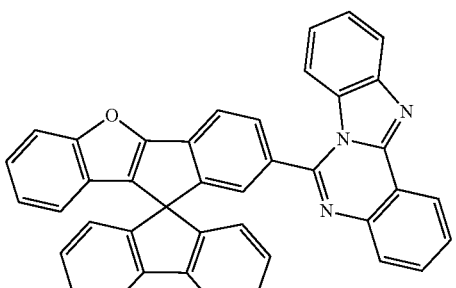
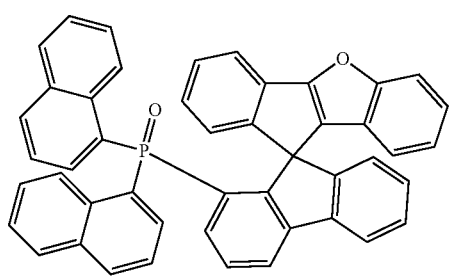
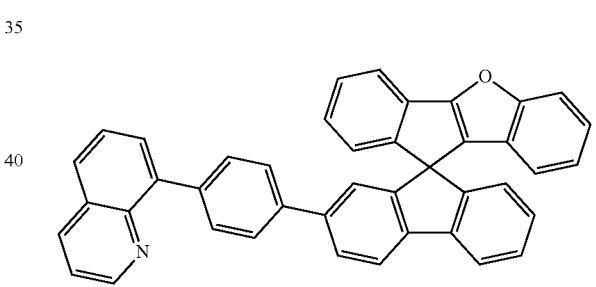
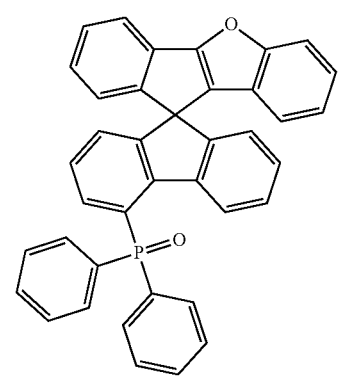
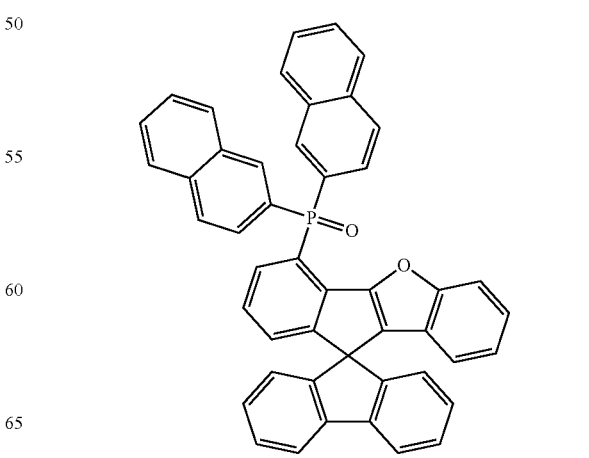

85
-continued
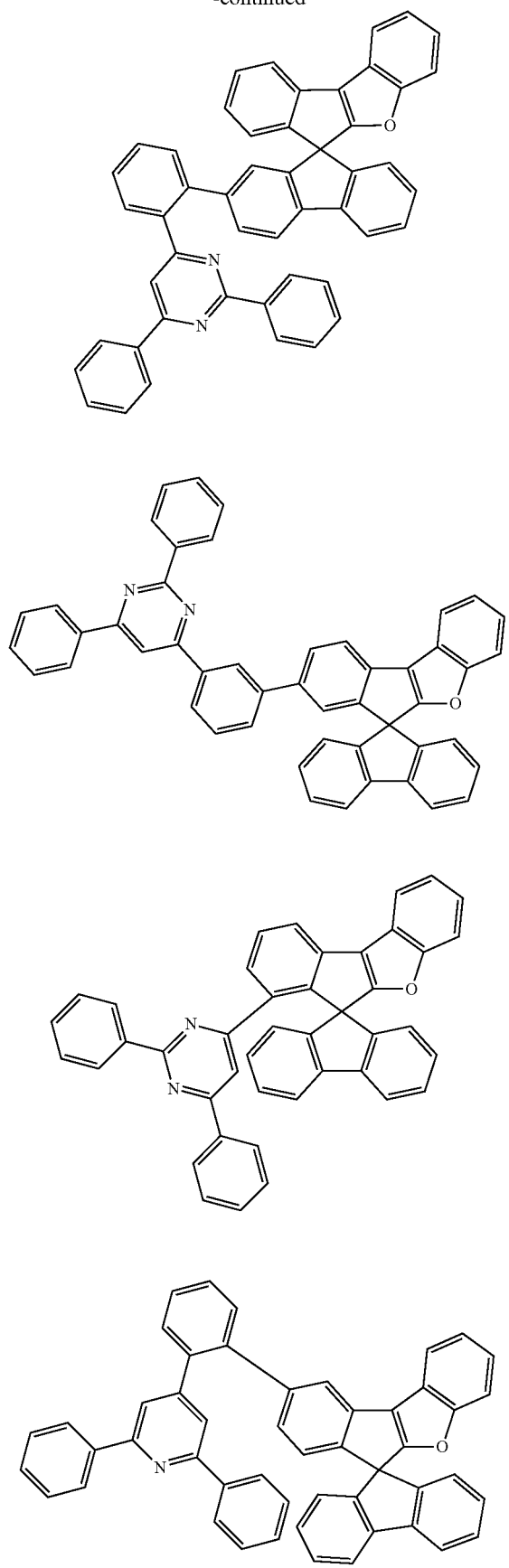
86
-continued
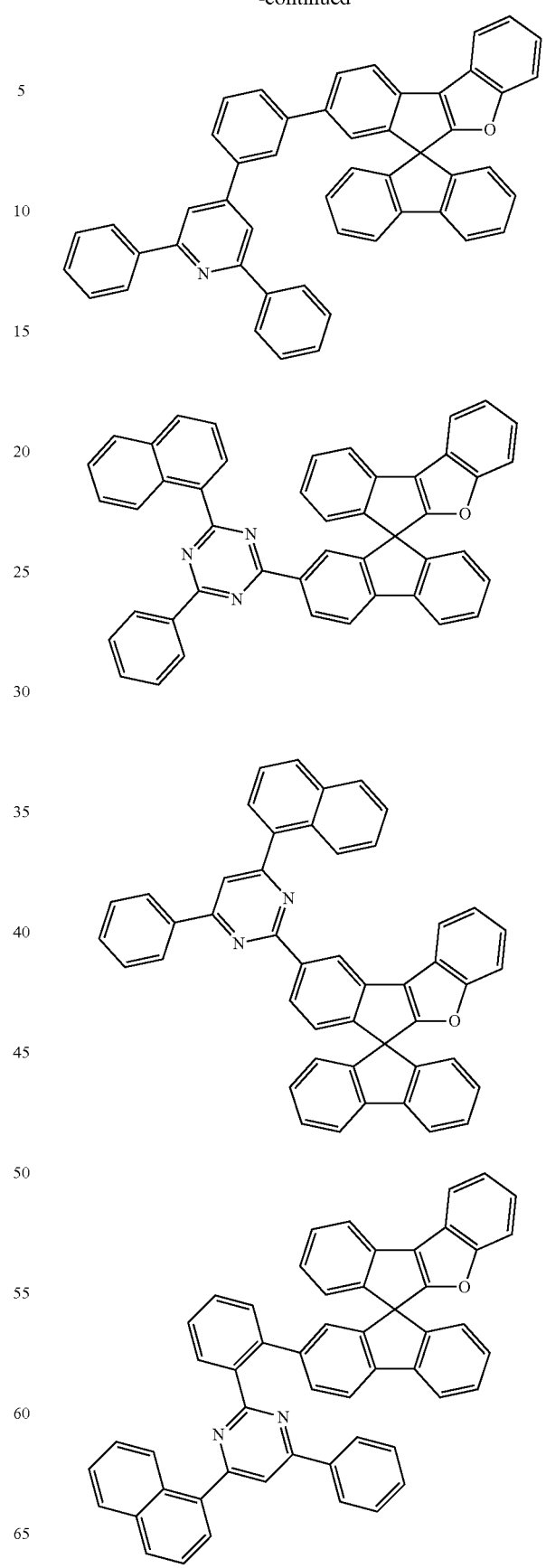

87
-continued
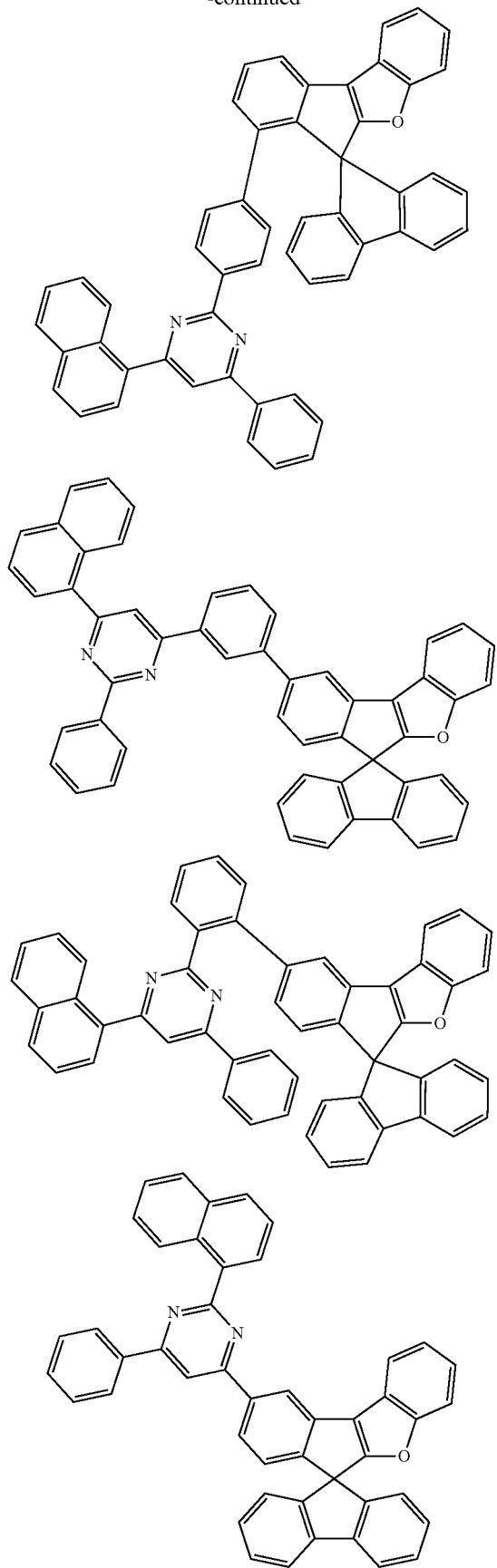
88
-continued
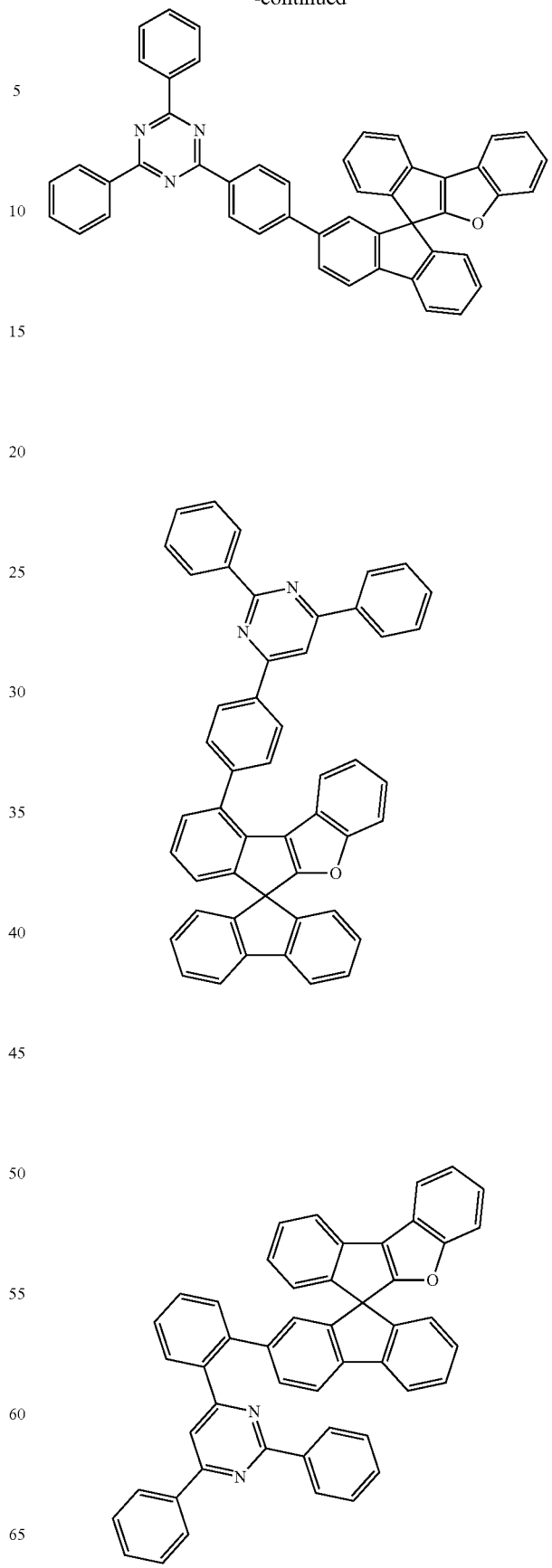

89
-continued
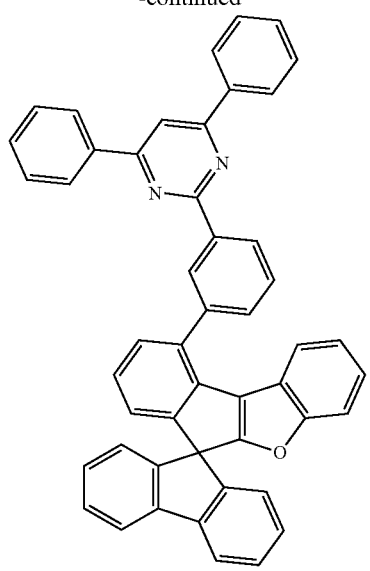
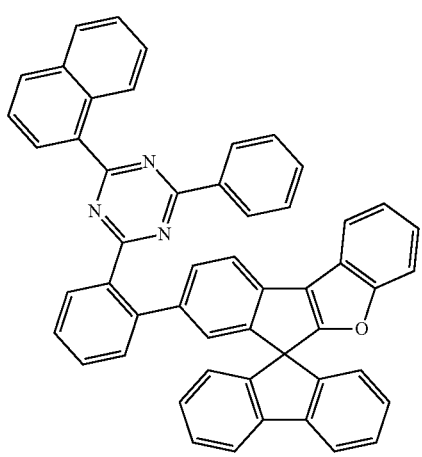
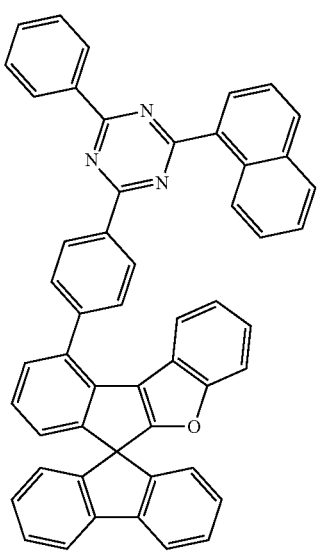
90
-continued
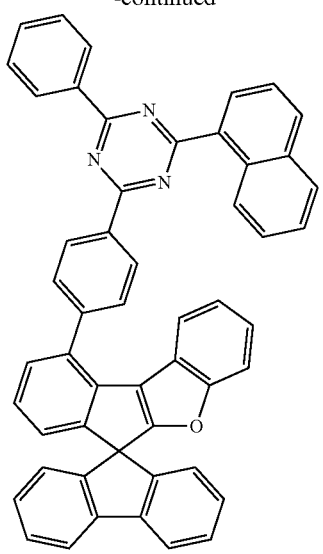
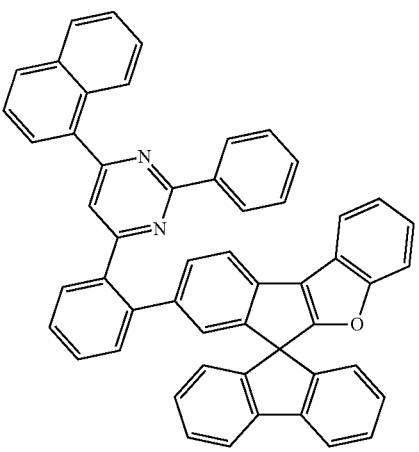
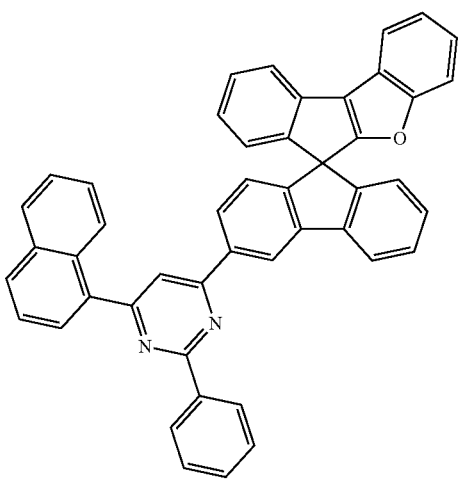

91
-continued
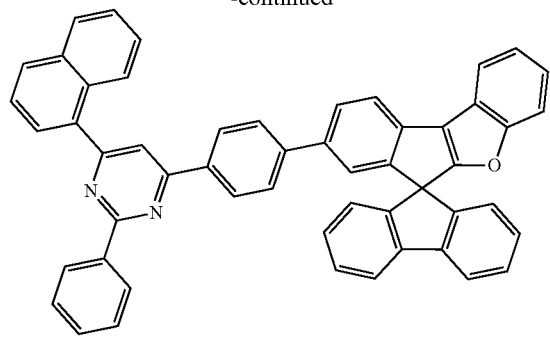
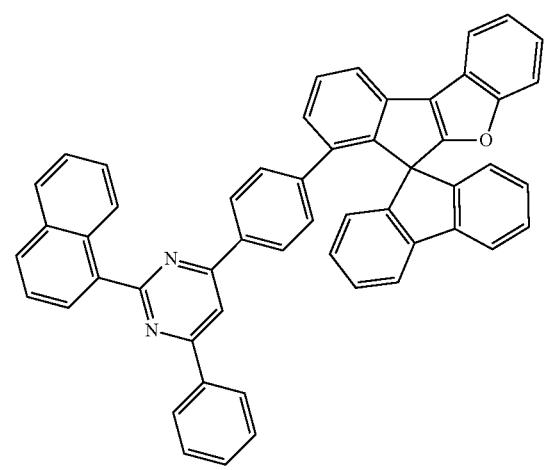
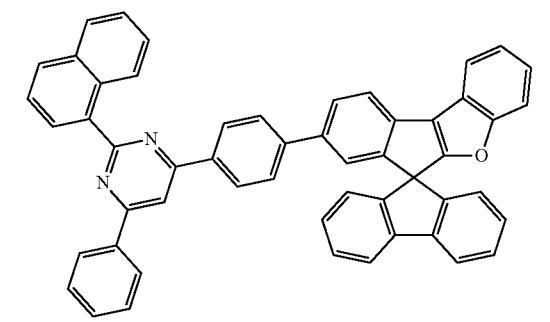
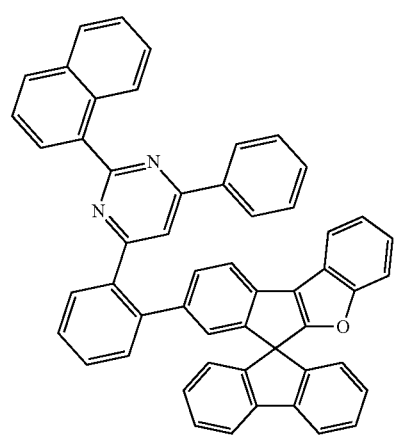
92
-continued
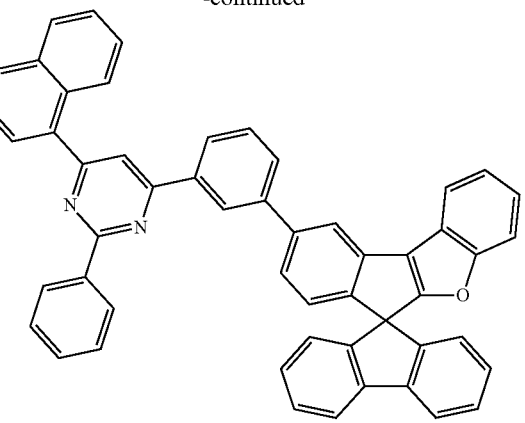
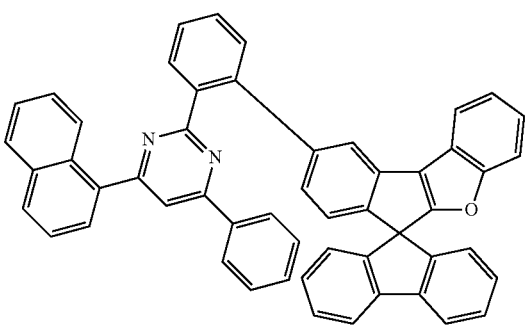
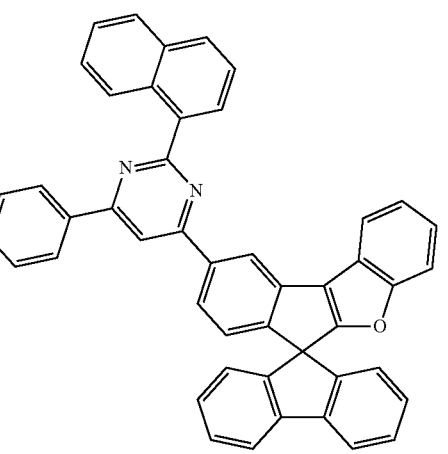
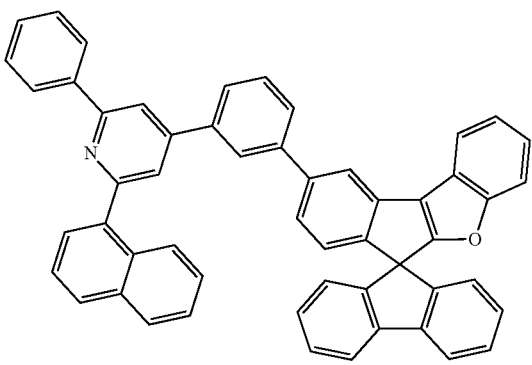

93
-continued
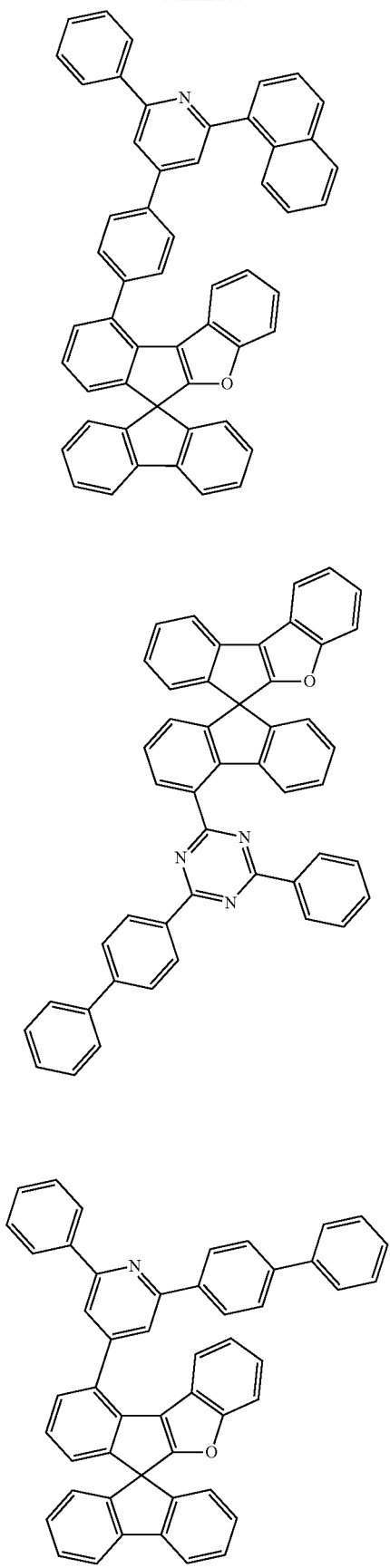
94
-continued
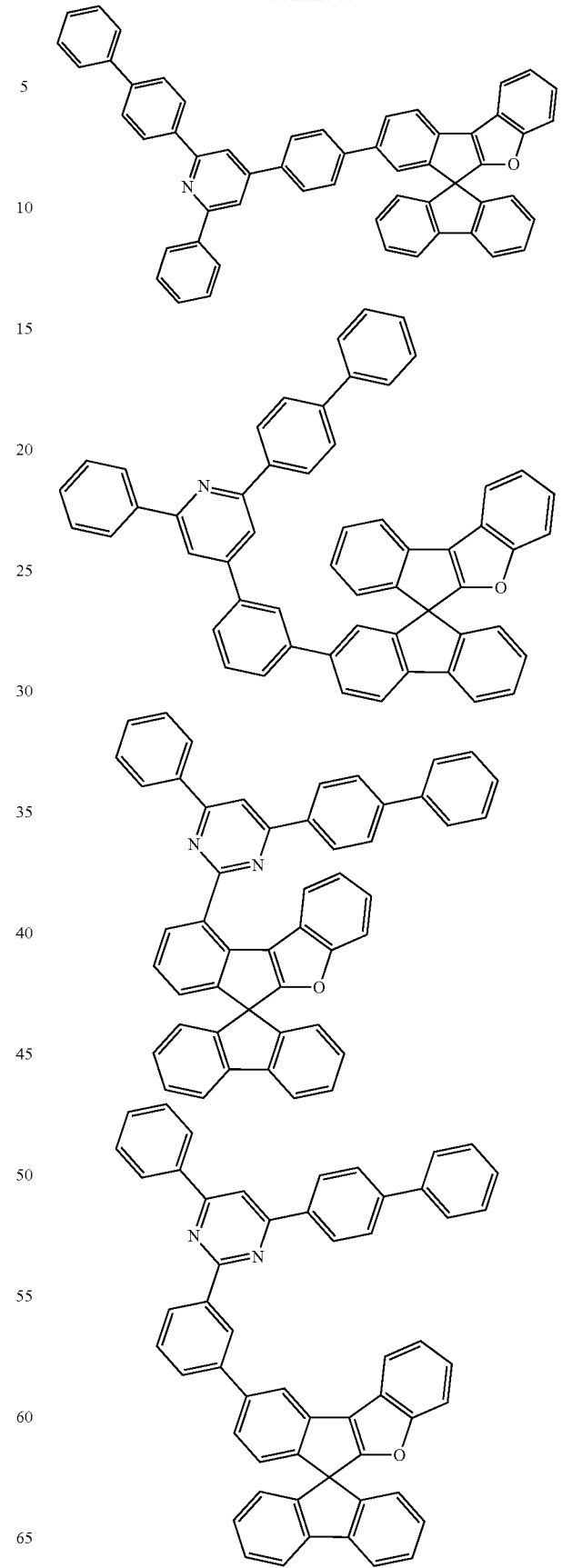

95
-continued
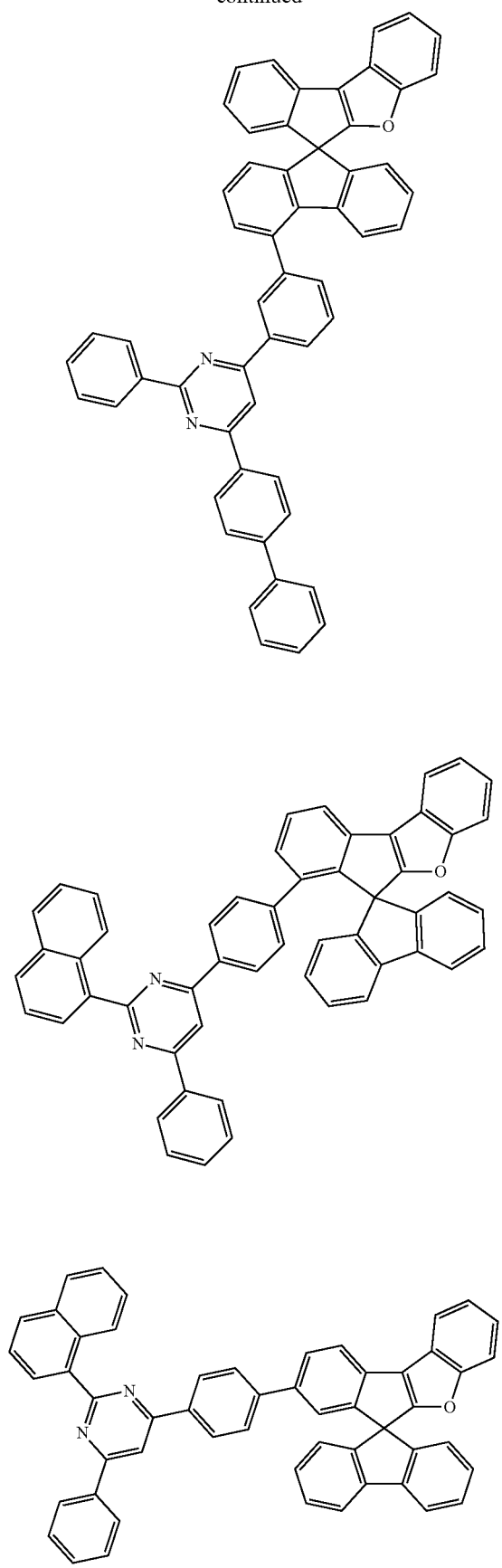
96
-continued
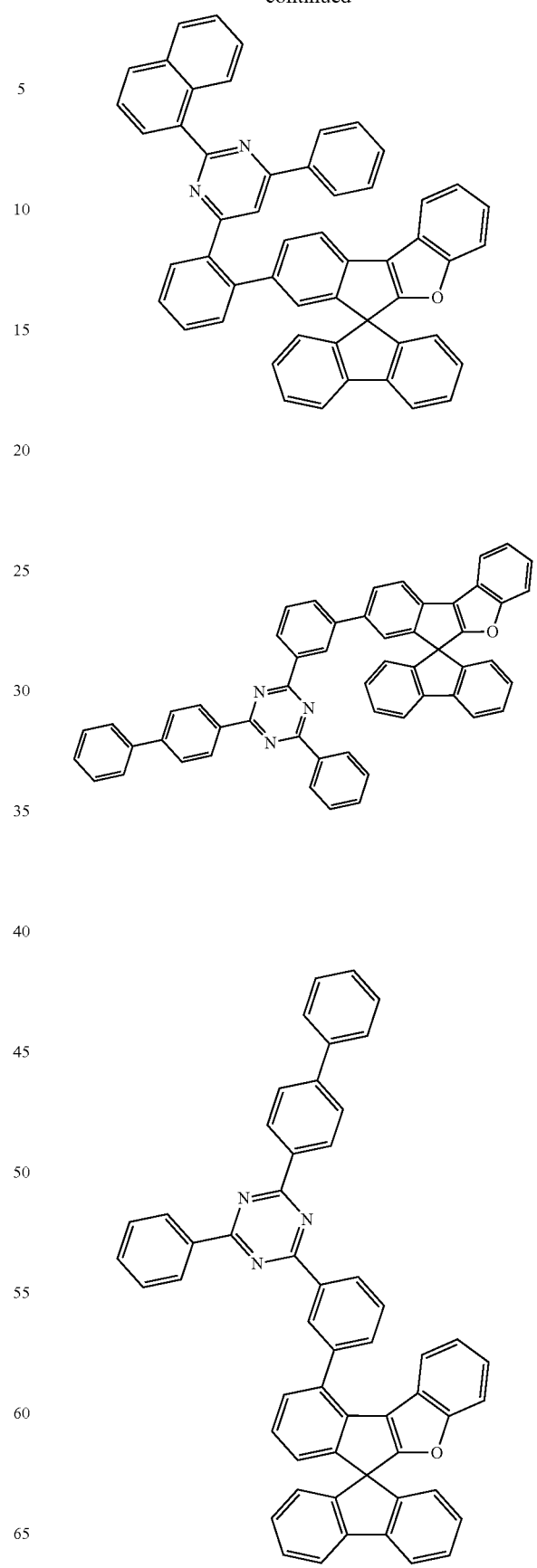

97
-continued
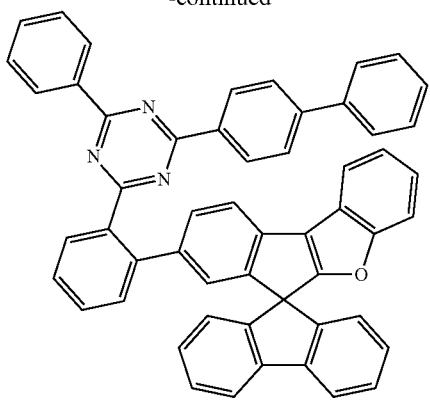
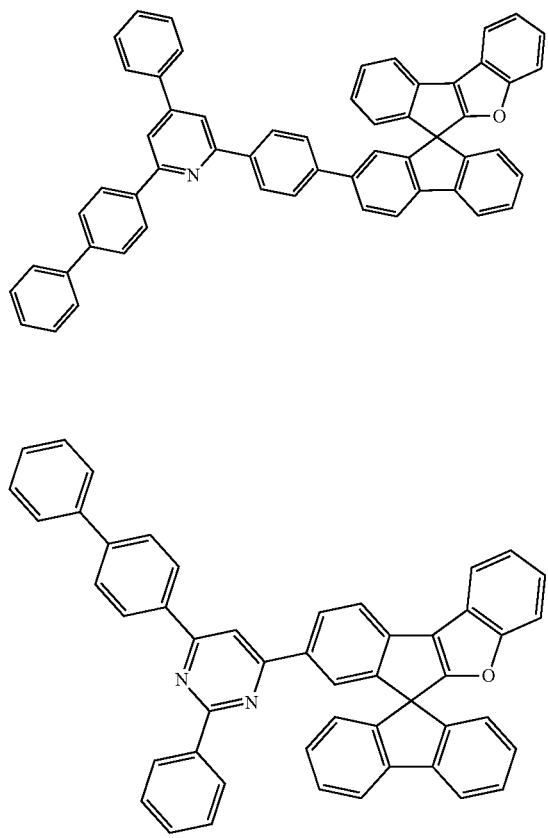
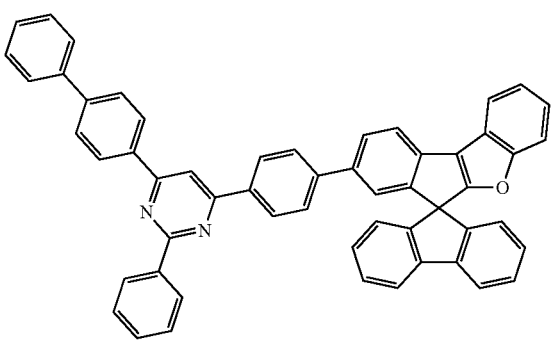
98
-continued
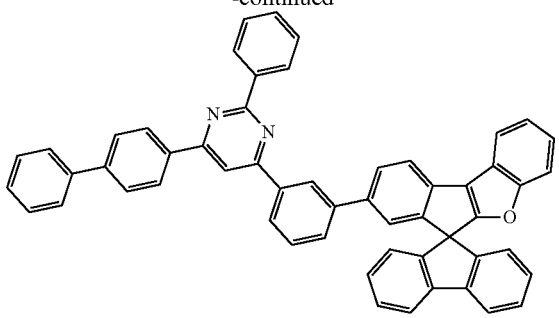
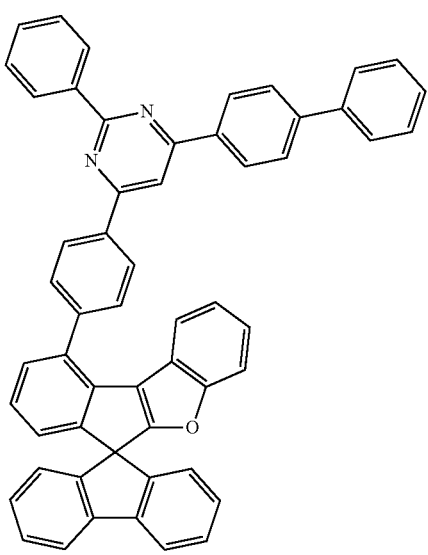
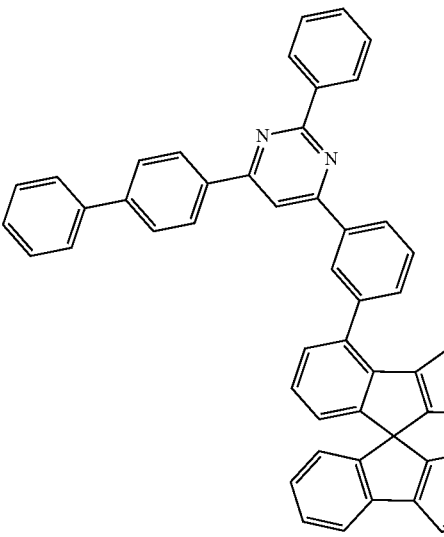

99
-continued
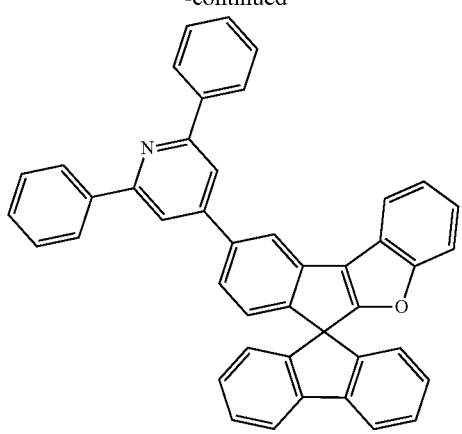
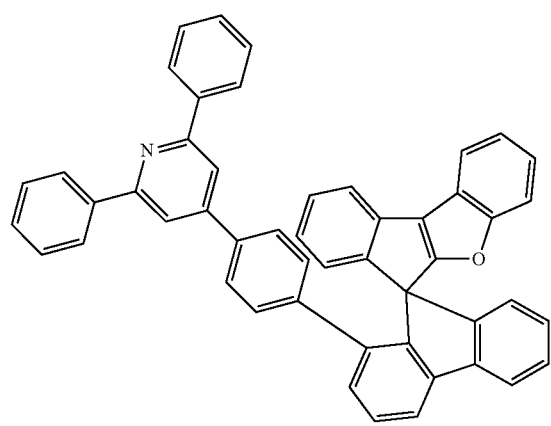
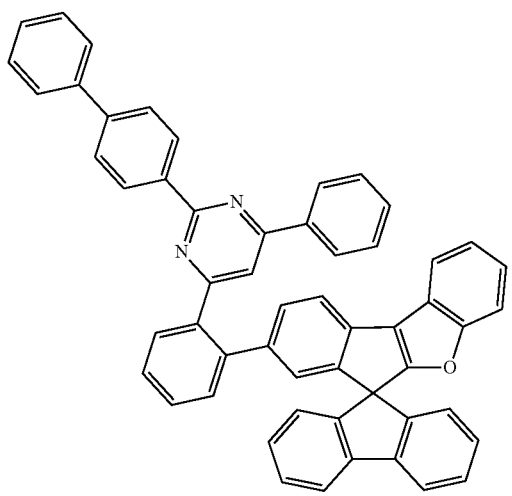
100
-continued
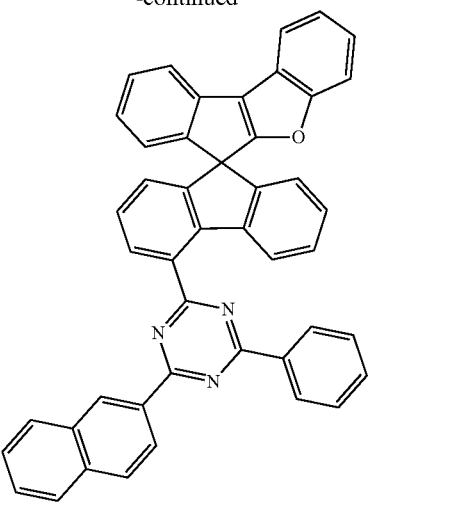
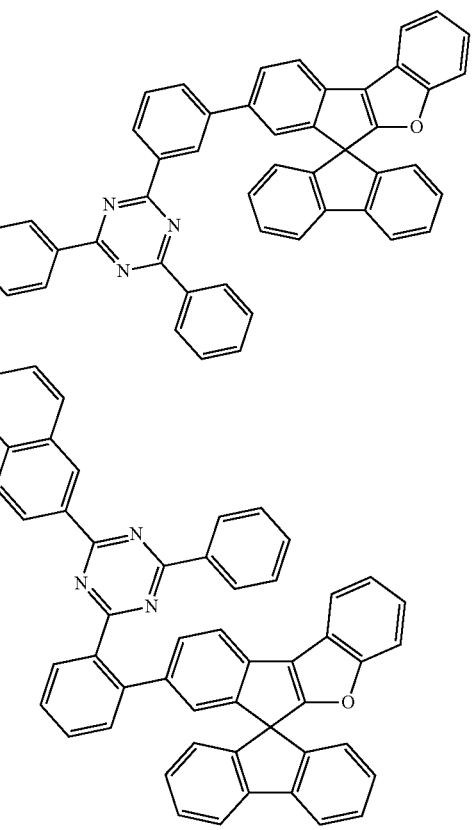
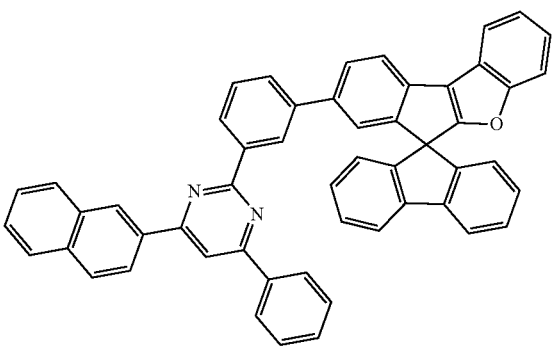

101
-continued
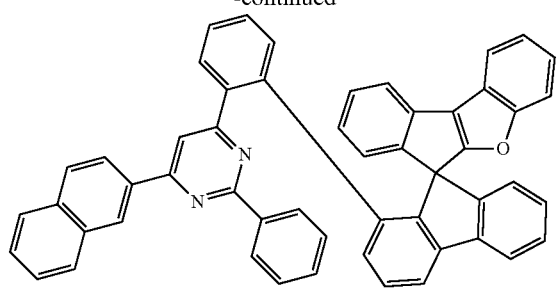
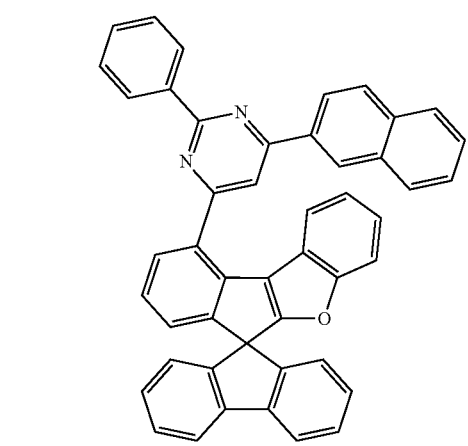
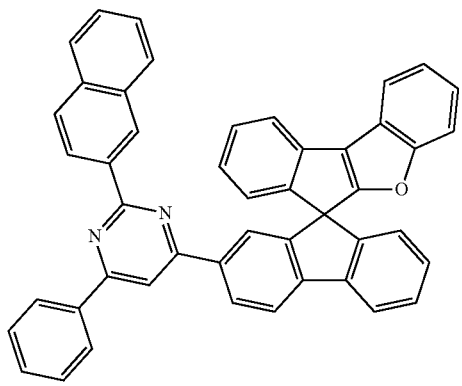
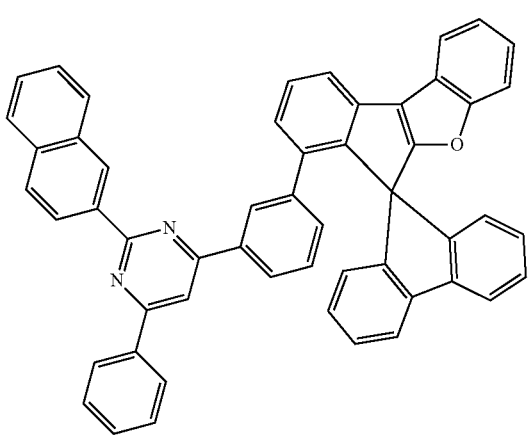
102
-continued
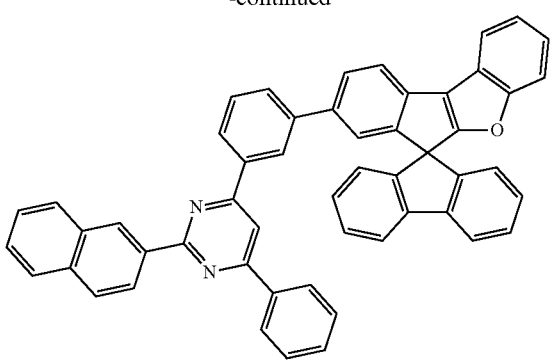
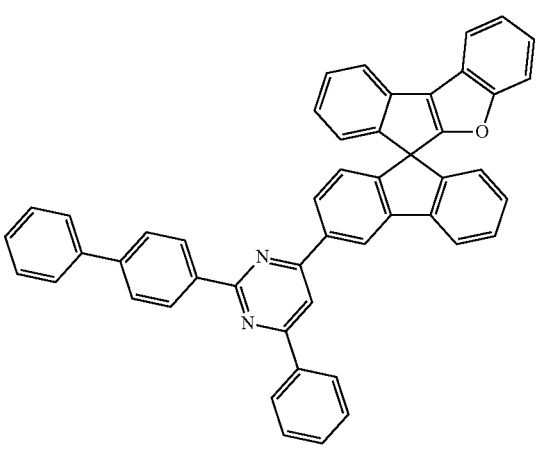
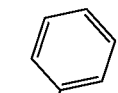
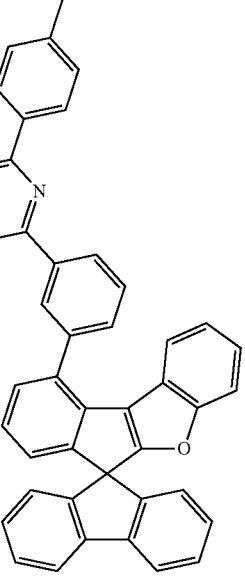

103
-continued
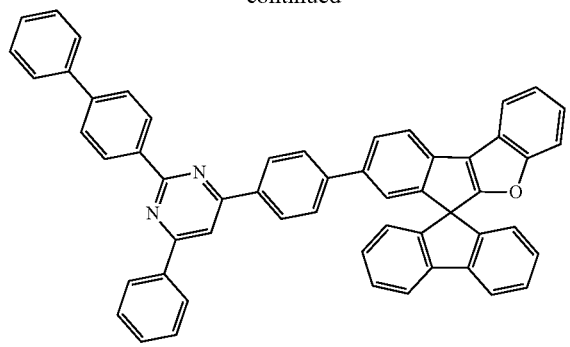
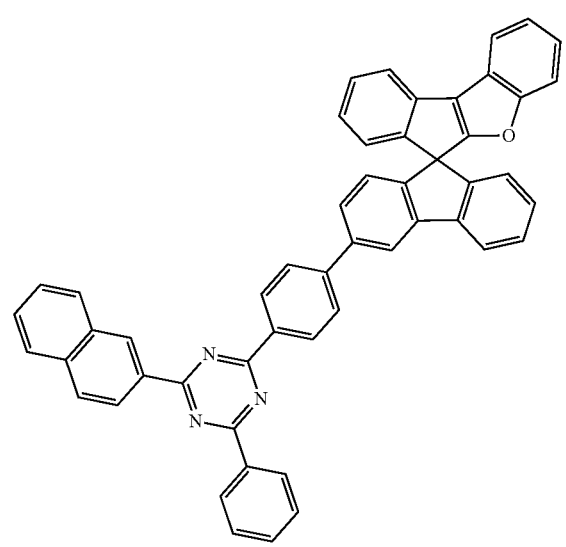
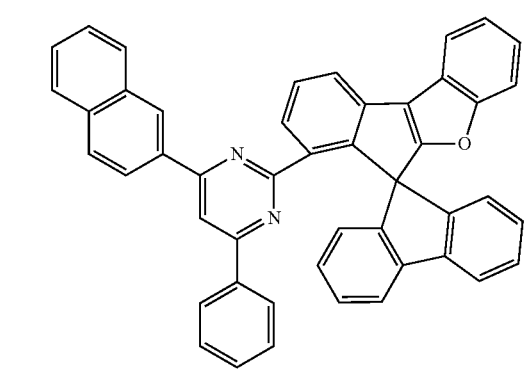
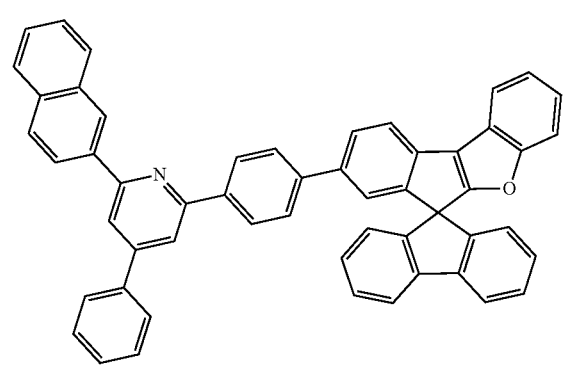
104
-continued
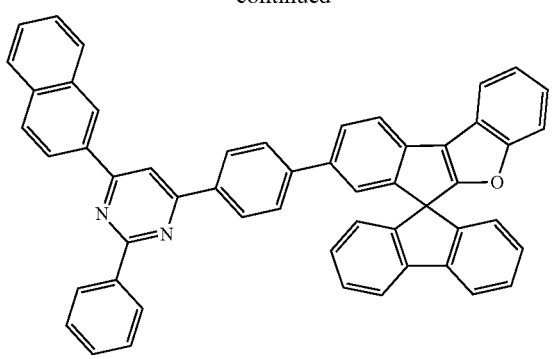
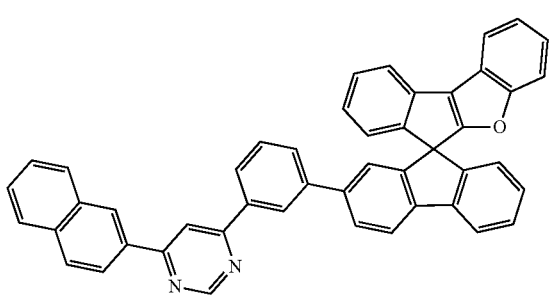
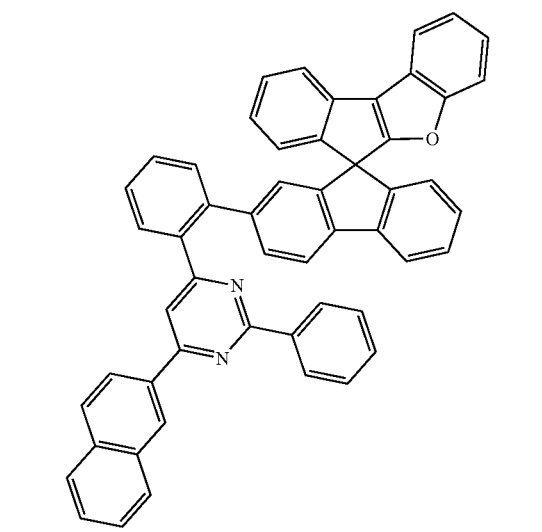
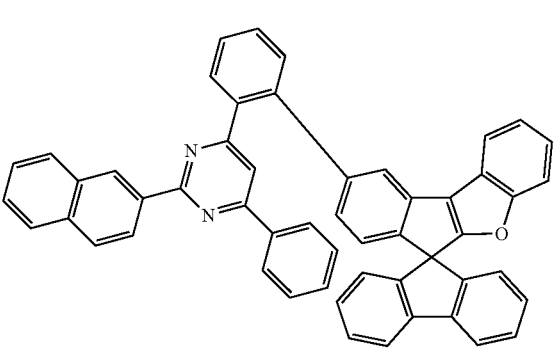

105
-continued
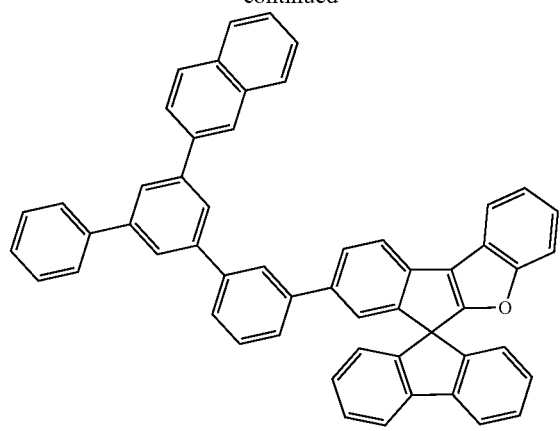
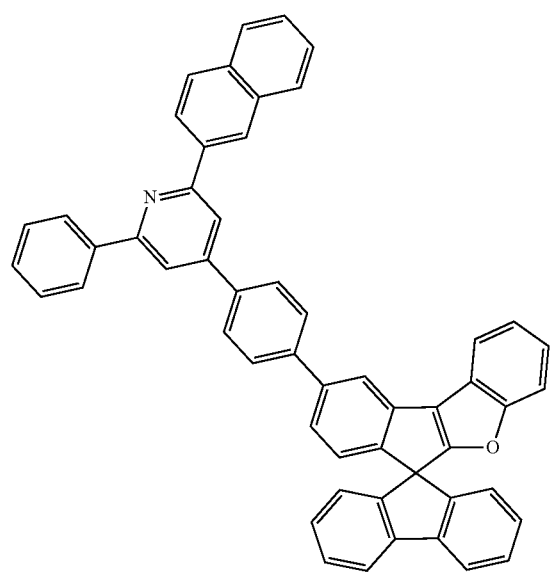
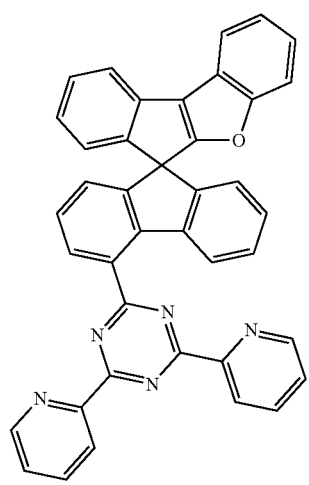
106
-continued
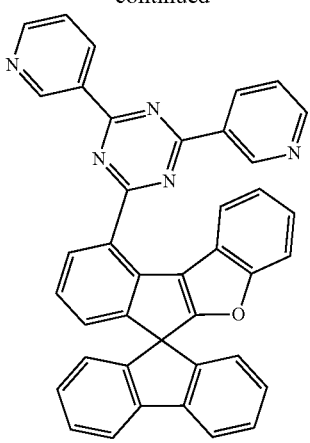
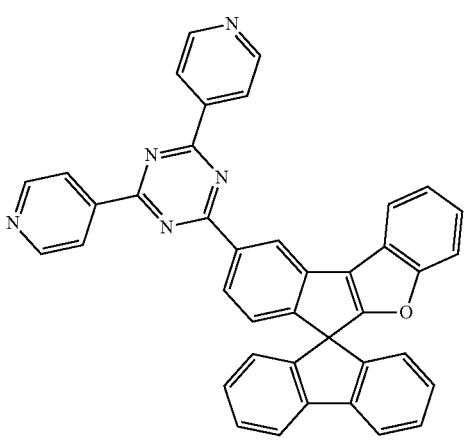
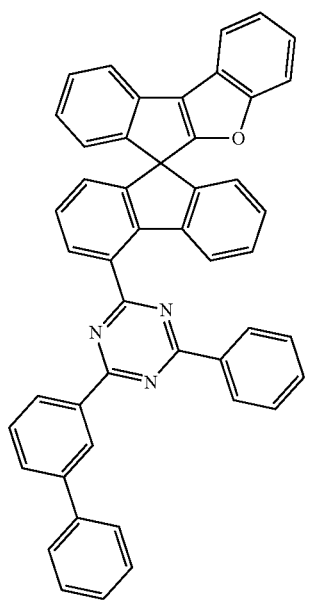

107
-continued
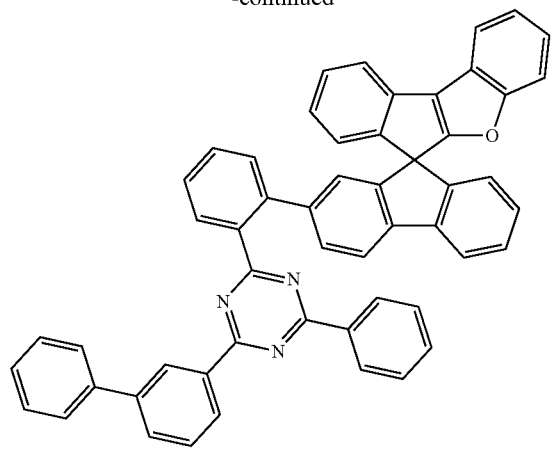
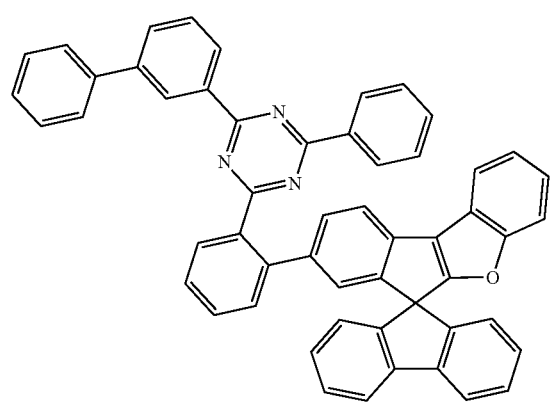
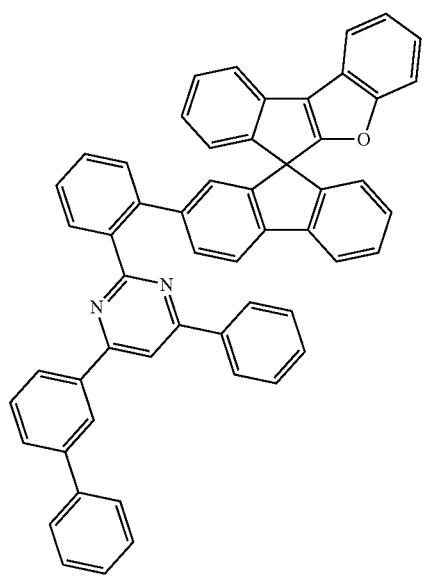
108
-continued
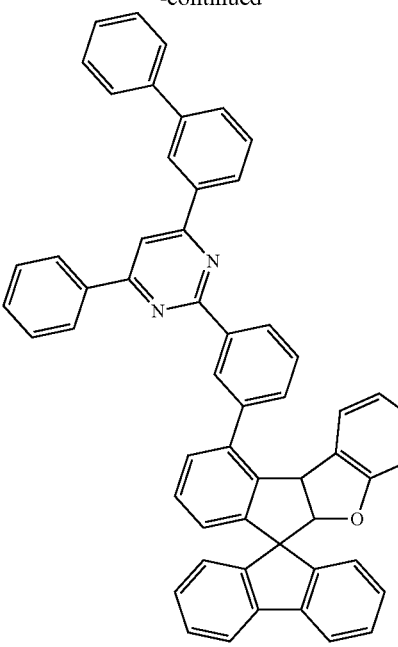
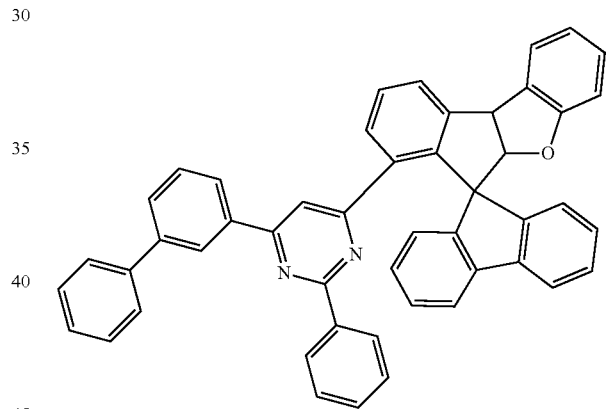
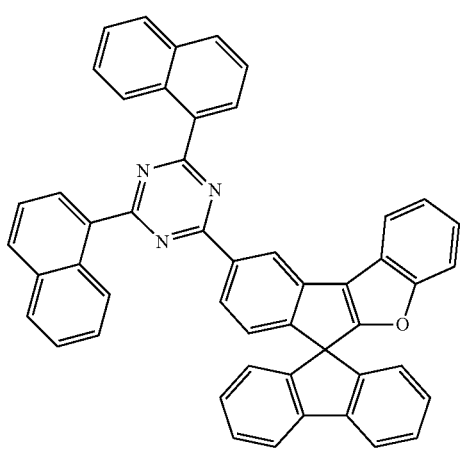

109
-continued
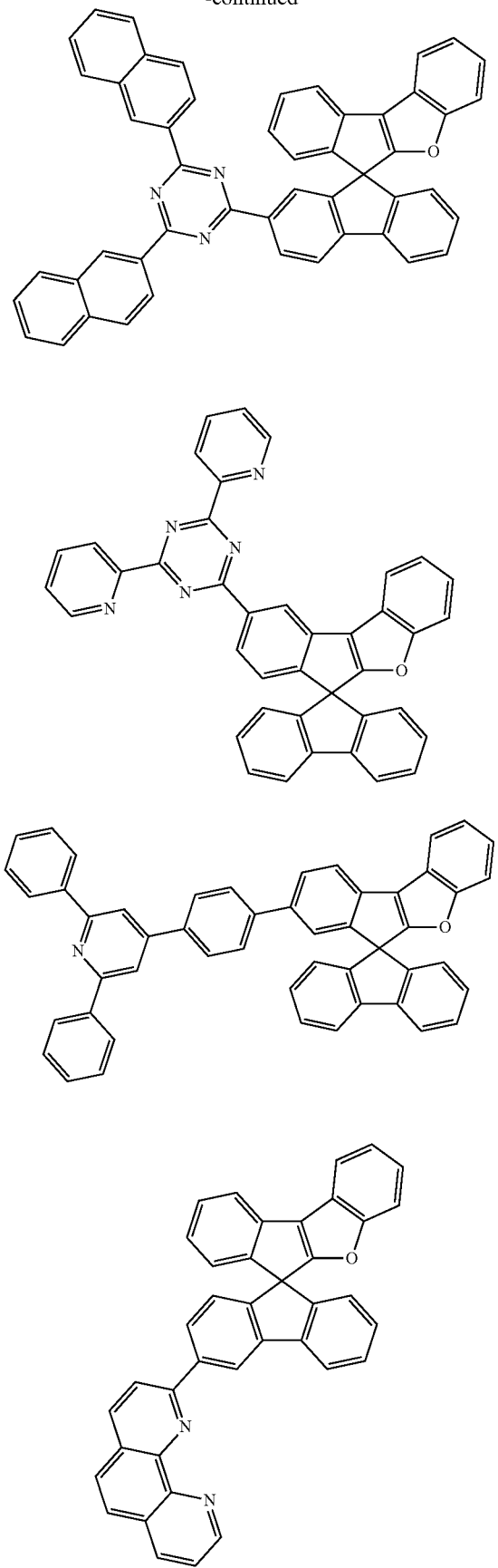
110
-continued
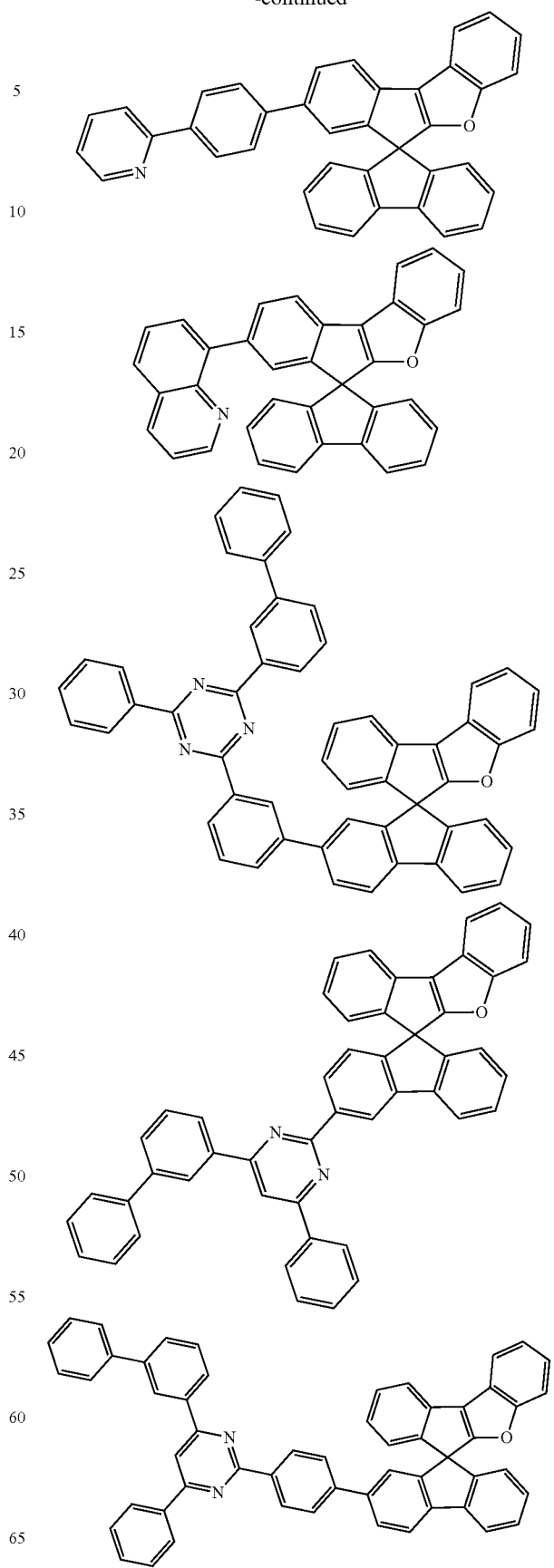

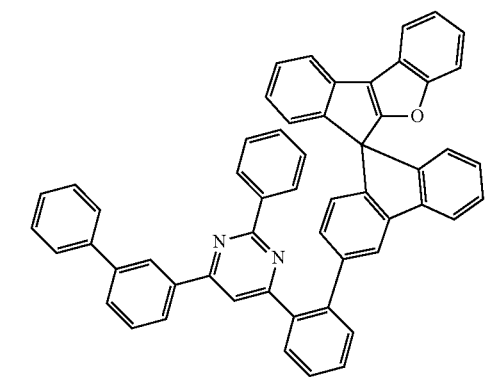
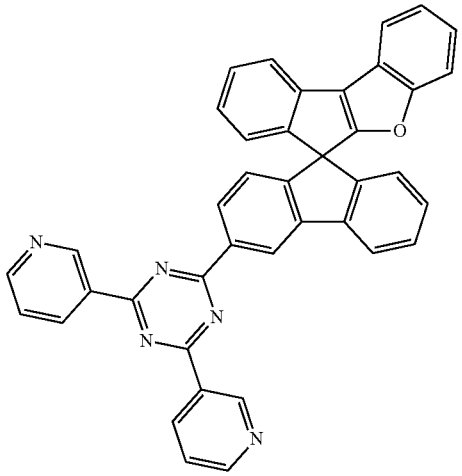
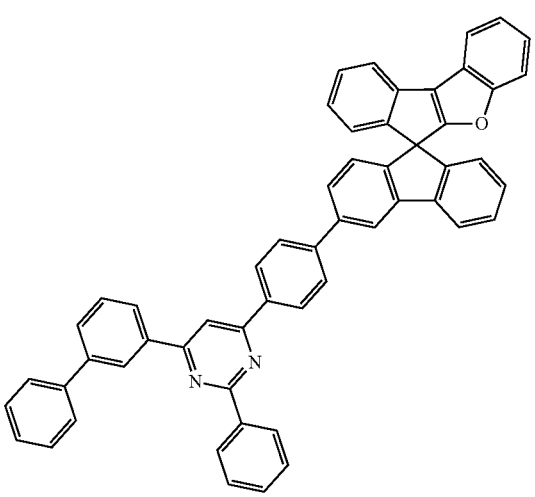
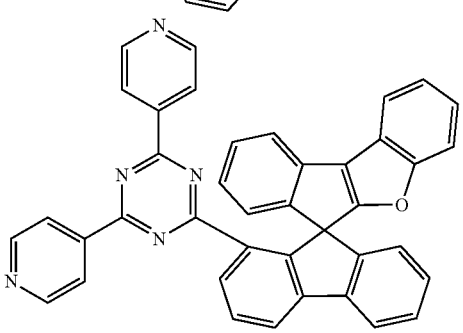
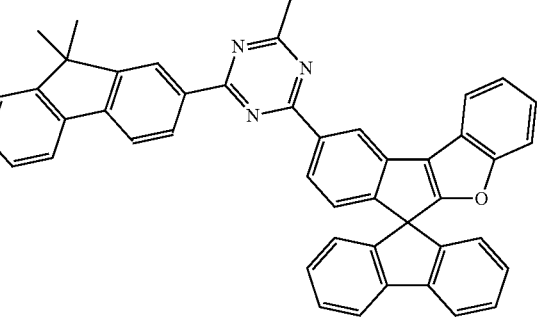
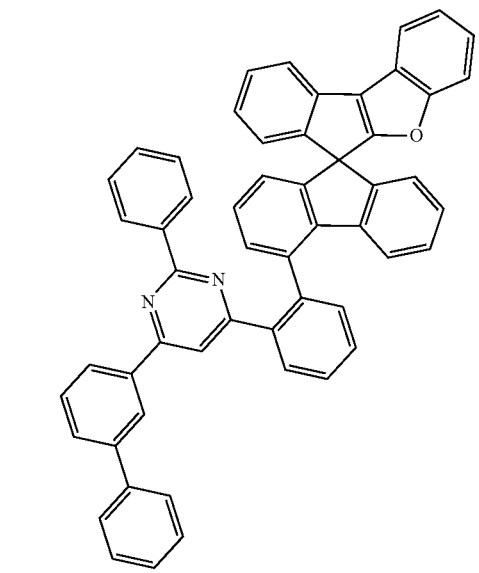
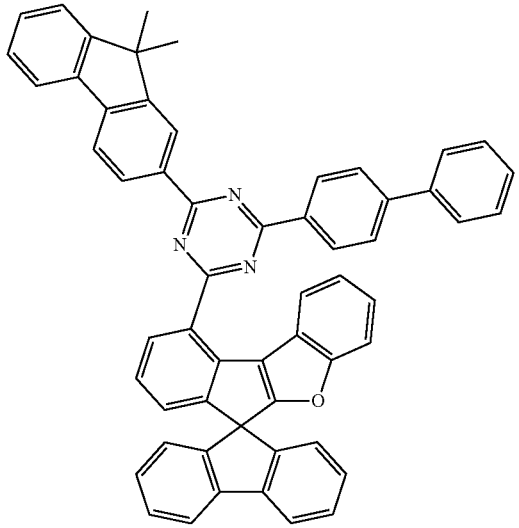

113
-continued
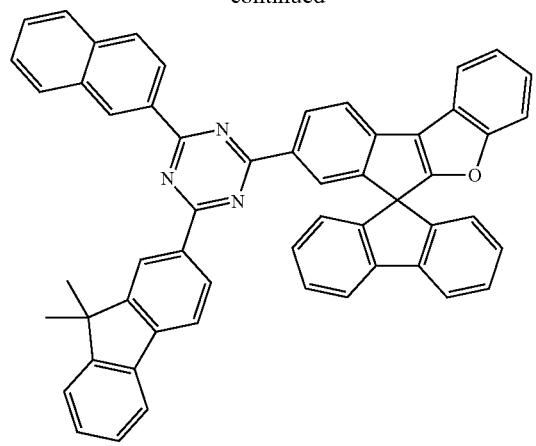
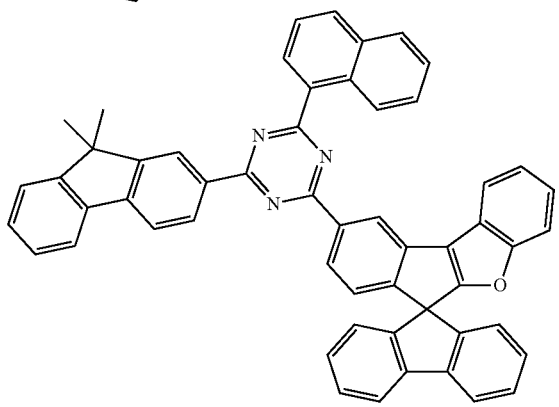
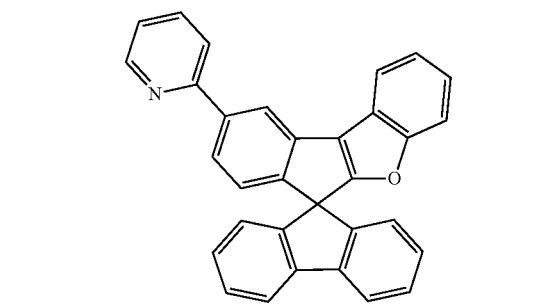
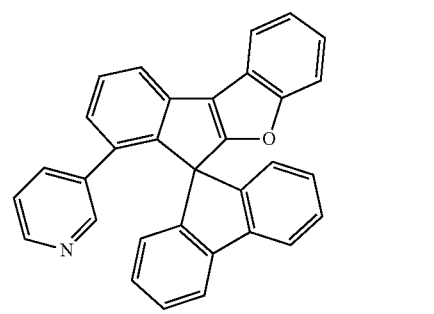
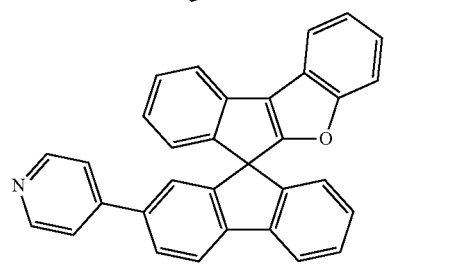
114
-continued
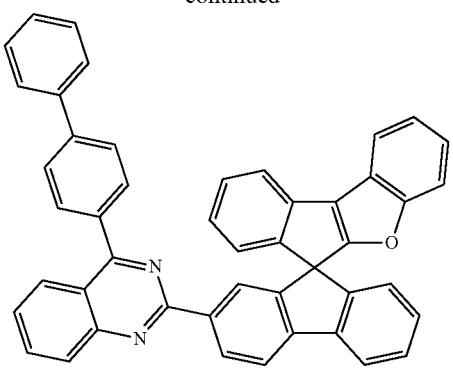
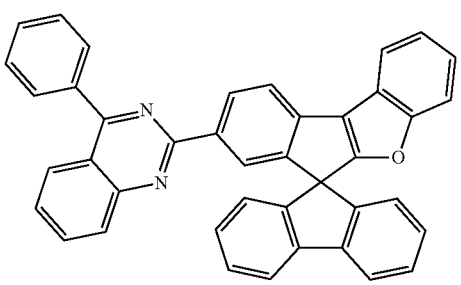
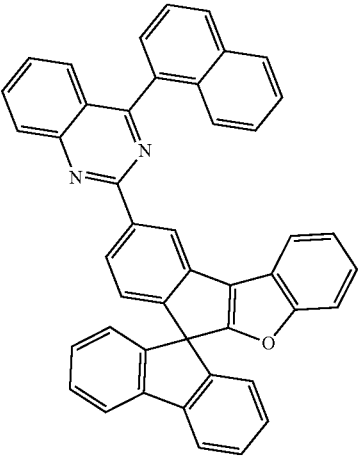
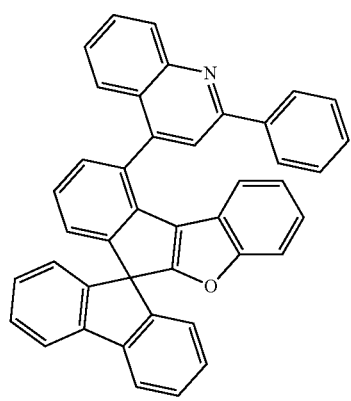

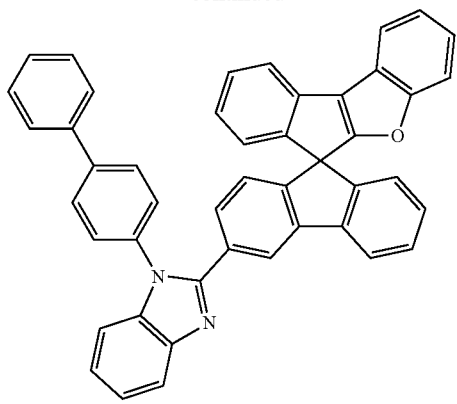
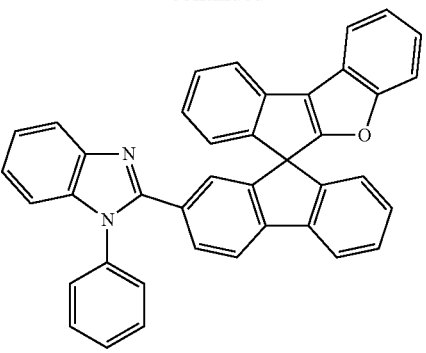
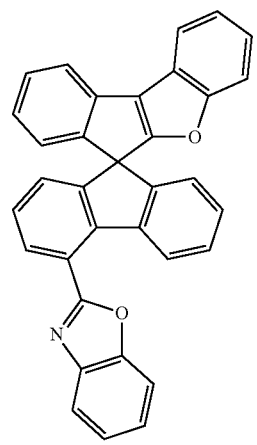
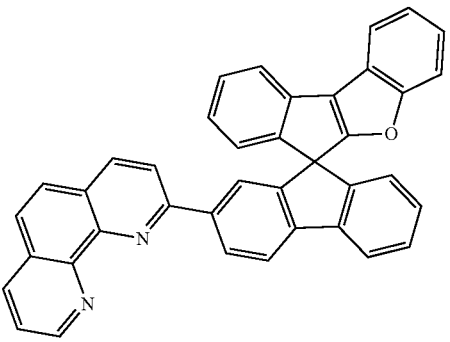
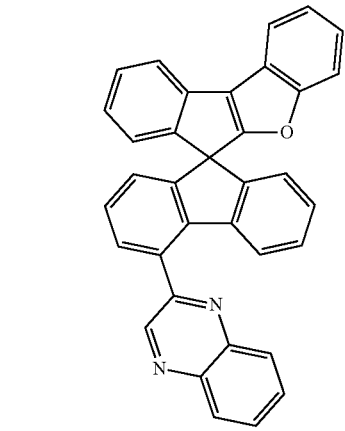
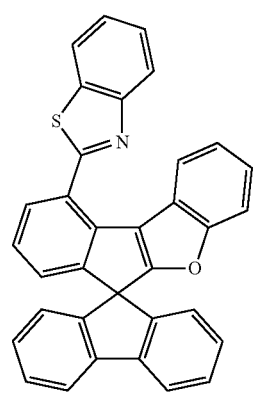
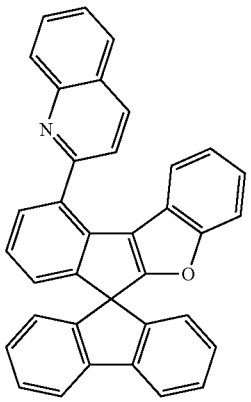

117
-continued
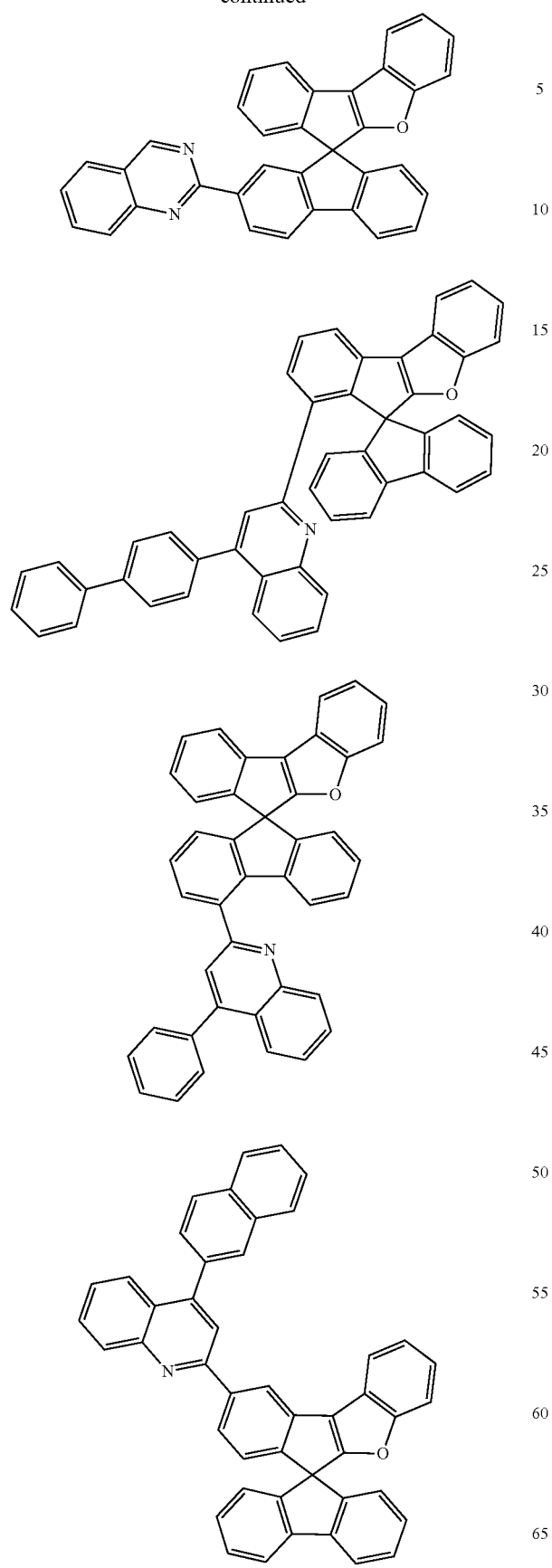
118
-continued
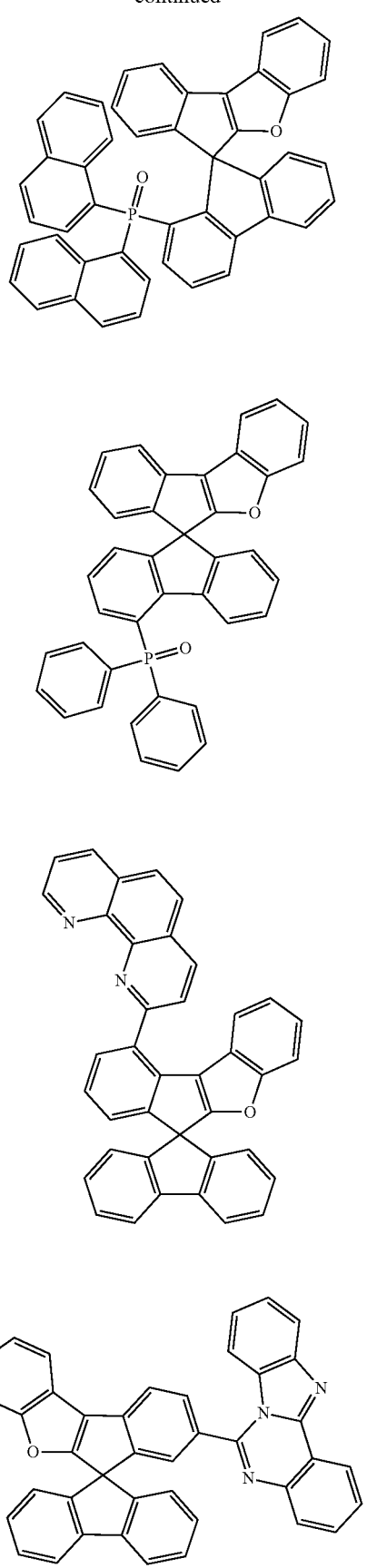

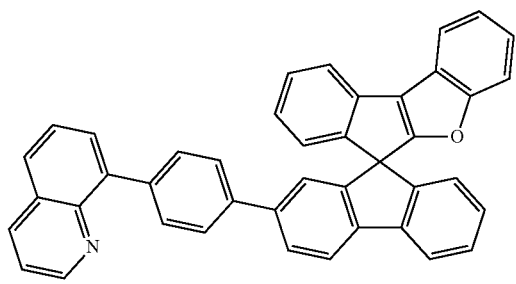
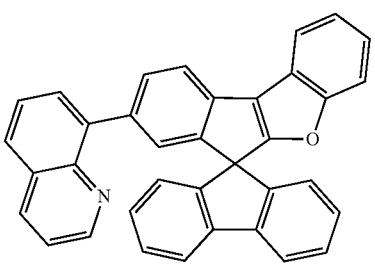
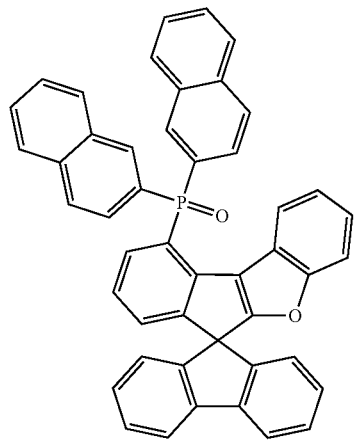
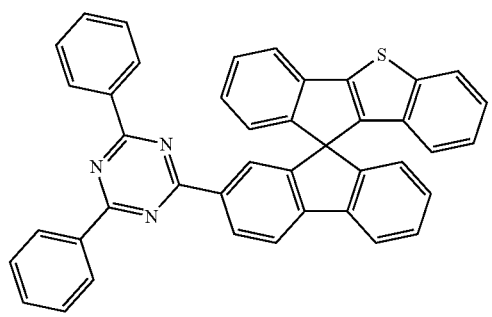
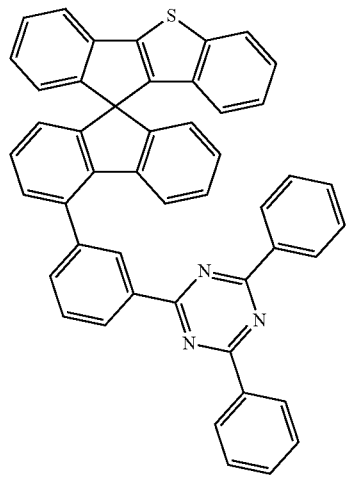
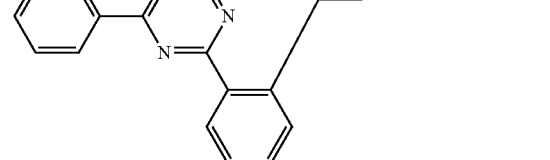
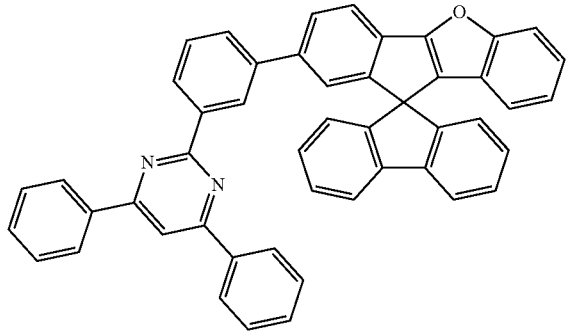
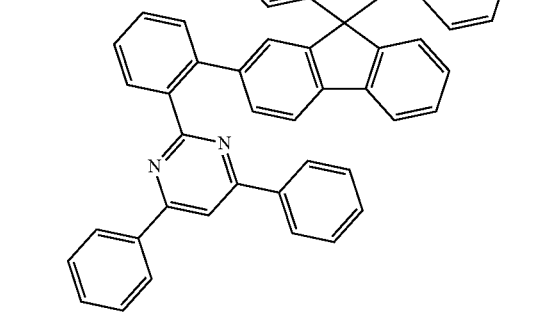

121
-continued
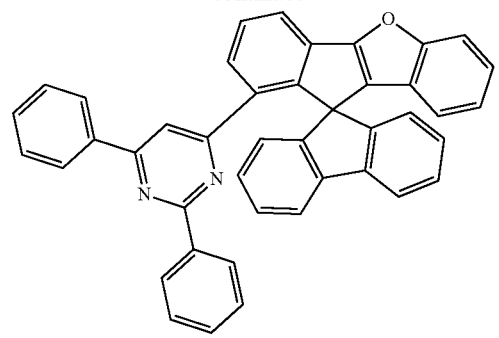
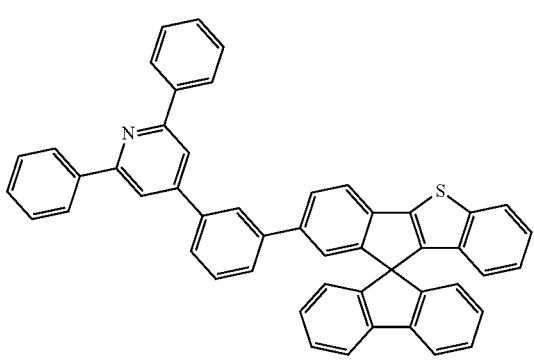
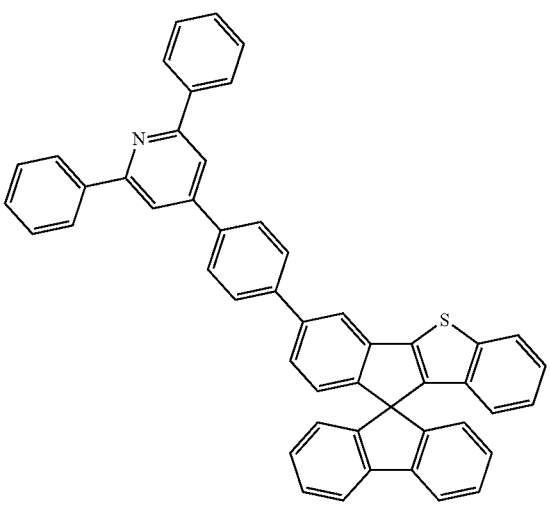
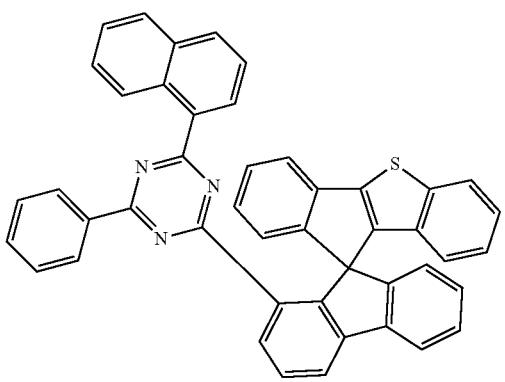
122
-continued
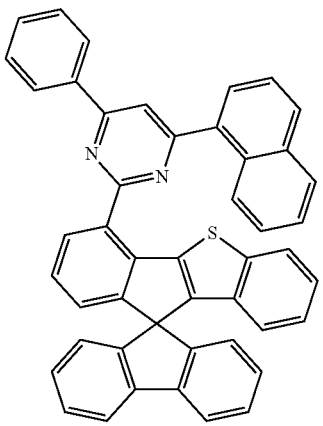
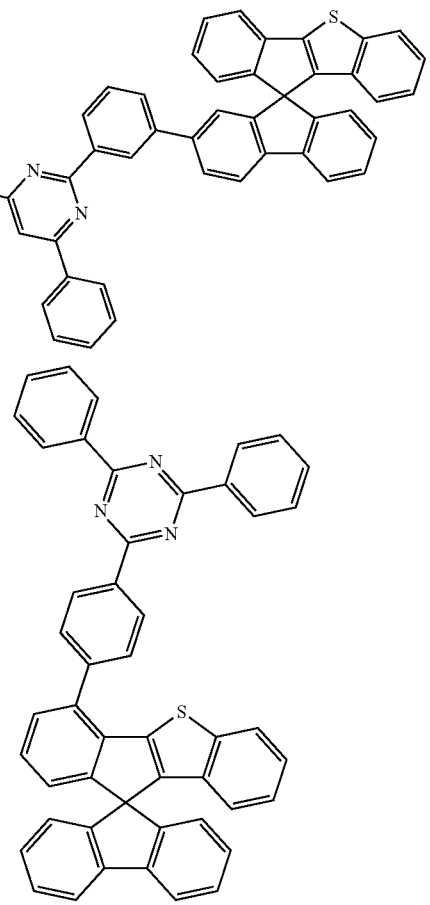

123
-continued
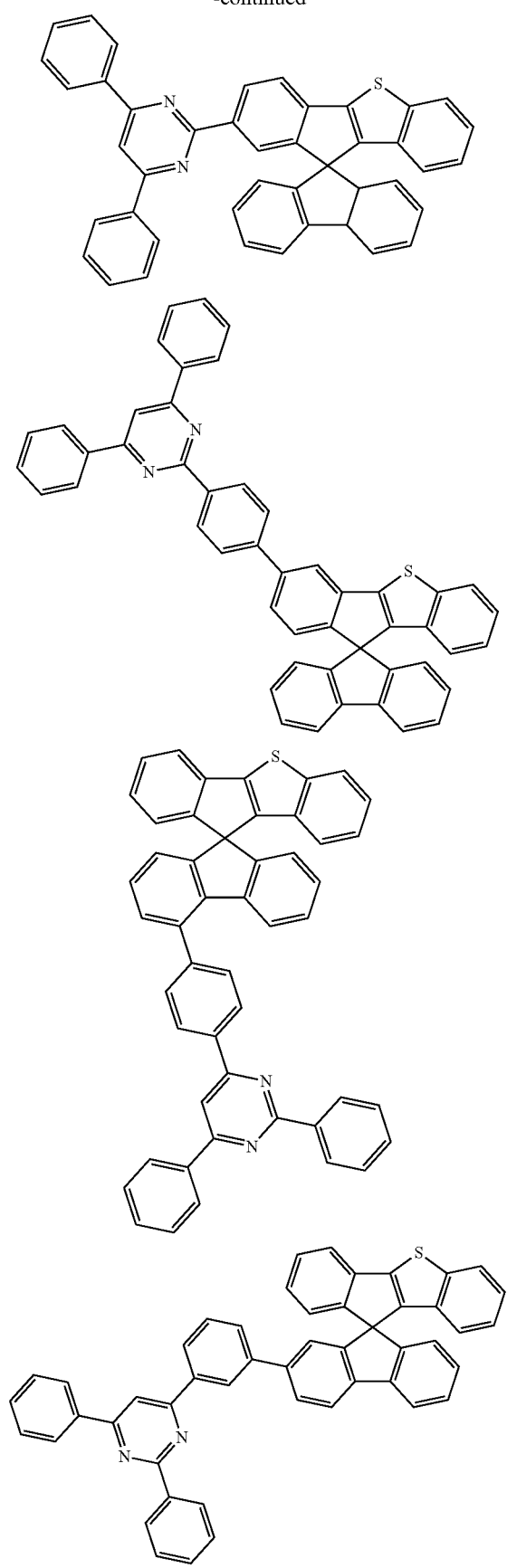
124
-continued
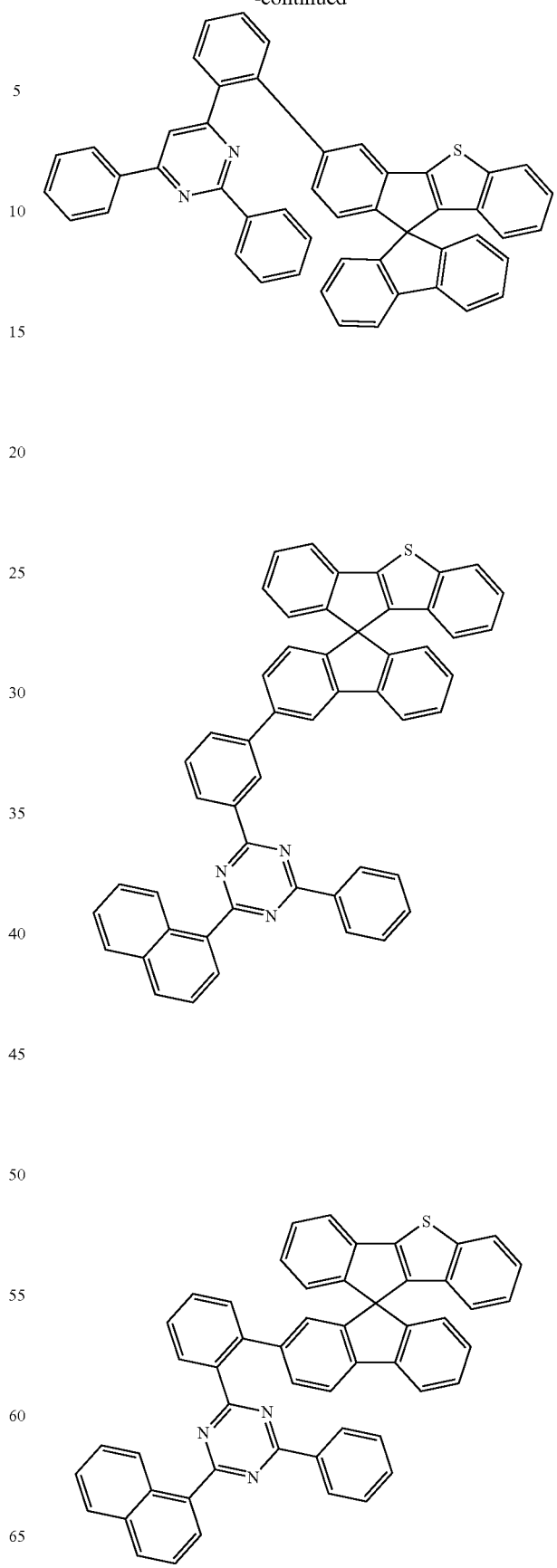

125
-continued
126
-continued
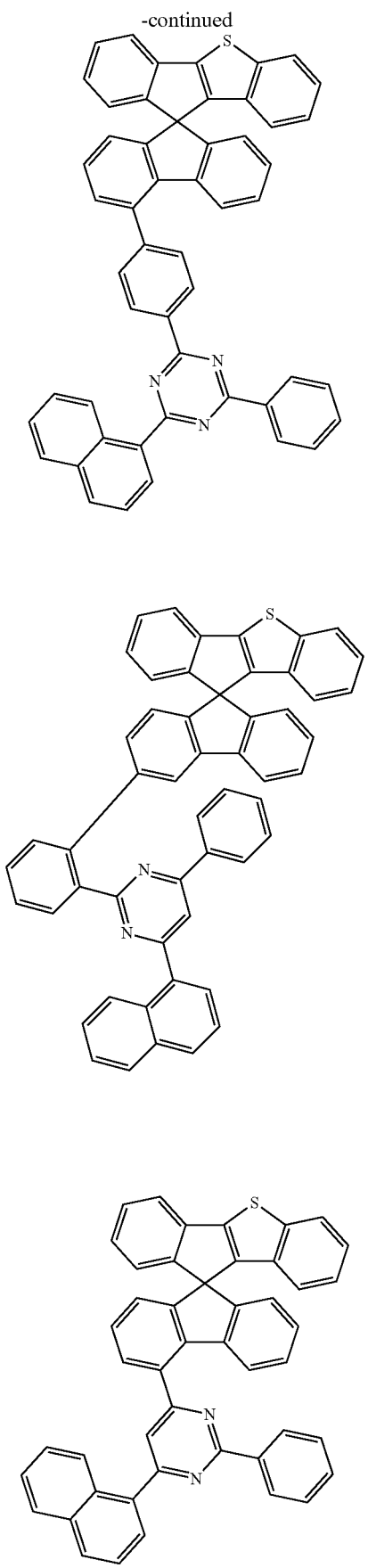
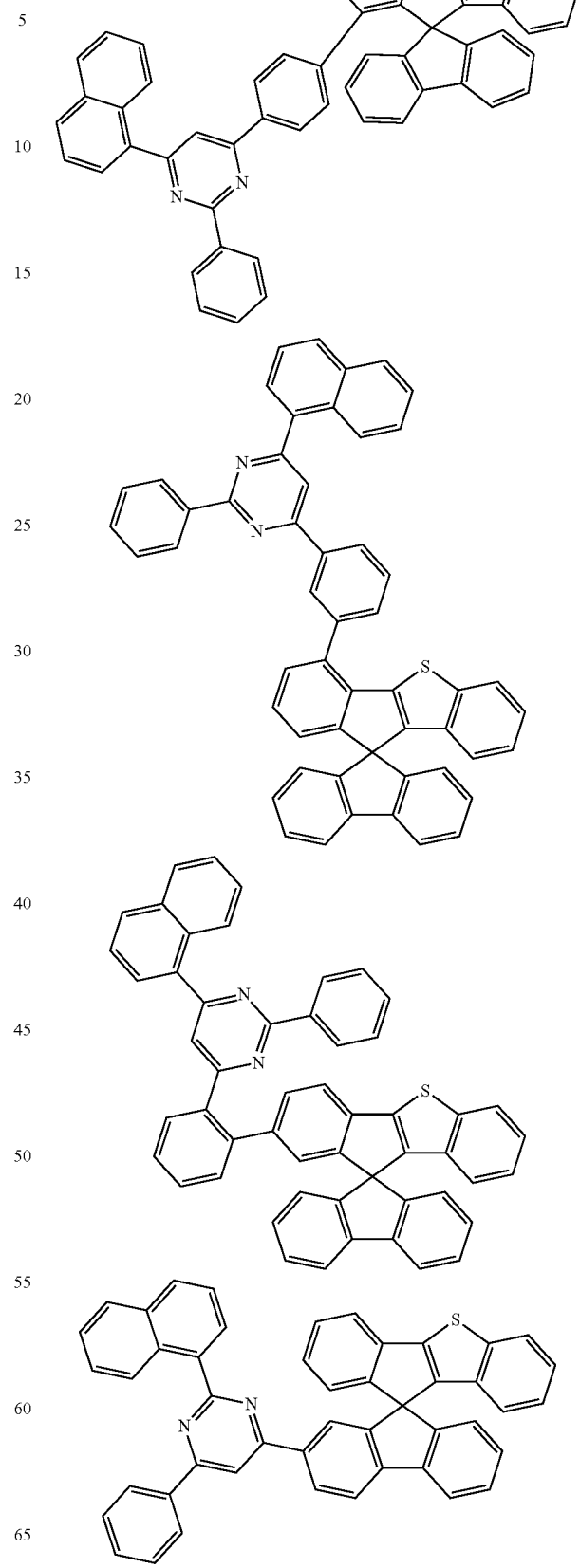

127
-continued
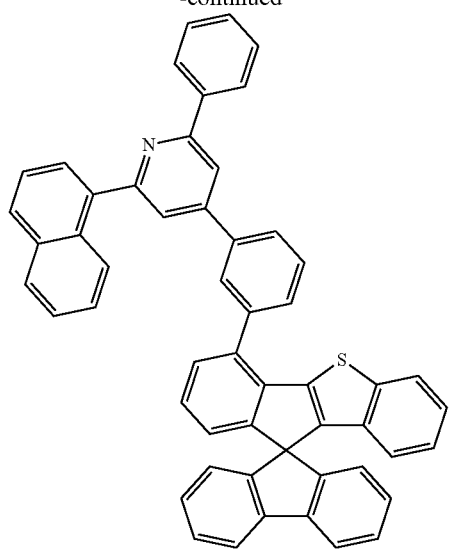
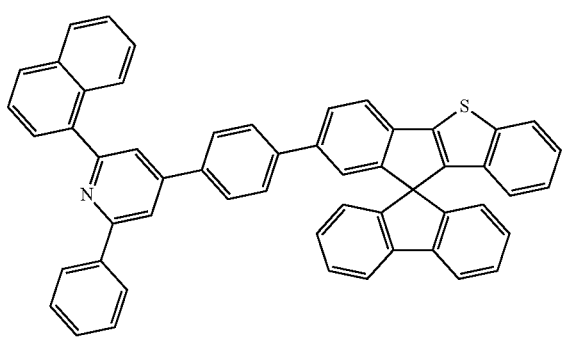
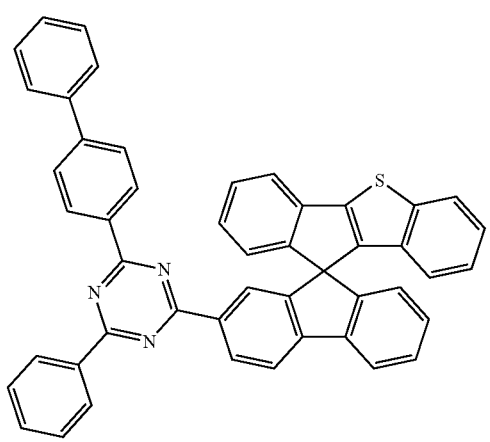
128
-continued
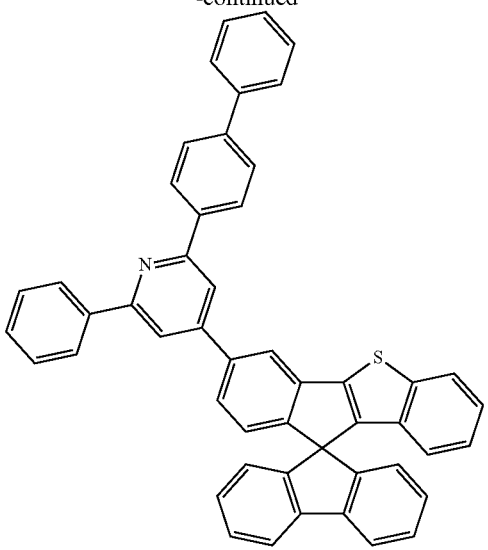
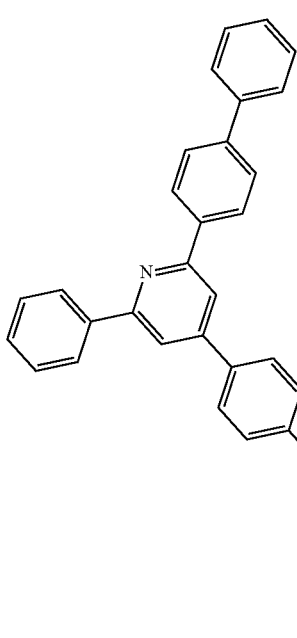
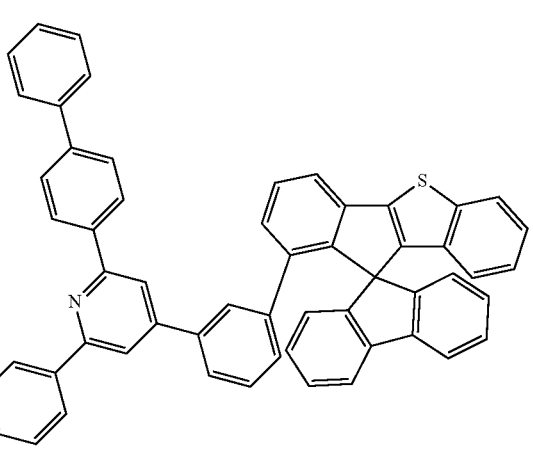

129
-continued
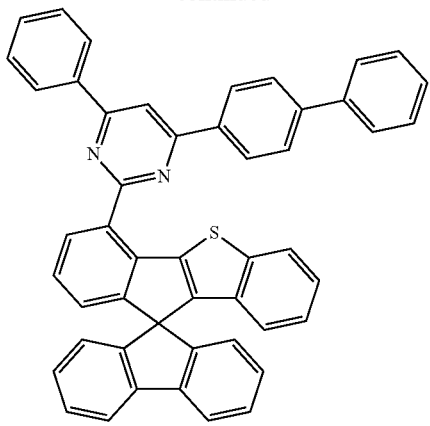
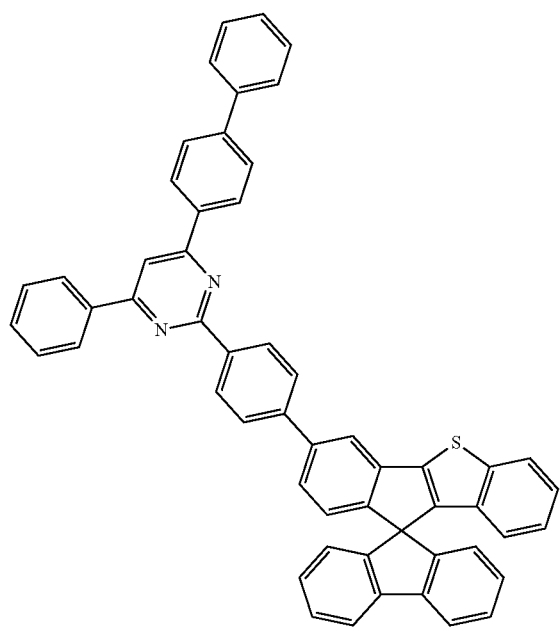
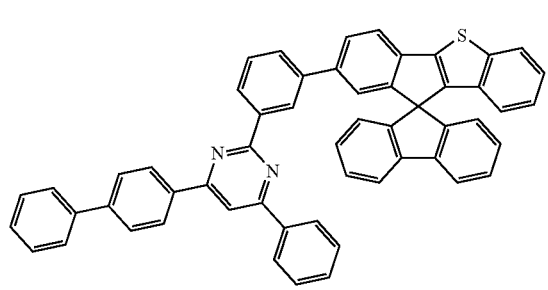
130
-continued
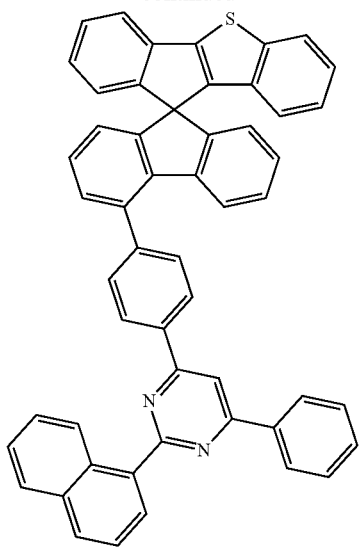
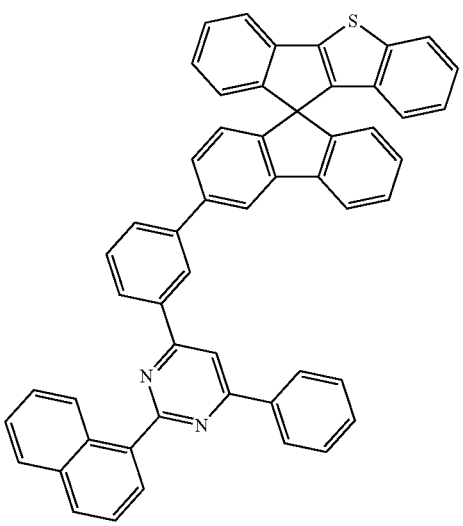
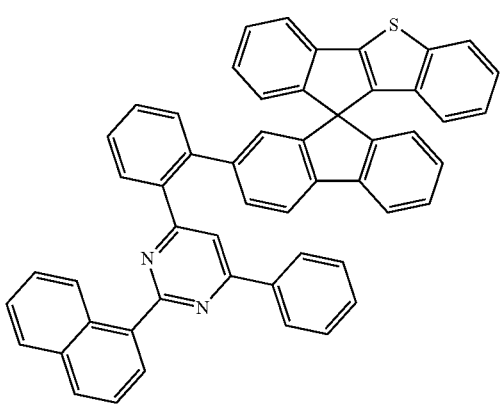

131
-continued
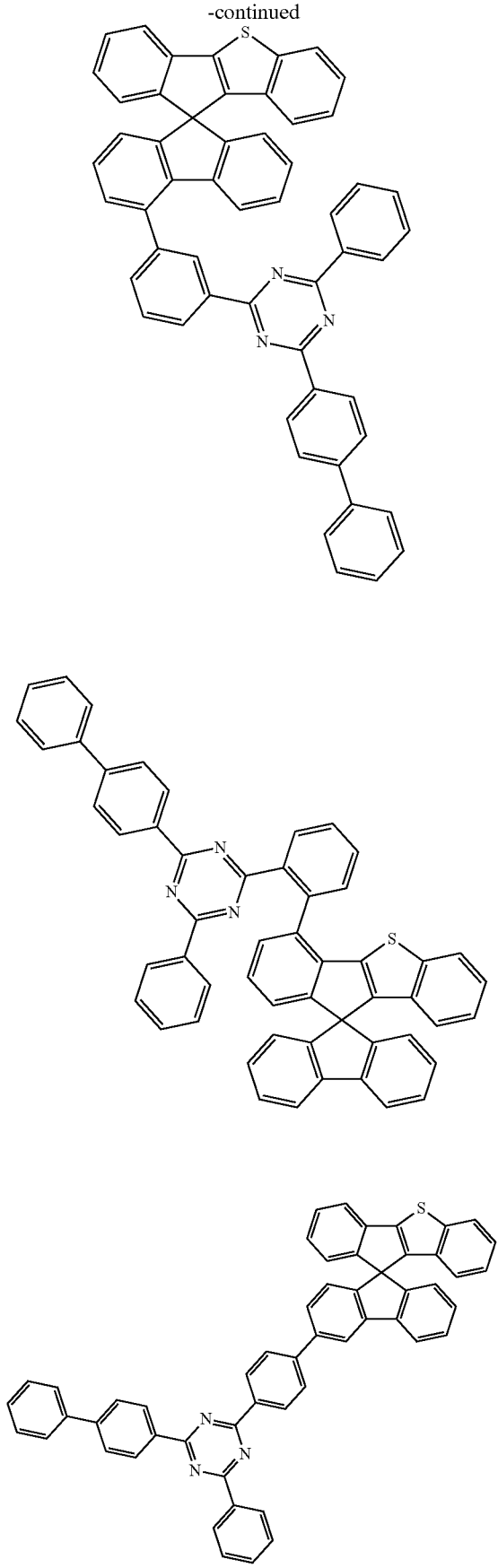
132
-continued
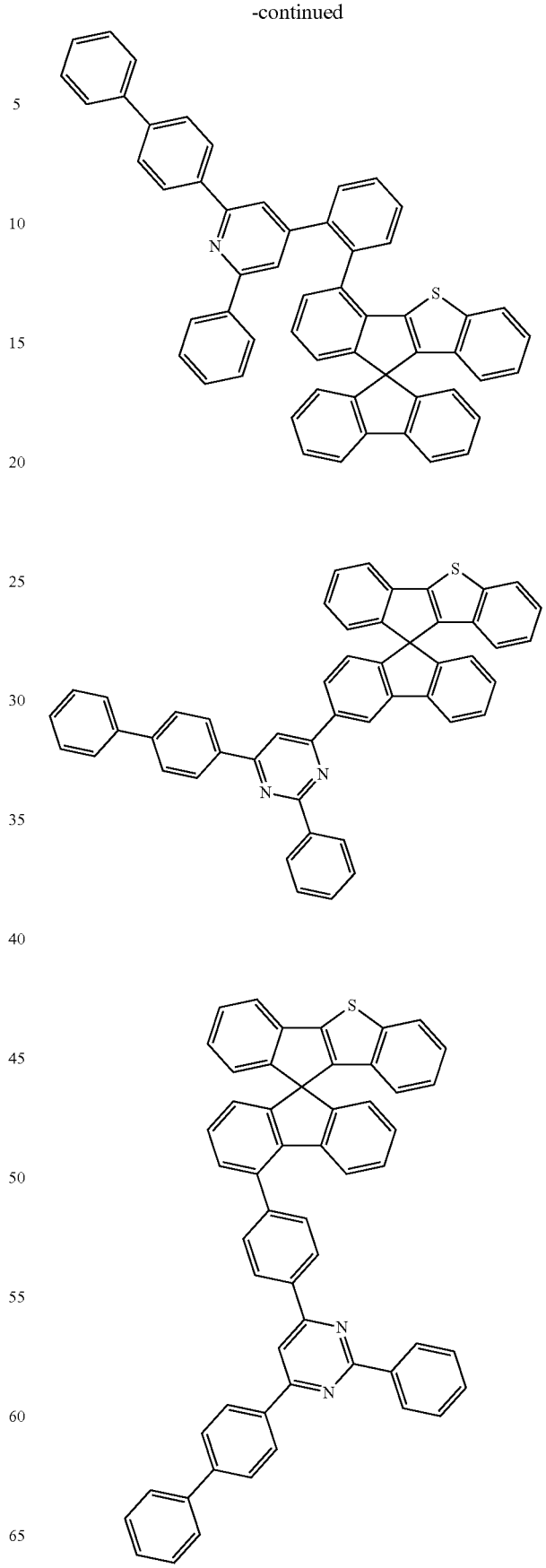

133
-continued
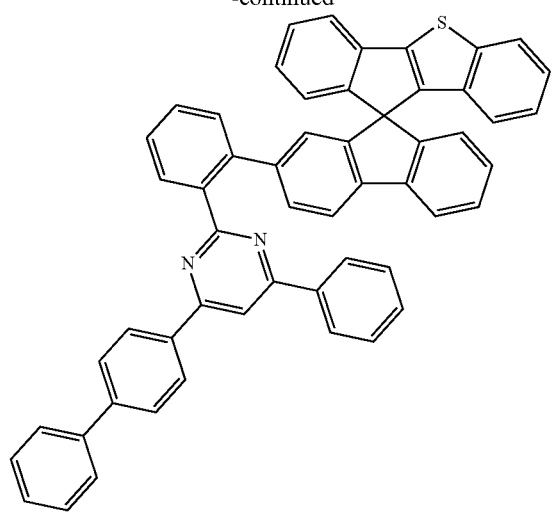
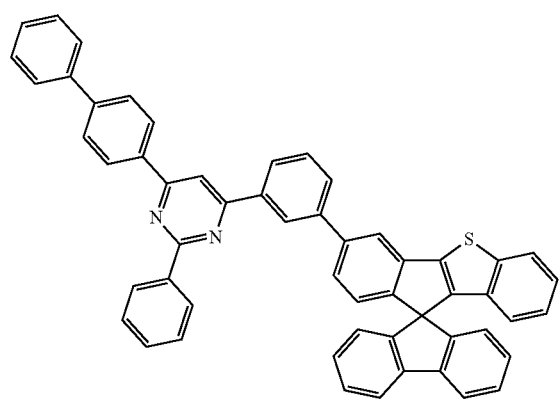
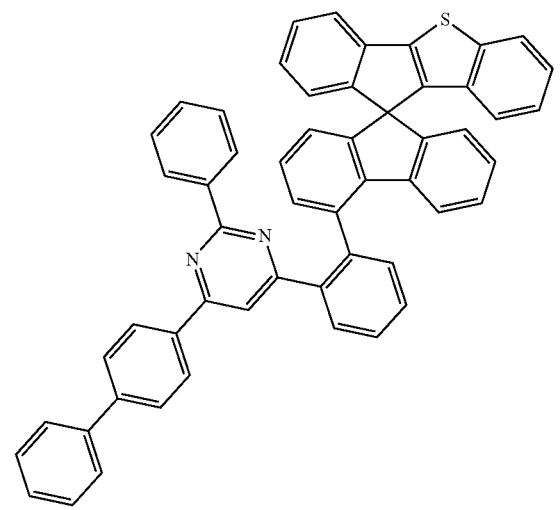
134
-continued
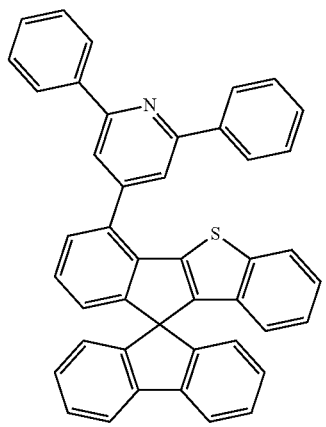
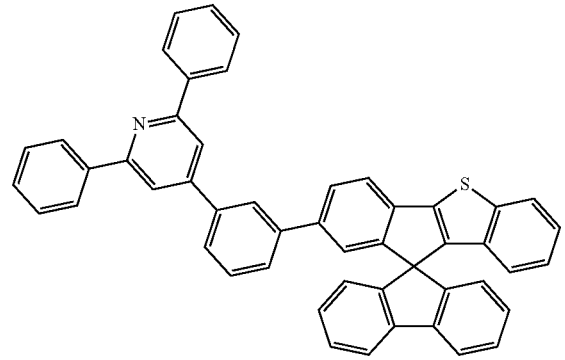
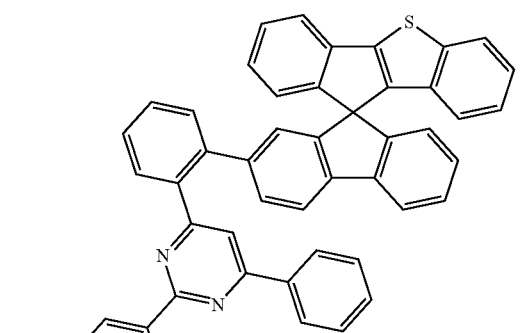
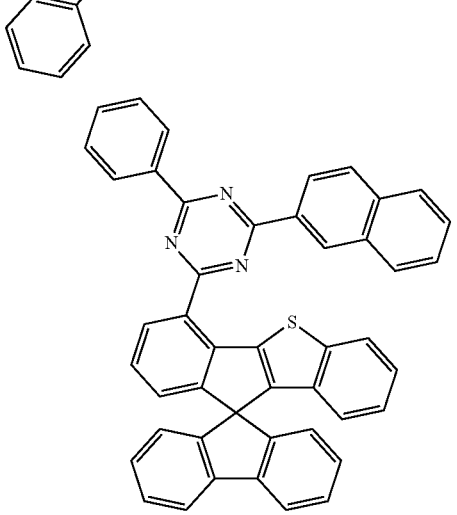

135
-continued
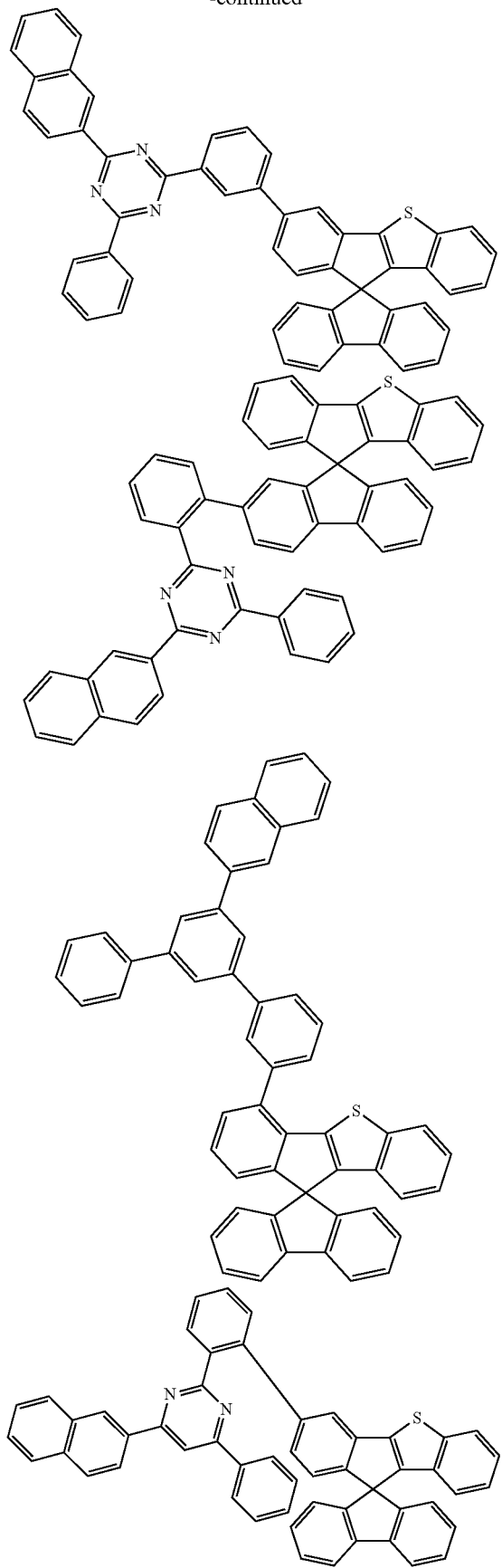
136
-continued
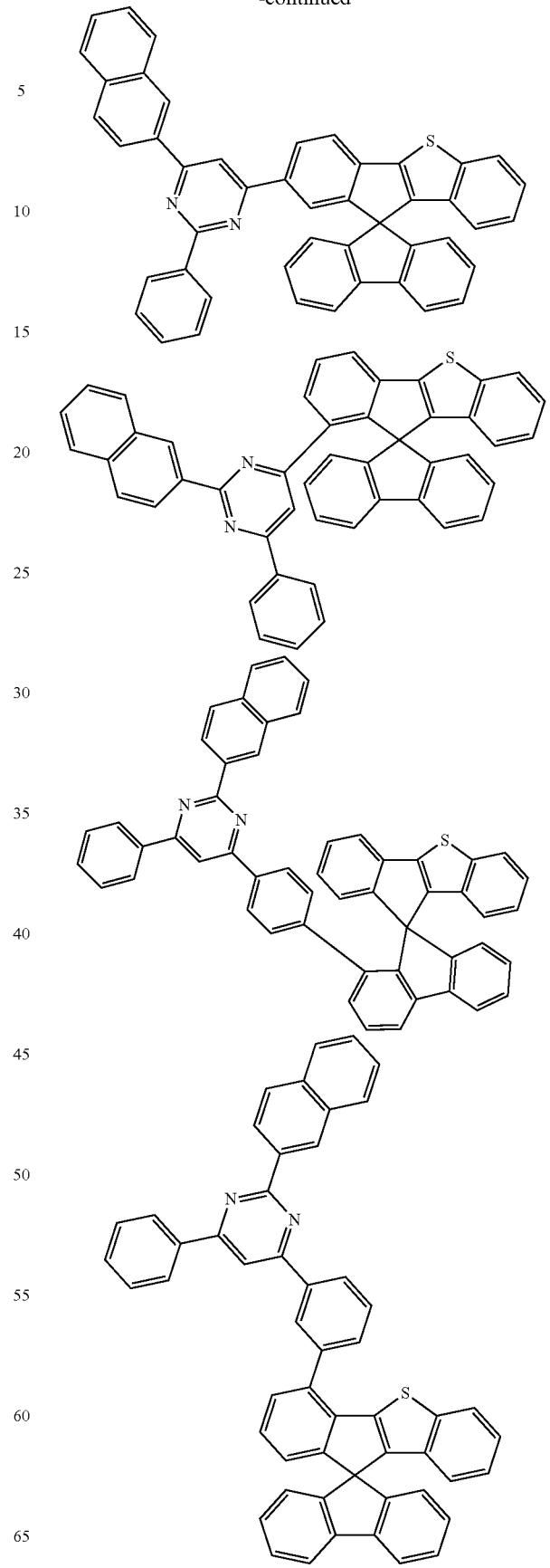

137
-continued
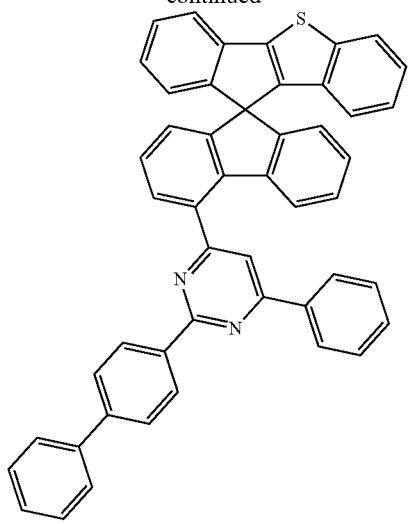
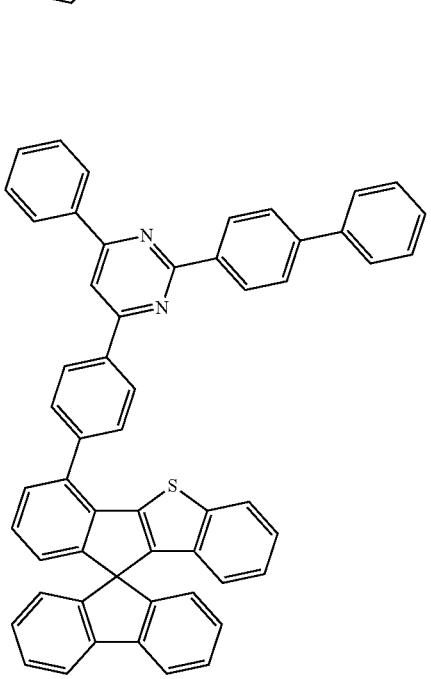
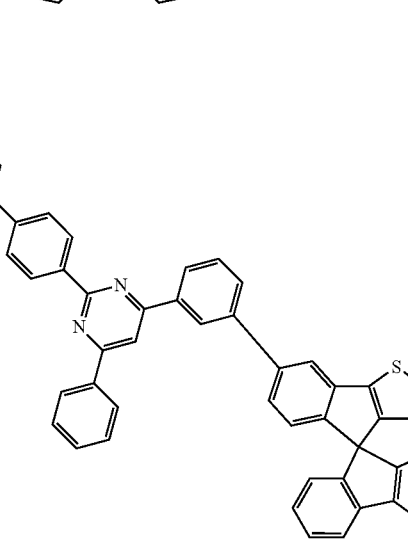
138
-continued
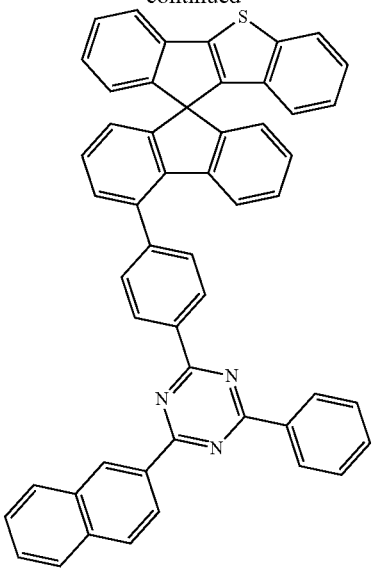
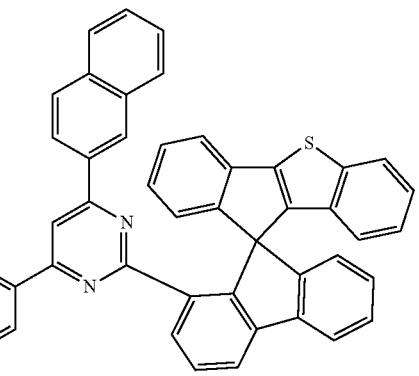
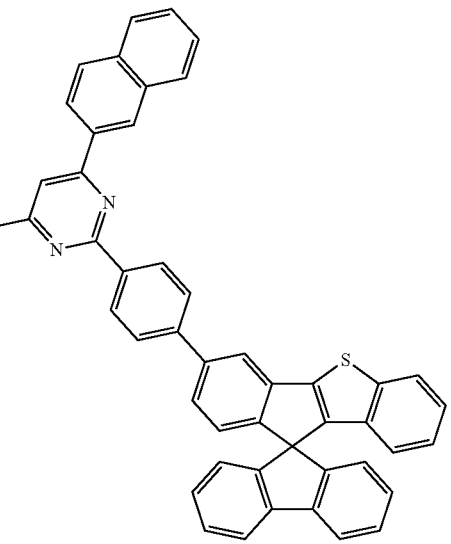

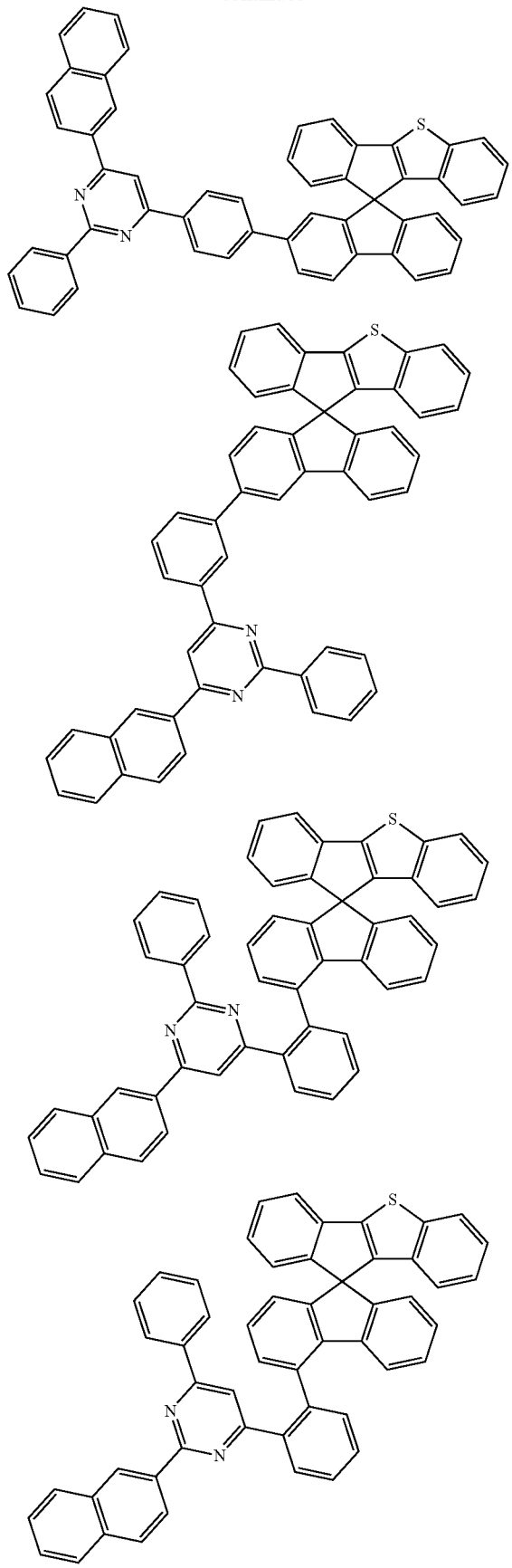
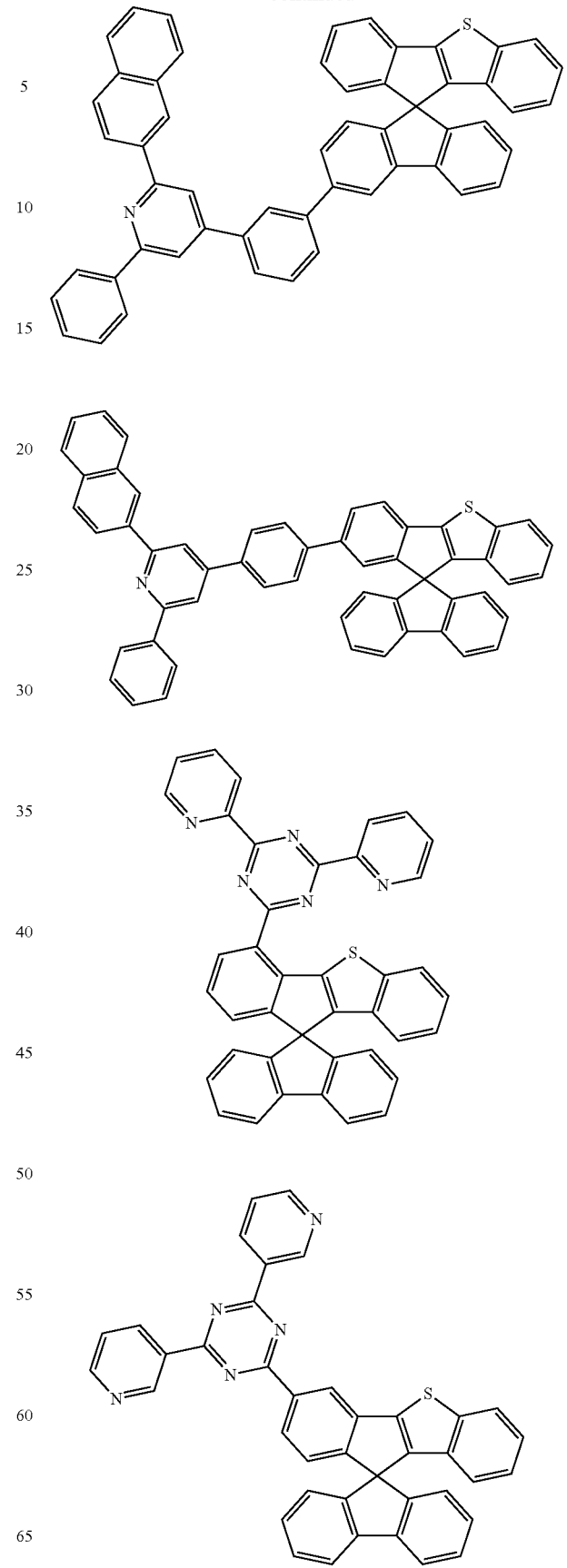

141
-continued
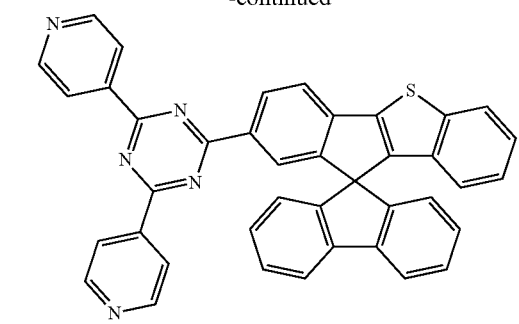
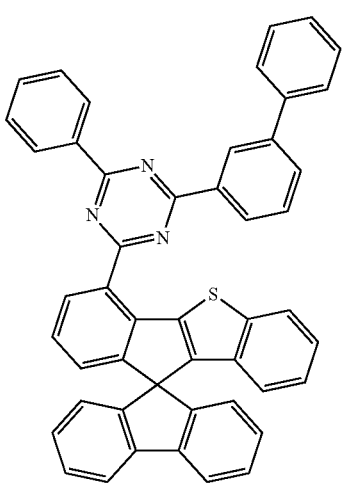
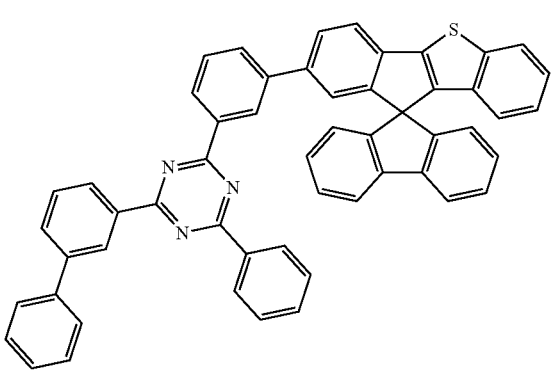
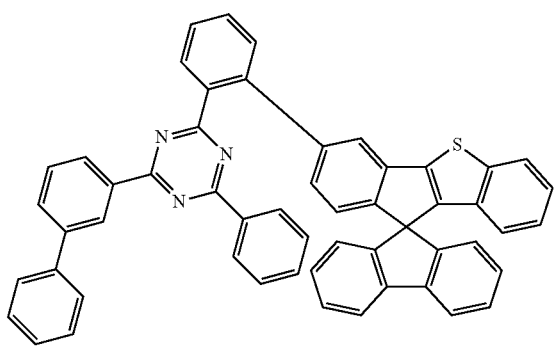
142
-continued
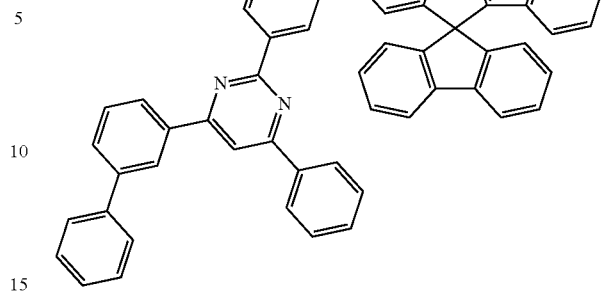
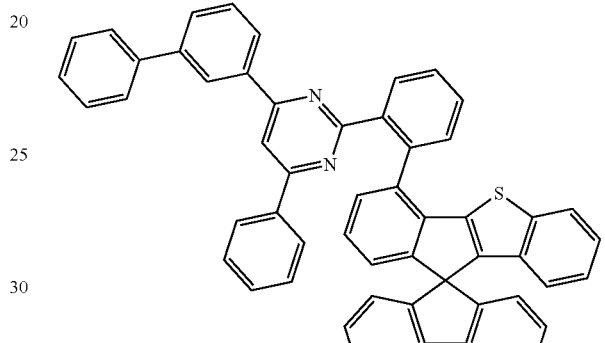
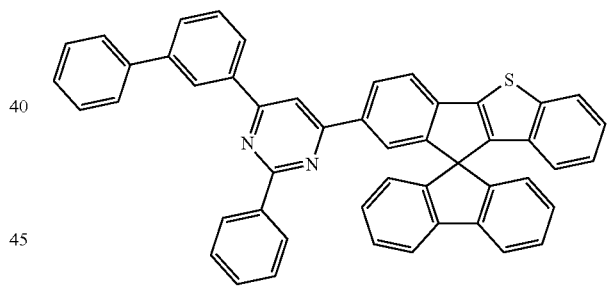
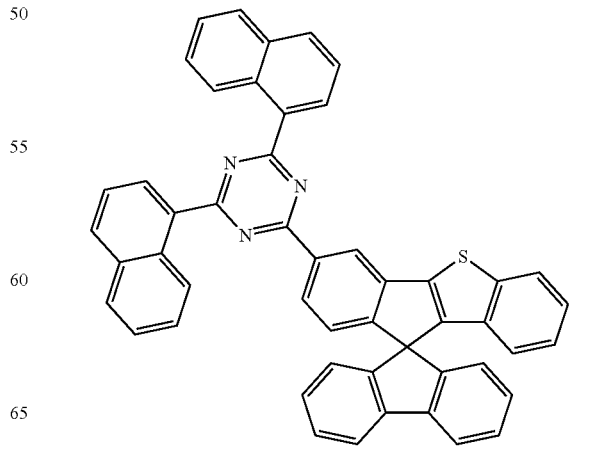

143
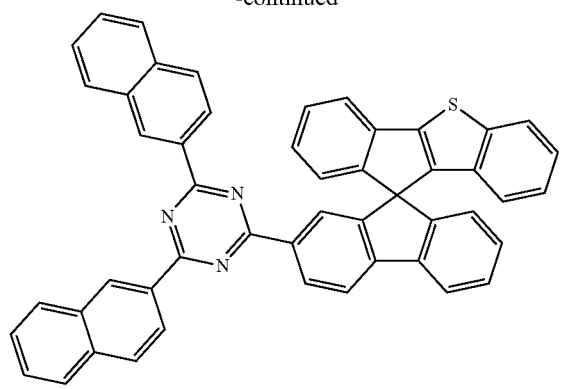
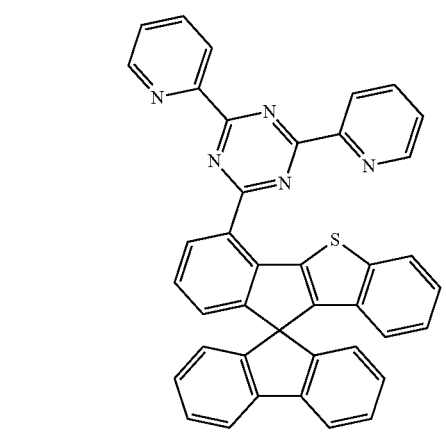
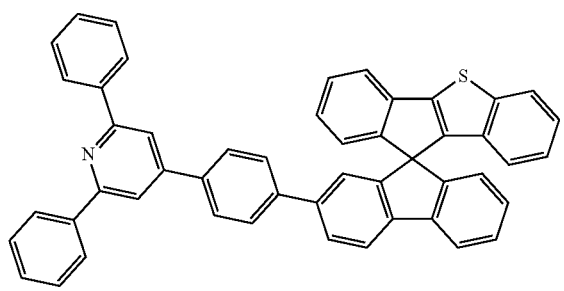
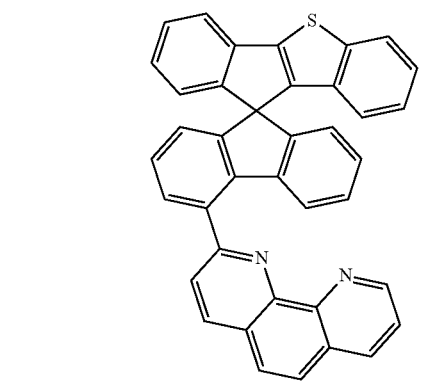
144
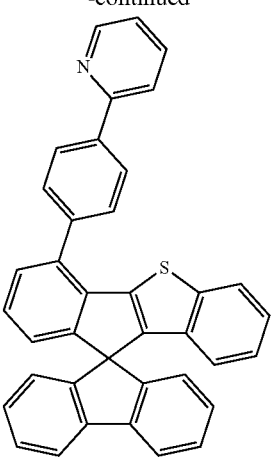
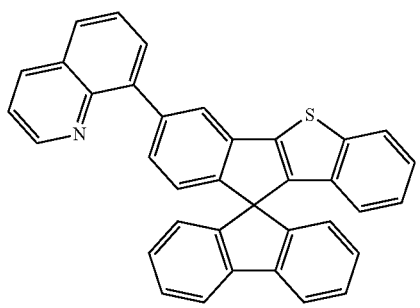
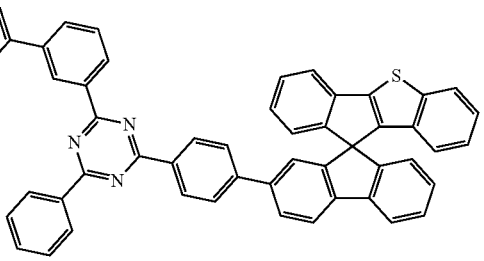
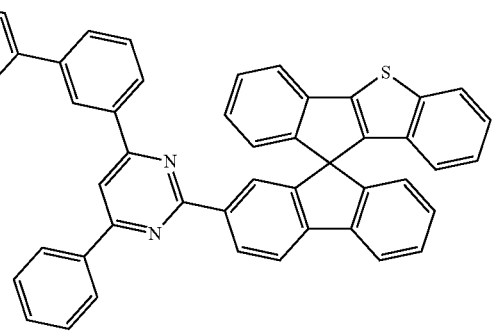

145
-continued
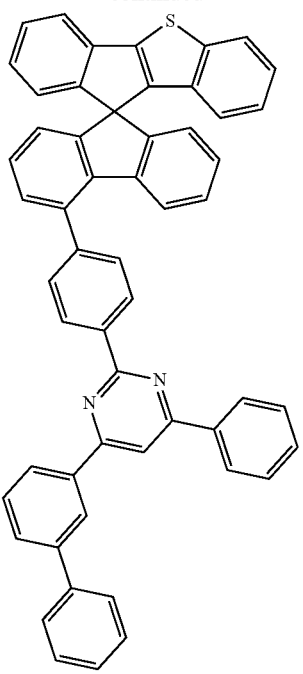
146
-continued
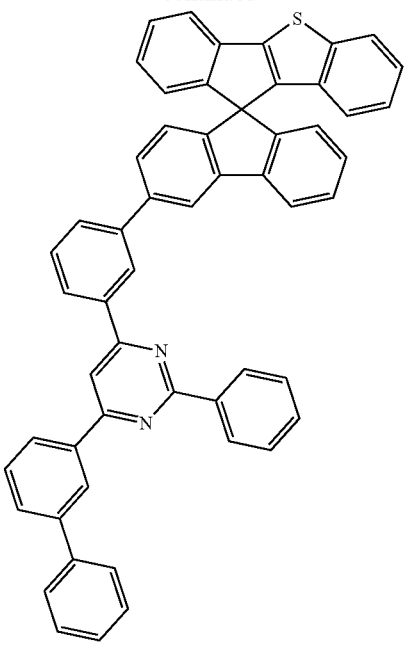
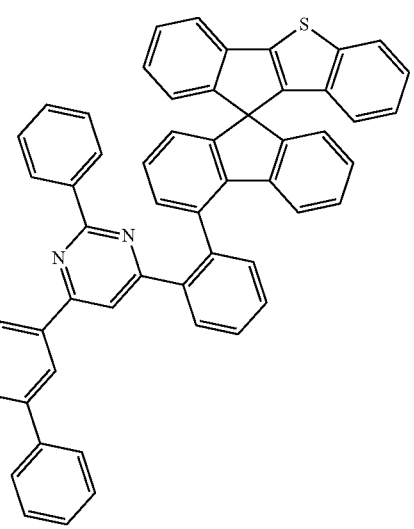
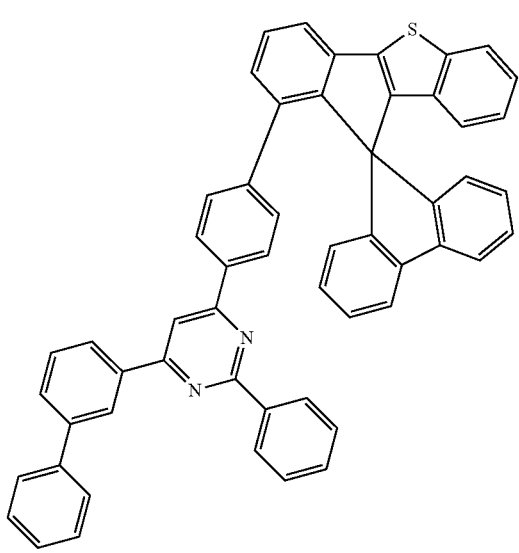
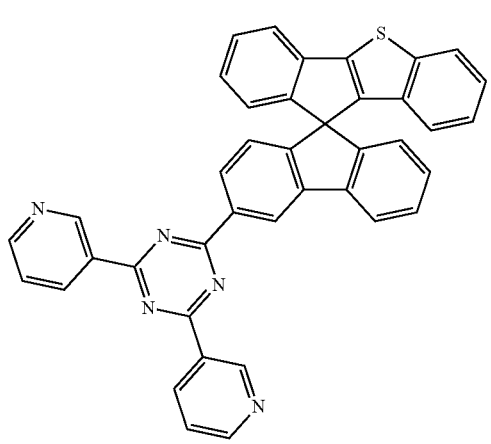

-continued
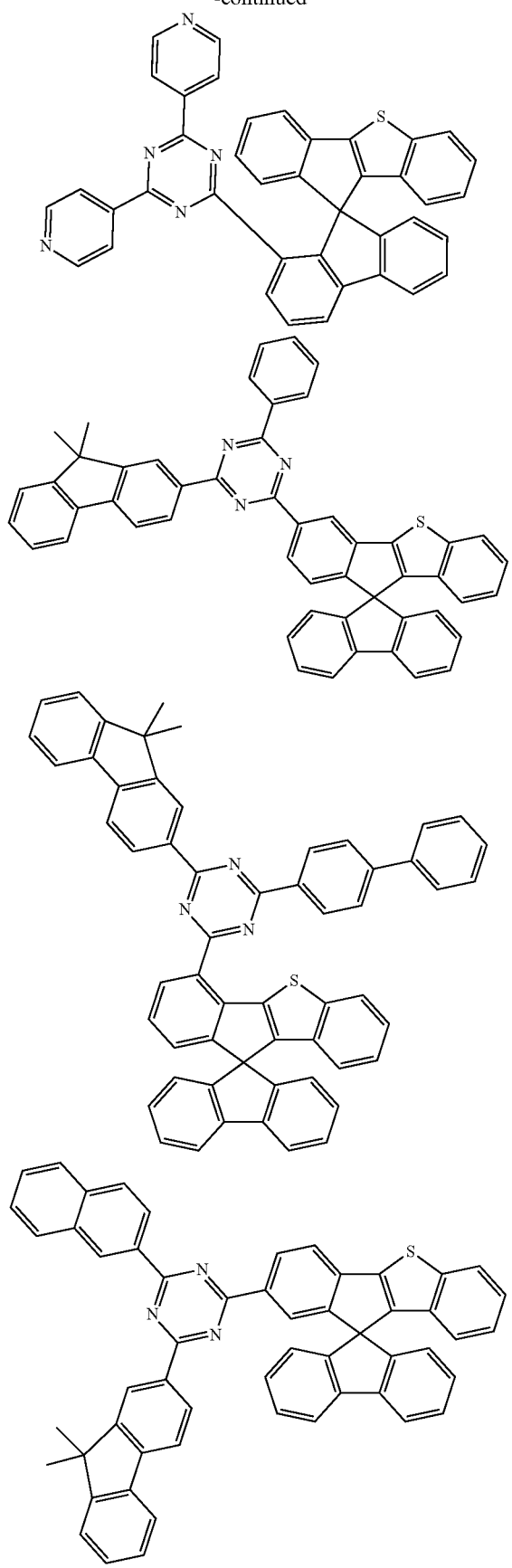
-continued
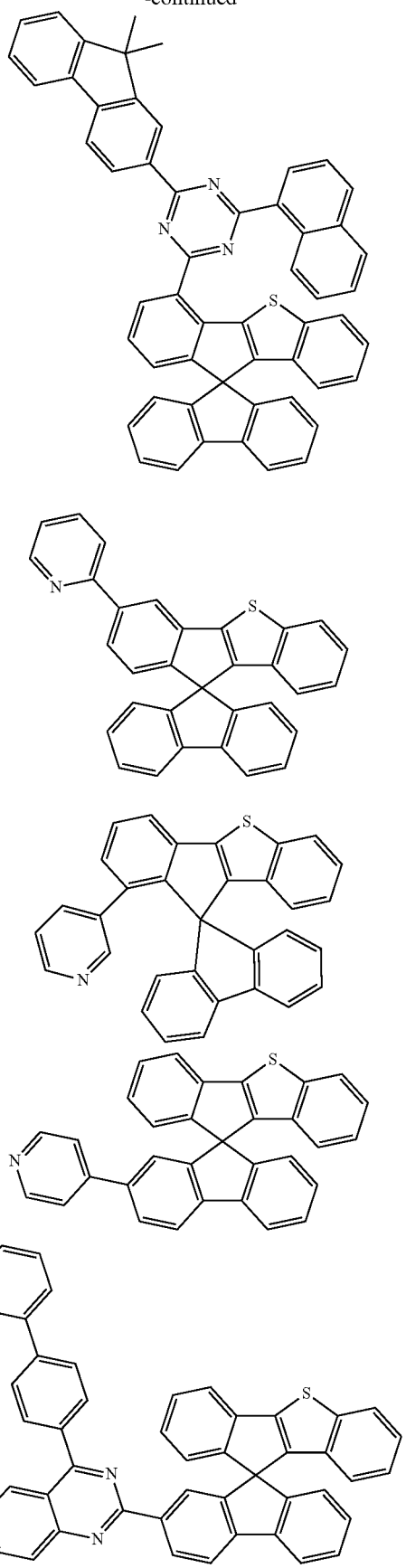

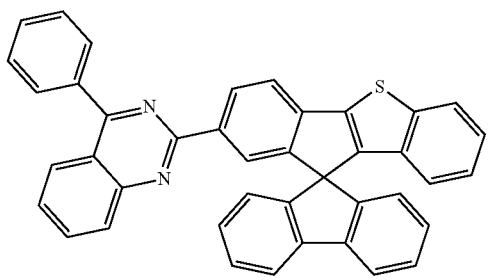
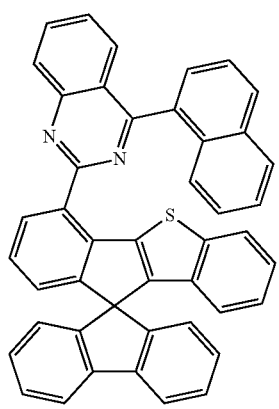
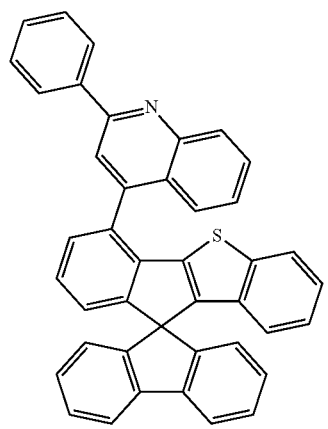
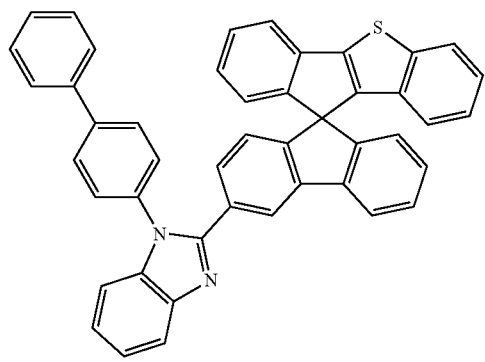
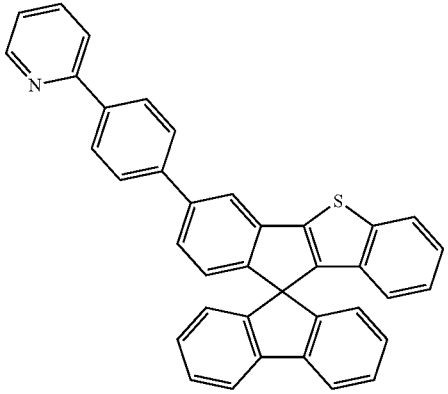
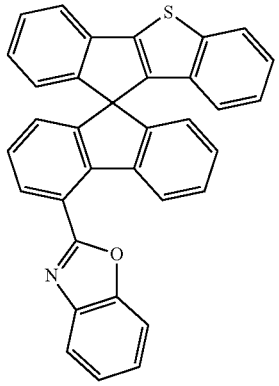
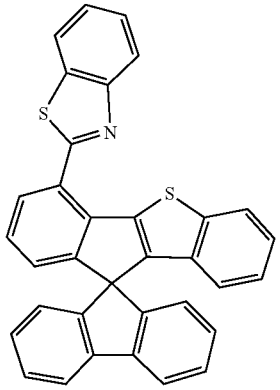
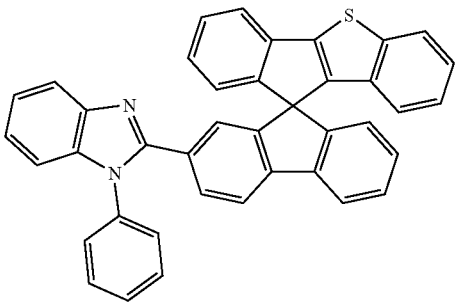

151
-continued
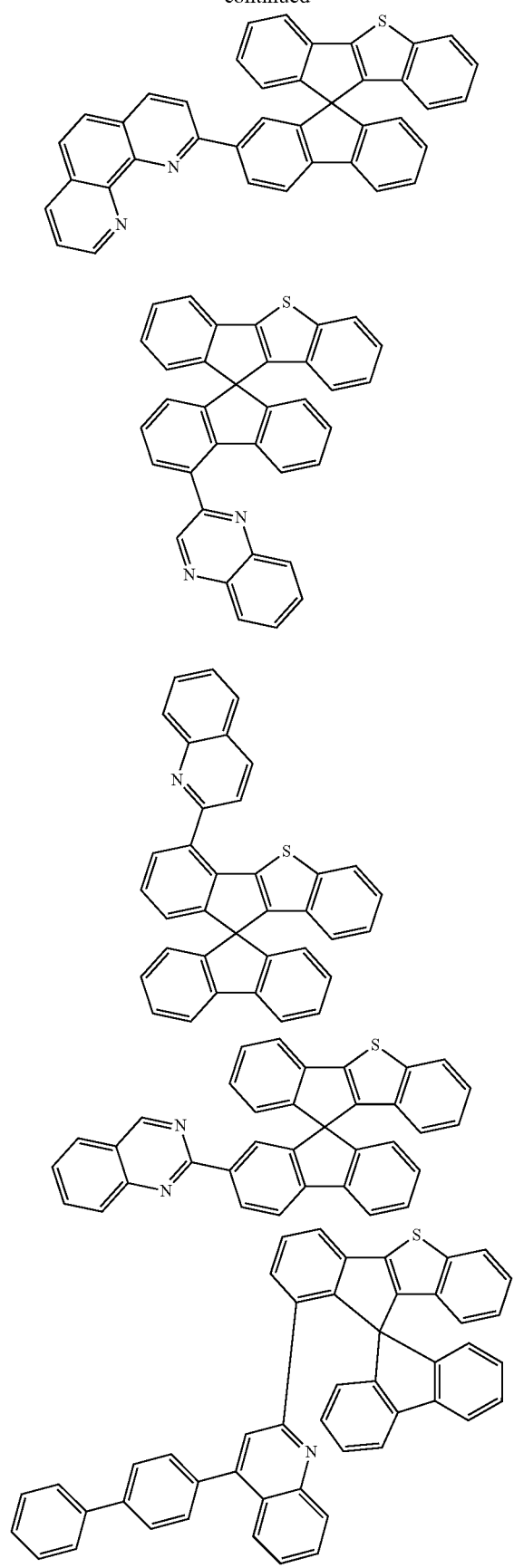
152
-continued
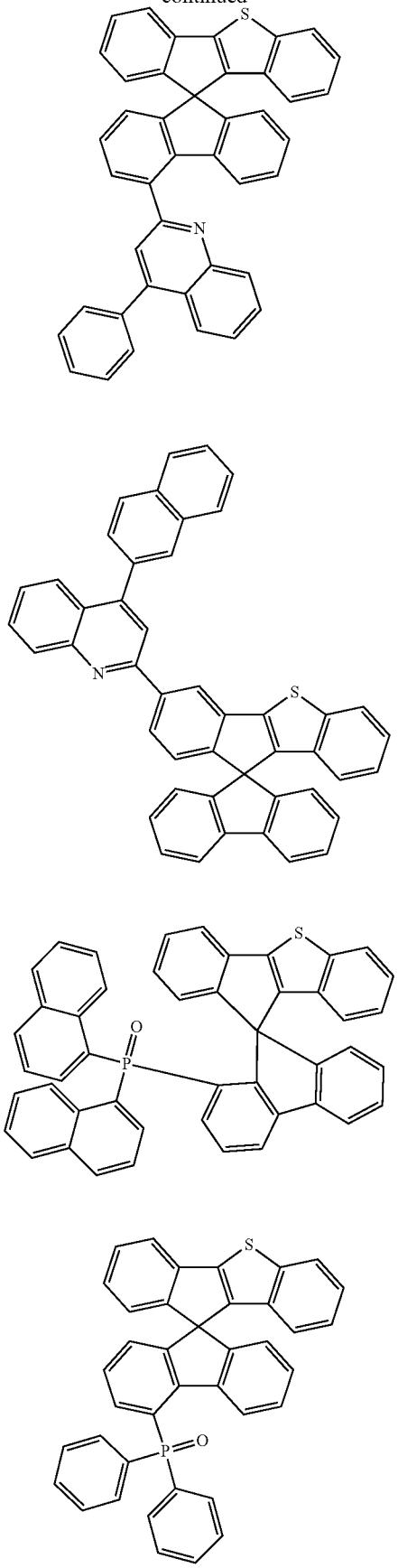

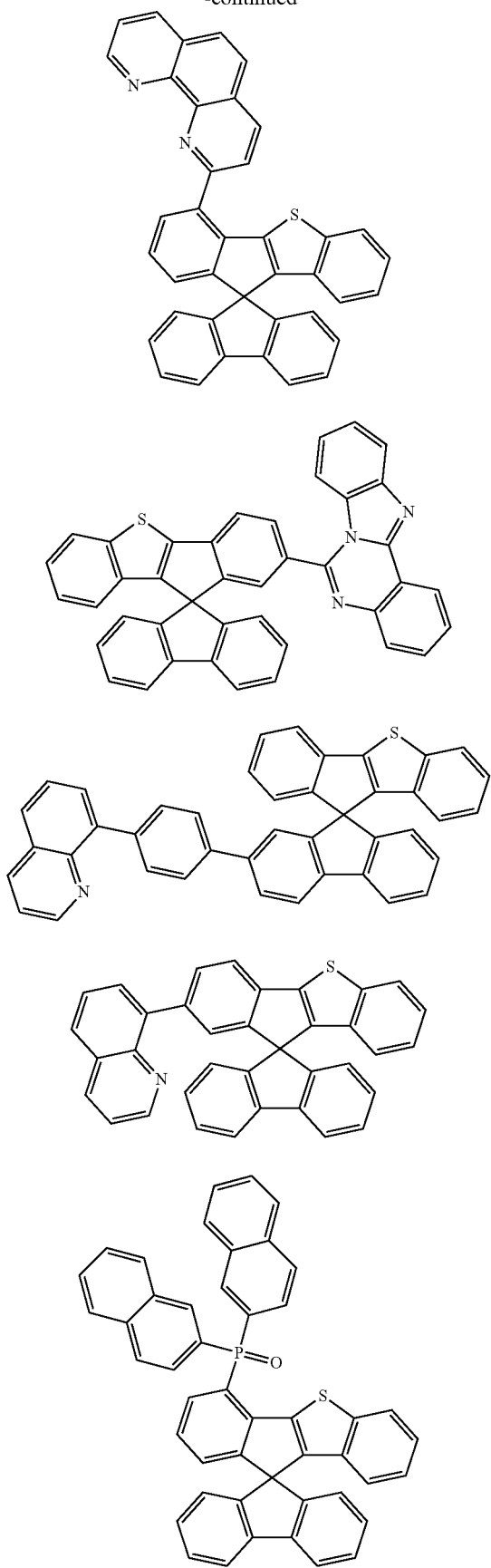
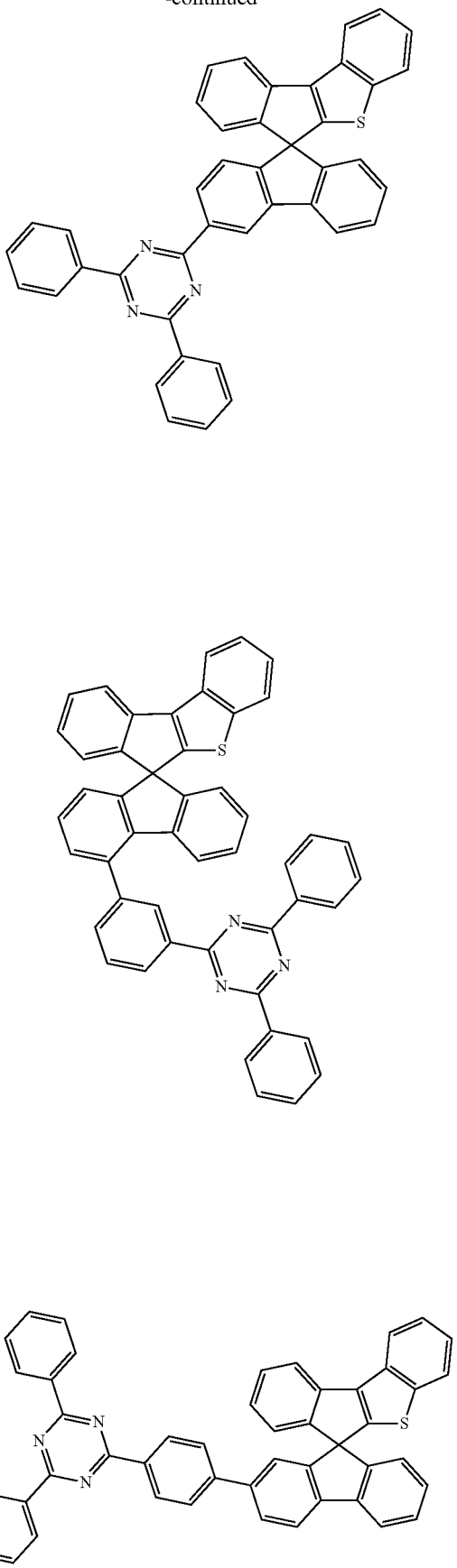

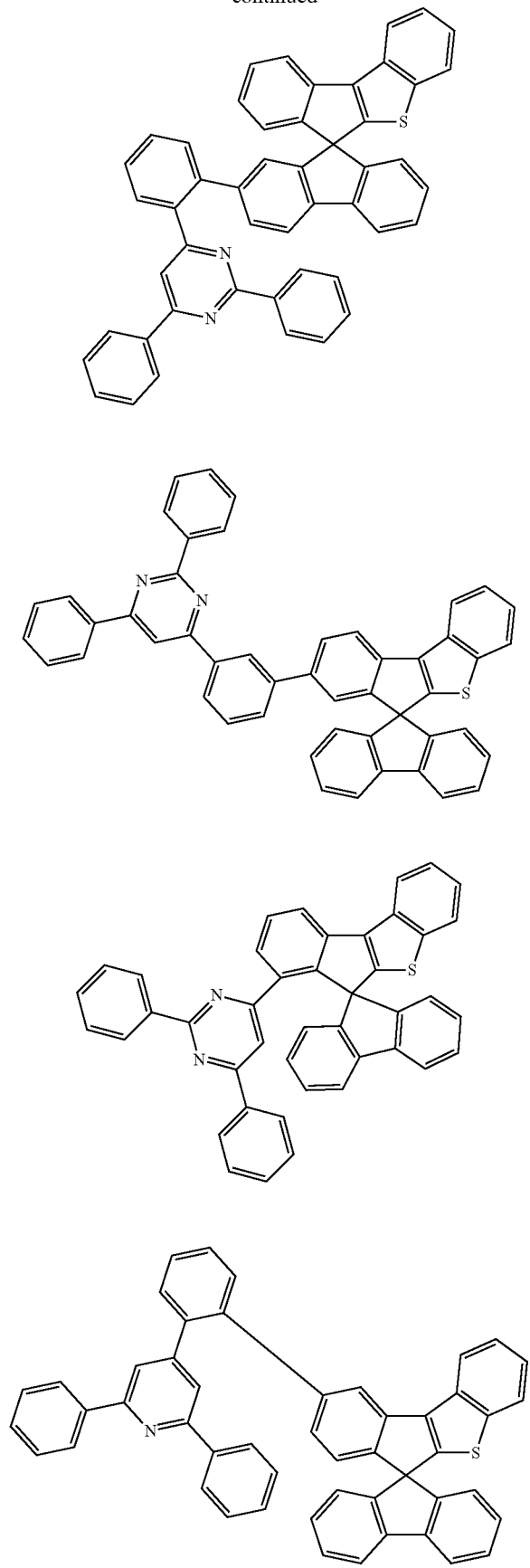
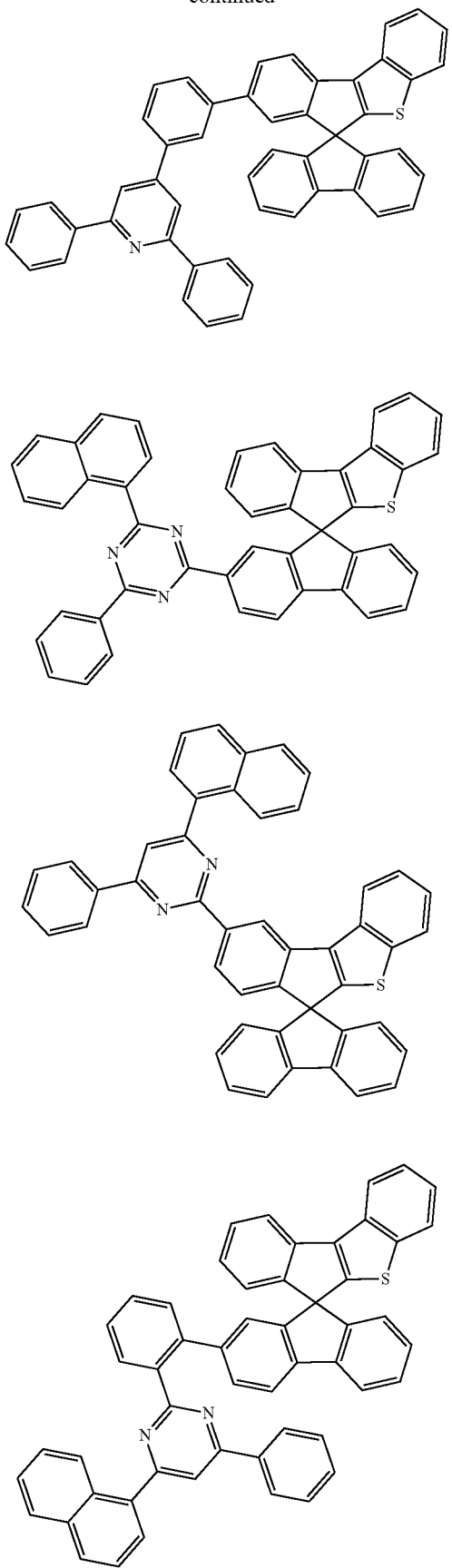

-continued
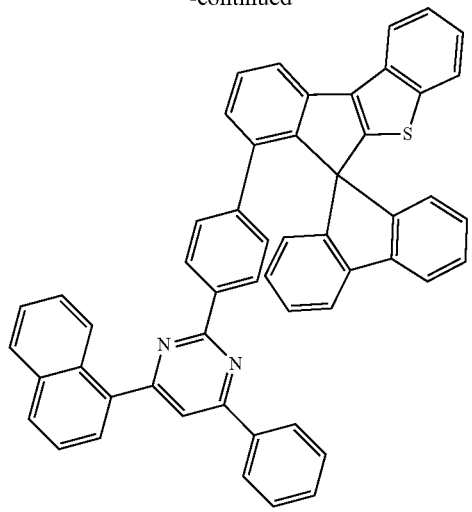
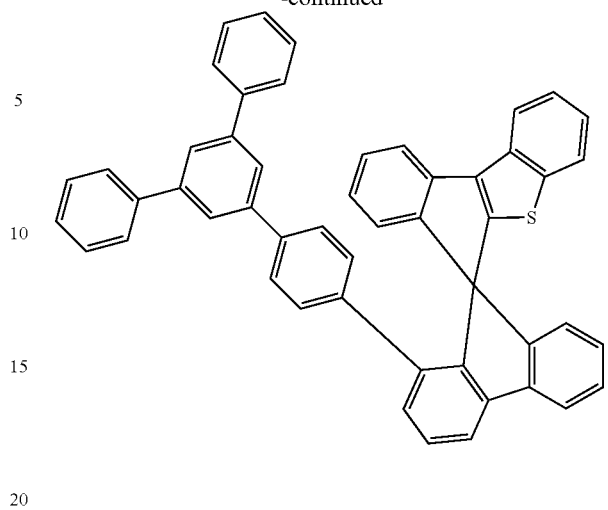
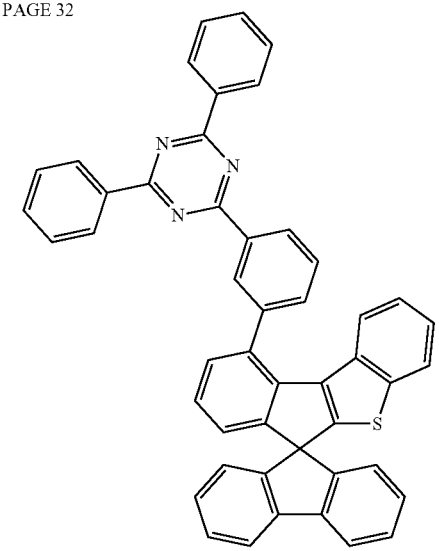
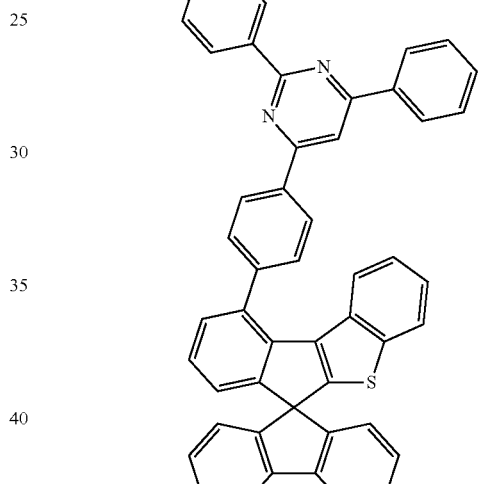
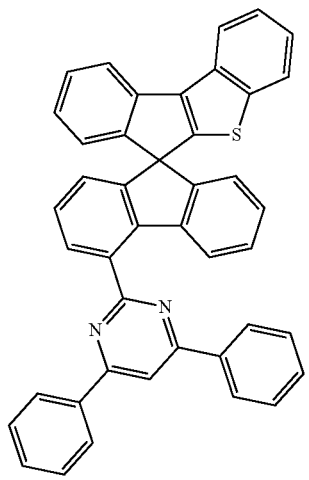
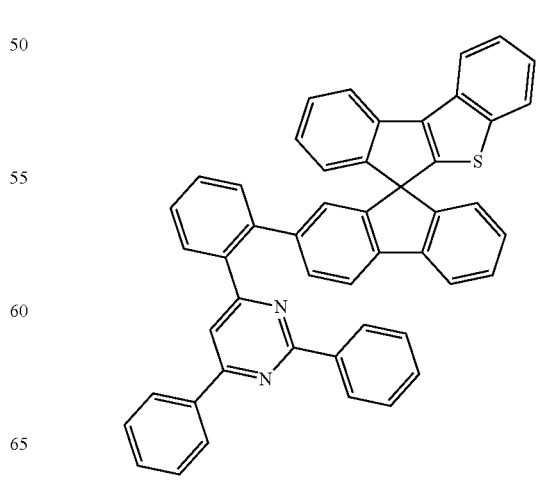

159
-continued
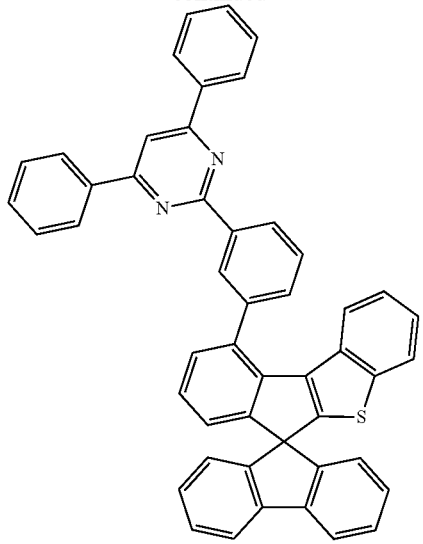
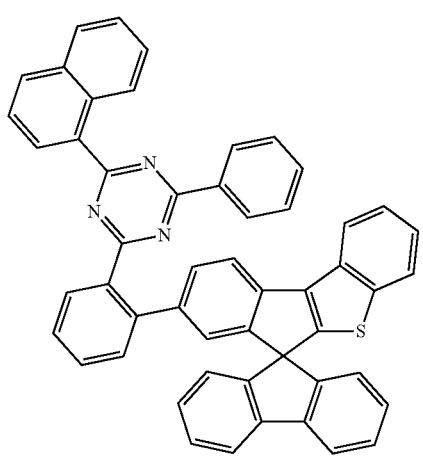
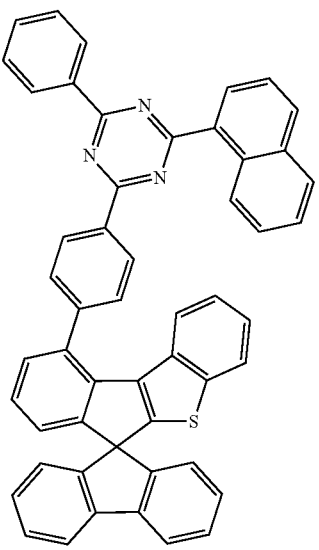
160
-continued
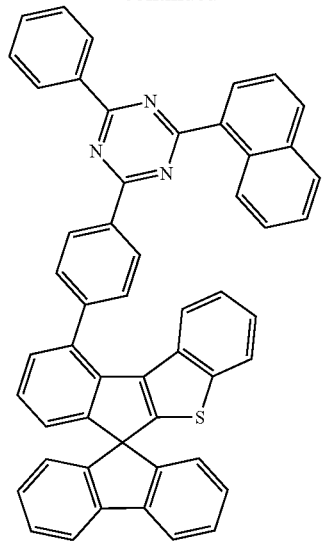
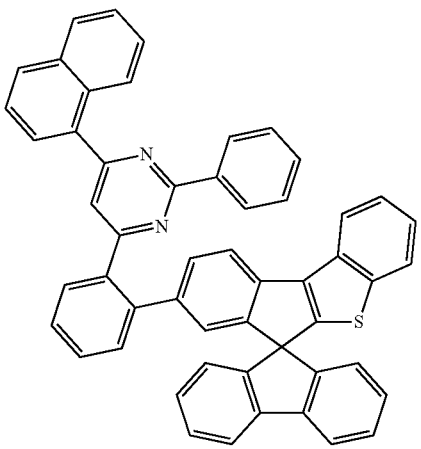
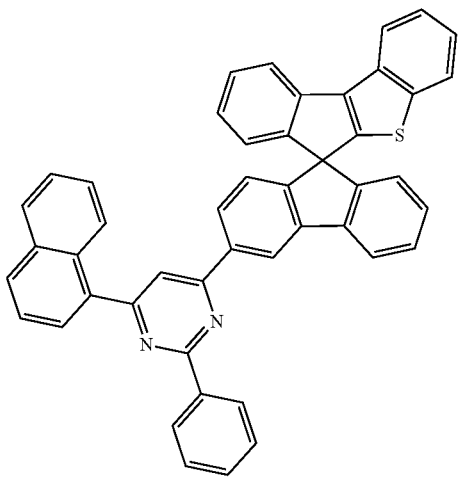

-continued
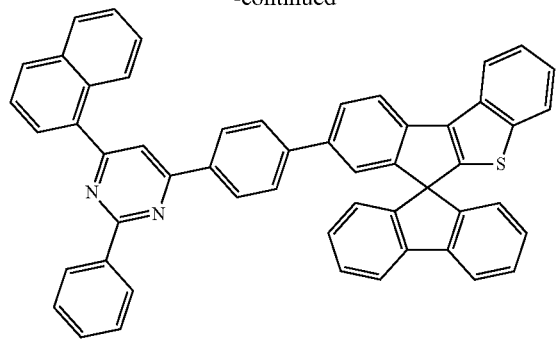
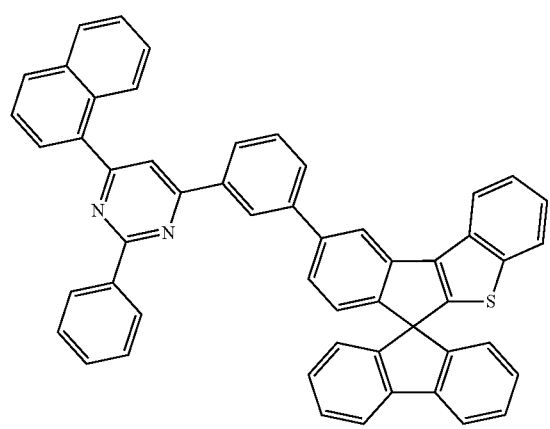
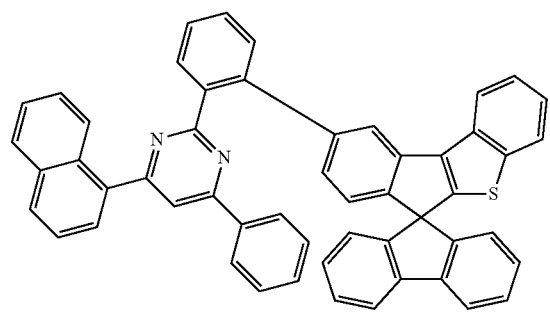
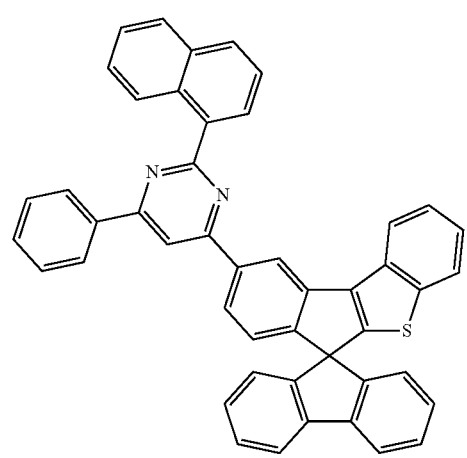
-continued
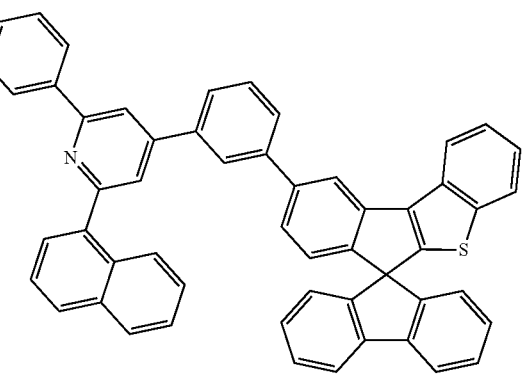
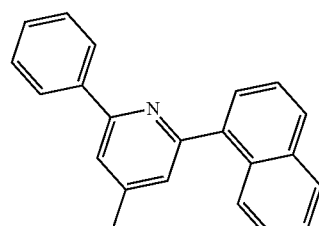
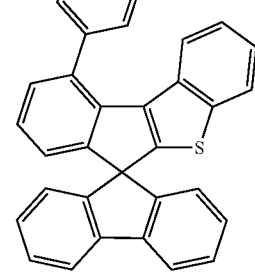
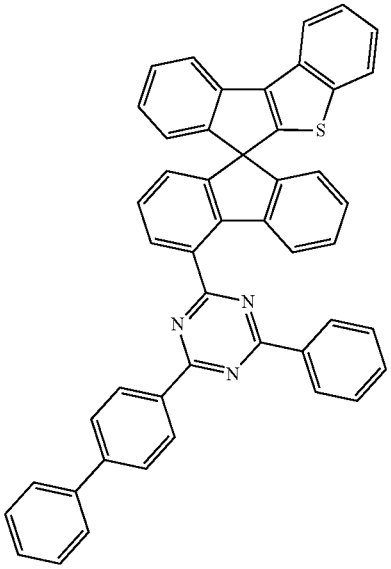

163
-continued
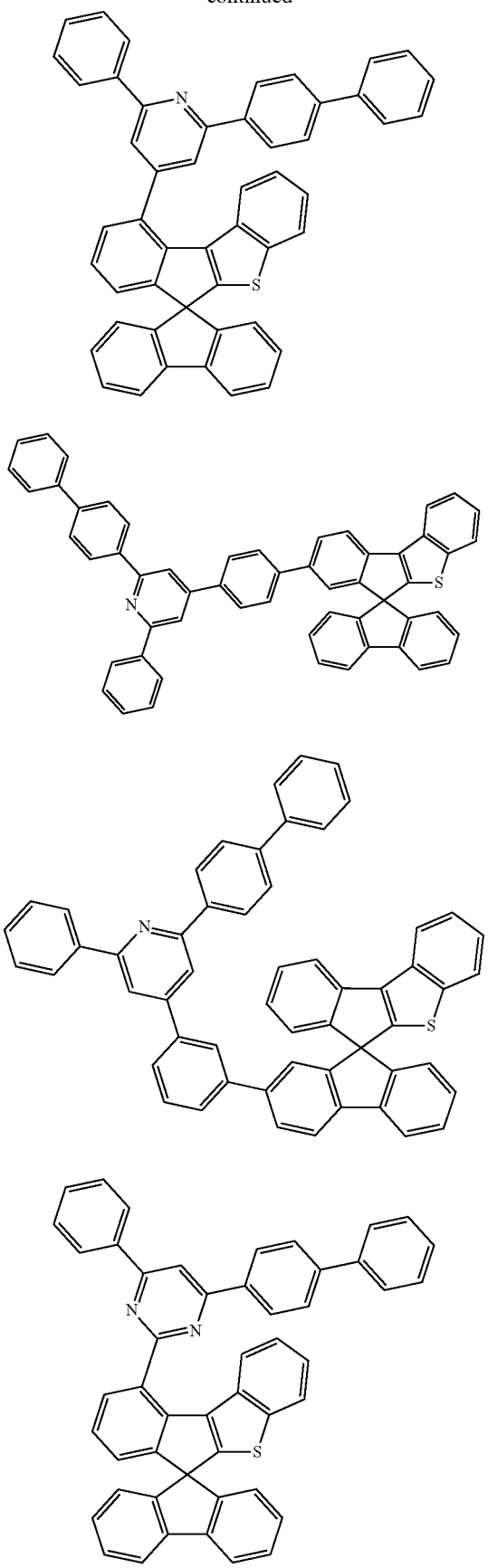
164
-continued
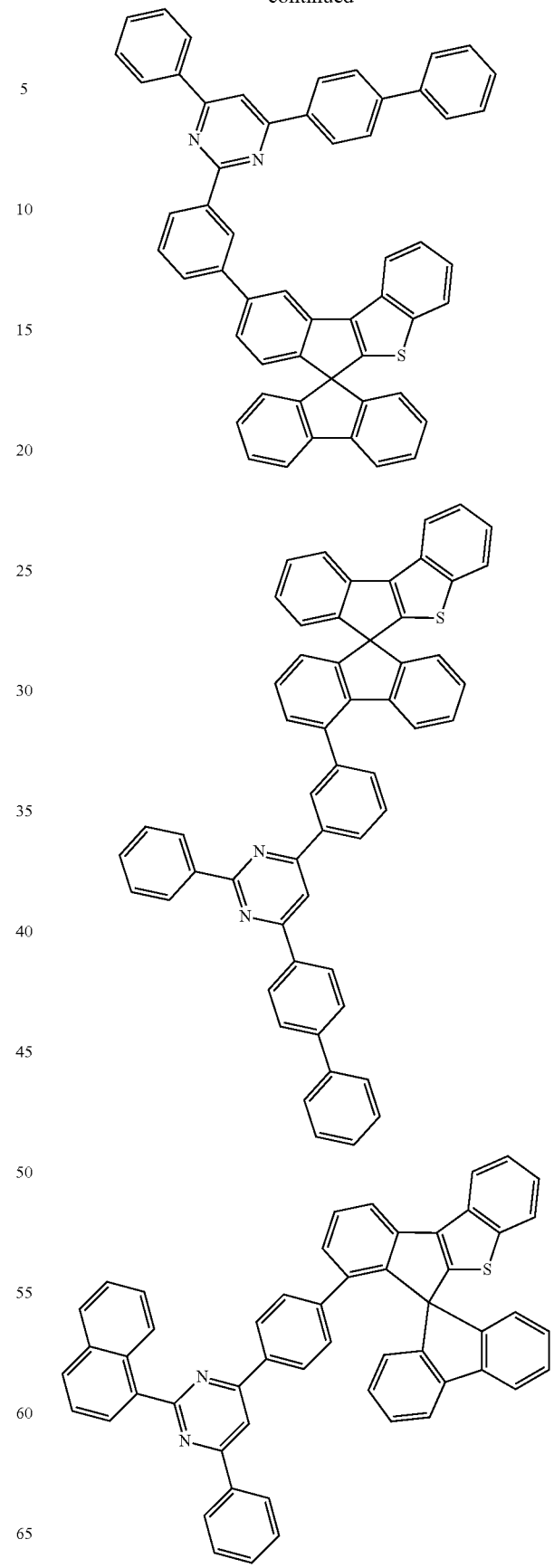

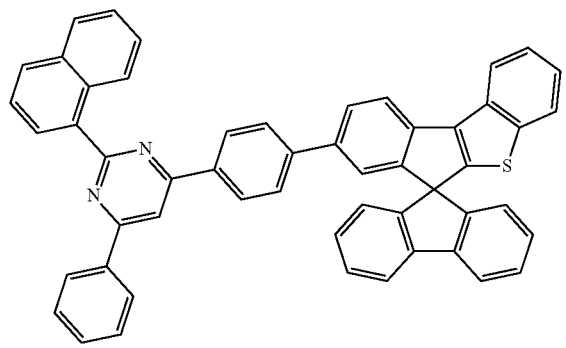
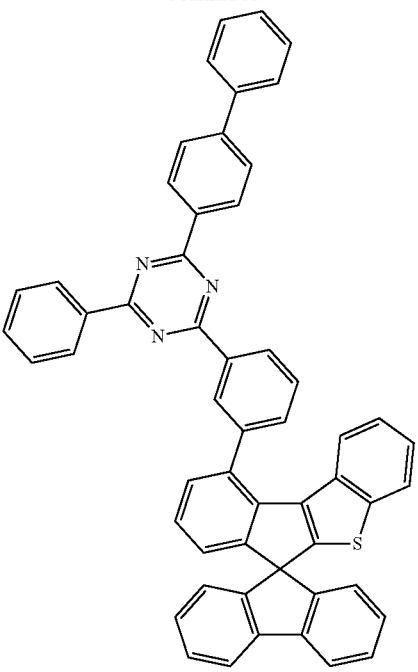
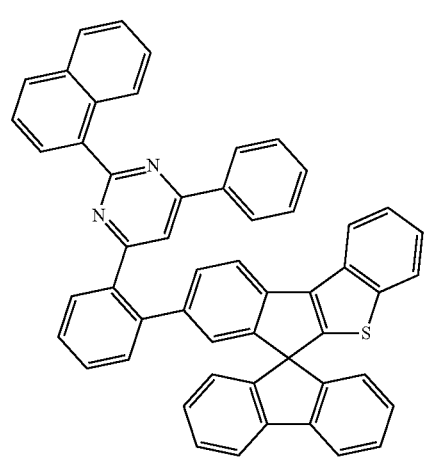
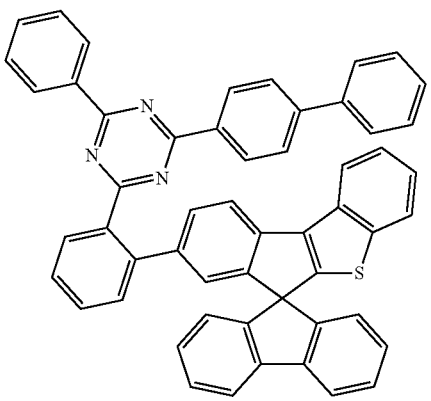
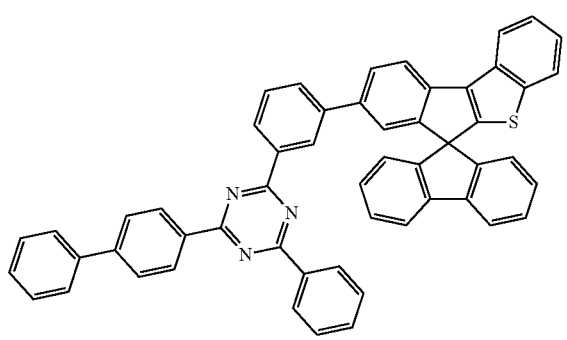
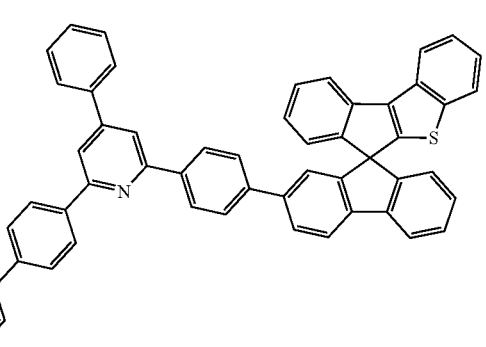

167
-continued
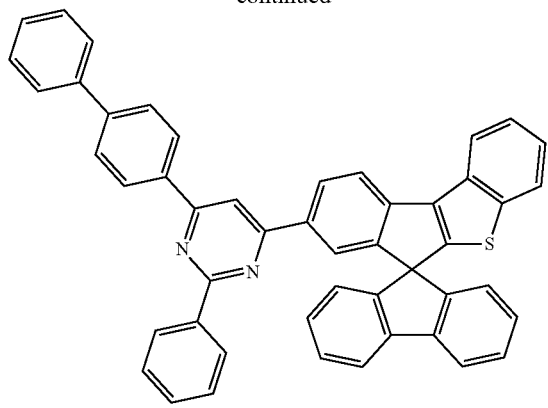
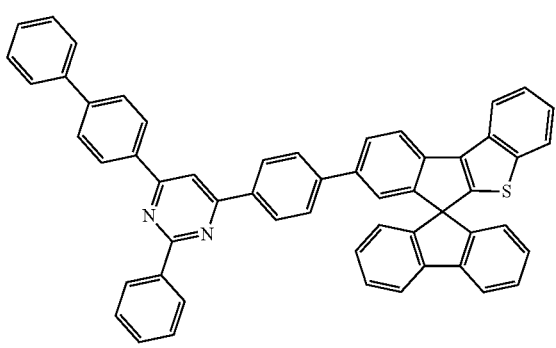
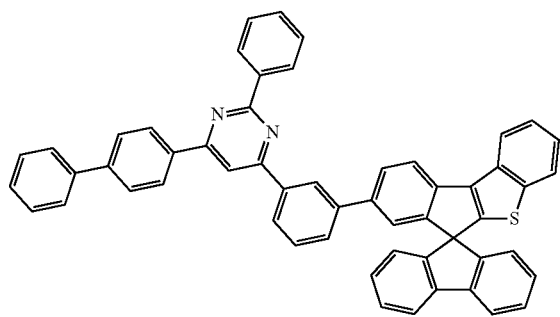
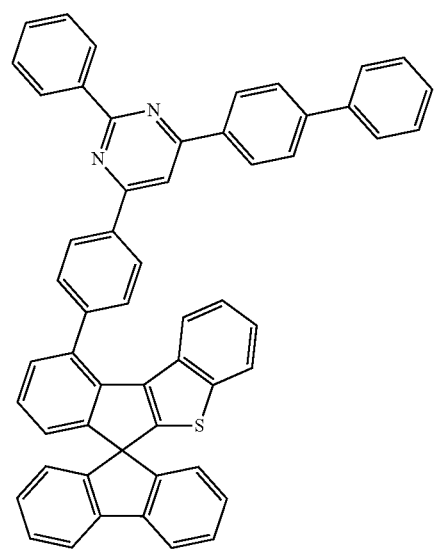
168
-continued
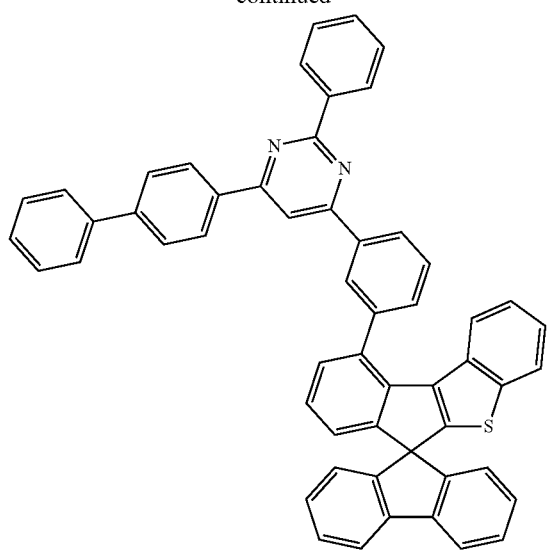
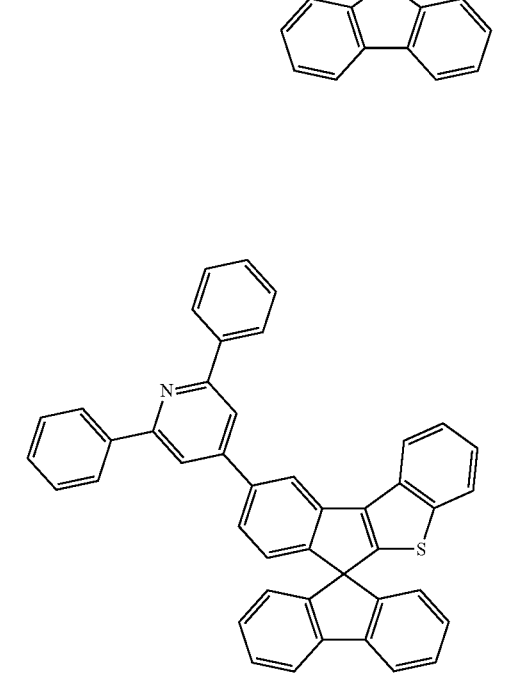
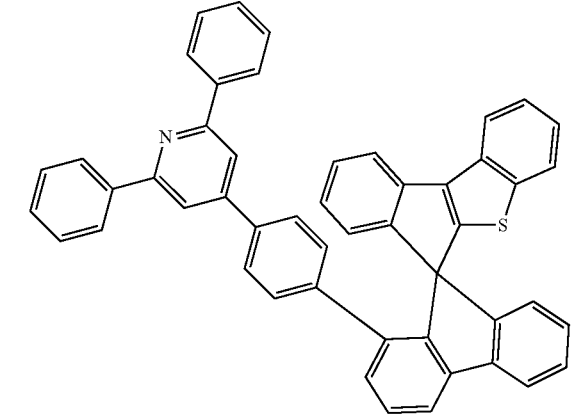

169
-continued
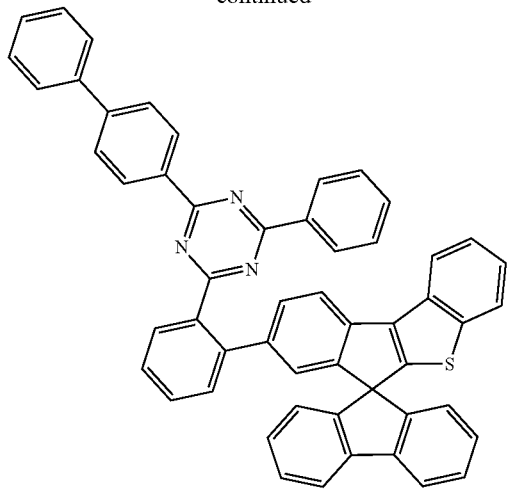
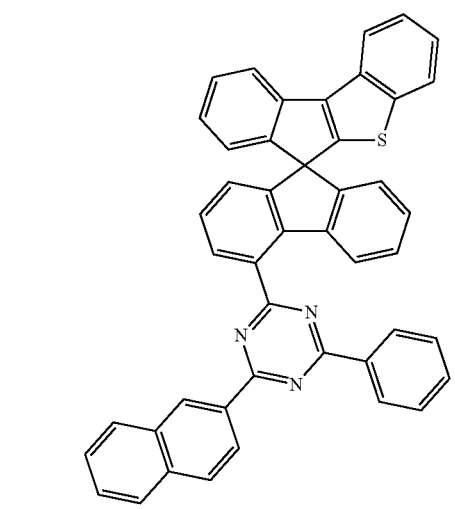
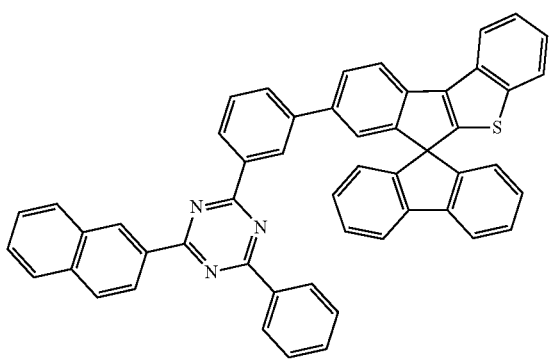
170
-continued
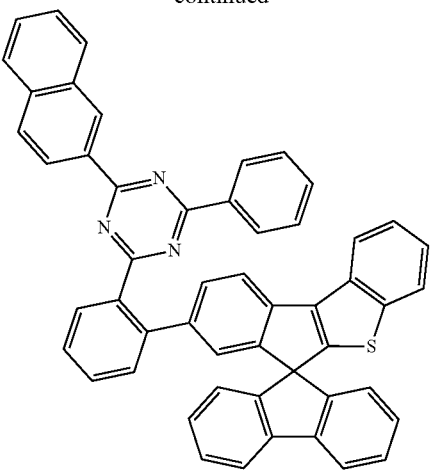
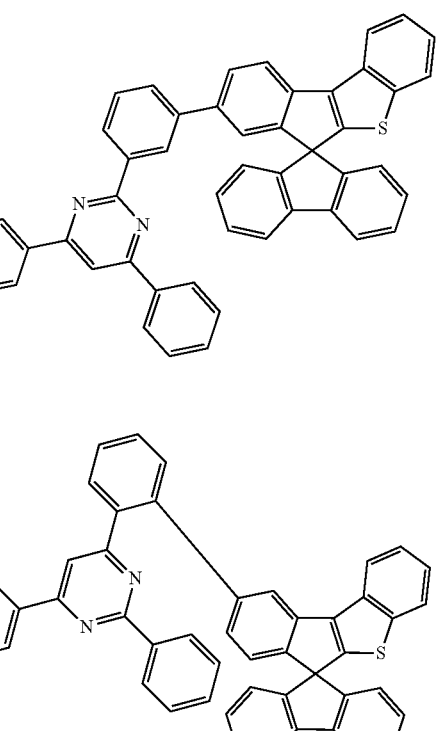
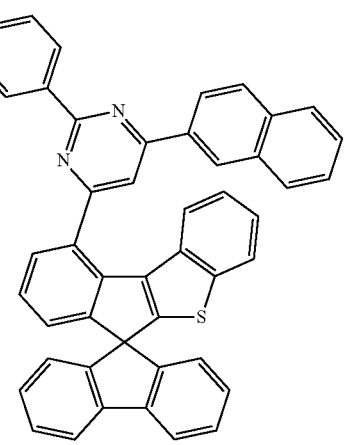

171
-continued
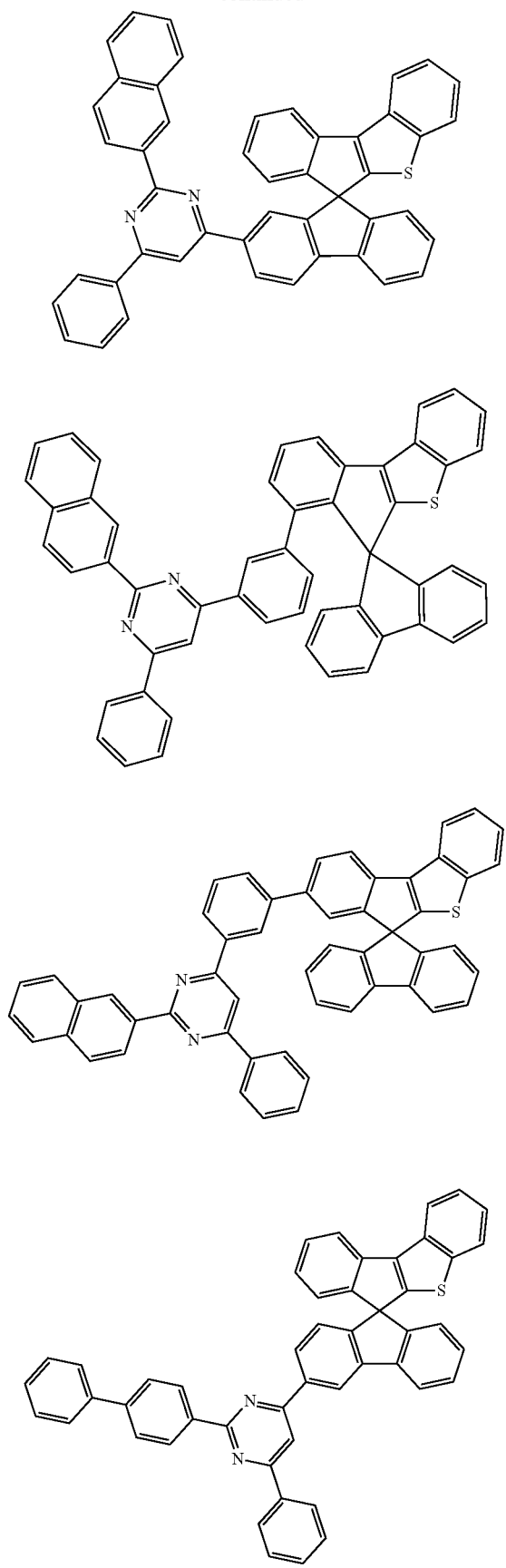
172
-continued
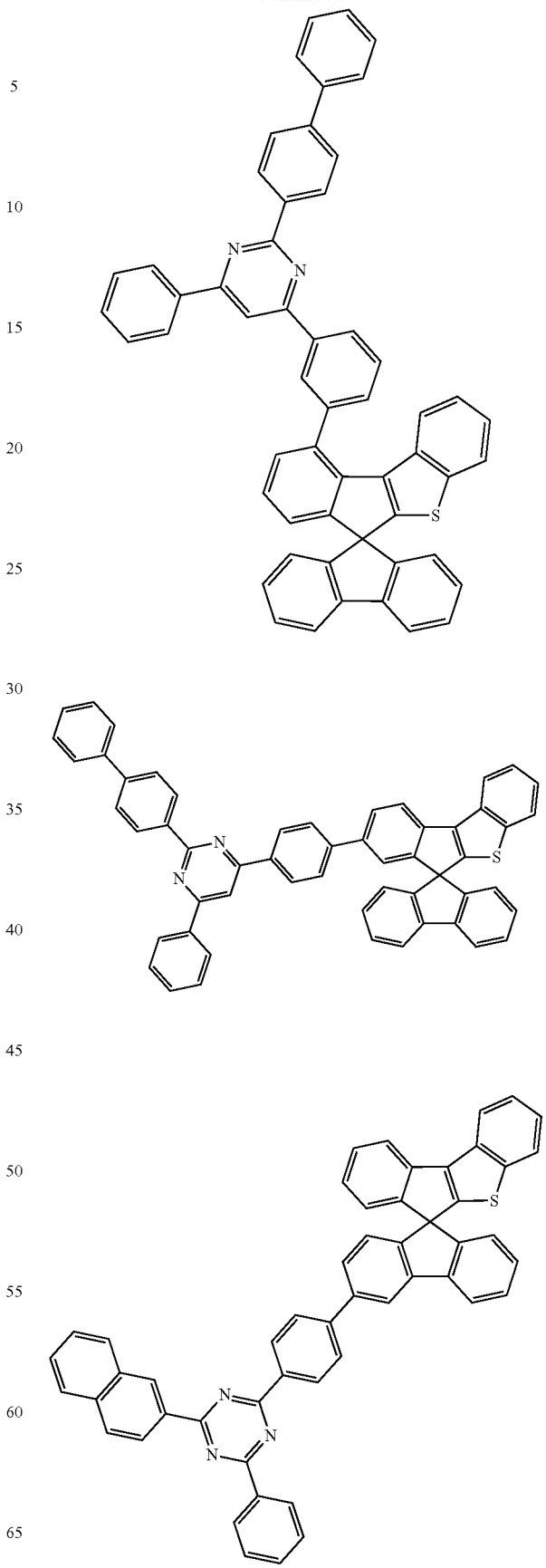

173
-continued
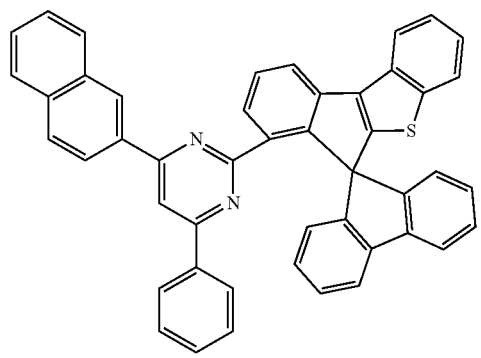
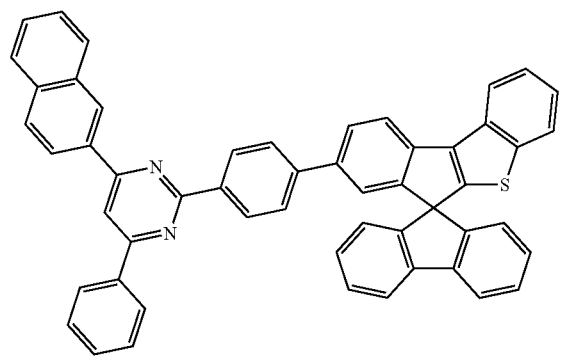
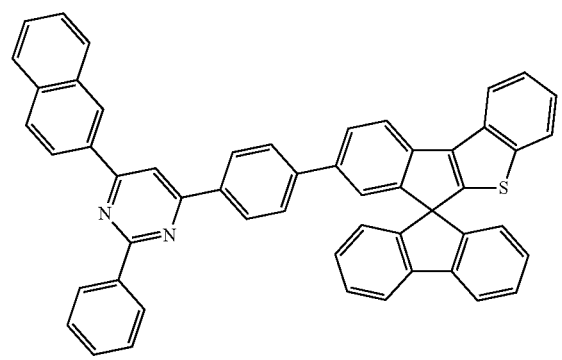
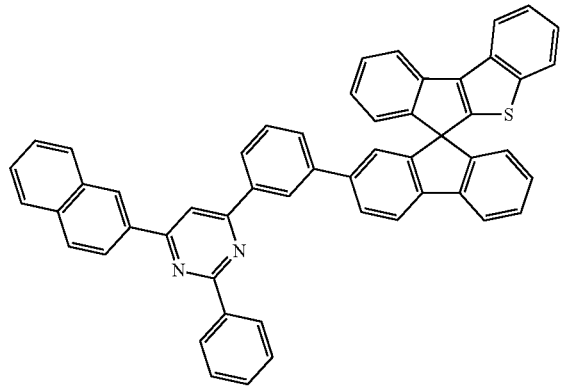
174
-continued
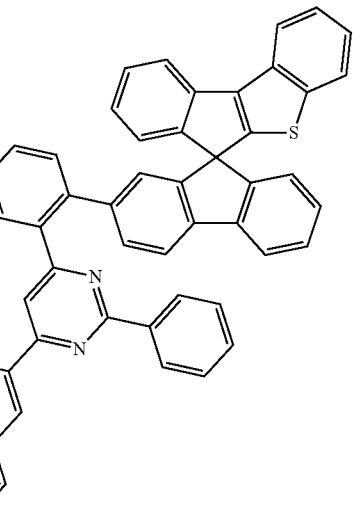
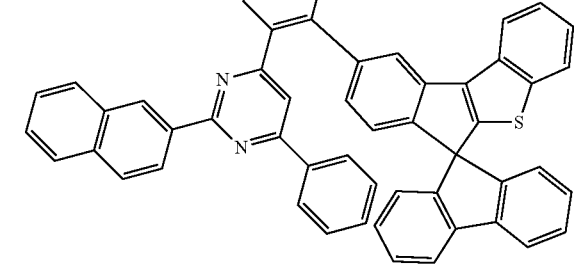
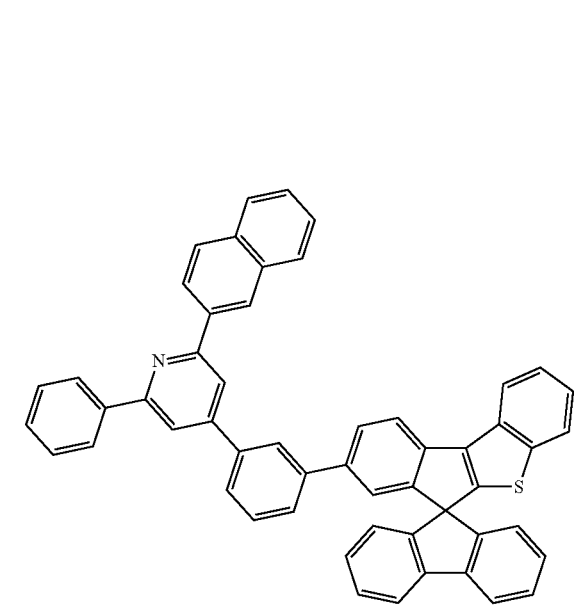

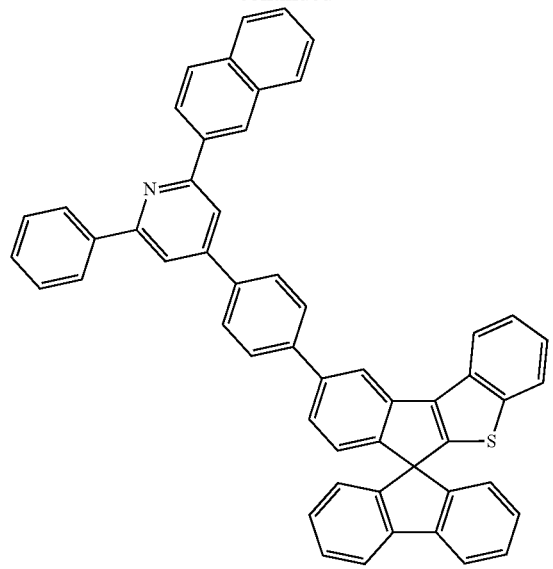
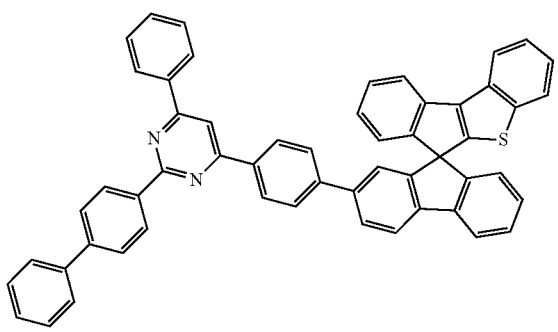 [SMILES: c1ccc(-c2ccc(-c3nc(-c4ccccc4)cc(-c4ccc(-c5ccc6c(c5)C5(c7ccccc7-6)c6ccccc6-c6c5sc5ccccc65)cc4)n3)cc2)cc1]
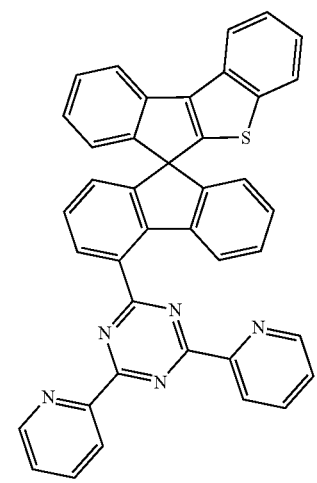
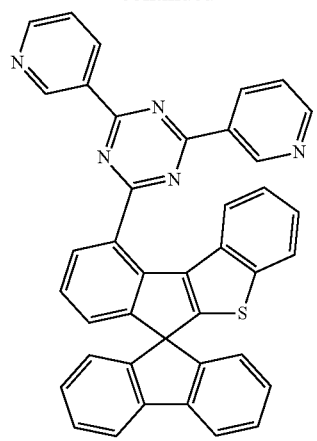
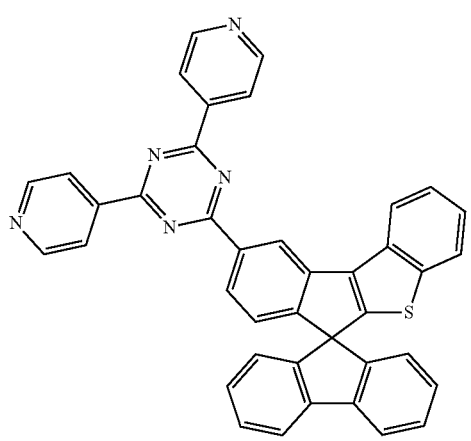
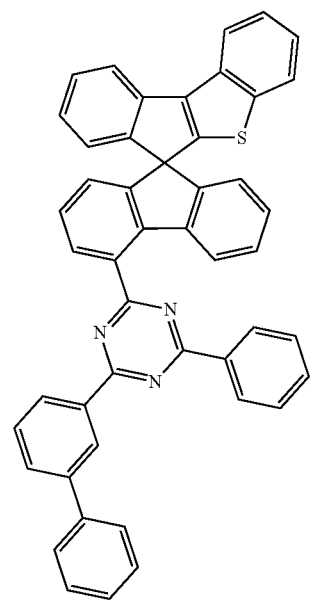

177
-continued
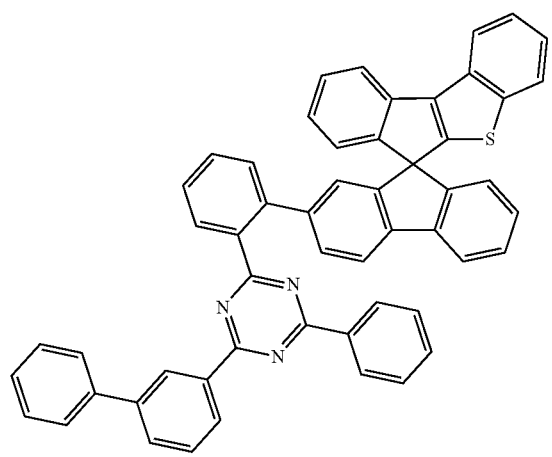
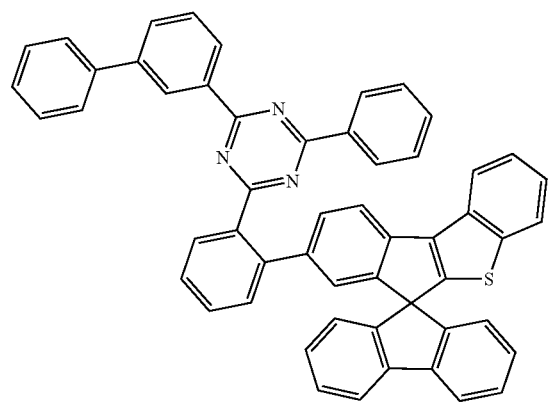
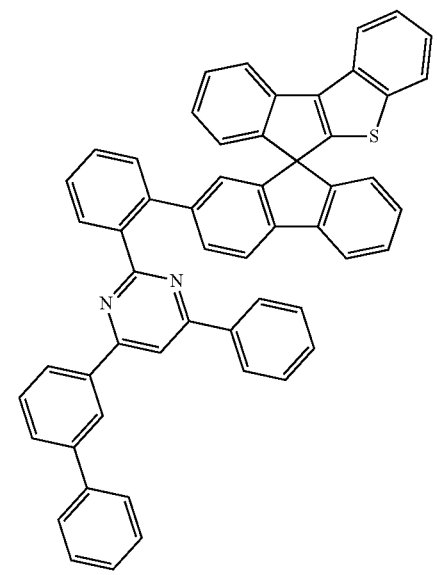
178
-continued
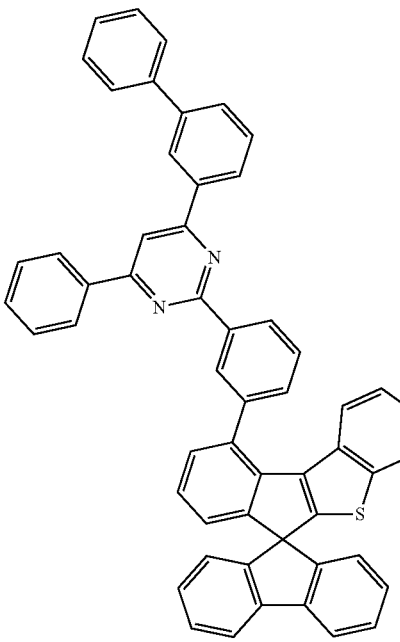
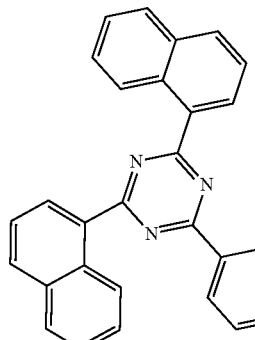
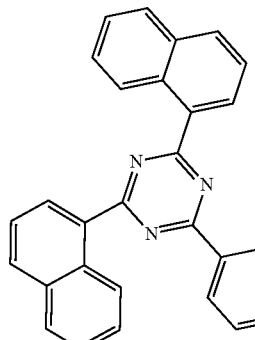
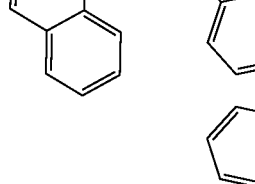

179
-continued
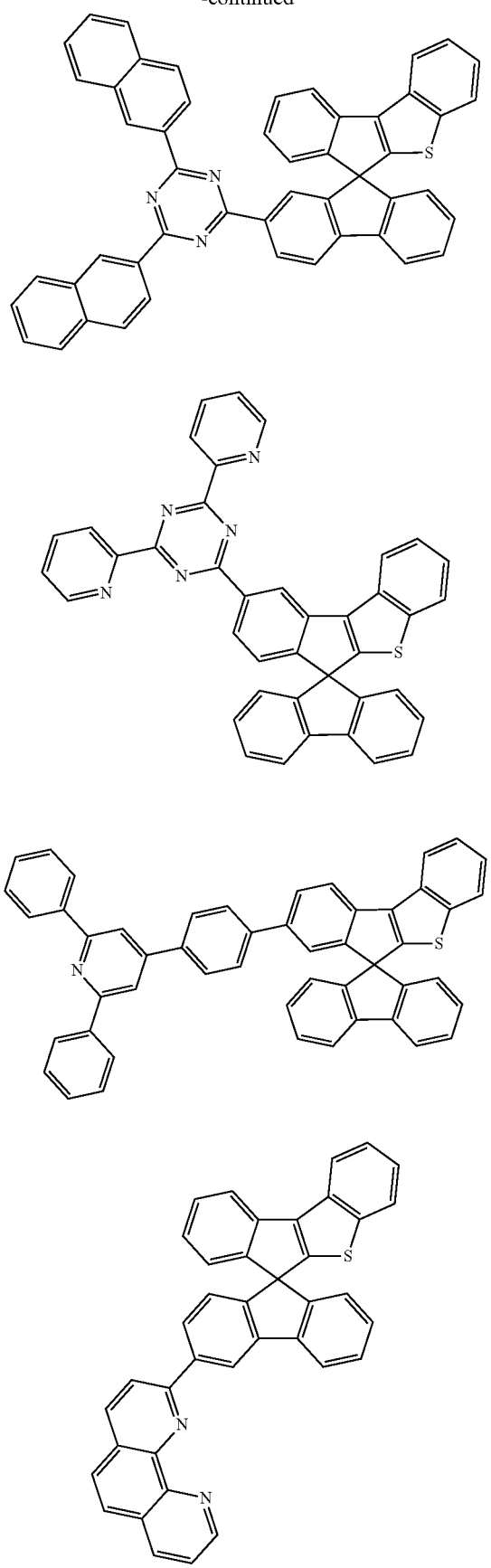
180
-continued
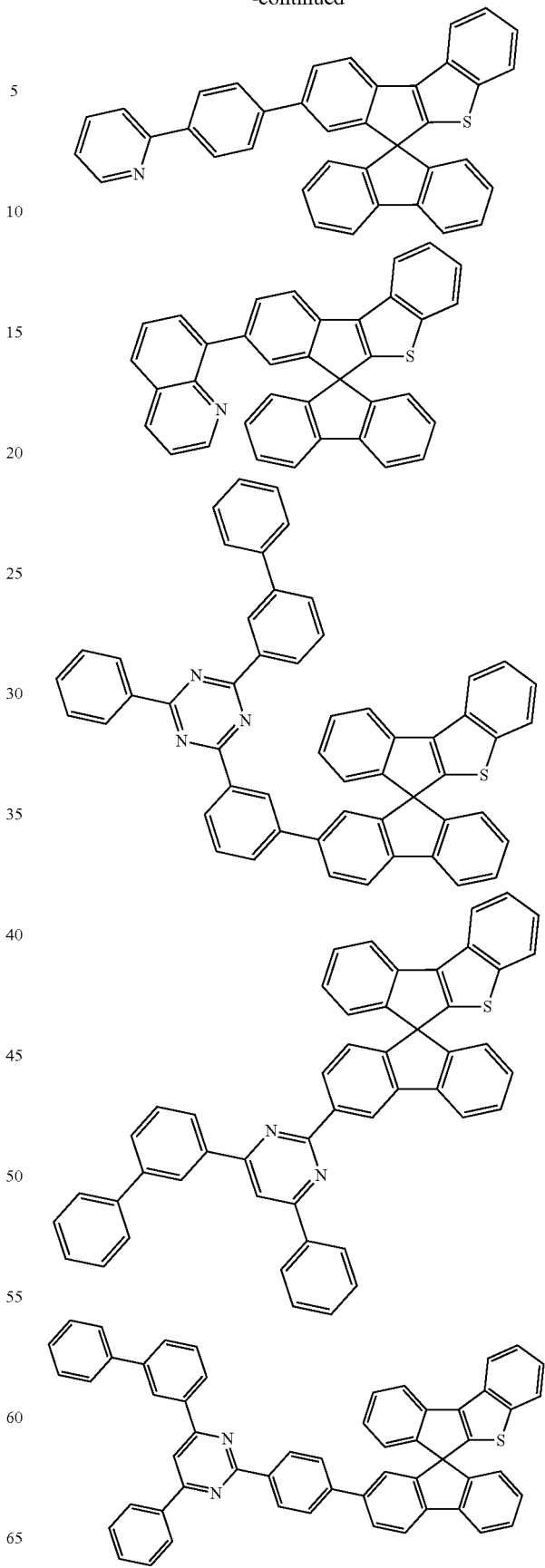

-continued
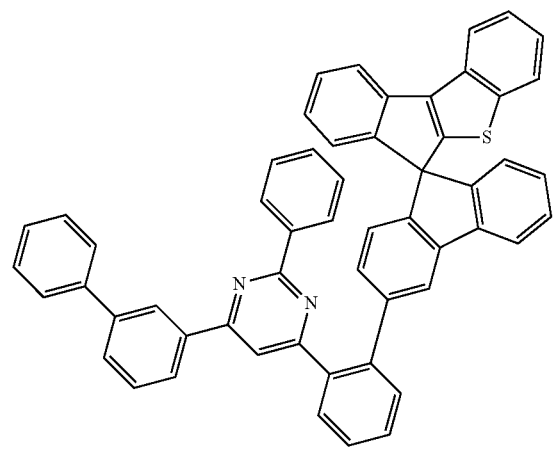
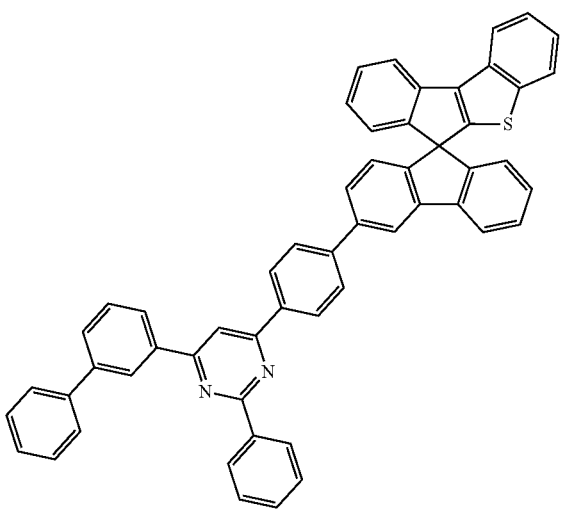
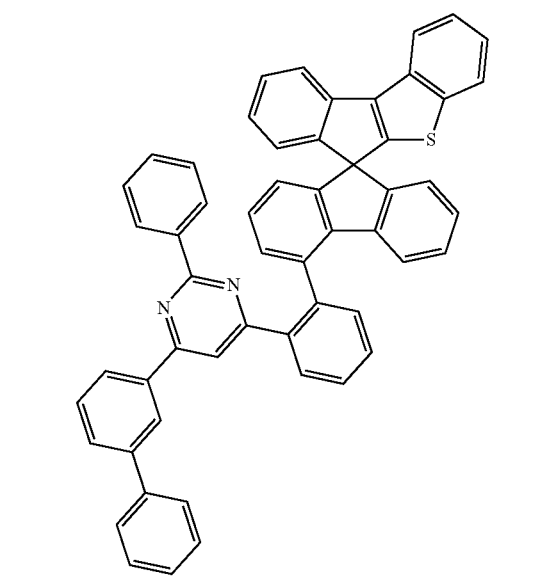
-continued
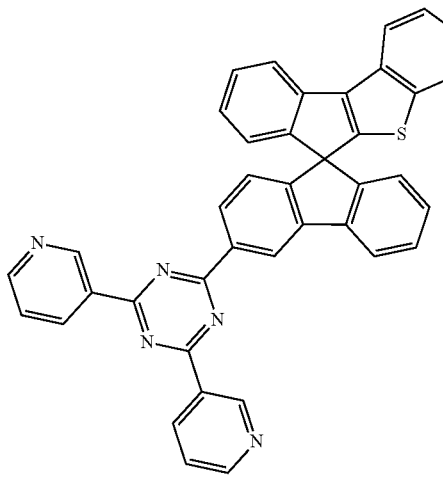
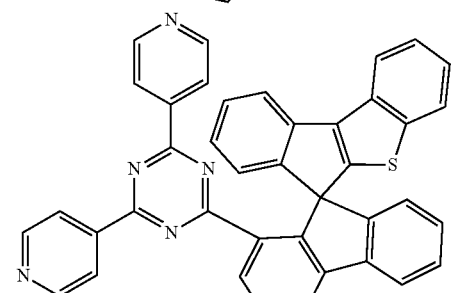
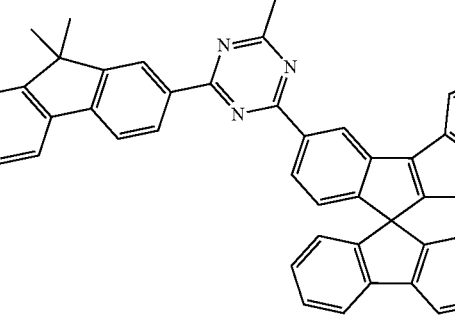
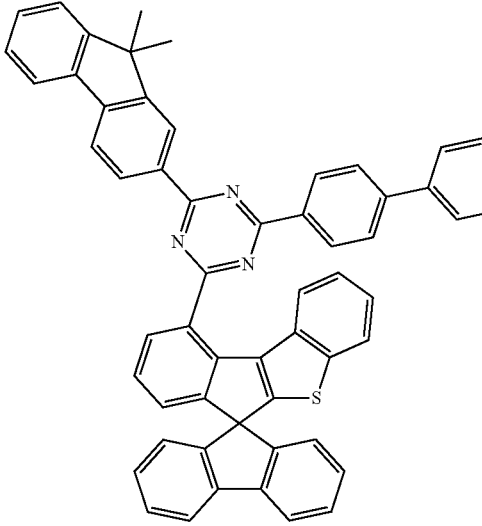

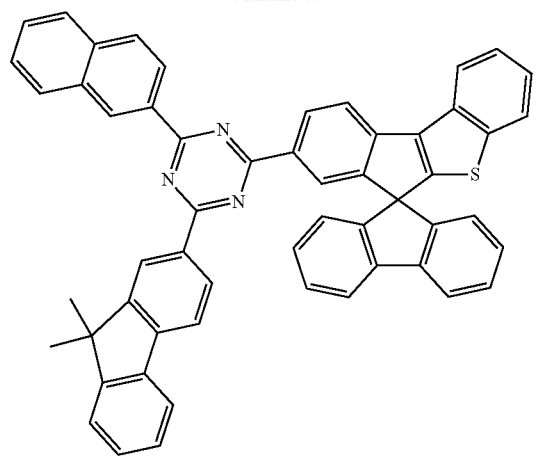
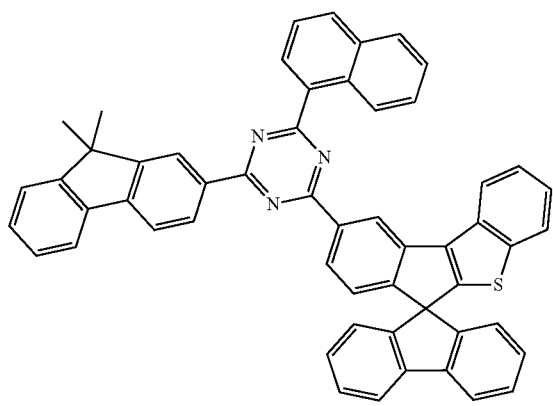
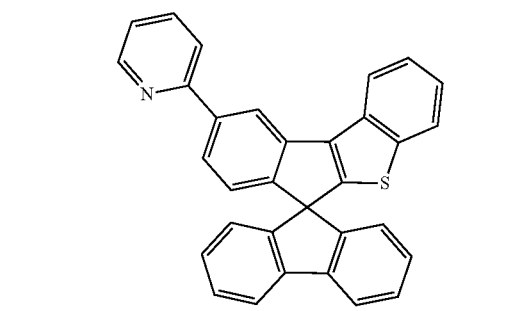
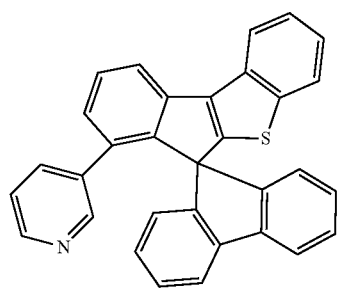
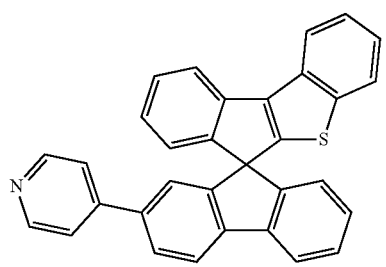
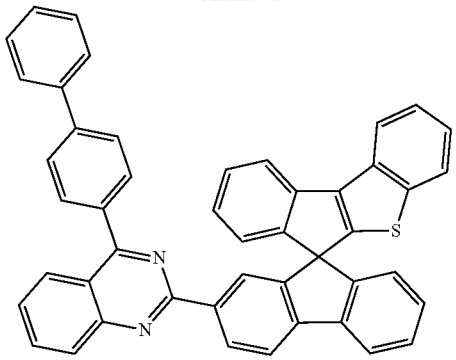
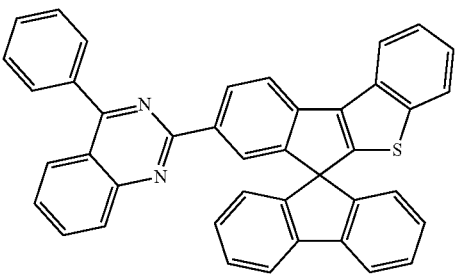
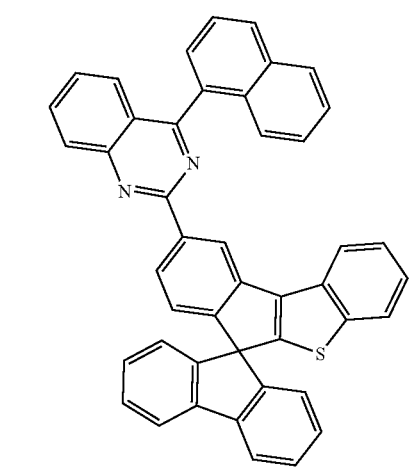
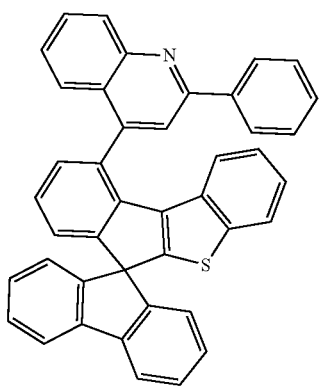

-continued
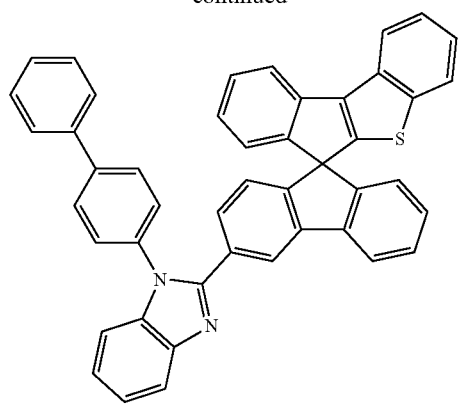
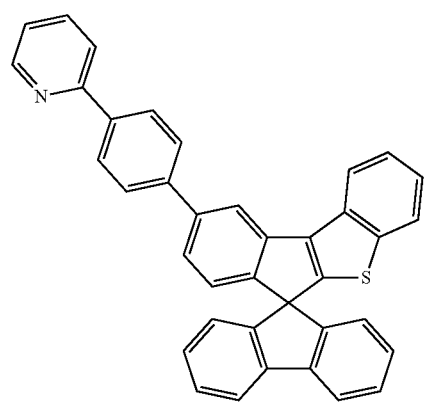
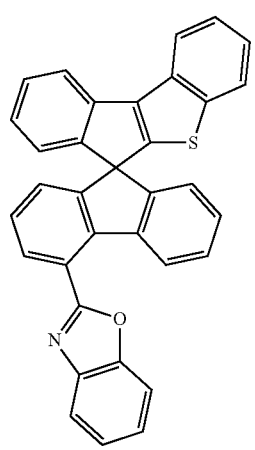
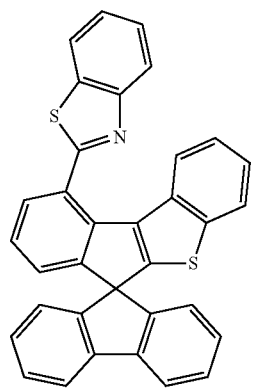
-continued
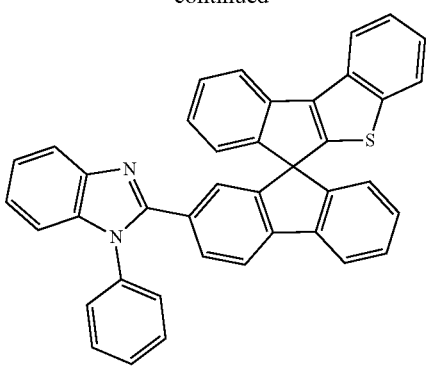
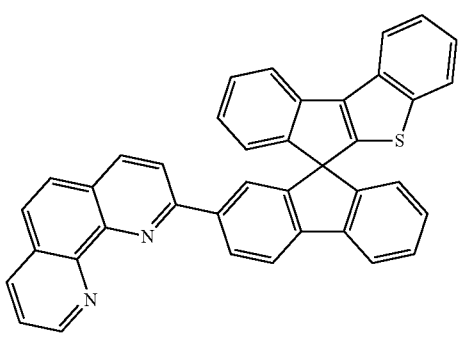
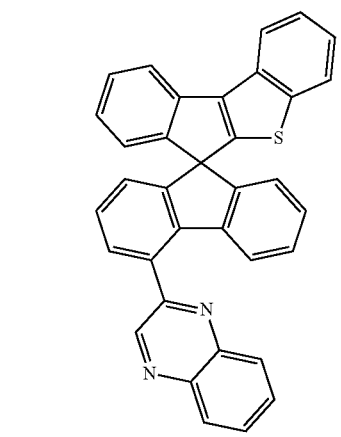
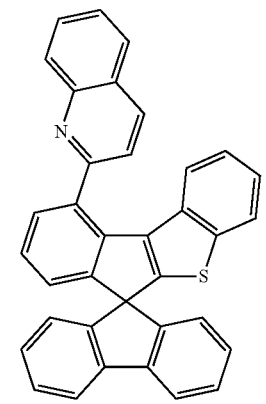

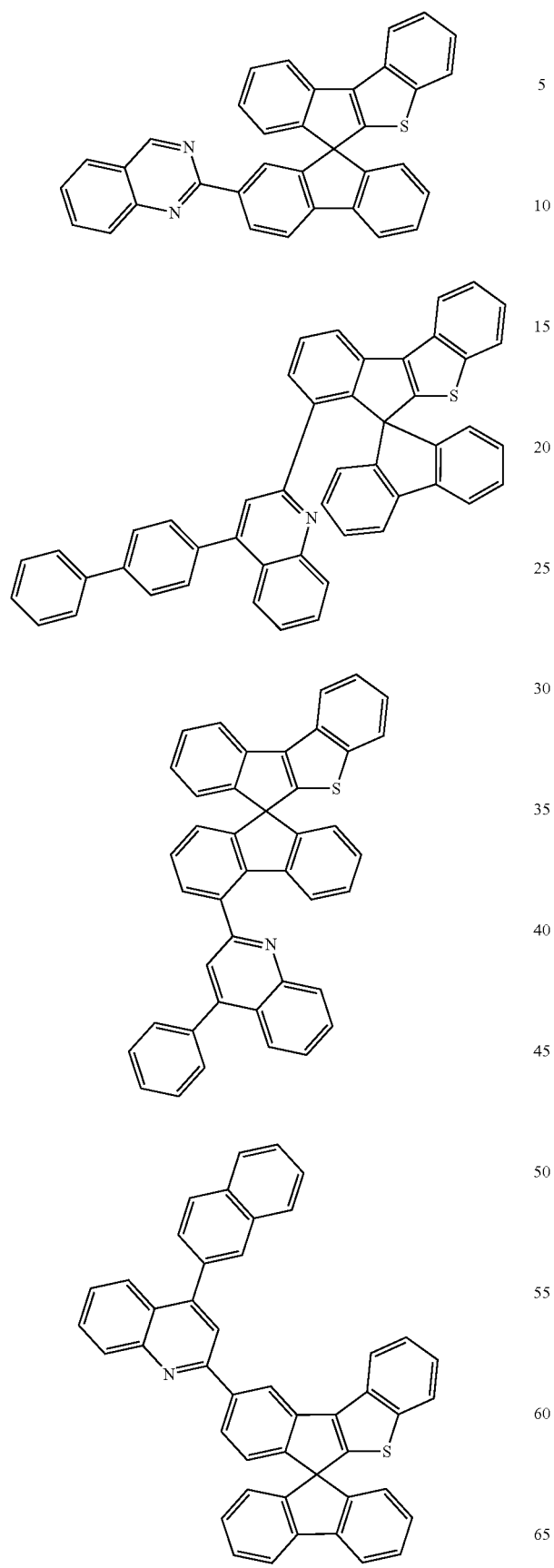
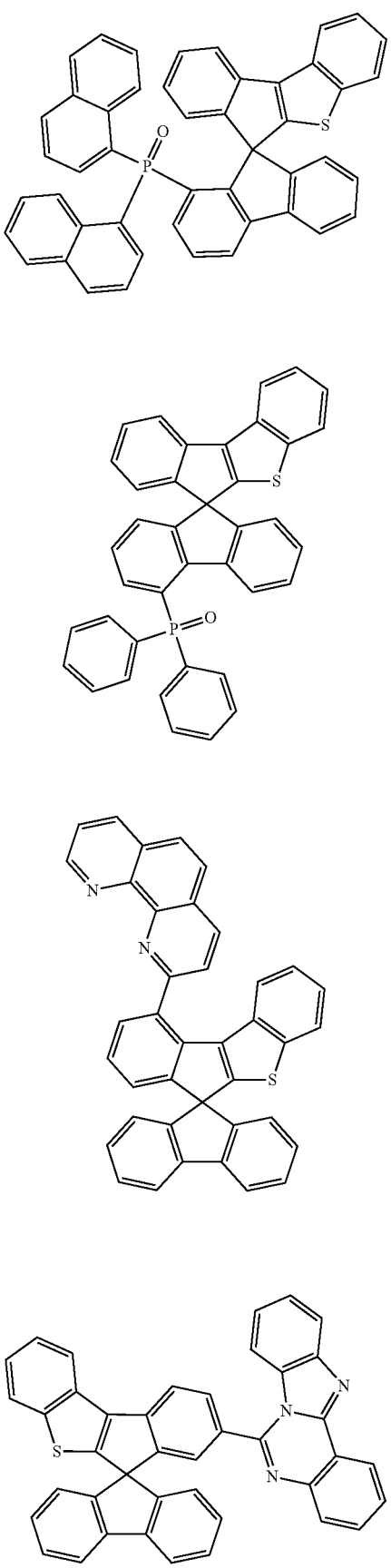

-continued

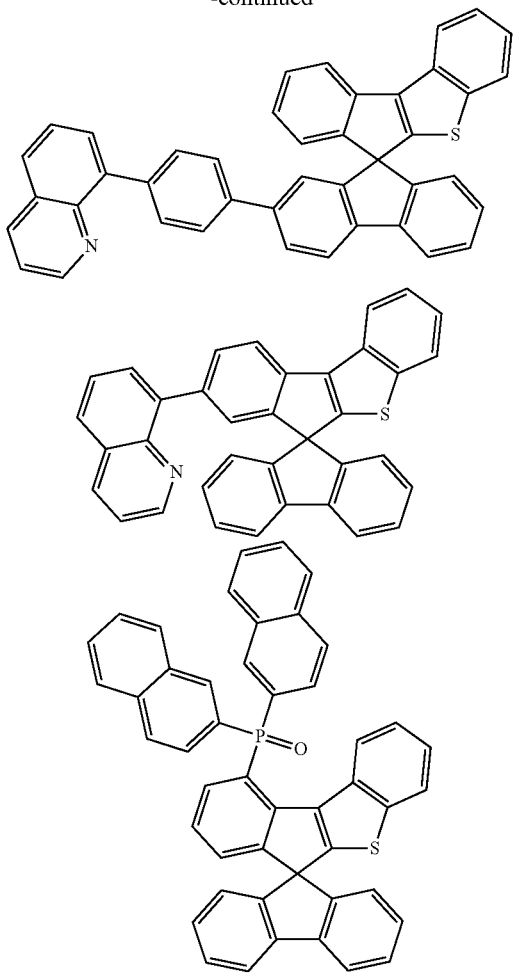

An exemplary embodiment of the present specification provides an organic light emitting device including: a first electrode; a second electrode provided to face the first electrode; and one or more organic material layers provided between the first electrode and the second electrode, in which one or more layers of the organic material layers include the above-described spiro structure compound.

According to an exemplary embodiment of the present specification, the organic material layer of the organic light emitting device of the present specification may also be composed of a single-layered structure, but may be composed of a multi-layered structure in which two or more organic material layers are stacked. For example, the organic light emitting device of the present invention may have a structure including a hole injection layer, a hole transport layer, an electron blocking layer, a light emitting layer, a hole blocking layer, an electron transport layer, an electron injection layer, and the like as organic material layers. However, the structure of the organic light emitting device is not limited thereto, and may include fewer or more organic layers.

For example, the structure of the organic light emitting device of the present specification may have a structure as illustrated in FIGS. 1 and 2, but is not limited thereto.

FIG. 1 exemplifies the structure of an organic light emitting device 10 in which a first electrode 30, a light emitting layer 40, and a second electrode 50 are sequentially stacked on a substrate 20. FIG. 1 is an exemplified structure of the organic light emitting device according to an exemplary embodiment of the present specification, and may further include other organic material layers.

FIG. 2 exemplifies the structure of an organic light emitting device in which a first electrode 30, a hole injection layer 60, a hole transport layer 70, a light emitting layer 40, an electron transport layer 80, an electron injection layer 90, and a second electrode 50 are sequentially stacked on a substrate 20. FIG. 2 is an exemplified structure according to exemplary embodiments of the present specification, and may further include other organic material layers.

According to an exemplary embodiment of the present specification, the organic material layer includes an electron injection layer, an electron transport layer, or a layer which injects and transports electrons simultaneously, and the electron injection layer, the electron transport layer, or the layer which injects and transports electrons simultaneously includes the spiro structure compound represented by Chemical Formula 1.

According to an exemplary embodiment of the present specification, the organic material layer includes a light emitting layer, and the light emitting layer includes a compound represented by the following Chemical Formula 1-A.

[Chemical Formula 1-A]

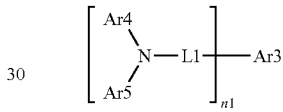

In Chemical Formula 1-A,
n1 is an integer of 1 or more,
Ar3 is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group,
L1 is a direct bond; a substituted or unsubstituted arylene group; or a substituted or unsubstituted heteroarylene group,
Ar4 and Ar5 are the same as or different from each other, and are each independently a substituted or unsubstituted aryl group; a substituted or unsubstituted silyl group; a substituted or unsubstituted alkyl group; a substituted or unsubstituted arylalkyl group; or a substituted or unsubstituted heteroaryl group, or may combine with each other to form a substituted or unsubstituted ring, and
when n1 is 2 or more, two or more structures in the parenthesis are the same as or different from each other.

According to an exemplary embodiment of the present specification, the organic material layer includes a light emitting layer, and the light emitting layer includes the compound represented by Chemical Formula 1-A as a dopant of the light emitting layer.

According to an exemplary embodiment of the present specification, L1 is a direct bond.

According to an exemplary embodiment of the present specification, n1 is 2.

In an exemplary embodiment of the present specification, Ar3 is a divalent pyrene group which is unsubstituted or substituted with deuterium, a methyl group, an ethyl group, an isopropyl group, or a tert-butyl group; or a divalent chrysene group which is unsubstituted or substituted with deuterium, a methyl group, an ethyl group, or a tert-butyl group.

According to an exemplary embodiment of the present specification, Ar4 and Ar5 are the same as or different from each other, and are each independently a substituted or unsubstituted aryl group having 6 to 30 carbon atoms.

According to an exemplary embodiment of the present specification, Ar4 and Ar5 are the same as or different from each other, and are each independently an aryl group which is unsubstituted or substituted with a silyl group which is substituted with a methyl group, an ethyl group, an isopropyl group, a tert-butyl group, a nitrile group, or an alkyl group.

According to an exemplary embodiment of the present specification, Ar4 and Ar5 are the same as or different from each other, and are each independently an aryl group which is unsubstituted or substituted with silyl group which is substituted with an alkyl group.

According to an exemplary embodiment of the present specification, Ar4 and Ar5 are the same as or different from each other, and are each independently an aryl group which is unsubstituted or substituted with a trimethylsilyl group.

According to an exemplary embodiment of the present specification, Ar4 and Ar5 are the same as or different from each other, and are each independently a substituted or unsubstituted phenyl group; a substituted or unsubstituted biphenyl group; or a substituted or unsubstituted terphenyl group.

According to an exemplary embodiment of the present specification, Ar4 and Ar5 are the same as or different from each other, and are each independently a phenyl group which is unsubstituted or substituted with a methyl group, an ethyl group, an isopropyl group, a tert-butyl group, a nitrile group, or a trimethylsilyl group.

According to an exemplary embodiment of the present specification, Ar4 and Ar5 are the same as or different from each other, and are each independently a biphenyl group which is unsubstituted or substituted with a methyl group, an ethyl group, a tert-butyl group, a nitrile group, or a trimethylsilyl group.

According to an exemplary embodiment of the present specification, Ar4 and Ar5 are the same as or different from each other, and are each independently a terphenyl group which is unsubstituted or substituted with a methyl group, an ethyl group, a tert-butyl group, a nitrile group, or a trimethylsilyl group.

According to an exemplary embodiment of the present specification, Ar4 and Ar5 are the same as or different from each other, and are each independently a substituted or unsubstituted heteroaryl group having 6 to 30 carbon atoms.

According to an exemplary embodiment of the present specification, Ar4 and Ar5 are the same as or different from each other, and are each independently a heteroaryl group which is unsubstituted or substituted with a methyl group, an ethyl group, a tert-butyl group, a nitrile group, a silyl group substituted with an alkyl group, or a phenyl group.

According to an exemplary embodiment of the present specification, Ar4 and Ar5 are the same as or different from each other, and are each independently a dibenzofuran group which is unsubstituted or substituted with a methyl group, an ethyl group, a tert-butyl group, a nitrile group, a trimethylsilyl group, or a phenyl group.

According to an exemplary embodiment of the present specification, Chemical Formula 1-A is selected from the following compounds.

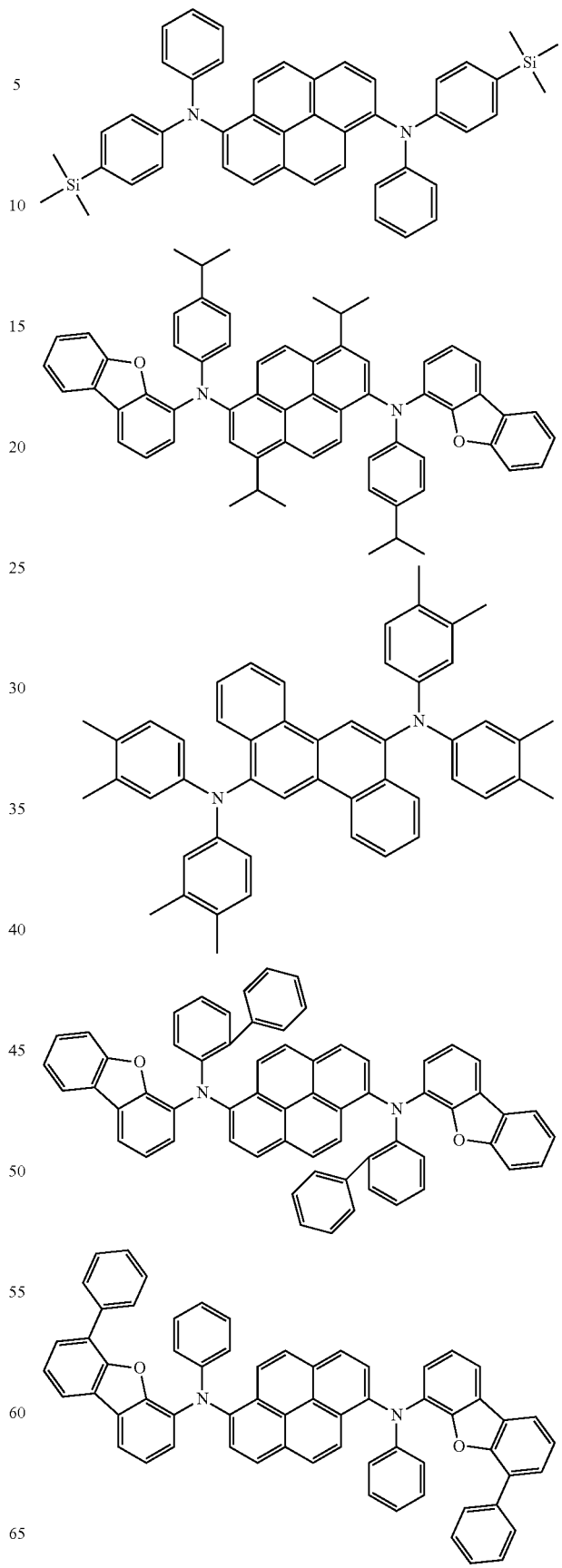

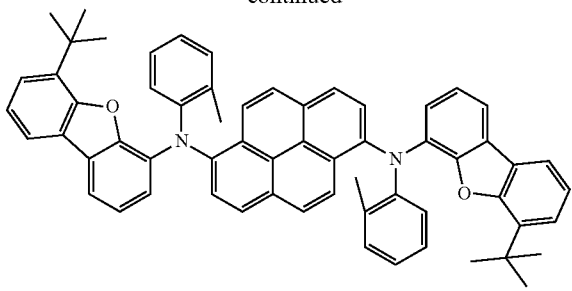

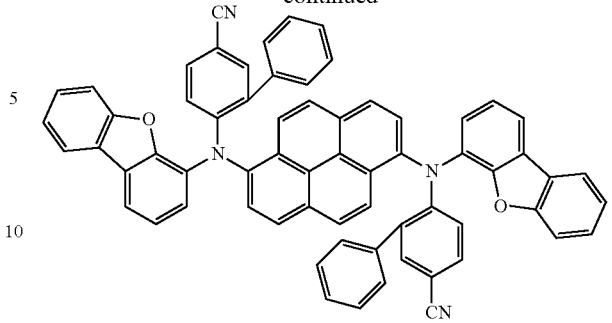

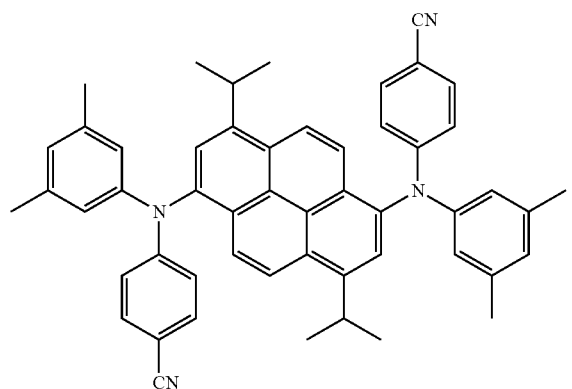

According to an exemplary embodiment of the present specification, the organic material layer includes a light emitting layer, and the light emitting layer includes a compound represented by the following Chemical Formula 2-A.

[Chemical Formula 2-A]

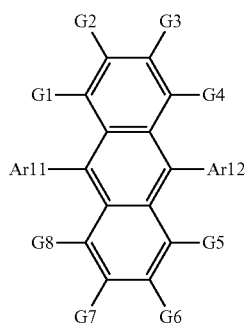

In Chemical Formula 2-A,

Ar11 and Ar12 are the same as or different from each other, and are each independently a substituted or unsubstituted monocyclic aryl group; or a substituted or unsubstituted polycyclic aryl group, and G1 to G8 are the same as or different from each other, and are each independently hydrogen; a substituted or unsubstituted monocyclic aryl group; or a substituted or unsubstituted polycyclic aryl group.

According to an exemplary embodiment of the present specification, the organic material layer includes a light emitting layer, and the light emitting layer includes the compound represented by Chemical Formula 2-A as a host of the light emitting layer.

According to an exemplary embodiment of the present specification, Ar11 and Ar12 are the same as or different from each other, and are each independently a substituted or unsubstituted polycyclic aryl group.

According to an exemplary embodiment of the present specification, Ar11 and Ar12 are the same as or different from each other, and are each independently a substituted or unsubstituted polycyclic aryl group having 10 to 30 carbon atoms.

According to an exemplary embodiment of the present specification, Ar11 and Ar12 are the same as or different from each other, and are each independently a substituted or unsubstituted naphthyl group.

According to an exemplary embodiment of the present specification, Ar11 and Ar12 are the same as or different from each other, and are each independently a substituted or unsubstituted 1-naphthyl group.

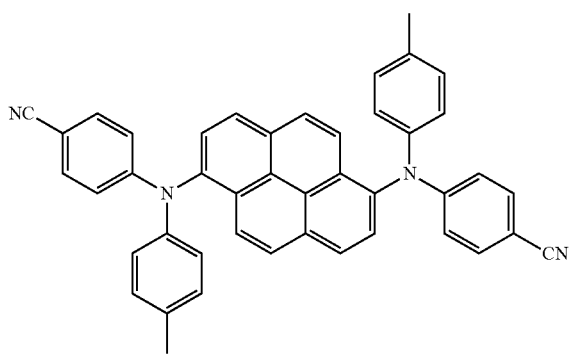

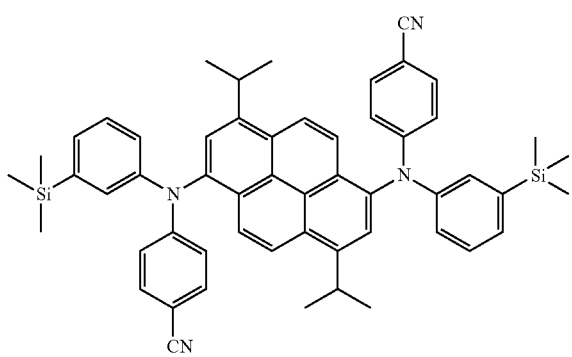

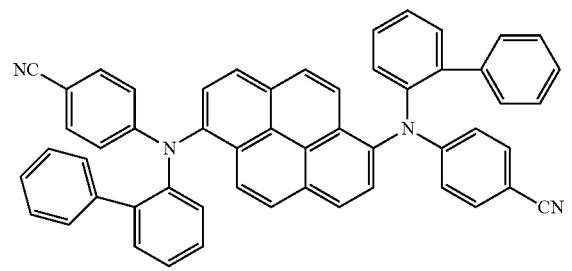

According to an exemplary embodiment of the present specification, Ar11 and Ar12 are a 1-naphthyl group. According to an exemplary embodiment of the present specification, G1 to G8 are hydrogen.

According to an exemplary embodiment of the present specification, Chemical Formula 2-A is selected from the following compound.

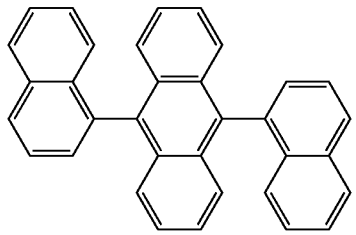 [SMILES: c1ccc2c(-c3c4ccccc4c(-c4cccc5ccccc45)c4ccccc34)cccc2c1]

According to an exemplary embodiment of the present specification, the organic material layer includes a light emitting layer, and the light emitting layer includes the compound represented by Chemical Formula 1-A as a dopant of the light emitting layer, and includes the compound represented by Chemical Formula 2-A as a host of the light emitting layer.

According to an exemplary embodiment of the present specification, the organic material layer may further include one or more layers selected from the group consisting of a hole injection layer, a hole transport layer, a light emitting layer, an electron transport layer, and an electron injection layer.

The organic light emitting device of the present specification may be manufactured by the materials and methods known in the art, except that one or more layers of the organic material layers include the spiro structure compound of the present specification, that is, the spiro structure compound represented by Chemical Formula 1.

When the organic light emitting device includes a plurality of organic material layers, the organic material layers may be formed of the same material or different materials.

For example, the organic light emitting device of the present specification may be manufactured by sequentially stacking a first electrode, an organic material layer, and a second electrode on a substrate. In this case, the organic light emitting device may be manufactured by depositing a metal or a metal oxide having conductivity, or an alloy thereof on a substrate to form a first electrode, forming an organic material layer including a hole injection layer, a hole transport layer, a light emitting layer, and an electron transport layer thereon, and then depositing a material, which may be used as a second electrode, thereon, by using a physical vapor deposition (PVD) method such as sputtering or e-beam evaporation. In addition to the method described above, an organic light emitting device may be made by sequentially depositing a second electrode material, an organic material layer, and a first electrode material on a substrate. Further, the spiro structure compound represented by Chemical Formula 1 may be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

According to an exemplary embodiment of the present specification, the first electrode is a positive electrode, and the second electrode is a negative electrode.

According to another exemplary embodiment of the present specification, the first electrode is a negative electrode, and the second electrode is a positive electrode.

As the positive electrode material, a material having a large work function is usually preferred so as to smoothly inject holes into an organic material layer. Specific examples of the positive electrode material which may be used in the present invention include: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as ZnO:Al or $SnO_2$:Sb; an electrically conductive polymer, such as poly(3-methylthiophene), poly [3,4-(ethylene-1,2-dioxy)thiophene] (PEDOT), polypyrrole, and polyaniline, and the like, but are not limited thereto.

As the negative electrode material, a material having a small work function is usually preferred so as to smoothly inject electrons into an organic material layer. Specific examples of the negative electrode material include: a metal, such as magnesium, calcium, sodium, potassium, titanium, indium, yttrium, lithium, gadolinium, aluminum, silver, tin, and lead, or alloys thereof; a multi-layered structural material, such as LiF/Al or $LiO_2$/Al and Mg/Ag, and the like, but are not limited thereto.

The hole injection layer is a layer which injects holes from an electrode, and a hole injection material is preferably a compound which has a capability of transporting holes and thus has an effect of injecting holes at a positive electrode and an excellent effect of injecting holes for a light emitting layer or a light emitting material, prevents excitons produced from the light emitting layer from moving to an electron injection layer or an electron injection material, and is also excellent in the ability to form a thin film. It is preferred that the highest occupied molecular orbital (HOMO) of the hole injection material is between the work function of the positive electrode material and the HOMO of a peripheral organic material layer. Specific examples of the hole injection material include metal porphyrin, oligothiophene, an arylamine-based organic material, a hexanitrile hexaazatriphenylene-based organic material, a quinacridone-based organic material, a perylene-based organic material, anthraquinone, a polyaniline and polythiophene-based electrically conductive polymer, and the like, but are not limited thereto.

The hole transport layer is a layer which receives holes from a hole injection layer and transports the holes to a light emitting layer, and a hole transport material is suitably a material which may receive holes from a positive electrode or a hole injection layer to transfer the holes to a light emitting layer, and has a large mobility for the holes. Specific examples thereof include an arylamine-based organic material, an electrically conductive polymer, a block copolymer in which a conjugate portion and a non-conjugate portion are present together, and the like, but are not limited thereto.

A light emitting material for the light emitting layer is a material which may receive holes and electrons from a hole transport layer and an electron transport layer, respectively, and combine the holes and the electrons to emit light in a visible ray region, and is preferably a material having good quantum efficiency to fluorescence or phosphorescence. Specific examples thereof include: an 8-hydroxy-quinoline aluminum complex ($Alq_3$); a carbazole-based compound; a dimerized styryl compound; BAlq; a 10-hydroxybenzoquinoline-metal compound; a benzoxazole, benzothiazole and benzimidazole-based compound; a poly(p-phenylenevinylene) (PPV)-based polymer; a spiro compound; polyfluorene, lubrene, and the like, but are not limited thereto.

The light emitting layer may include a host material and a dopant material. Examples of the host material include a fused aromatic ring derivative, or a hetero ring-containing compound, and the like. Specifically, examples of the fused aromatic ring derivative include an anthracene derivative, a pyrene derivative, a naphthalene derivative, a pentacene derivative, a phenanthrene compound, a fluoranthene compound, and the like, and examples of the hetero ring-containing compound include a carbazole derivative, a dibenzofuran derivative, a ladder-type furan compound, a pyrimidine derivative, and the like, but the examples thereof are not limited thereto.

Examples of the dopant material include an aromatic amine derivative, a styrylamine compound, a boron complex, a fluoranthene compound, a metal complex, and the like. Specifically, the aromatic amine derivative is a fused aromatic ring derivative having a substituted or unsubstituted arylamino group, and examples thereof include a pyrene, an anthracene, a chrysene, a periflanthene, and the like, which have an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transport layer is a layer which receives electrons from an electron injection layer and transports the electrons to a light emitting layer, and an electron transport material is suitably a material which may receive electrons well from a negative electrode and transfer the electrons to a light emitting layer and has large mobility for the electrons. Specific examples thereof include: an Al complex of 8-hydroxyquinoline; a complex including $Alq_3$; an organic radical compound; a hydroxyflavone-metal complex, and the like, but are not limited thereto. The electron transport layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a negative electrode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris (2-methyl-8-hydroxyquinolinato) aluminum, tris(8-hydroxyquinolinato) gallium, bis(10-hydroxybenzo[h] quinolinato) beryllium, bis(10-hydroxybenzo[h] quinolinato) zinc, bis(2-methyl-8-quinolinato) chlorogallium, bis(2-methyl-8-quinolinato)(o-cresolato) gallium, bis(2-methyl-8-quinolinato)(1-naphtholato) aluminum, bis(2-methyl-8-quinolinato)(2-naphtholato) gallium, and the like, but are not limited thereto.

The organic light emitting device according to the present specification may be a top emission type, a bottom emission type, or a dual emission type according to the material to be used.

According to an exemplary embodiment of the present specification, the spiro structure compound represented by Chemical Formula 1 may be included in an organic solar cell or an organic transistor in addition to the organic light emitting device.

Hereinafter, the present specification will be described in detail with reference to Examples in order to specifically explain the present specification. However, the Examples according to the present specification may be modified in various forms, and it is not interpreted that the scope of the present specification is limited to the Examples described below in detail. The Examples of the present specification are provided to more completely explain the present specification to a person with ordinary skill in the art.

PREPARATION EXAMPLES

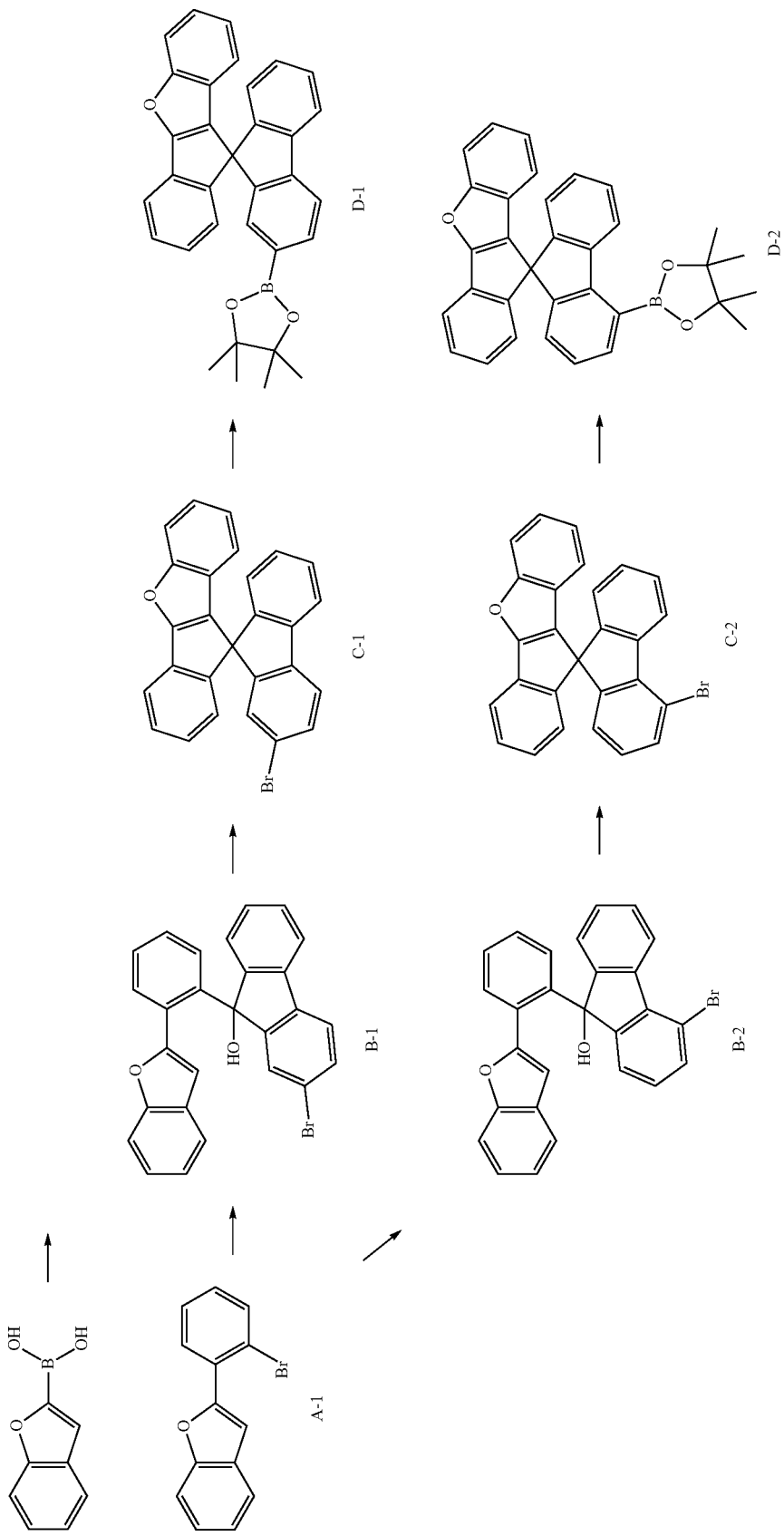

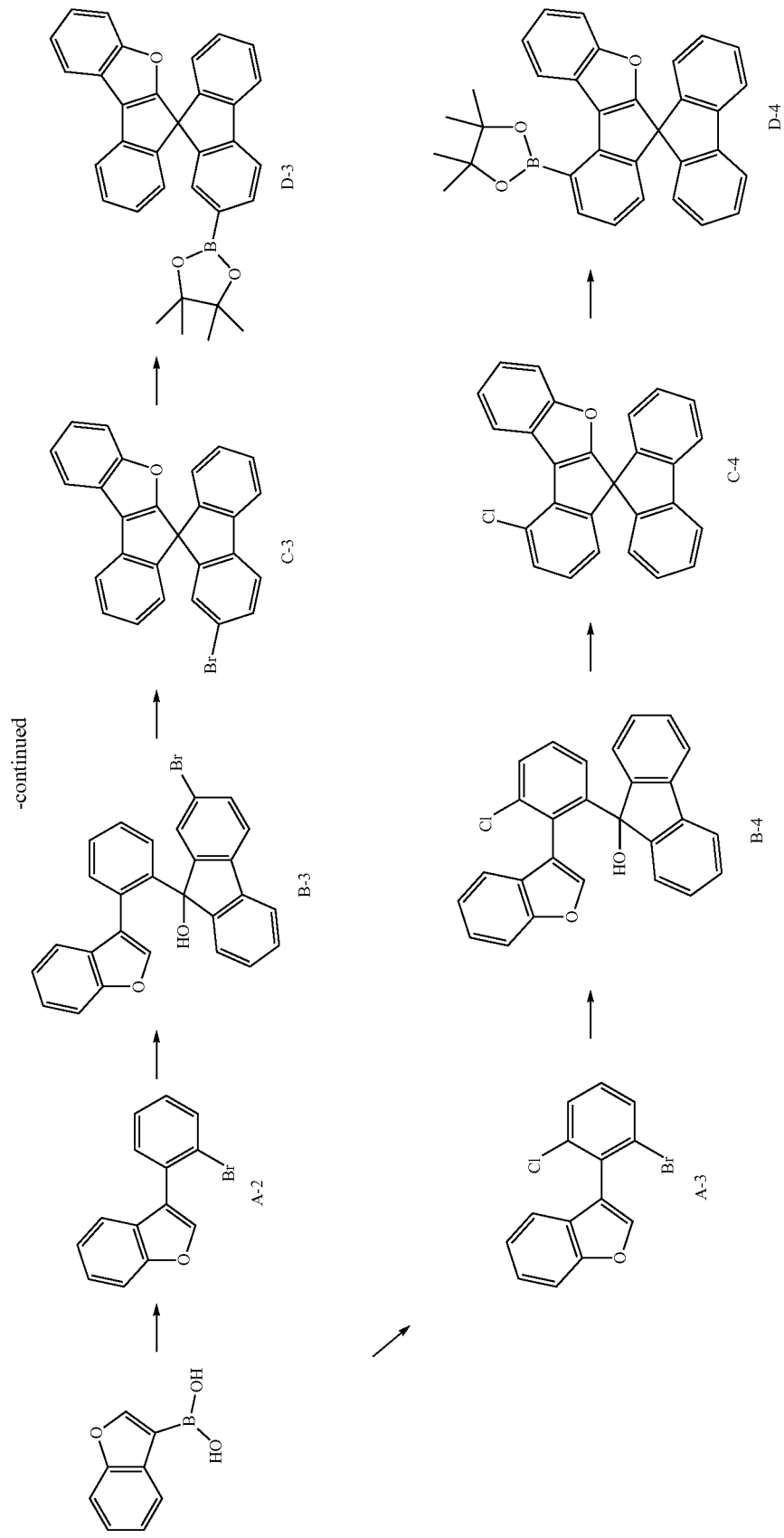

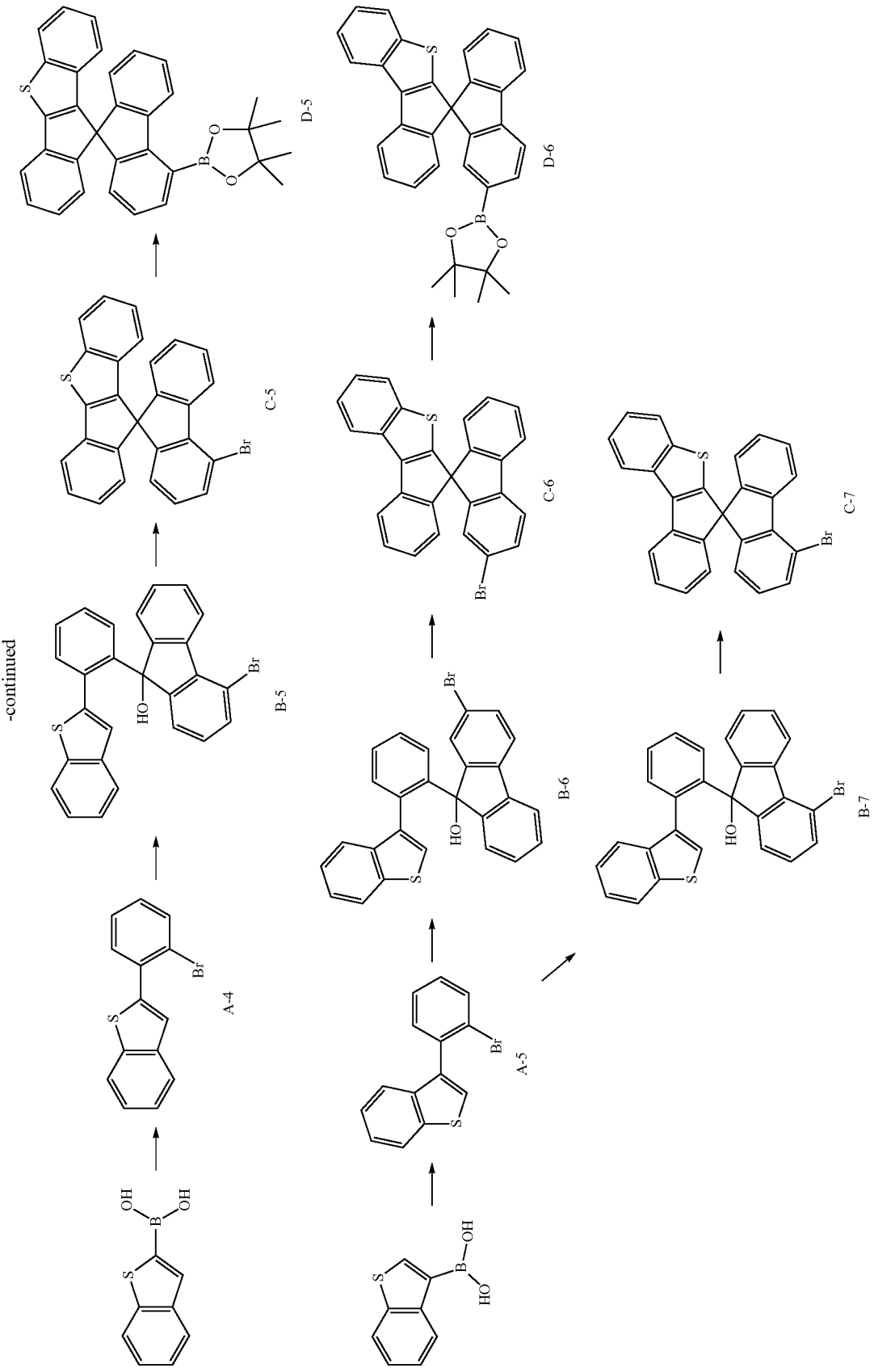

Preparation Example A-1. Preparation of Compound A-1

After benzofuran-2-boronic acid (30 g, 185 mmol) and 1-bromo-2-iodobenzene (53.2 g, 189 mmol) were added to dioxane (300 ml), a 2M aqueous potassium carbonate solution (100 ml) was added thereto, tetrakistriphenyl-phosphinopalladium (4.28 g, 2 mol %) was put thereinto, and then the resulting mixture was heated and stirred for 4 hours. The temperature was lowered to normal temperature, the reaction was terminated, and then the potassium carbonate solution was removed to separate the layers. After the solvent was removed, the residue was columned with hexane to prepare Compound A-1, which is a colorless oil (42.7 g, 85%).
MS[M+H]$^+$=272.98

Preparation Example A-2. Preparation of Compound A-2

Compound A-2 was prepared by performing the synthesis in the same manner as in Preparation Example A-1, except that benzofuran-3-boronic acid was used instead of benzofuran-2-boronic acid.
MS[M+H]$^+$=272.98

Preparation Example A-3. Preparation of Compound A-3

Compound A-3 was prepared by performing the synthesis in the same manner as in Preparation Example A-2, except that 1-bromo-3-chloro-2-iodobenzene was used instead of 1-bromo-2-iodobenzene.
MS[M+H]$^+$=306.94

Preparation Example A-4. Preparation of Compound A-4

Compound A-4 was prepared by performing the synthesis in the same manner as in Preparation Example A-1, except that benzothiophene-2-boronic acid was used instead of benzofuran-2-boronic acid.
MS[M+H]$^+$=288.96

Preparation Example A-5. Preparation of Compound A-5

Compound A-5 was prepared by performing the synthesis in the same manner as in Preparation Example A-1, except that benzothiophene-3-boronic acid was used instead of benzofuran-2-boronic acid.
MS[M+H]$^+$=288.96

Preparation Example B-1. Preparation of Compound B-1

After Compound A-1 (30 g, 110 mmol) was dissolved in THF (250 ml), the temperature was lowered to −78° C., and then 2.5 M n-BuLi (57 ml) was added dropwise thereto, and after 30 minutes, 2-bromo-9H-fluoren-9-one (28.3 g, 109 mmol) was put thereinto, the temperature was increased to RT, and then the resulting mixture was stirred for 1 hour. After 1 N HCl (ml) was put thereinto and the resulting mixture was stirred for 30 minutes, the layers were separated to remove the solvent, and then the residue was recrystallized with hexane to prepare Compound B-1 (47.2 g, 95%).
MS[M+H]$^+$=453.04

Preparation Example B-2. Preparation of Compound B-2

Compound B-2 was prepared by performing the synthesis in the same manner as in Preparation Example B-1, except that 4-bromo-9H-fluoren-9-one was used instead of 2-bromo-9H-fluoren-9-one.
MS[M+H]$^+$=453.04

Preparation Example B-3. Preparation of Compound B-3

Compound B-3 was prepared by performing the synthesis in the same manner as in Preparation Example B-1, except that Compound A-2 was used instead of Compound A-1.
MS[M+H]$^+$=453.04

Preparation Example B-4. Preparation of Compound B-4

Compound B-4 was prepared by performing the synthesis in the same manner as in the synthesis of Preparation Example B-3, except that Compound A-3 was used instead of Compound A-2, and 4-bromo-9H-fluoren-9-one was used instead of 2-bromo-9H-fluoren-9-one.
MS[M+H]$^+$=453.04

Preparation Example B-5. Preparation of Compound B-5

Compound B-5 was prepared by performing the synthesis in the same manner as in Preparation Example B-1, except that Compound A-4 was used instead of Compound A-1, and 4-bromo-9H-fluoren-9-one was used instead of 2-bromo-9H-fluoren-9-one.
MS[M+H]+=469.02

Preparation Example B-6. Preparation of Compound B-6

Compound B-6 was prepared by performing the synthesis in the same manner as in Preparation Example B-1, except that Compound A-5 was used instead of Compound A-1.
MS[M+H]$^+$=469.02

Preparation Example B-7. Preparation of Compound B-7

Compound B-7 was prepared by performing the synthesis in the same manner as in Preparation Example B-6, except that 4-bromo-9H-fluoren-9-one was used instead of 2-bromo-9H-fluoren-9-one.
MS[M+H]$^+$=469.02

Preparation Example C-1. Preparation of Compound C-1

After Compound B-1 (30 g, 66.4 mmol) was put into acetic acid (250 ml), 10 ml of trifluoroacetic acid was added dropwise thereto, and the resulting mixture was stirred and refluxed. The temperature was lowered to normal temperature, the resulting product was neutralized with water, and then the filtered solid was recrystallized with ethyl acetate to prepare Compound C-1 (20 g, 70%).
MS[M+H]$^+$=435.03

Preparation Example C-2. Preparation of Compound C-2

Compound C-2 was prepared by performing the synthesis in the same manner as in Preparation Example C-1, except that Compound B-2 was used instead of Compound B-1.
MS[M+H]$^+$=435.03

Preparation Example C-3. Preparation of Compound C-3

Compound C-3 was prepared by performing the synthesis in the same manner as in Preparation Example C-1, except that Compound B-3 was used instead of Compound B-1.
MS[M+H]$^+$=435.03

Preparation Example C-4. Preparation of Compound C-4

Compound C-4 was prepared by performing the synthesis in the same manner as in Preparation Example C-1, except that Compound B-4 was used instead of Compound B-1.
MS[M+H]$^+$=391.08

Preparation Example C-5. Preparation of Compound C-5

Compound C-5 was prepared by performing the synthesis in the same manner as in Preparation Example C-1, except that Compound B-5 was used instead of Compound B-1.
MS[M+H]$^+$=451.01

Preparation Example C-6. Preparation of Compound C-6

Compound C-6 was prepared by performing the synthesis in the same manner as in Preparation Example C-1, except that Compound B-6 was used instead of Compound B-1.
MS[M+H]$^+$=451.01

Preparation Example C-7. Preparation of Compound C-7

Compound C-7 was prepared by performing the synthesis in the same manner as in Preparation Example C-1, except that Compound B-7 was used instead of Compound B-1.
MS[M+H]$^+$=451.01

Preparation Example D-1. Preparation of Compound D-1

Compound C-1 (20 g, 46.1 mmol), bis(pinacolato)diboron (11.7 g, 46.1 mmol), and potassium acetate (19.1 g, 138 mmol) were mixed under a nitrogen atmosphere, and the resulting mixture was added to 200 ml of dioxane, and heated while being stirred.
Bis(dibenzylidineacetone)palladium (15 mg, 0.92 mmol) and tricyclohexylphosphine (10 mg, 1.84 mmol) were put into the mixture under reflux, and the resulting mixture was heated and stirred for 10 hours. After the reaction was terminated, the temperature of the mixture was lowered to normal temperature, and then the mixture was filtered. Water was poured into the filtrate, extraction was performed with chloroform, and the organic layer was dried over anhydrous magnesium sulfate. After distillation under reduced pressure, recrystallization was performed with ethanol to prepare Compound D-1 (20 g, 90%).
MS[M+H]$^+$=345.16

Preparation Example D-2. Preparation of Compound D-2

Compound D-2 was prepared by performing the synthesis in the same manner as in Preparation Example D-1, except that Compound C-2 was used instead of Compound C-1.
MS[M+H]$^+$=345.16

Preparation Example D-3. Preparation of Compound D-3

Compound D-3 was prepared by performing the synthesis in the same manner as in Preparation Example D-1, except that Compound C-3 was used instead of Compound C-1.
MS[M+H]$^+$=345.16

Preparation Example D-4. Preparation of Compound D-4

Compound D-4 was prepared by performing the synthesis in the same manner as in Preparation Example D-1, except that Compound C-4 was used instead of Compound C-1.
MS[M+H]$^+$=345.16

Preparation Example D-5. Preparation of Compound D-5

Compound D-5 was prepared by performing the synthesis in the same manner as in Preparation Example D-1, except that Compound C-5 was used instead of Compound C-1.
MS[M+H]$^+$=499.18

Preparation Example D-6. Preparation of Compound D-6

Compound D-6 was prepared by performing the synthesis in the same manner as in Preparation Example D-1, except that Compound C-6 was used instead of Compound C-1.
MS[M+H]$^+$=499.18

Preparation Example 1. Preparation of Compound 1

-continued

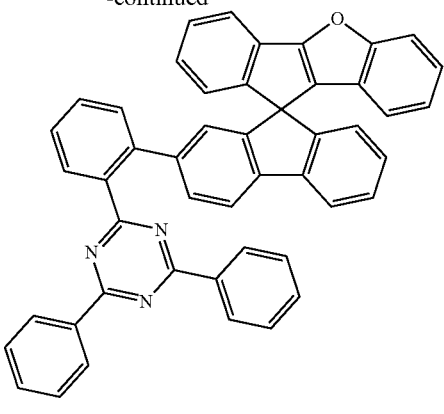

1

Compound D-1 (15 g, 31.1 mmol) and 2-(2-chlorophenyl)-4,6-diphenyl-1,3,5-triazine (10.8 g, 31.7 mmol) were put into THF (300 ml), a 2M aqueous potassium carbonate solution (70 ml) was added thereto, tetrakistriphenyl-phosphinopalladium (71.9 mg, 2 mol %) was put thereinto, and then the resulting mixture was heated and stirred for 10 hours. The temperature was lowered to normal temperature, the reaction was terminated, and then the layers were separated. Recrystallization was performed with tetrahydrofuran and ethyl acetate to prepare Compound 1 (10.31 g, 50%).

MS[M+H]$^+$=664.24

Preparation Example 2. Preparation of Compound 2

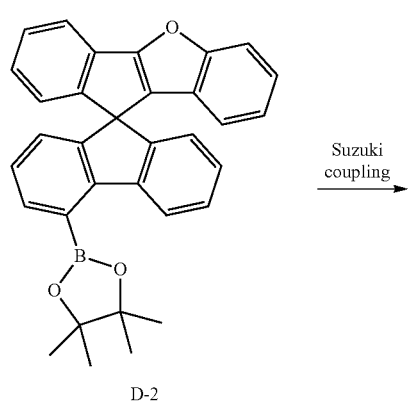

D-2

-continued

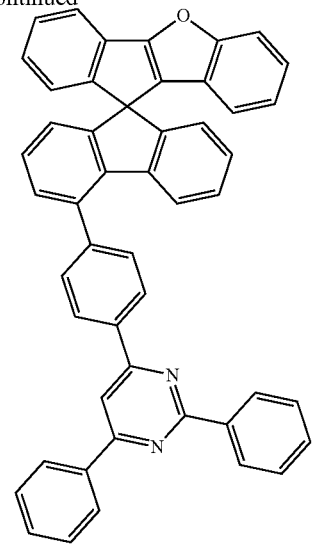

2

Compound 2 was prepared by performing the synthesis in the same manner as in Preparation Example 1, except that Compound D-2 was used instead of Compound D-1, and 4-(4-chlorophenyl)-2,6-diphenylpyrimidine was used instead of 2-(2-chlorophenyl)-4,6-diphenyl-1,3,5-triazine.

MS[M+H]$^+$=663.24

Preparation Example 3. Preparation of Compound 3

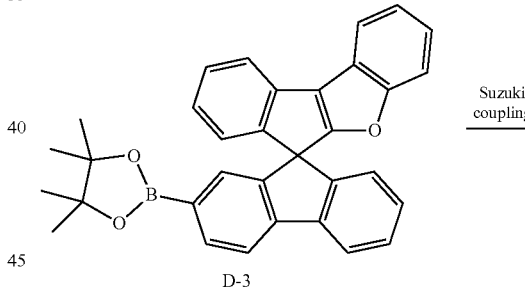

D-3

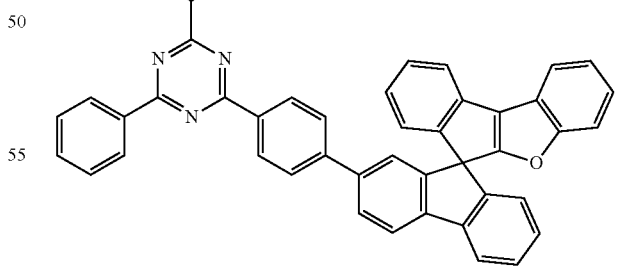

3

Compound 3 was prepared by performing the synthesis in the same manner as in Preparation Example 1, except that Compound D-3 was used instead of Compound D-1, and 2-(4-chlorophenyl)-4,6-diphenyl-1,3,5-triazine was used instead of 2-(2-chlorophenyl)-4,6-diphenyl-1,3,5-triazine.

MS[M+H]$^+$=664.23

Preparation Example 4. Preparation of Compound 4

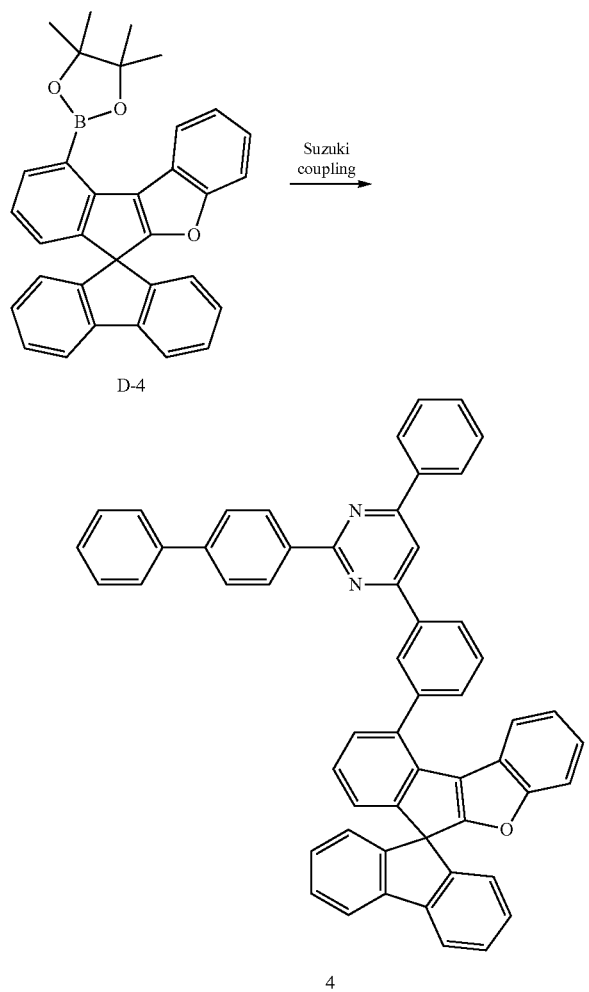

Compound 4 was prepared by performing the synthesis in the same manner as in Preparation Example 1, except that Compound D-4 was used instead of Compound D-1, and 2-([1,1'-biphenyl]-4-(3-chlorophenyl)-6-phenylpyrimidine was used instead of 2-(2-chlorophenyl)-4,6-diphenyl-1,3,5-triazine.

MS[M+H]$^+$=739.27

Preparation Example 5. Preparation of Compound 5

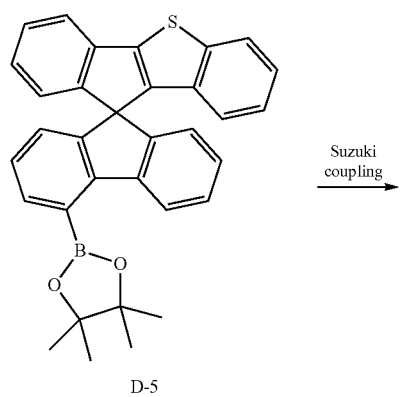

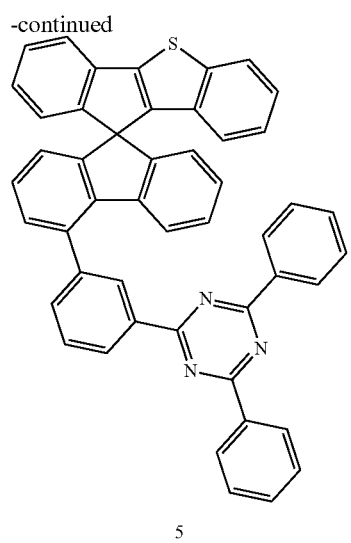

Compound 5 was prepared by performing the synthesis in the same manner as in Preparation Example 1, except that Compound D-5 was used instead of Compound D-1, and 2-(3-chlorophenyl)-4,6-diphenyl-1,3,5-triazine was used instead of 2-(2-chlorophenyl)-4,6-diphenyl-1,3,5-triazine.

MS[M+H]$^+$=680.21

Preparation Example 6. Preparation of Compound 6

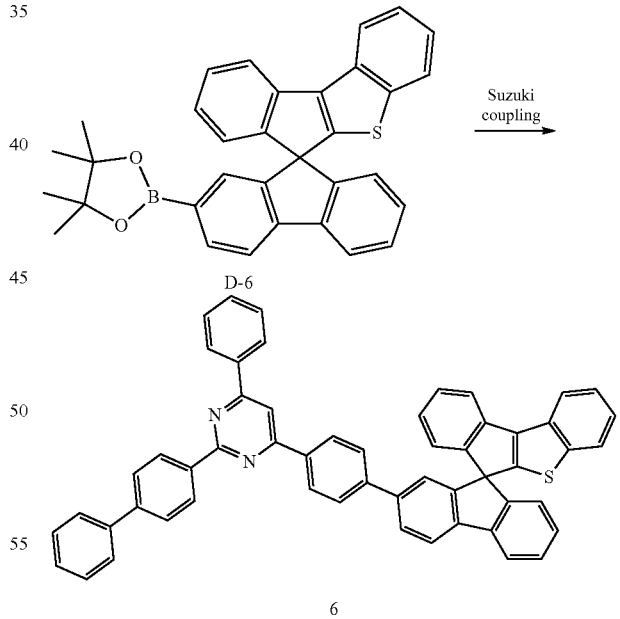

Compound 6 was prepared by performing the synthesis in the same manner as in Preparation Example 1, except that Compound D-6 was used instead of Compound D-1, and 2-([1,1'-biphenyl]-4-(4-chlorophenyl)-6-phenylpyrimidine was used instead of 2-(2-chlorophenyl)-4,6-diphenyl-1,3,5-triazine.

MS[M+H]$^+$=755.24

Preparation Example 7. Preparation of Compound 7

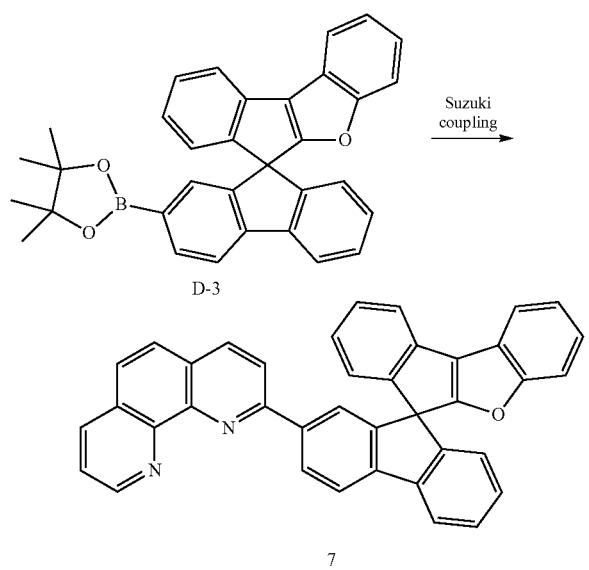

Compound 6 was prepared by performing the synthesis in the same manner as in Preparation Example 1, except that Compound D-3 was used instead of Compound D-1, and 2-bromo-1,10-phenanthroline was used instead of 2-(2-chlorophenyl)-4,6-diphenyl-1,3,5-triazine.

MS[M+H]+=535.17

Preparation Example 8. Preparation of Compound 8

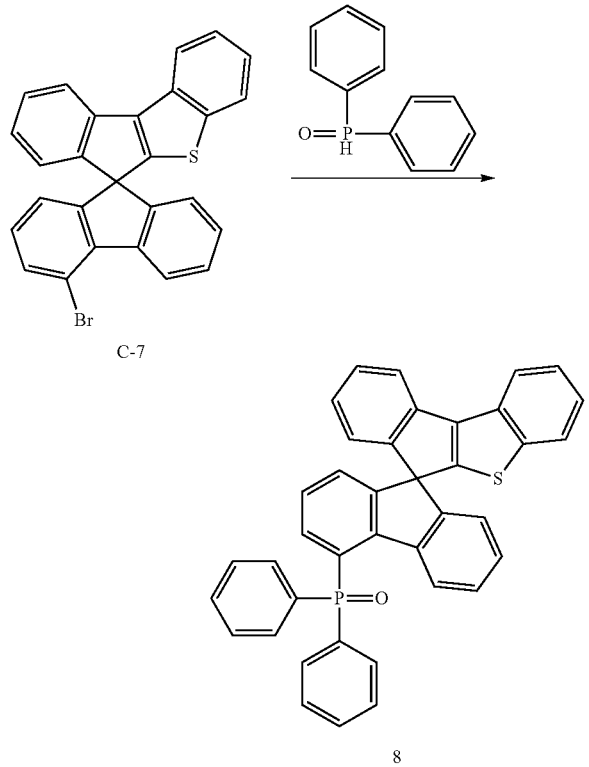

After Compound C-7 (15 g, 33.3 mmol) was dissolved in tetrahydrofuran (200 mL) and the resulting solution was heated, a solution in which cesium carbonate (30 g, 99.9 mmol) was dissolved in water (100 mL) was added thereto, and then [nickel(1,3-bis(diphenylphosphino)propane)chloride] ([Ni(dppp)Cl$_2$]) (153 mg, 2.1 mmol) was added thereto. When the solution was boiled, a structural formula diphenylphosphine oxide was put thereinto, the resulting solution was stirred for 8 hours, the temperature was cooled to normal temperature, and then the produced solid was filtered and recrystallized with tetrahydrofuran and ethyl acetate to prepare Compound 8 (9.52 g, 50%).

MS[M+H]$^+$=573.14

Example 1

A glass substrate (Corning 7059 glass) thinly coated with indium tin oxide (ITO) to have a thickness of 1,000 Å was put into distilled water in which a dispersant was dissolved, and ultrasonically washed. A product manufactured by Fischer Co., was used as the detergent, and distilled water twice filtered using a filter manufactured by Millipore Co., was used as the distilled water. After the ITO was washed for 30 minutes, ultrasonic washing was conducted twice repeatedly using distilled water for 10 minutes. After the washing using distilled water was completed, ultrasonic washing was conducted using isopropyl alcohol, acetone, and methanol solvents in this order, and drying was then conducted.

Hexanitrile hexaazatriphenylene was thermally vacuum deposited to have a thickness of 500 Å on a transparent ITO electrode thus prepared, thereby forming a hole injection layer. HT1 (900 Å) was vacuum deposited as a hole transport layer thereon, and then HT2 was vacuum deposited to have a film thickness of 100 Å on the hole transport layer, thereby forming a hole adjusting layer. As a light emitting layer, a compound of host H1 and dopant D1 (25:1) was vacuum deposited to have a thickness of 300 Å. Compound 1 and [LiQ] (lithium quinolate) were vacuum deposited at a weight ratio of 1:1 on the light emitting layer, thereby forming an electron injection and transport layer having a thickness of 350 Å. Lithium fluoride (LiF) and aluminum were sequentially deposited to have a thickness of 10 Å and 1,000 Å, respectively, on the electron injection and transport layer, thereby forming a negative electrode.

In the aforementioned procedure, the deposition rates of the organic material, lithium fluoride, and aluminum were maintained at 1 Å/sec, 0.2 Å/sec, and 3 to 7 Å/sec, respectively.

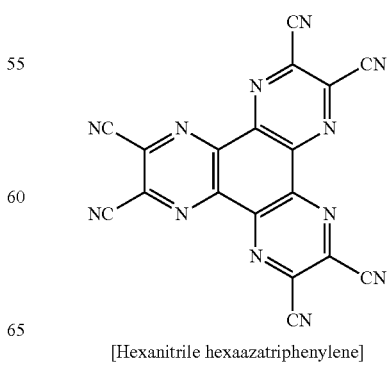

[Hexanitrile hexaazatriphenylene]

-continued

[HT1]
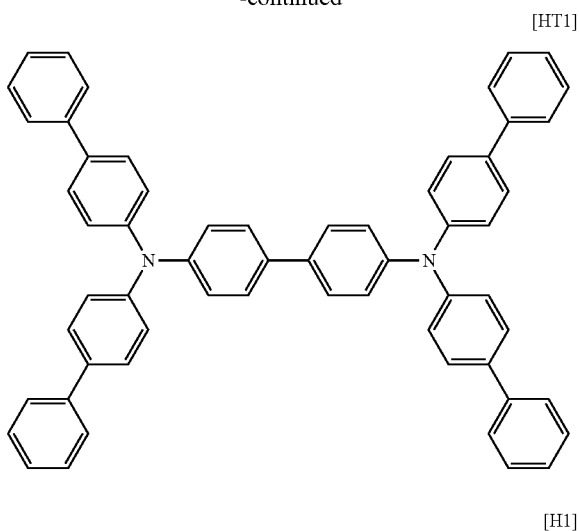

[H1]
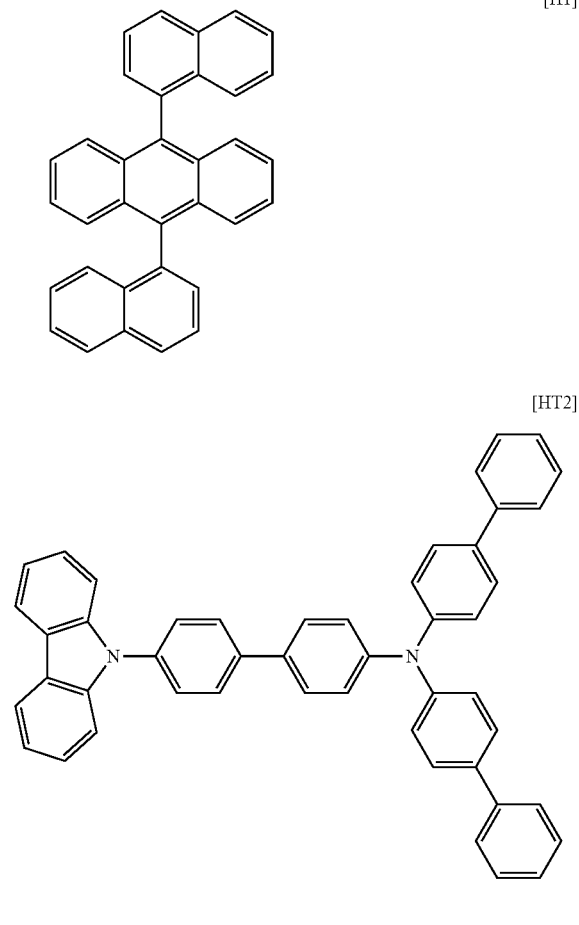

[HT2]

[D1]
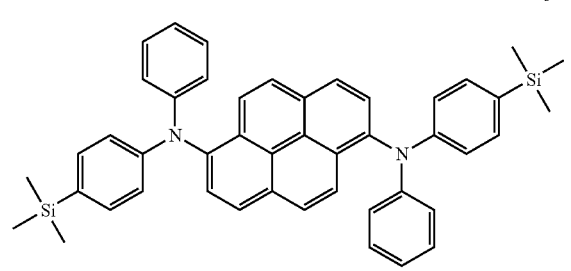

Example 2

An experiment was performed in the same manner as in Example 1, except that as the electron injection and transport layer, Compound 2 was used instead of Compound 1.

Example 3

An experiment was performed in the same manner as in Example 1, except that as the electron injection and transport layer, Compound 3 was used instead of Compound 1.

Example 4

An experiment was performed in the same manner as in Example 1, except that as the electron injection and transport layer, Compound 4 was used instead of Compound 1.

Example 5

An experiment was performed in the same manner as in Example 1, except that as the electron injection and transport layer, Compound 5 was used instead of Compound 1.

Example 6

An experiment was performed in the same manner as in Example 1, except that as the electron injection and transport layer, Compound 6 was used instead of Compound 1.

Example 7

An experiment was performed in the same manner as in Example 1, except that as the electron injection and transport layer, Compound 7 was used instead of Compound 1.

Example 8

An experiment was performed in the same manner as in Example 1, except that as the electron injection and transport layer, Compound 8 was used instead of Compound 1.

Example 9

An experiment was performed in the same manner as in Example 1, except that as the electron injection and transport layer, Compound 1 was used alone instead of the mixture of Compound 1 and LiQ.

Comparative Example 1

An experiment was performed in the same manner as in Example 1, except that as the electron injection and transport layer, E1 was used instead of Compound 1.

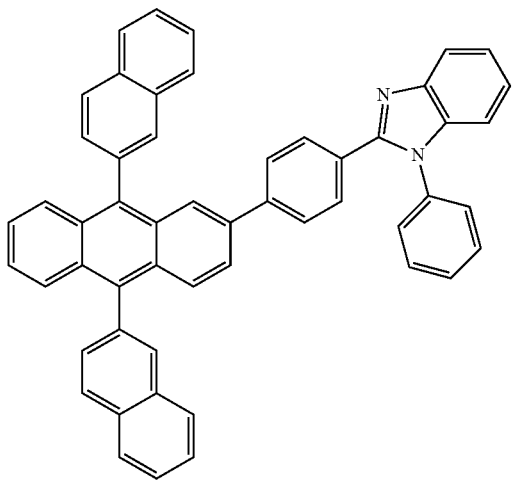

[E1]

Comparative Example 2

An experiment was performed in the same manner as in Example 1, except that as the electron injection and transport layer, E1 was used alone instead of the mixture of Compound 1 and LiQ.

For the organic light emitting devices of Examples 1 to 9 and Comparative Examples 1 to 2, the driving voltage and the light emitting efficiency were measured at a current density of 10 mA/cm$^2$, and a time ($T_{90}$) for reaching a 90% value compared to the initial luminance was measured at a current density of 20 mA/cm$^2$, and the results are shown in the following Table 1.

TABLE 1

| 10 mA/cm$^2$ | Electron injection and transport material | Voltage (V) | Current efficiency (cd/A) | Lifetime (h) $T_{90}$ at 20 mA/cm$^2$ |
|---|---|---|---|---|
| Comparative Example 1 | E1 + LiQ (1:1) | 4.11 | 5.32 | 90 |
| Comparative Example 2 | E1 (alone) | 4.32 | 5.00 | 101 |
| Example 1 | Compound 1 + LiQ (1:1) | 3.88 | 5.32 | 180 |
| Example 2 | Compound 2 + LiQ (1:1) | 3.78 | 5.35 | 150 |
| Example 3 | Compound 3 + LiQ (1:1) | 3.59 | 5.88 | 162 |
| Example 4 | Compound 4 + LiQ (1:1) | 3.66 | 5.91 | 172 |
| Example 5 | Compound 5 + LiQ (1:1) | 3.91 | 5.23 | 169 |
| Example 6 | Compound 6 + LiQ (1:1) | 3.55 | 5.89 | 181 |
| Example 7 | Compound 7 + LiQ (1:1) | 3.71 | 5.55 | 169 |
| Example 8 | Compound 8 + LiQ (1:1) | 3.55 | 5.89 | 175 |
| Example 9 | Compound 1 (alone) | 3.98 | 5.40 | 130 |

From the results of Table 1, it can be confirmed that the organic light emitting device in Example 9, which was manufactured by using the spiro structure compound represented by Chemical Formula 1 according to an exemplary embodiment of the present specification, can be used for an organic material layer which can inject and transport electrons simultaneously, and better device characteristics are exhibited in Examples 1 to 8, which are the organic light emitting devices manufactured by mixing the spiro structure compound with LiQ.

Through the Examples and the Comparative Examples, it can be confirmed that it is possible to provide an organic light emitting device having a long lifetime as in an exemplary embodiment of the present specification.

In particular, when an oxygen group element is formed as in Compounds 3, 4, 6, 7, and 8 in the molecular structure of the spiro structure compound represented by Chemical Formula 1 according to an exemplary embodiment of the present specification, there is an effect in that the performance of the device is enhanced because the oxygen group element has high triplet energy.

The spiro structure compound represented by Chemical Formula 1 according to an exemplary embodiment of the present specification has excellent thermal stability, a deep HOMO level of 5.7 eV or more, a high triplet energy (ET), and hole stability, and thus may exhibit excellent characteristics.

When the spiro structure compound according to an exemplary embodiment of the present specification is used in the organic material layer which may inject and transport electrons simultaneously, the compound can be used in a mixture with an n-type dopant.

EXPLANATION OF REFERENCE NUMERALS AND SYMBOLS 10, 11: Organic light emitting device
20: Substrate
30: First electrode
40: Light emitting layer
50: Second electrode
60: Hole injection layer
70: Hole transport layer
80: Electron transport layer
90: Electron injection layer

The invention claimed is:

1. A spiro structure compound represented by the following Chemical Formula 1:

[Chemical Formula 1]

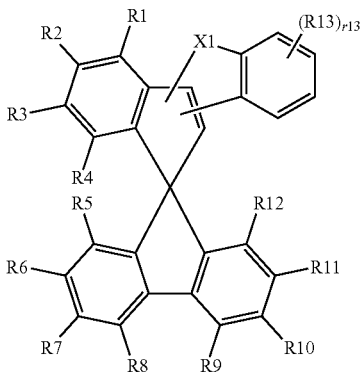

in Chemical Formula 1,
X1 is O or S,
at least one of R1 to R12 is -L1-Ar1, and the others and R13 are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, r13 is an integer of 1 to 4, when r13 is 2 or more, two or more R13's are the same as or different from each other, L1 is a direct bond; a substituted or unsubstituted arylene group; or a substituted or unsubstituted heteroarylene group, Ar1 is a substituted or unsubstituted phosphine oxide group; or is represented by any one of the following Chemical Formulae 2 to 6,

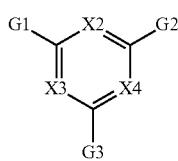

[Chemical Formula 2]

in Chemical Formula 2,

X2 is N or CR14, X3 is N or CR15, and X4 is N or CR16, at least one of X2 to X4 is N, any one of G1 to G3 and R14 to R16 is a moiety bonded to L1 of Chemical Formula 1, and the others of G1 to G3 and R14 to R16 are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, wherein when R2, R6 or R11 is -L1-Ar1, Ar1 is Chemical Formula 2, the other of G1 to G3 or R14 to R16 are each independently hydrogen, or a substituted or unsubstituted aryl group, and at least one of G1 to G3 or R14 to R16 is a substituted or unsubstituted aryl group, the at least one of G1-G3 or R14-R16 is a substituted or unsubstituted polycyclic aryl group,

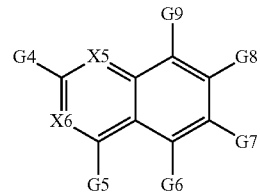

[Chemical Formula 3]

in Chemical Formula 3,

X5 is N or CR17, and X6 is N or CR18, at least one of X5 and X6 is N, any one of G4 to G9, R17, and R18 is a moiety bonded to L1 of Chemical Formula 1, and the others are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, or adjacent groups combine with each other to form a substituted or unsubstituted ring,

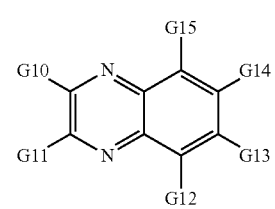

[Chemical Formula 4]

in Chemical Formula 4, any one of G10 to G15 is a moiety bonded to L1 of Chemical Formula 1, and the others are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group,

[Chemical Formula 5]

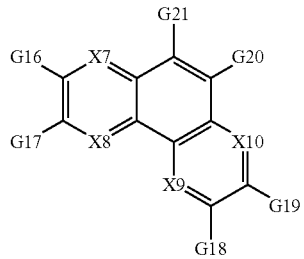

in Chemical Formula 5,
X7 is N or CR19, X8 is N or CR20, X9 is N or CR21, and X10 is N or CR22,
at least one of X7 to X10 is N,
any one of G16 to G21 and R19 to R22 is a moiety bonded to L1 of Chemical Formula 1, and the others are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group,

[Chemical Formula 6]

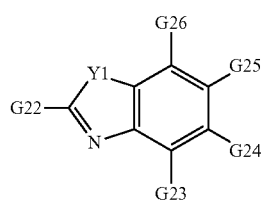

in Chemical Formula 6,
Y1 is O, S, NQ1, or CQ2Q3, and
any one of G22 to G26 is a moiety bonded to L1 of Chemical Formula 1, and the others and Q1 to Q3 are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group.

2. The spiro structure compound of claim 1, wherein Chemical Formula 1 is represented by any one of the following Chemical Formulae 1-1 to 1-3:

[Chemical Formula 1-1]

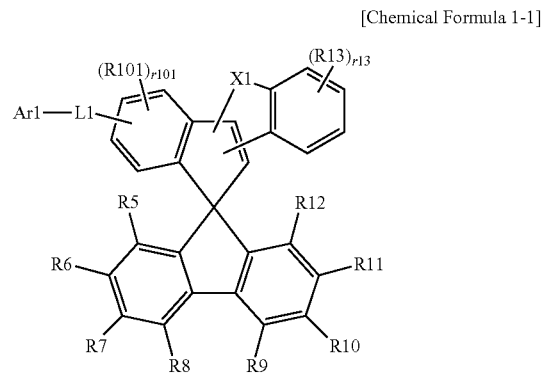

[Chemical Formula 1-2]

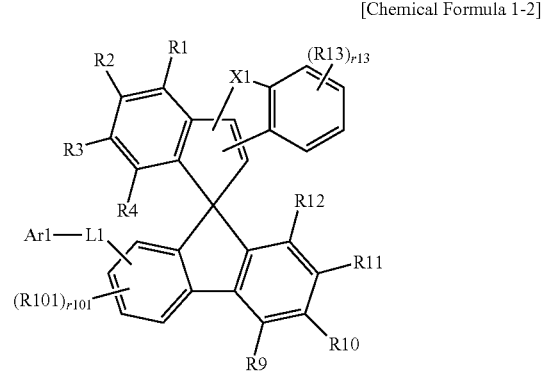

[Chemical Formula 1-3]

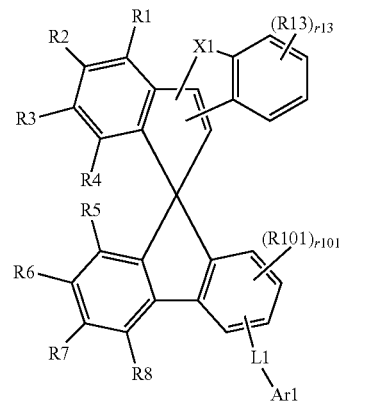

in Chemical Formulae 1-1 to 1-3,
the definitions of X1, R1 to R13, L1, Ar1, and r13 are the same as those in Chemical Formula 1,
R101 is hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, r101 is 1 to 3, and when r101 is 2 or more, two or more R101's are the same as or different from each other.

3. The spiro structure compound of claim 1, wherein Chemical Formula 1 is represented by any one of the following Chemical Formulae 1-4 to 1-15:

[Chemical Formula 1-4]

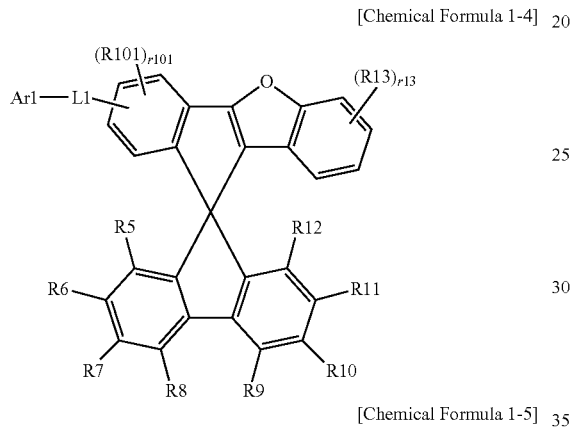

[Chemical Formula 1-5]

[Chemical Formula 1-6]

[Chemical Formula 1-7]

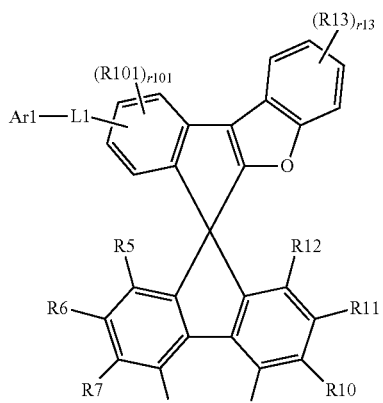

[Chemical Formula 1-8]

[Chemical Formula 1-9]

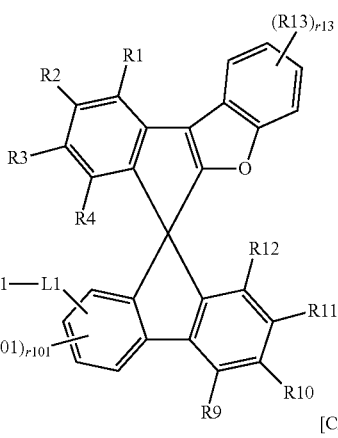

[Chemical Formula 1-10]

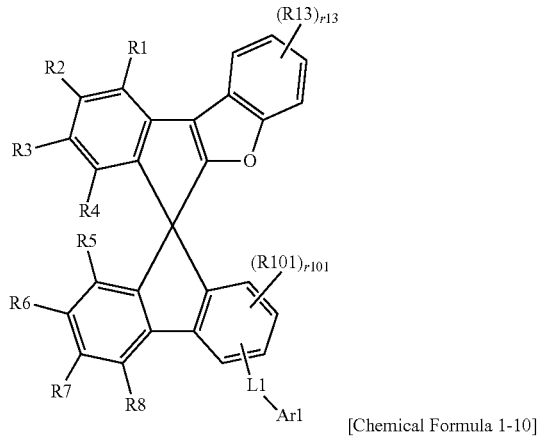

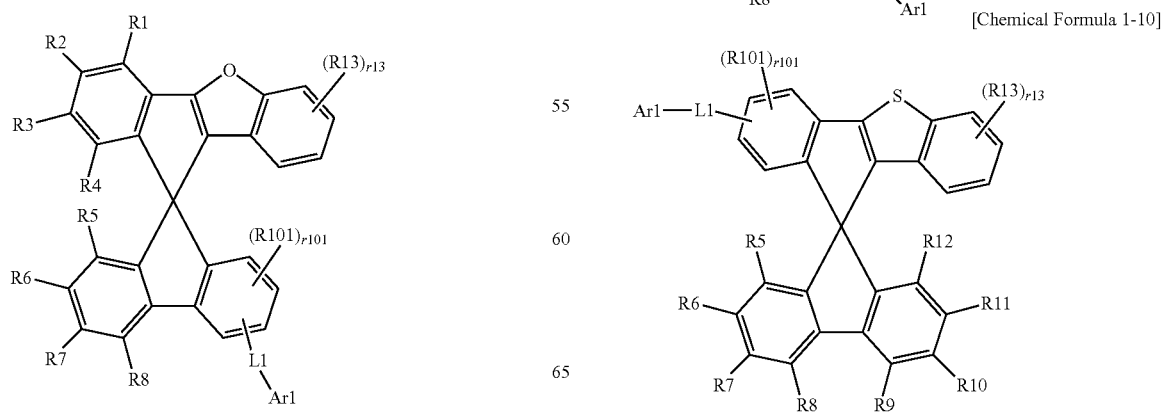

[Chemical Formula 1-11]

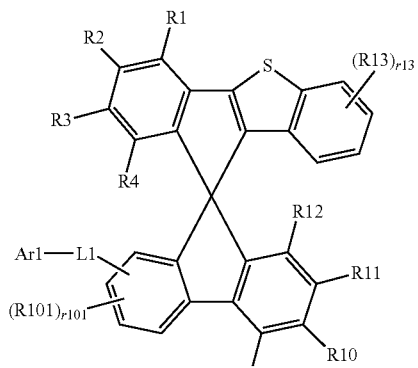

[Chemical Formula 1-12]

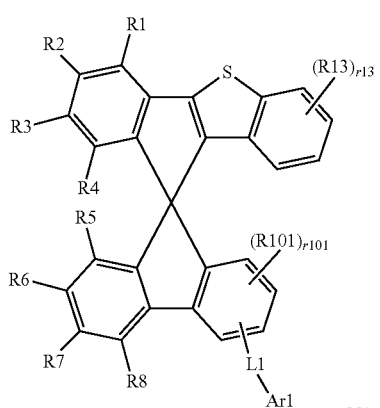

[Chemical Formula 1-13]

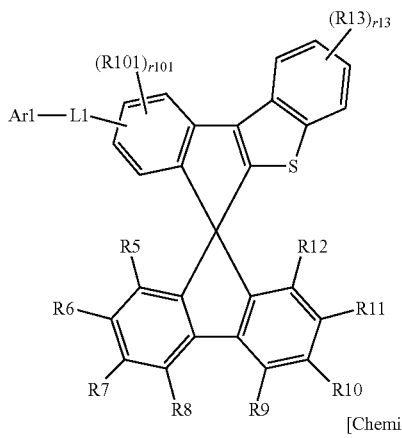

[Chemical Formula 1-14]

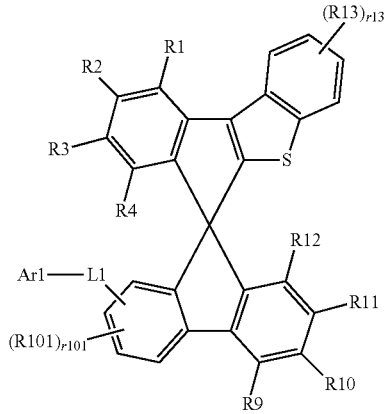

[Chemical Formula 1-15]

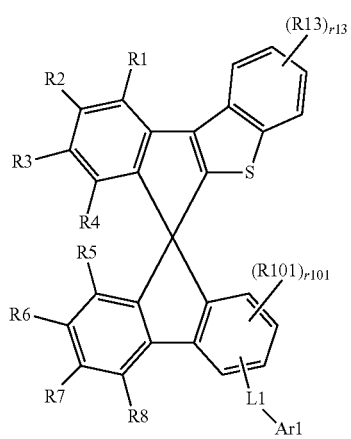

in Chemical Formulae 1-4 to 1-15, the definitions of R1 to R13, L1, Ar1, and r13 are the same as those in Chemical Formula 1, R101 is hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, r101 is 1 to 3, and when r101 is 2 or more, two or more R101's are the same as or different from each other.

4. The spiro structure compound of claim 1, wherein L1 is a direct bond; or a substituted or unsubstituted phenylene group.

5. The spiro structure compound of claim 1, wherein -L1-Ar1 is selected from the following structures:

B-1

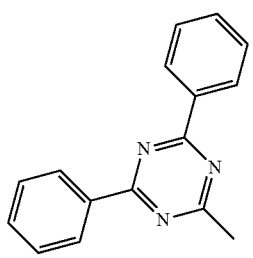

B-2
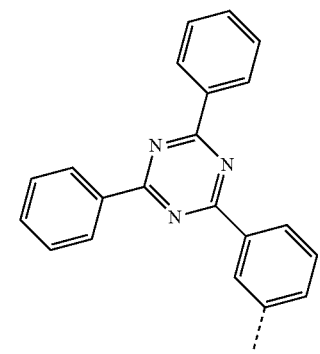
B-3
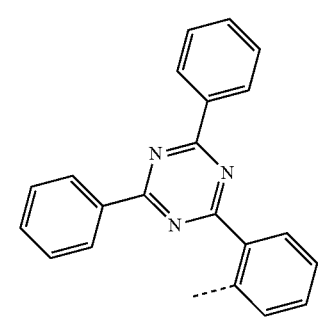
B-4
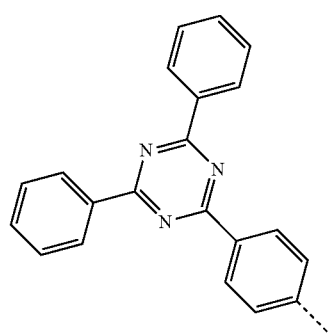
B-5
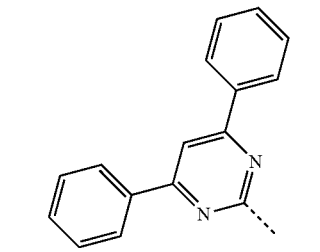
B-6
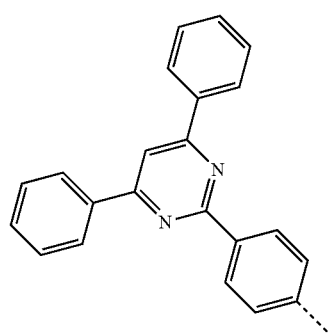
B-7
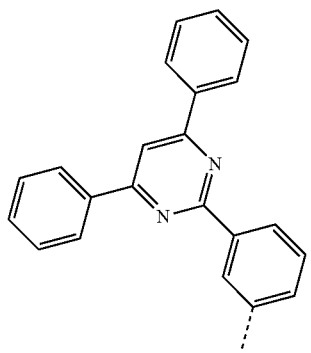
B-8
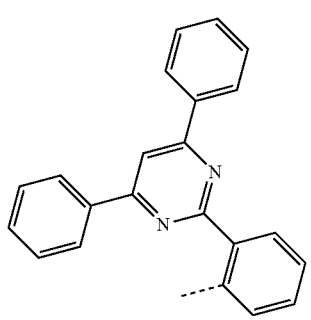
B-9
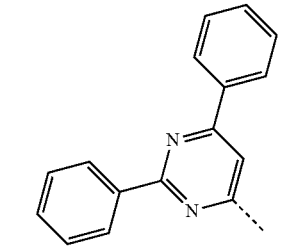
B-10
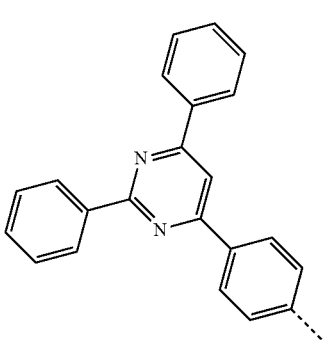
B-11
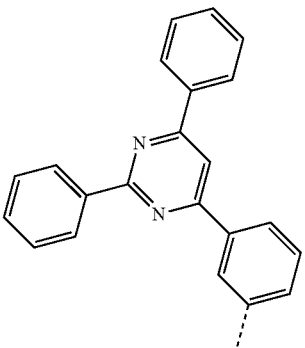

B-12
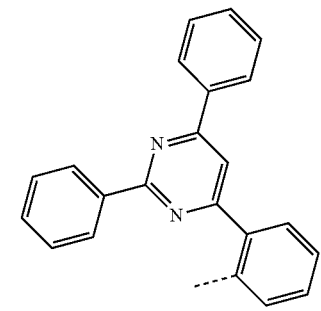
B-13
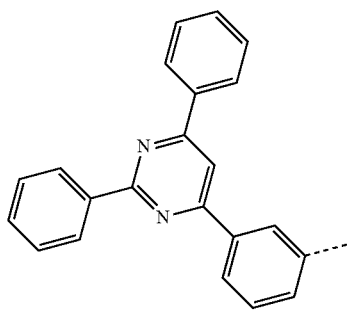
B-14
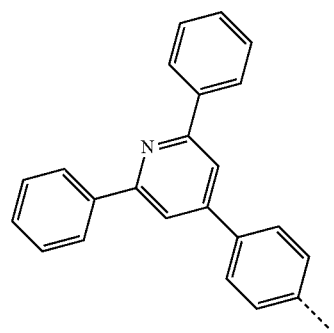
B-15
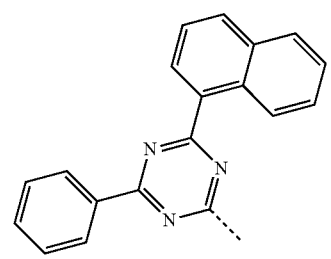
B-16
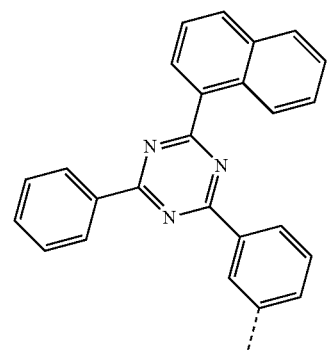
B-17
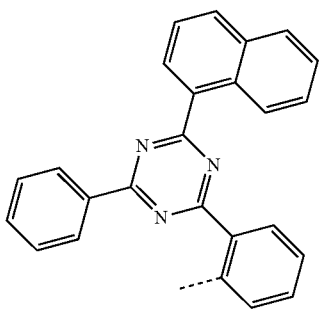
B-18
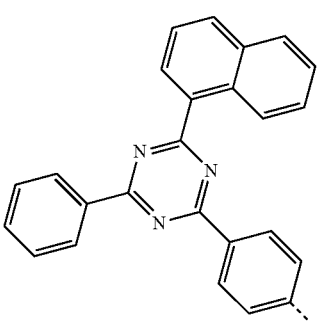
B-19
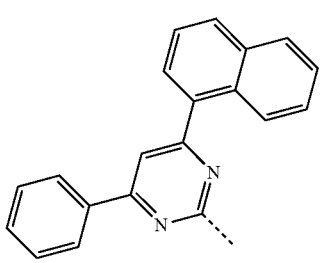
B-20
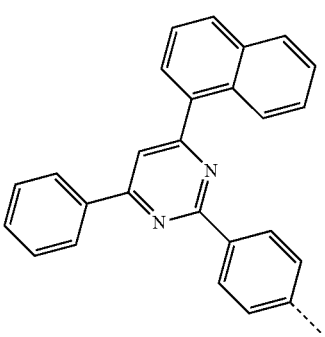
B-21
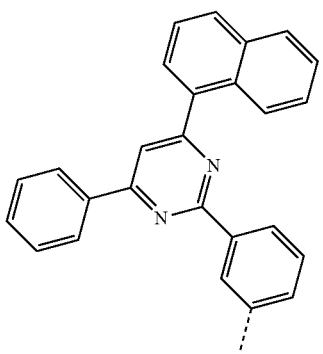

B-22 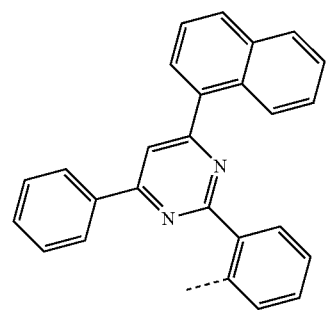
B-23 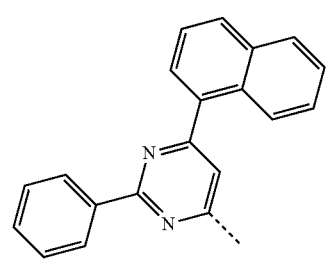
B-24 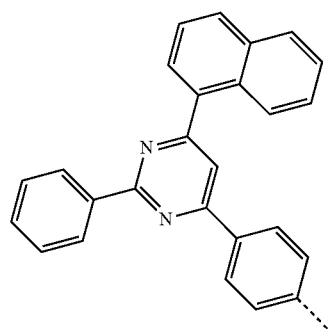
B-25 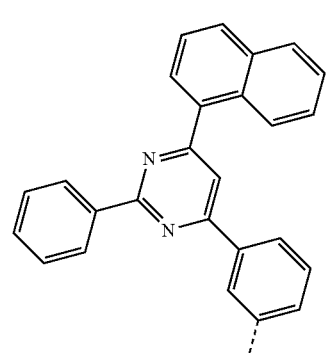
B-26 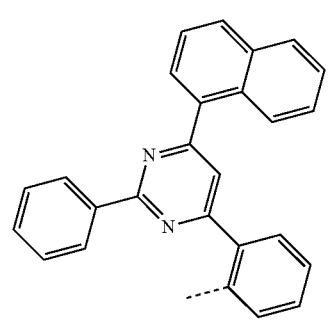
B-27 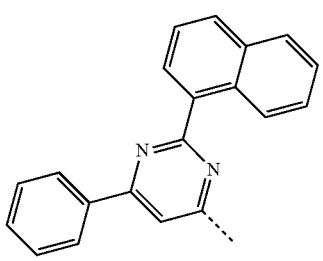
B-28 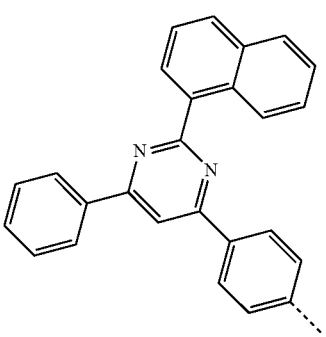
B-29 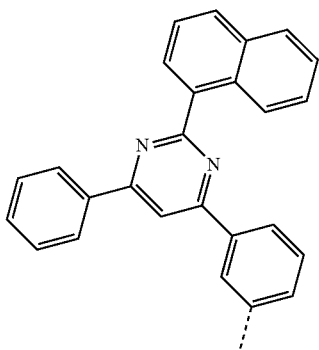
B-30 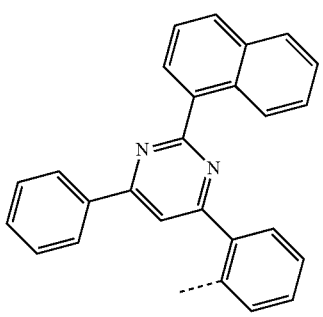
B-31 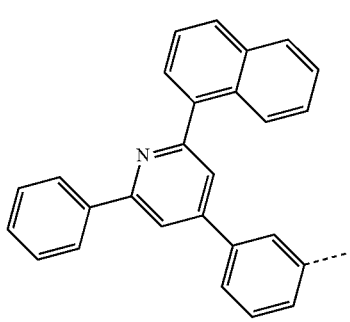

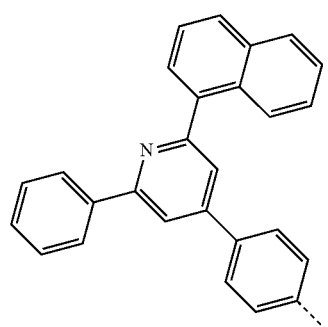
B-32
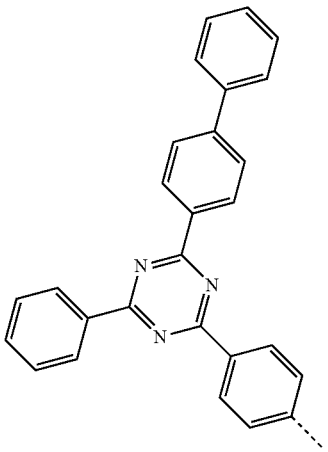
B-36
B-33
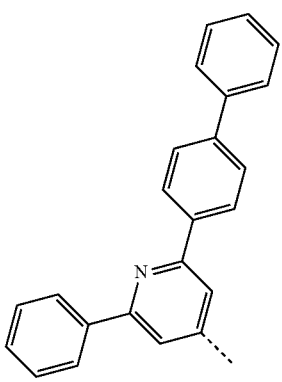
B-37
B-34
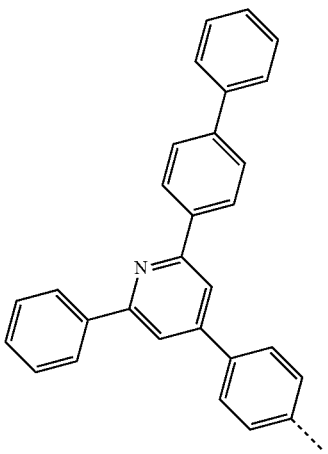
B-38
B-35

-continued
B-39
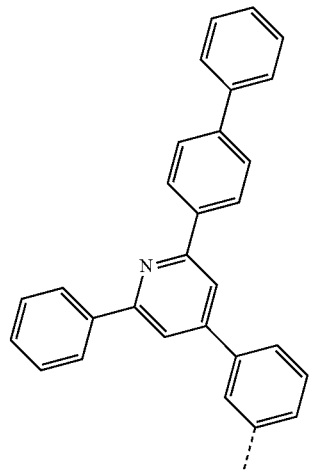
B-40
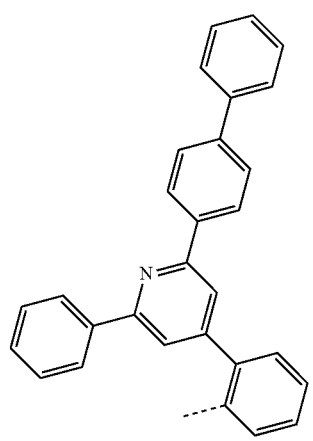
B-41
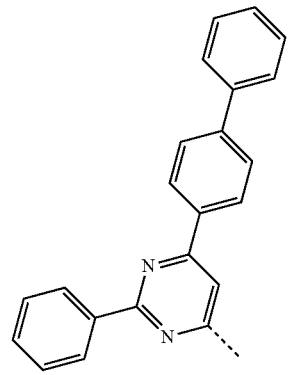
-continued
B-42
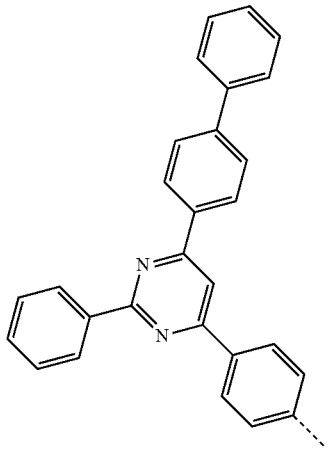
B-43
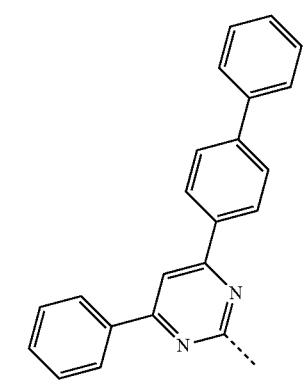
B-44
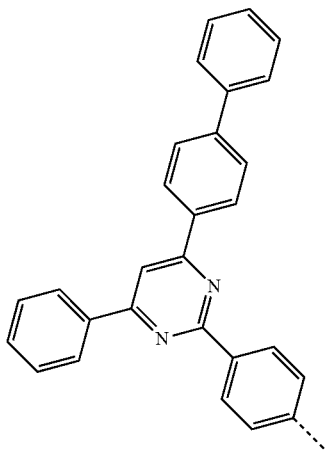

B-45
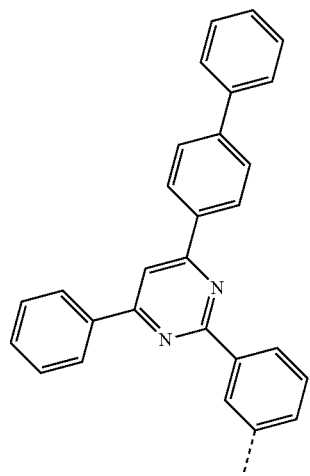
B-46
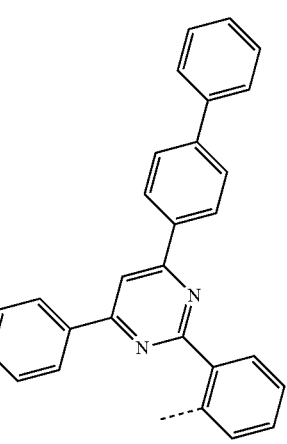
B-47
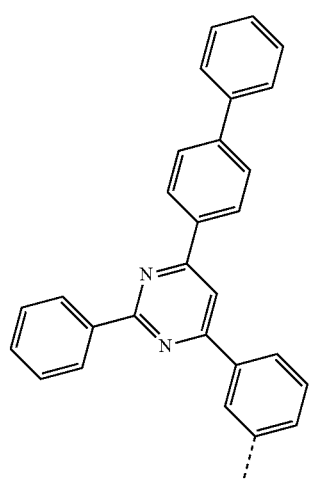
B-48
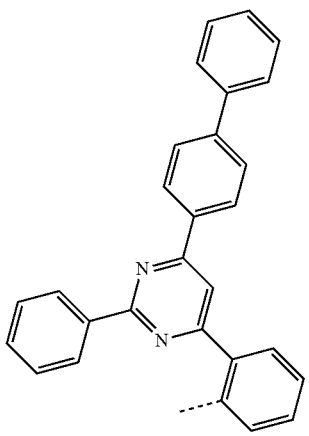
B-49
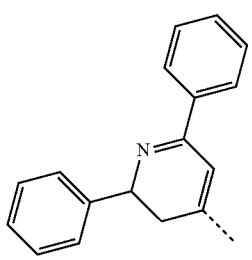
B-50
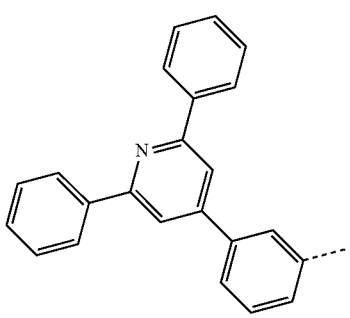
B-51
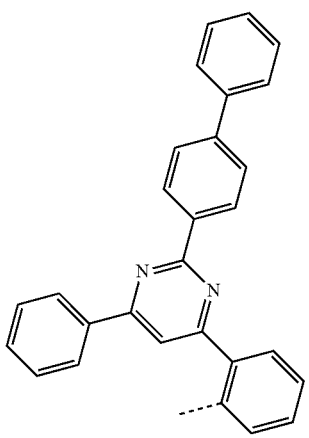

B-52 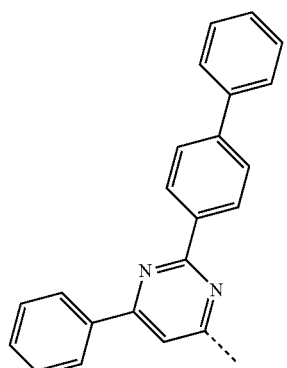
B-53 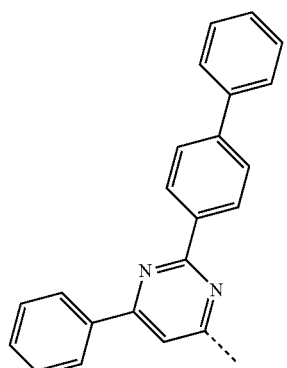
B-54
B-55
B-56 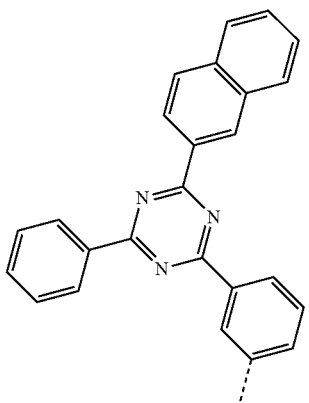
B-57 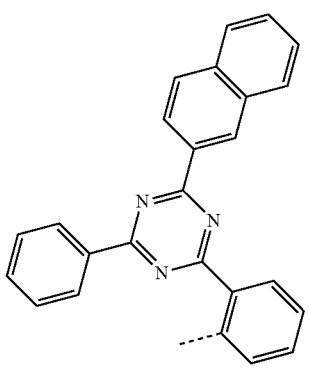
B-58 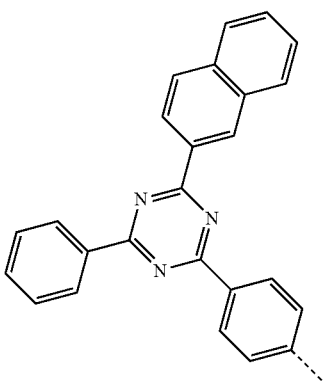
B-59 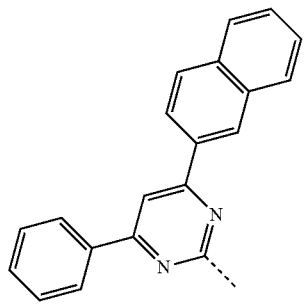

B-60
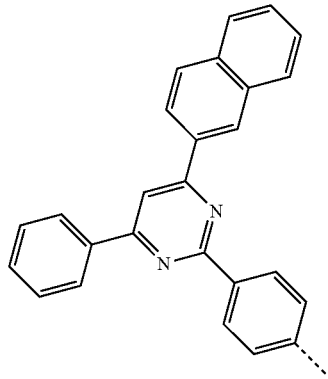
B-61
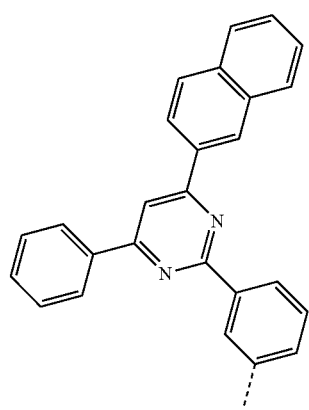
B-62
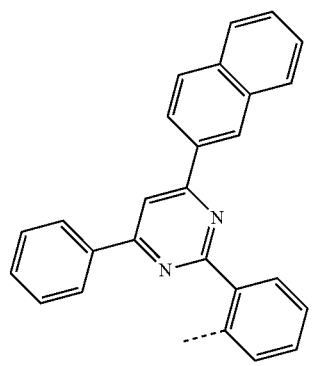
B-63
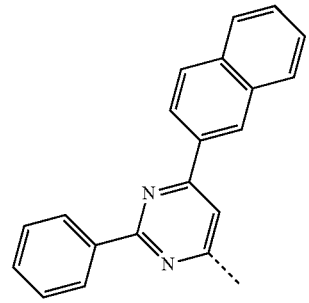
B-64
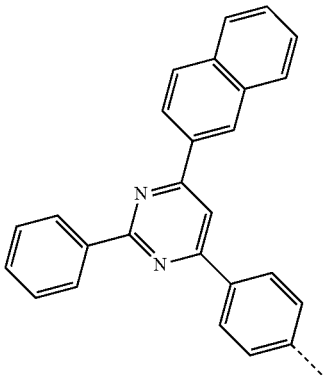
B-65
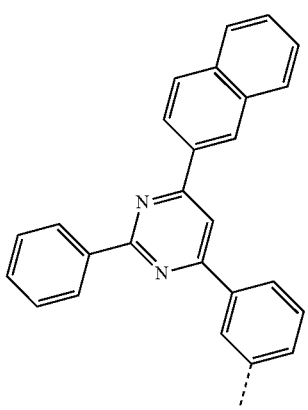
B-66
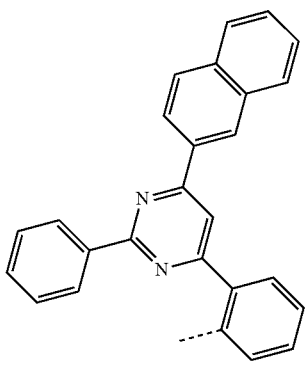
B-67
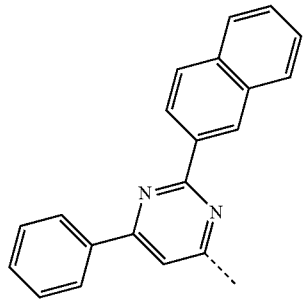

-continued
B-68
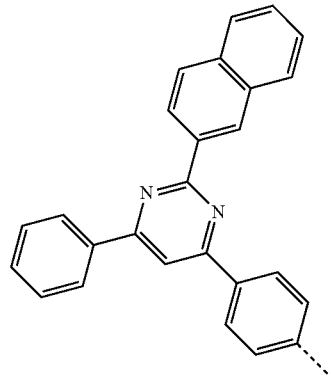
B-69
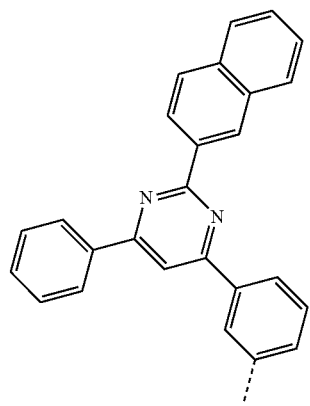
B-70
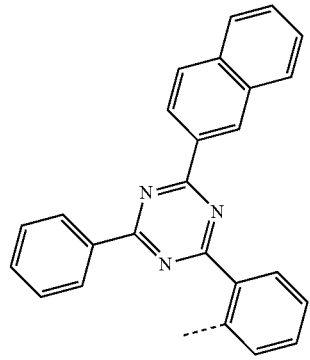
B-71
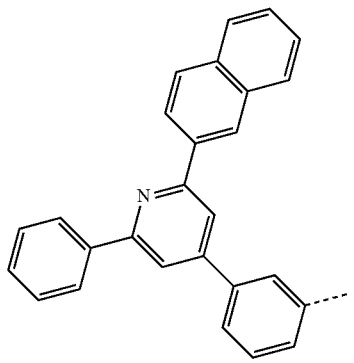
-continued
B-72
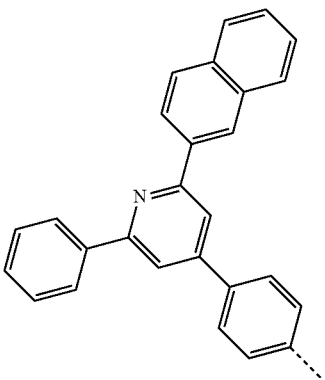
B-73
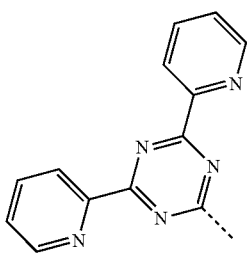
B-74
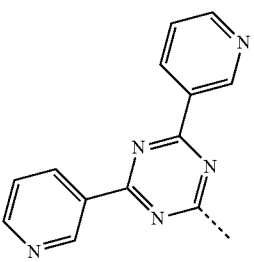
B-75
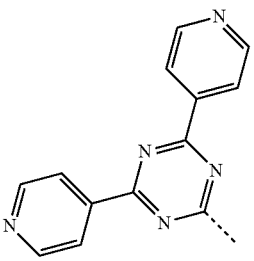
B-76
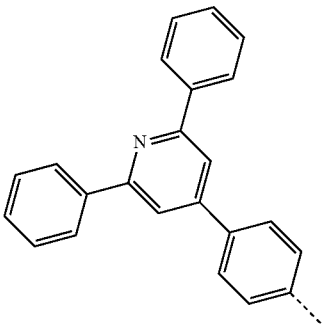

B-77 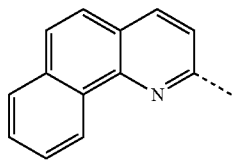
B-78 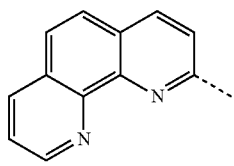
B-79 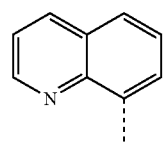
B-80 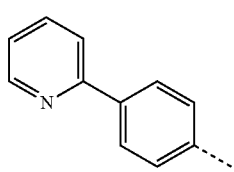
B-81 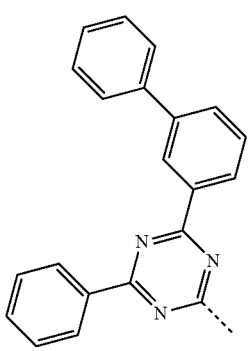
B-82 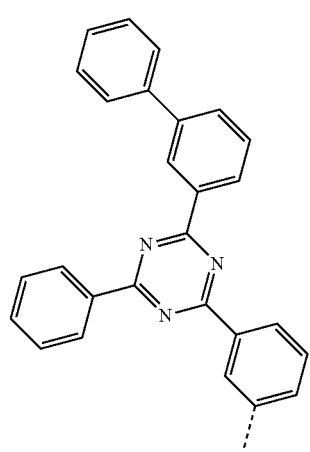
B-83 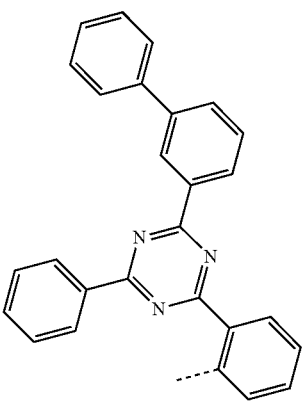
B-84 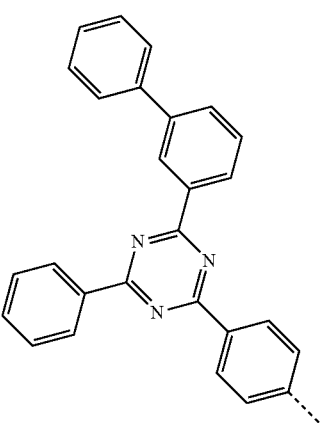
B-85 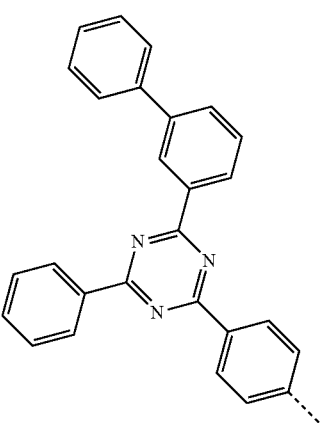

-continued
B-87
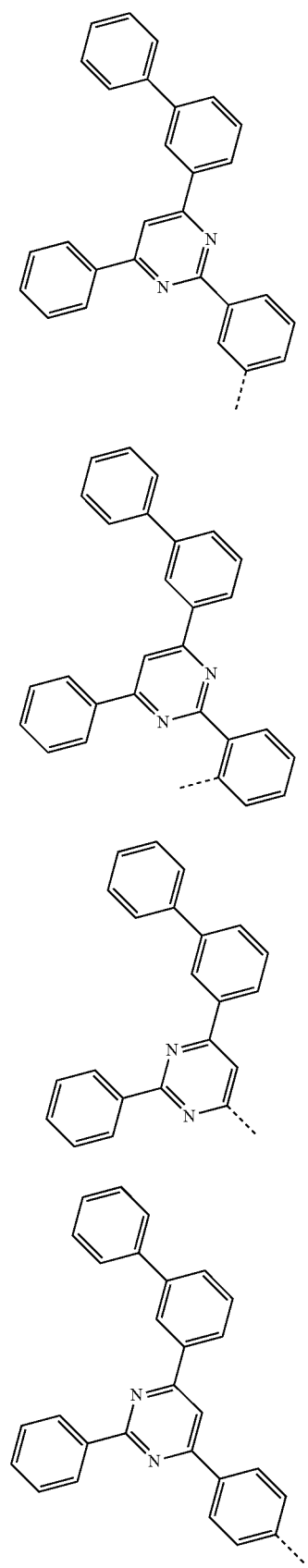
B-88
B-89
B-90
B-91
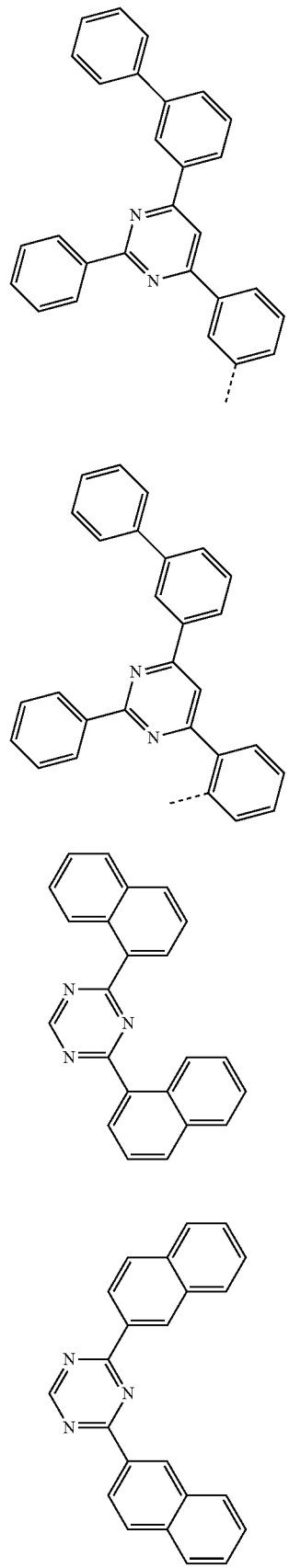
B-92
B-93
B-94

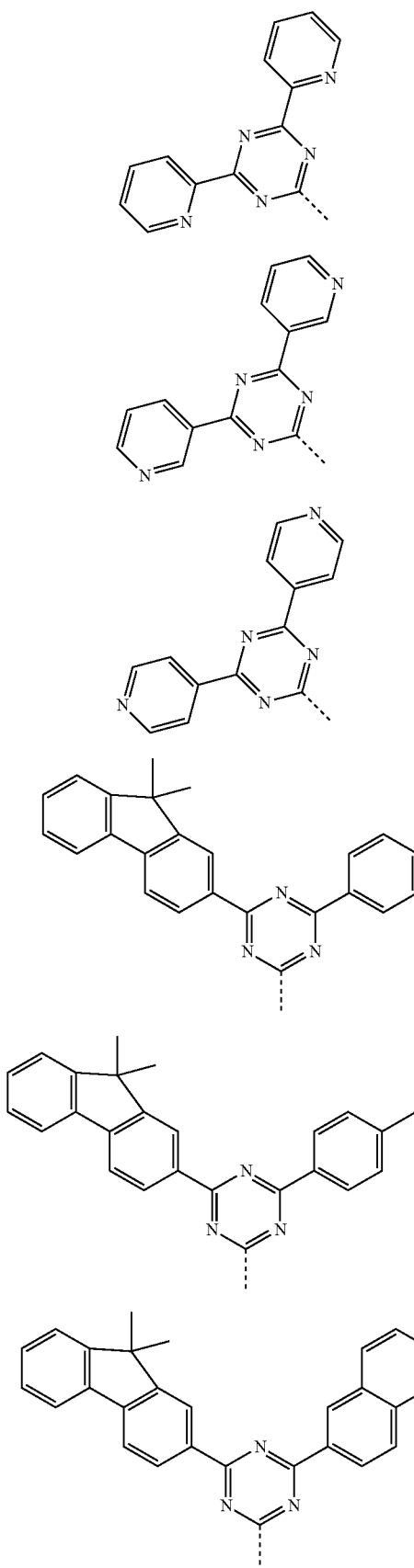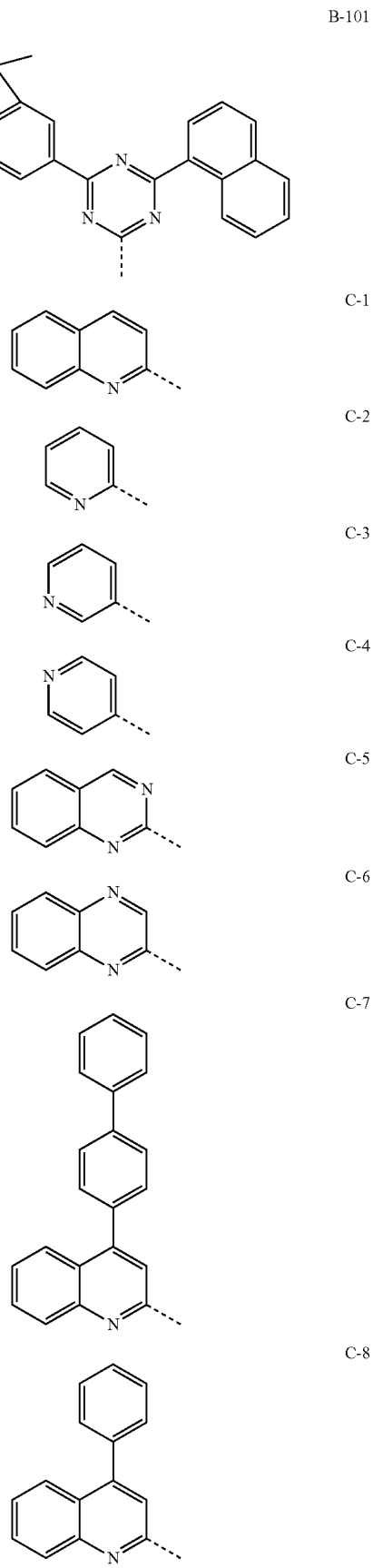

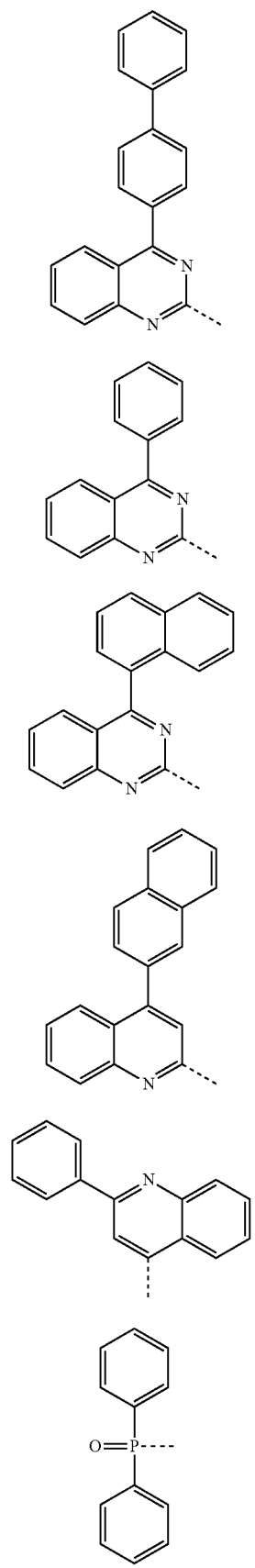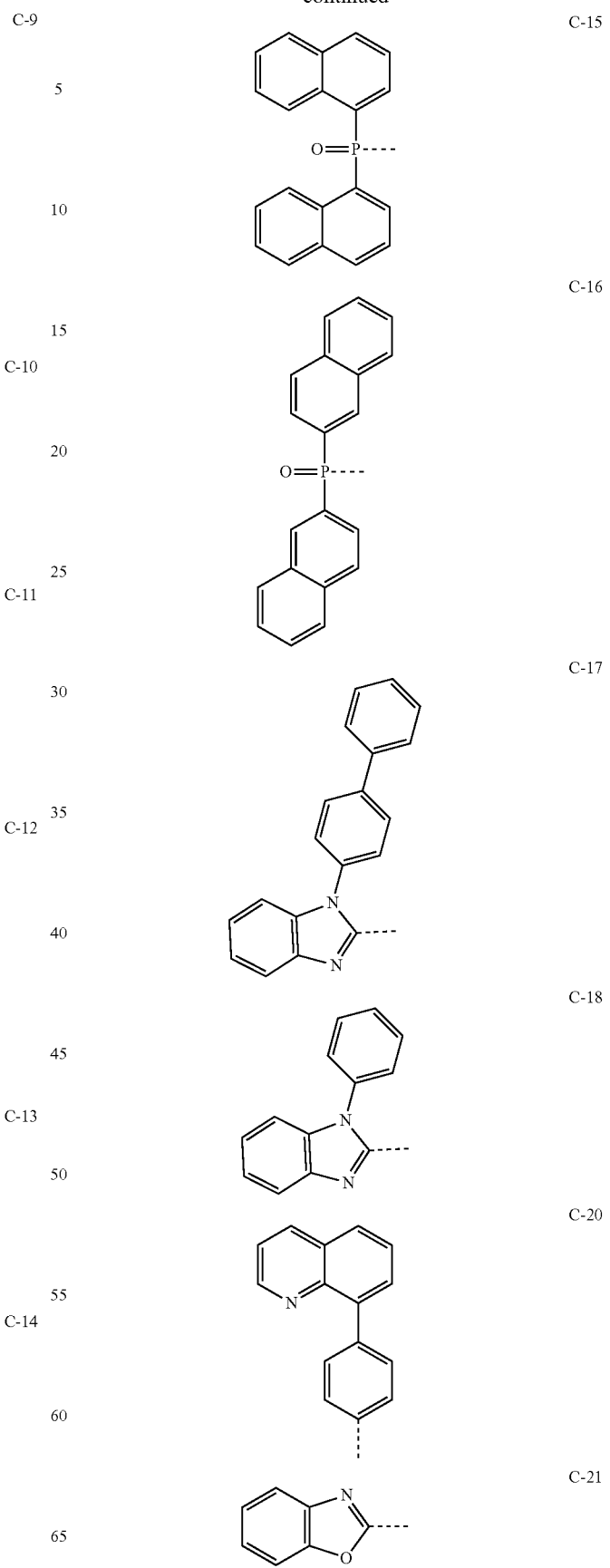

in the structures, - - - is a moiety linked to Chemical Formula 1.

6. The spiro structure compound of claim 1, wherein Chemical Formula 1 is selected from the following compounds:

255
-continued
256
-continued
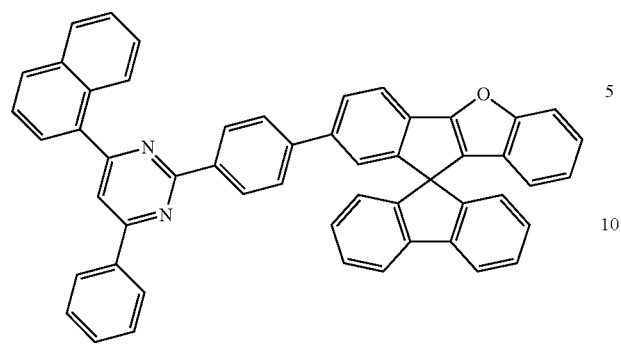
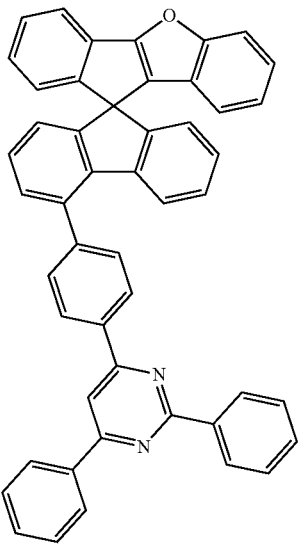
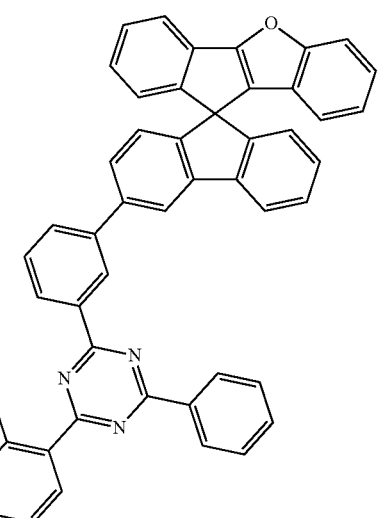
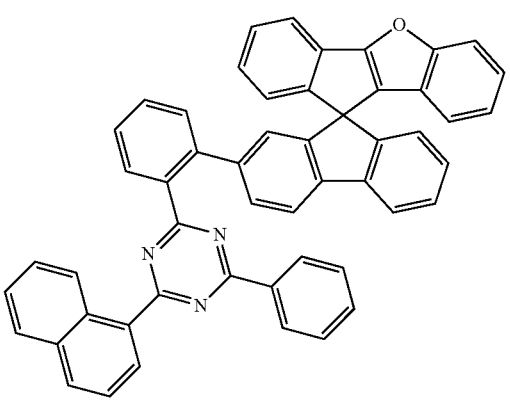

257
-continued
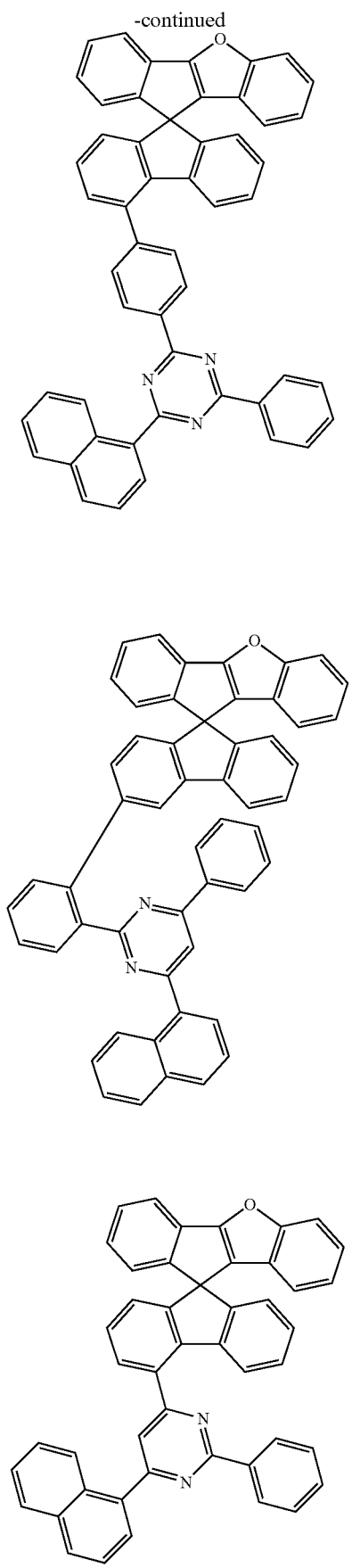
258
-continued
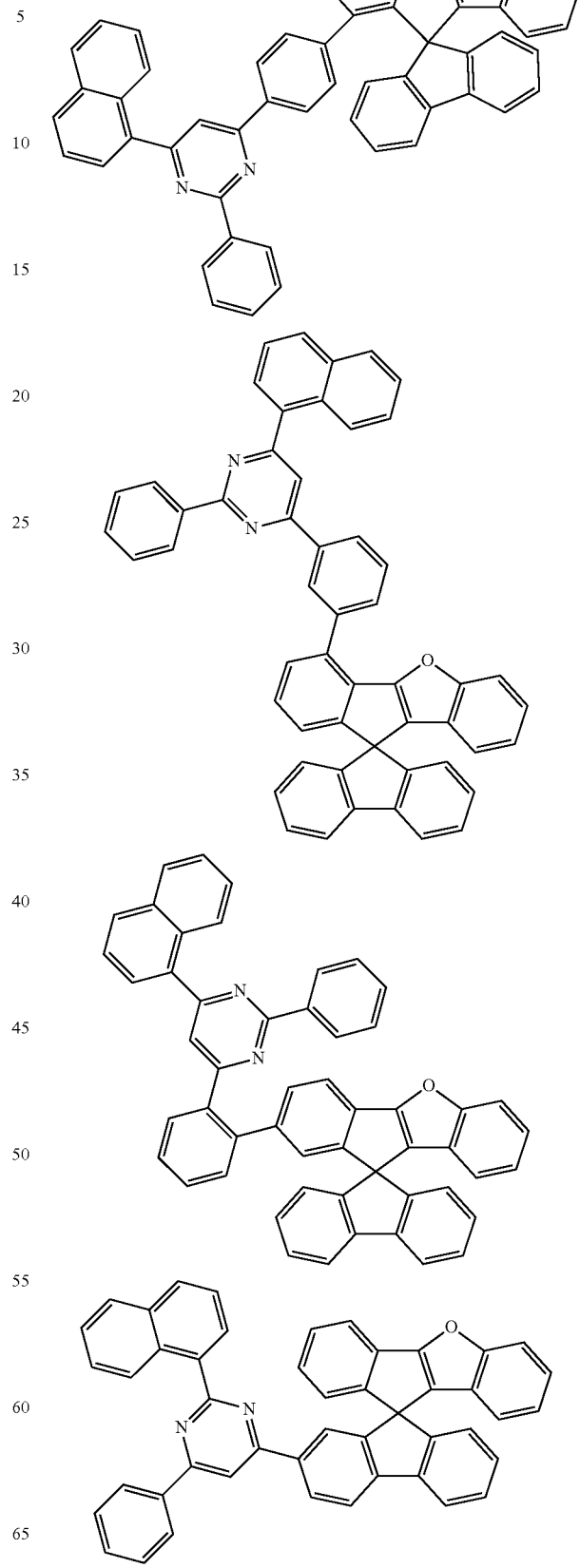

259
-continued
260
-continued
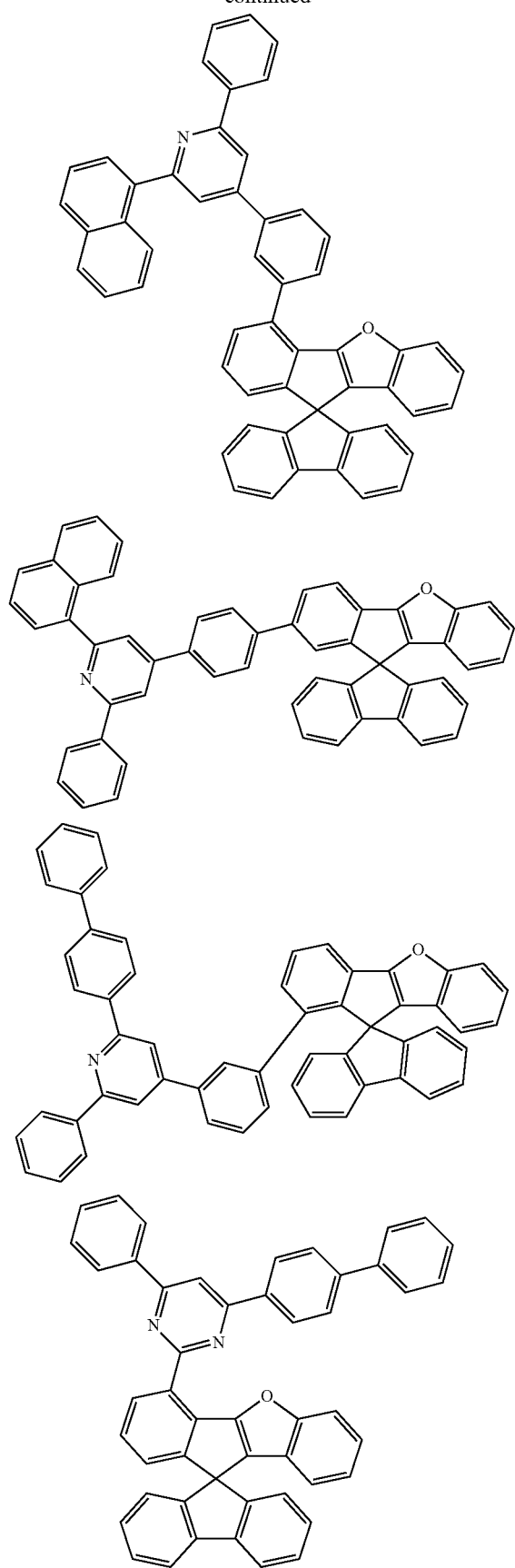
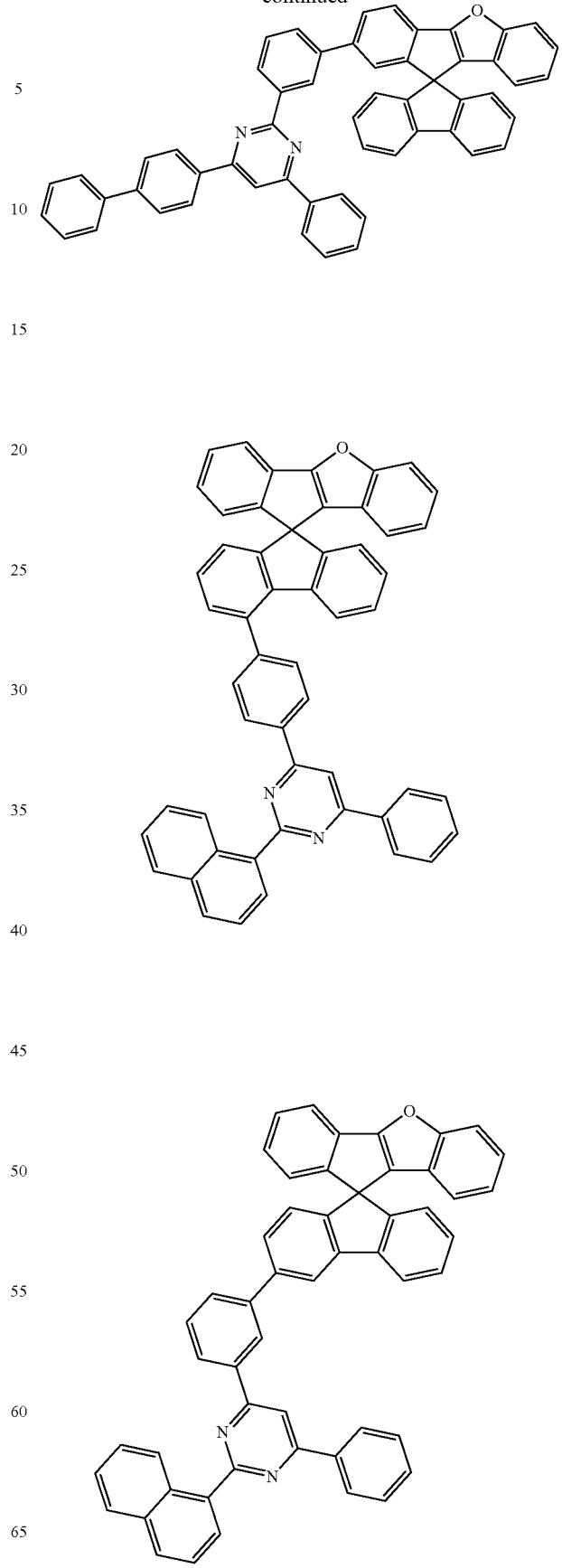

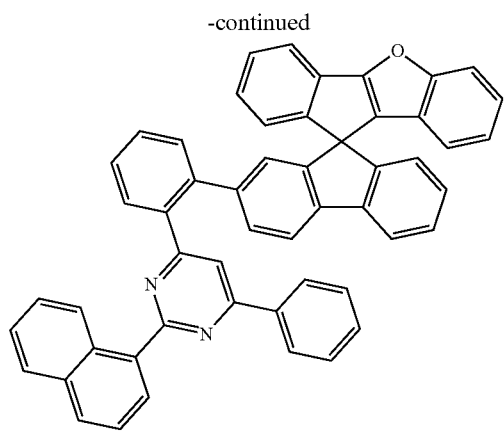
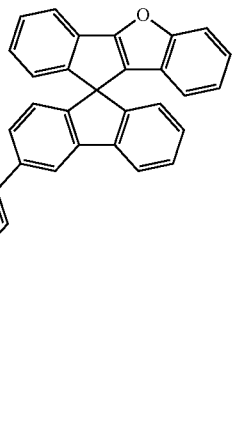
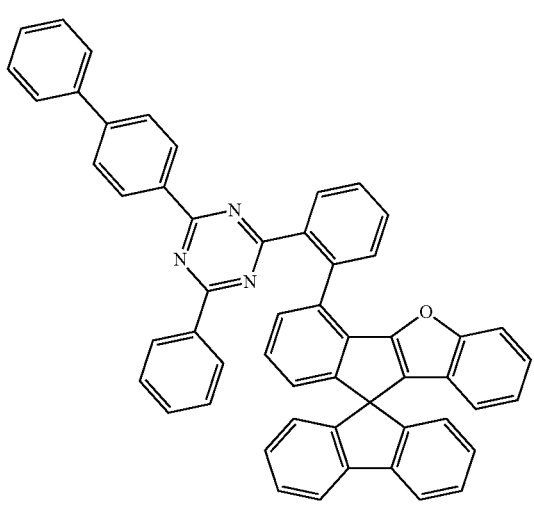
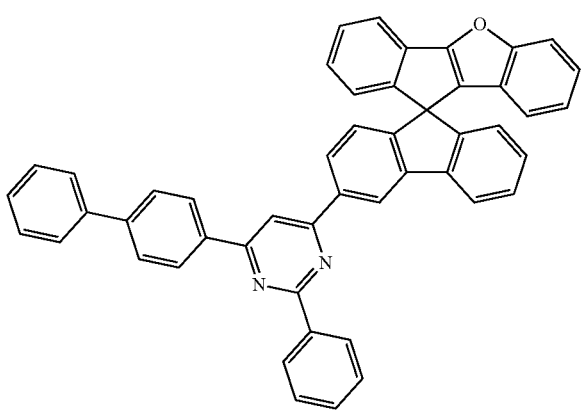

263
-continued
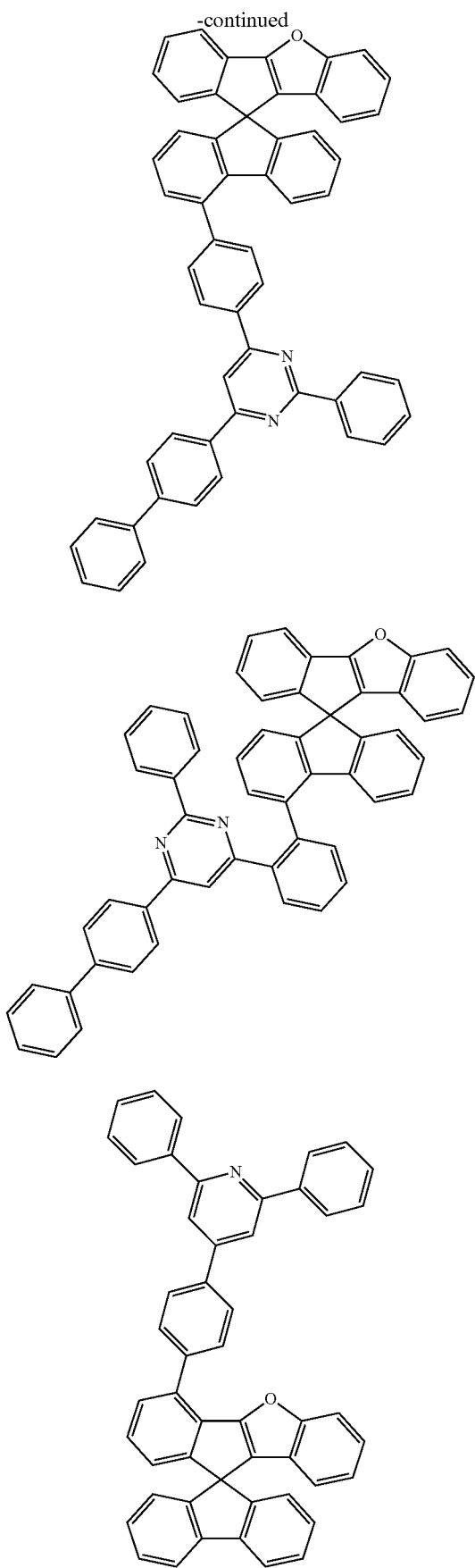
264
-continued
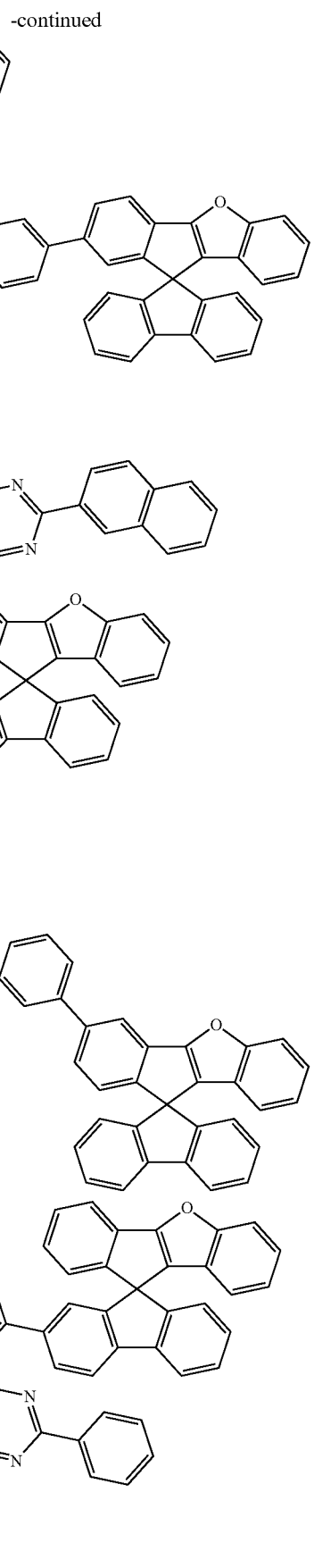

265
-continued
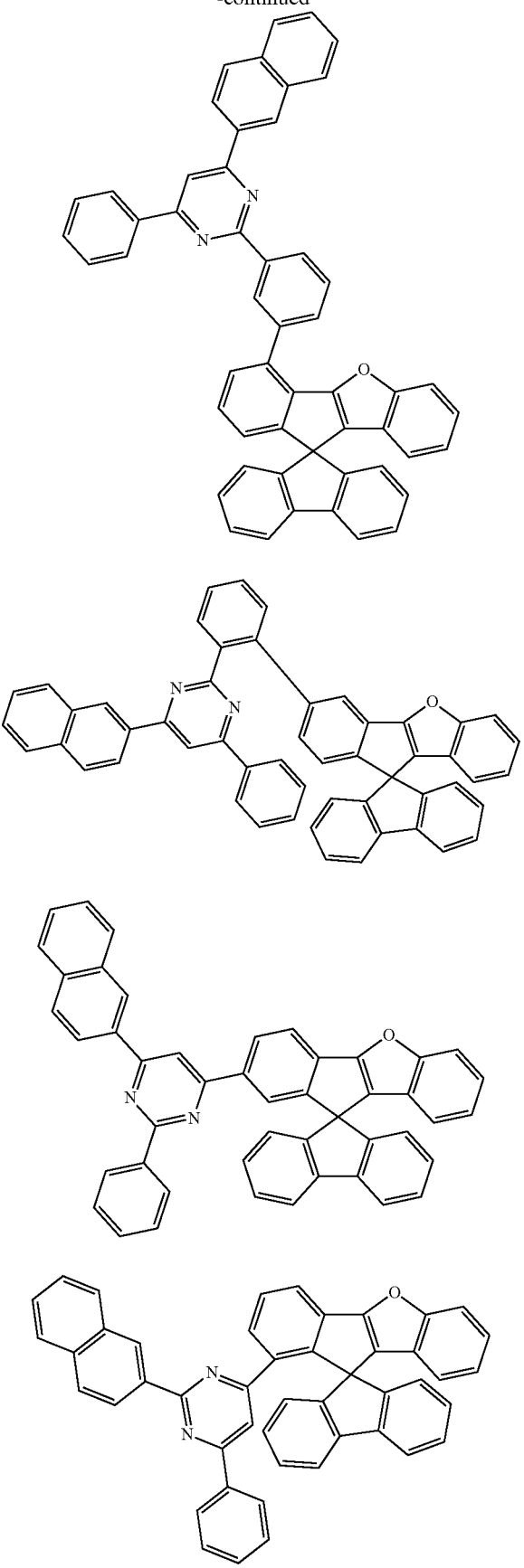
266
-continued
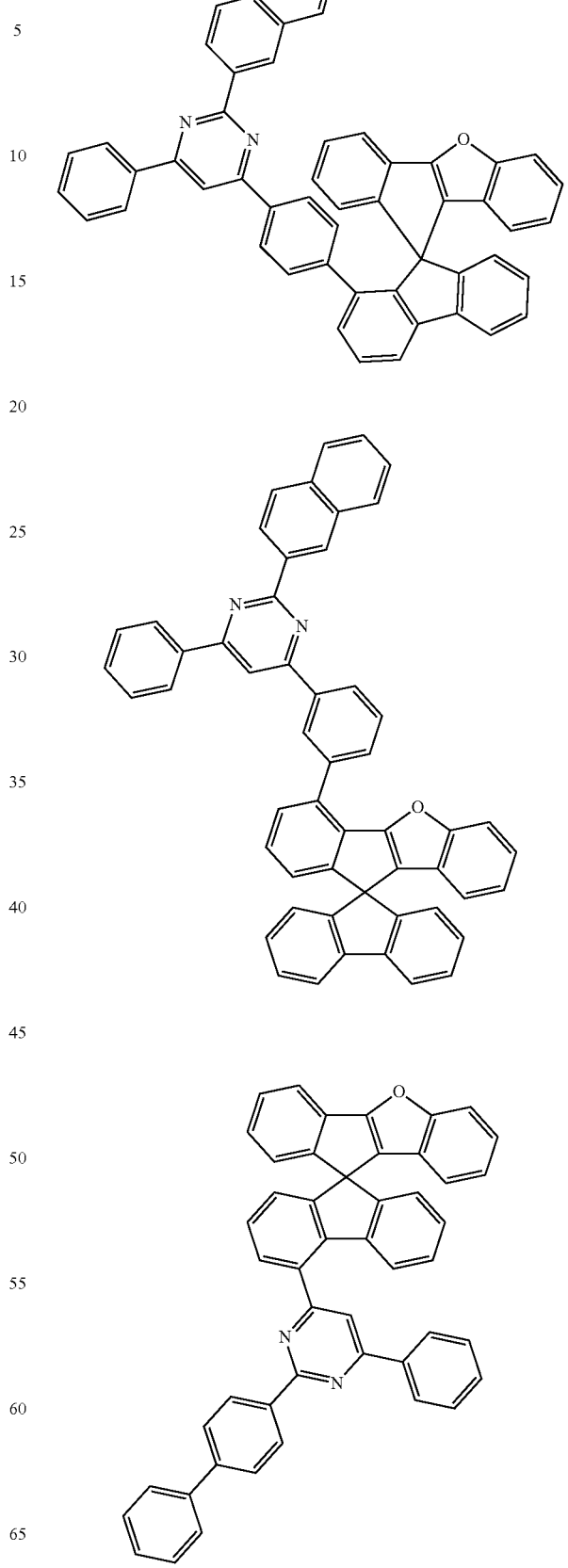

267
-continued
268
-continued
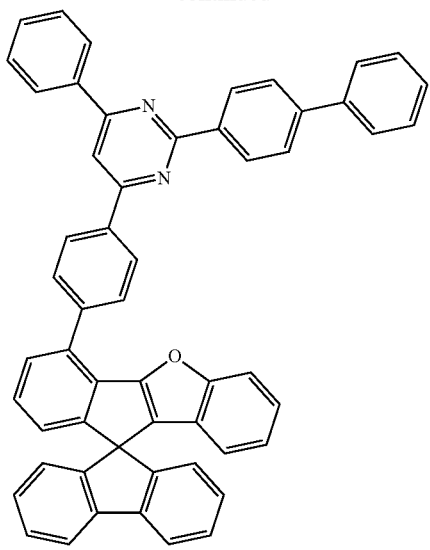
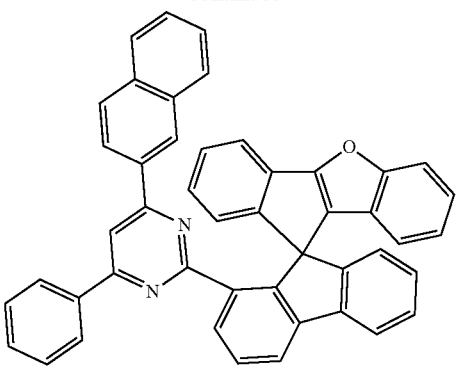
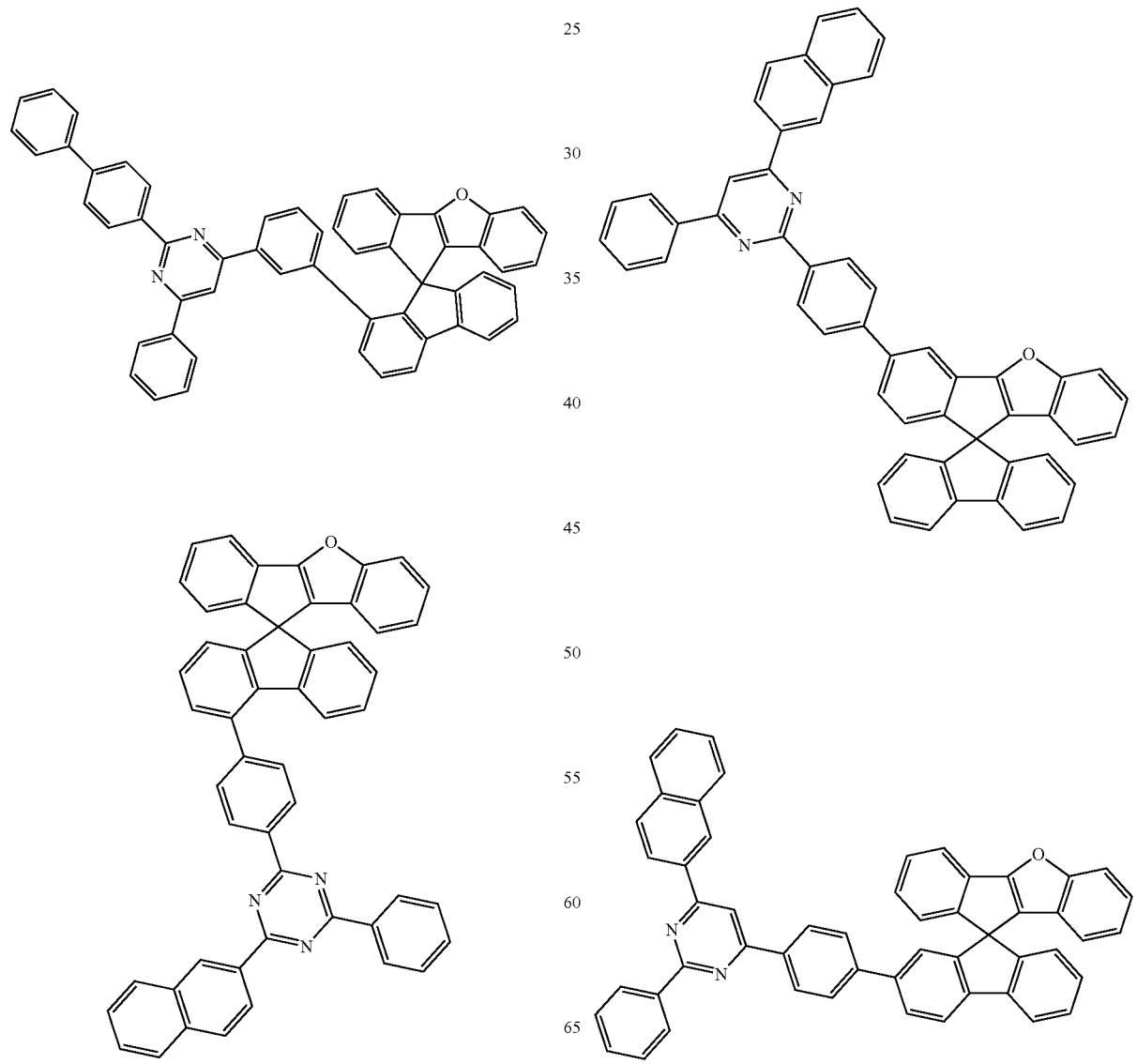

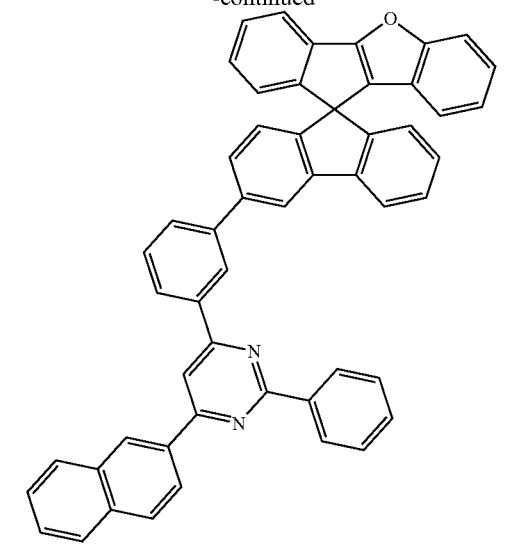
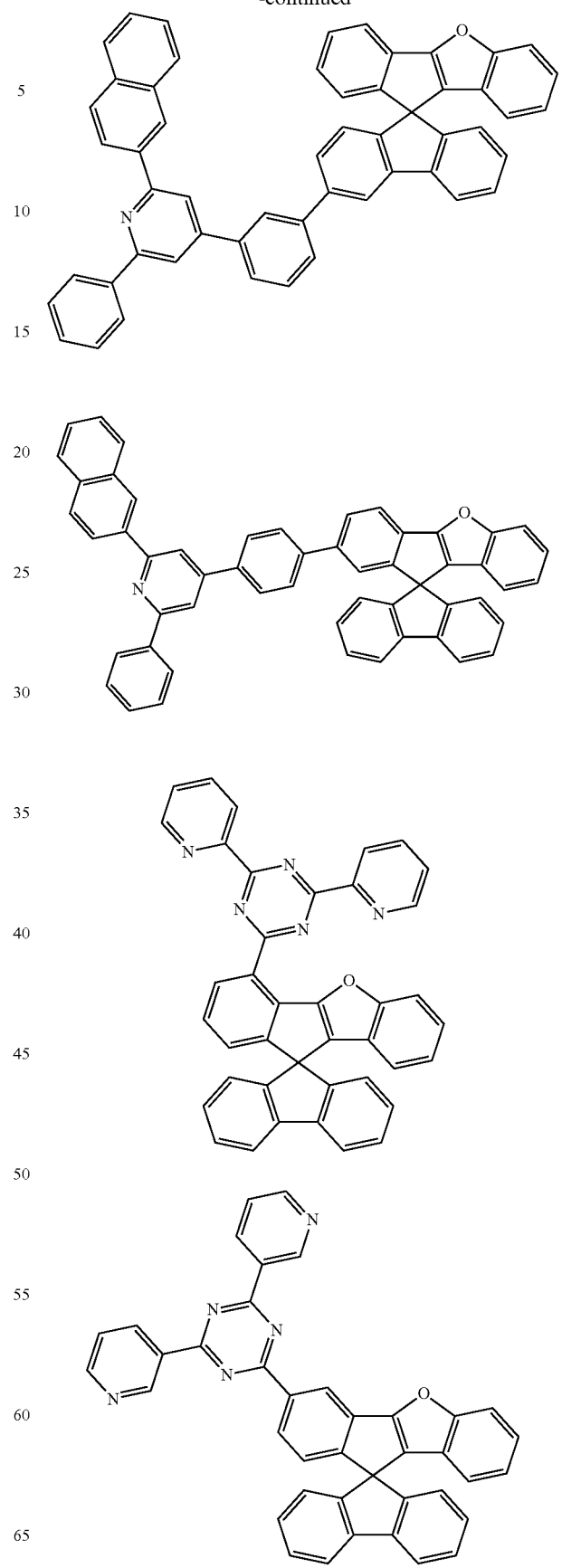

271
-continued
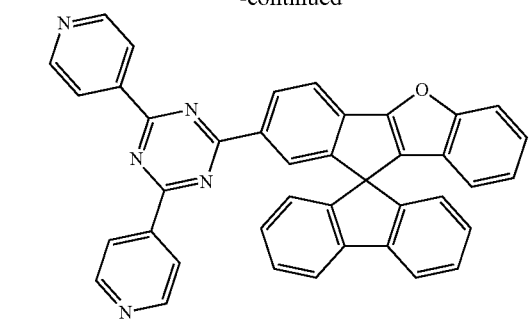
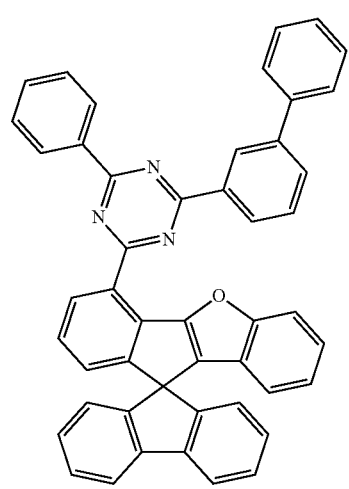
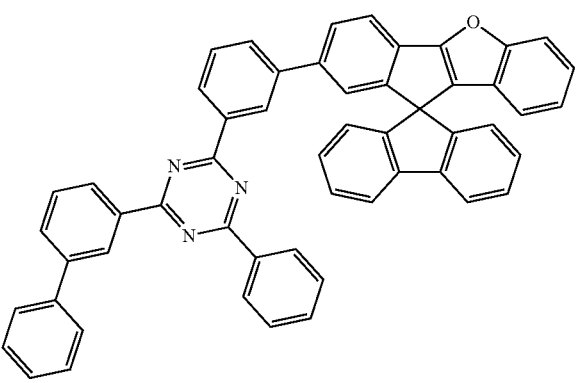
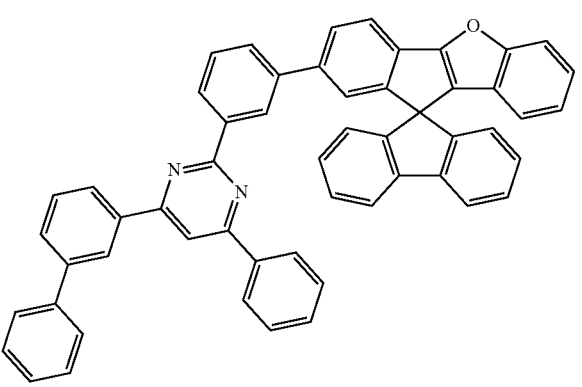
272
-continued
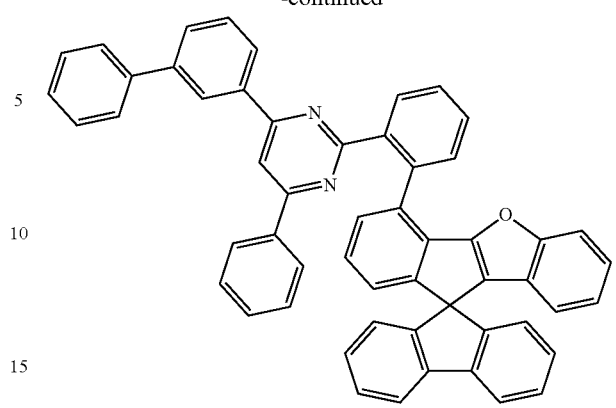
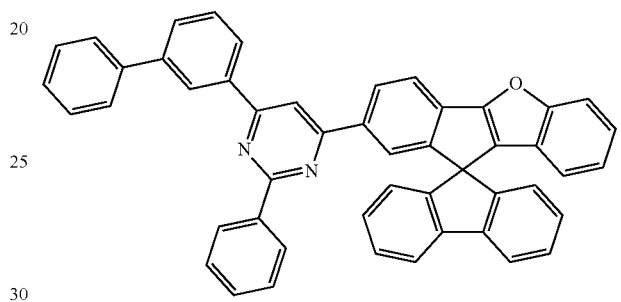
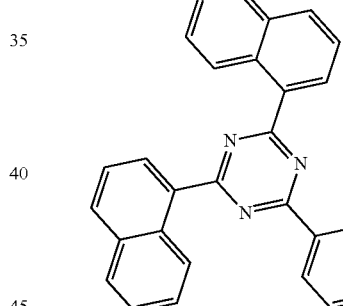
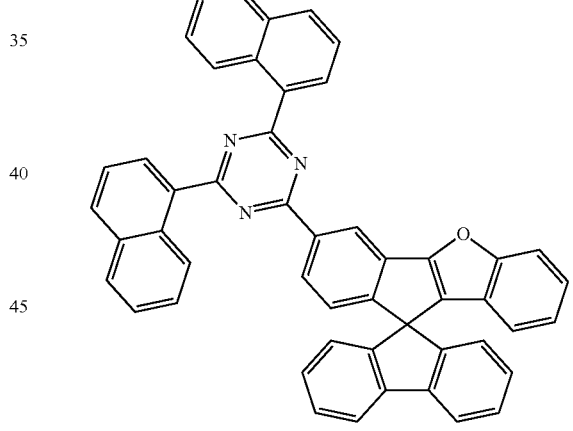
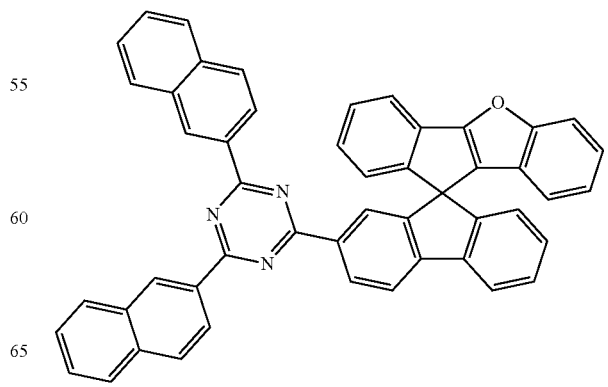

273
-continued
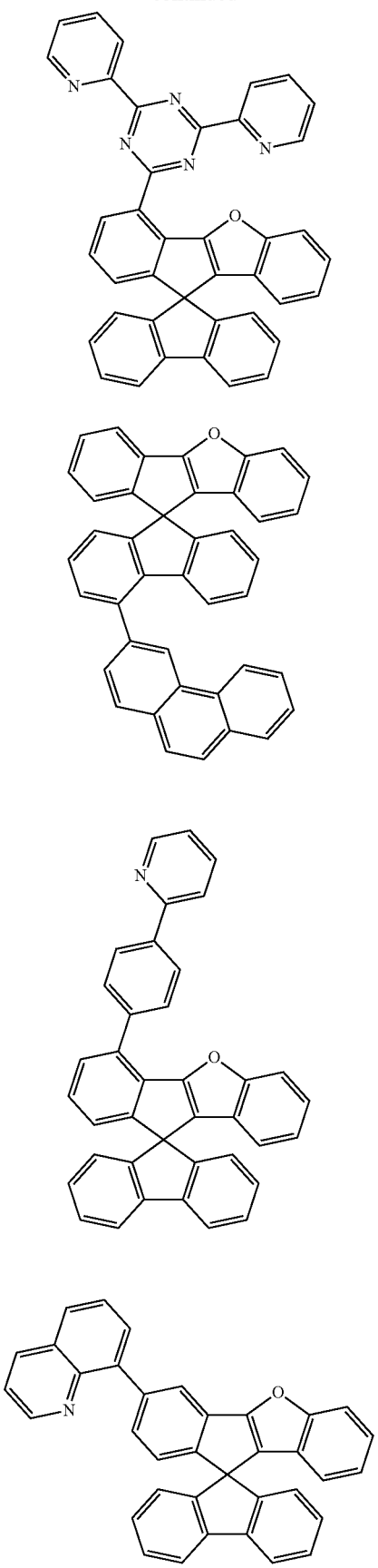
274
-continued
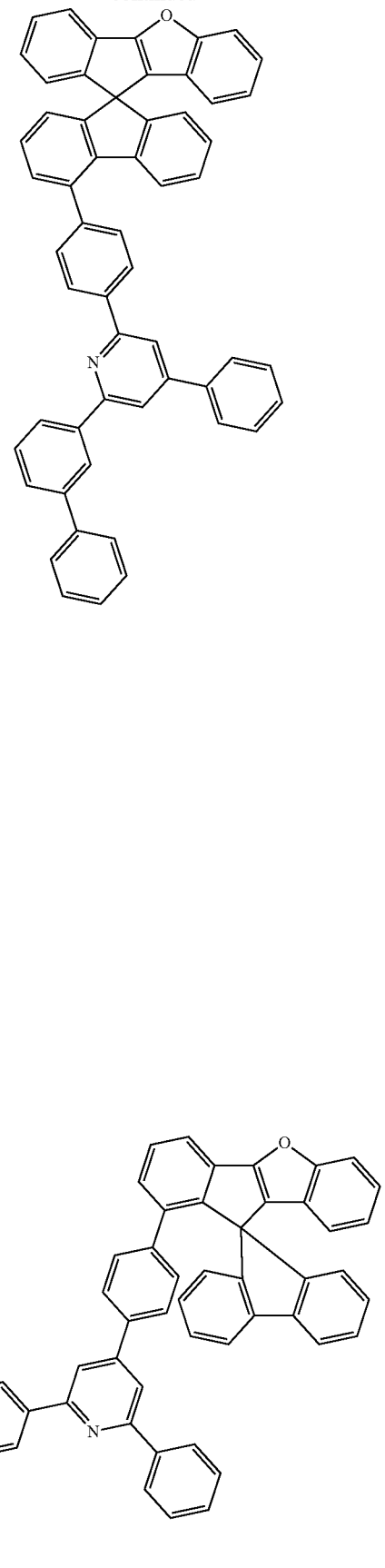

275
-continued
276
-continued
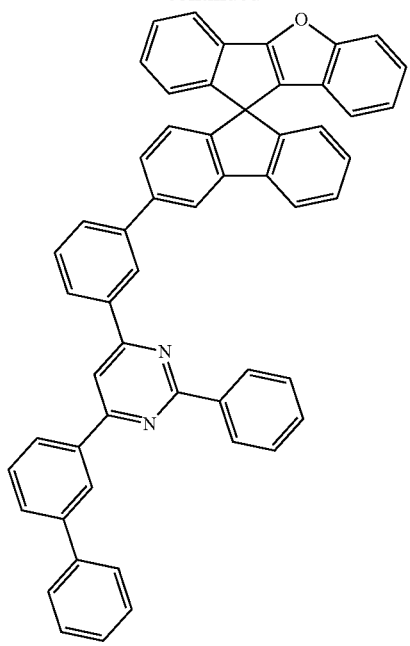
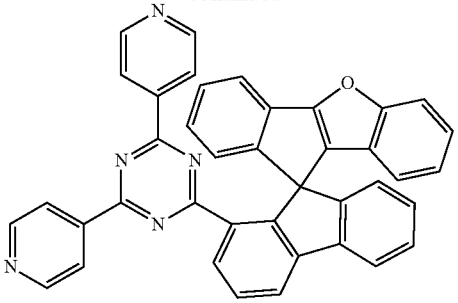
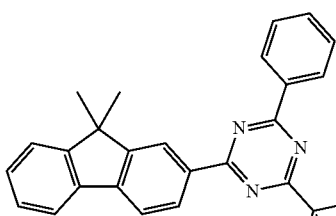
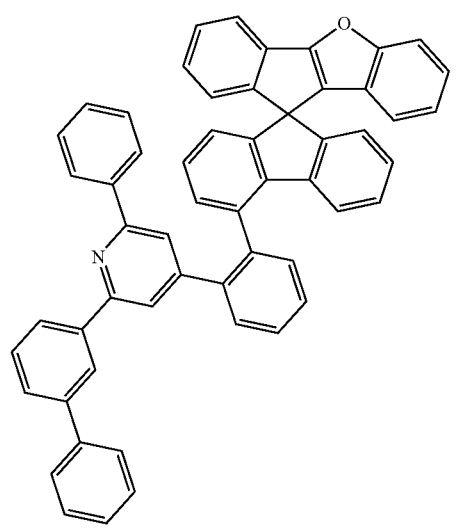
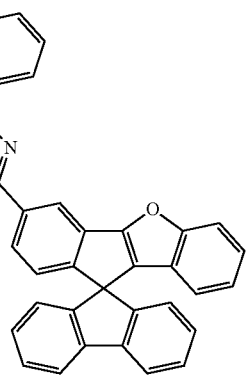
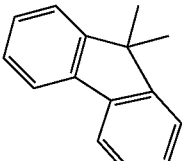
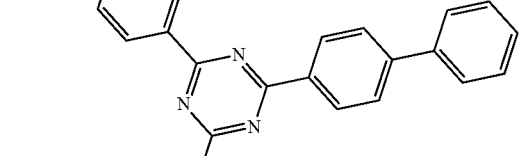
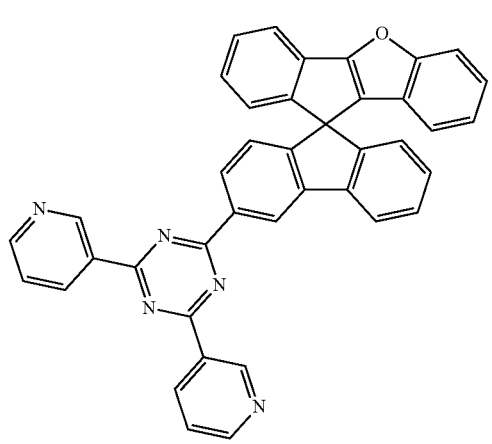
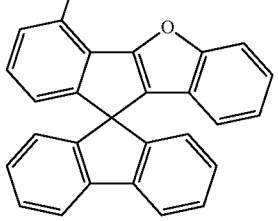

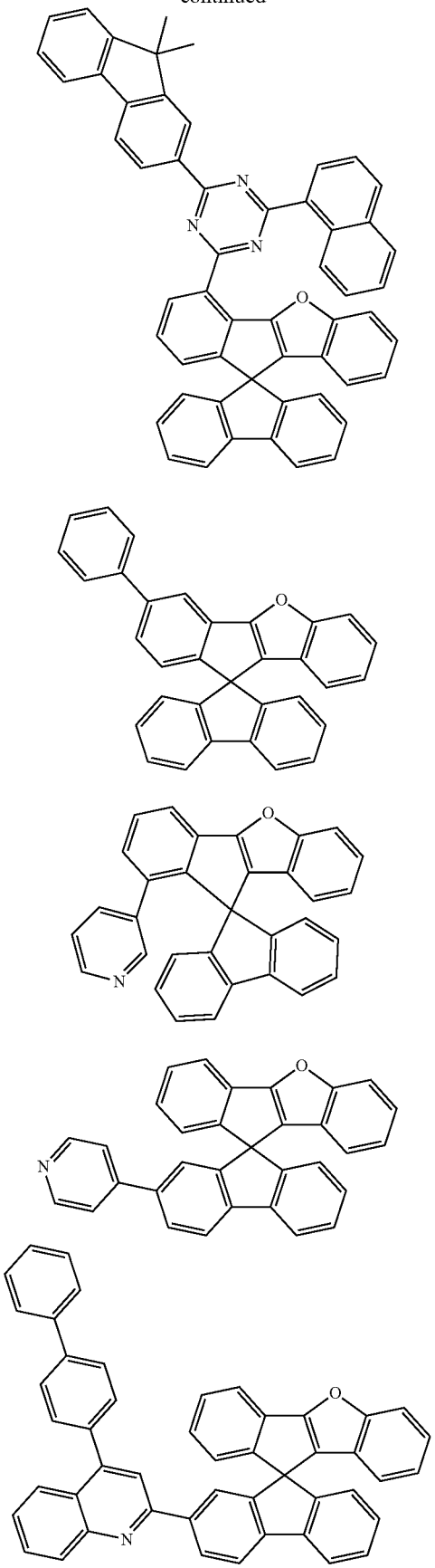
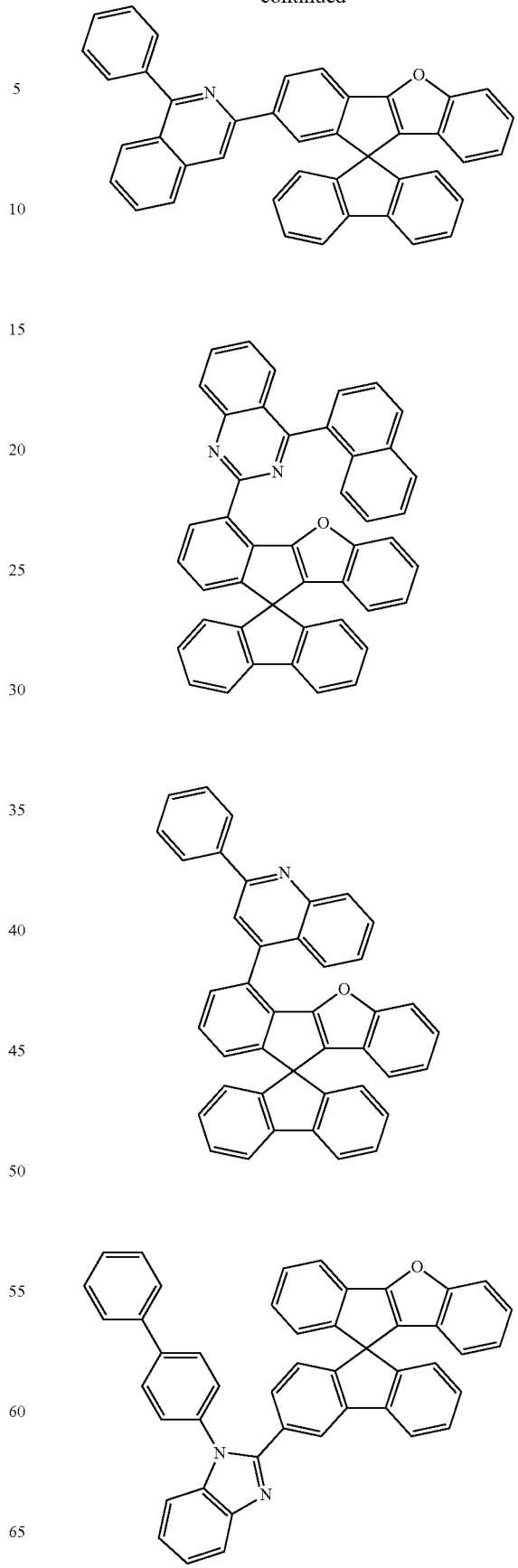

279
-continued
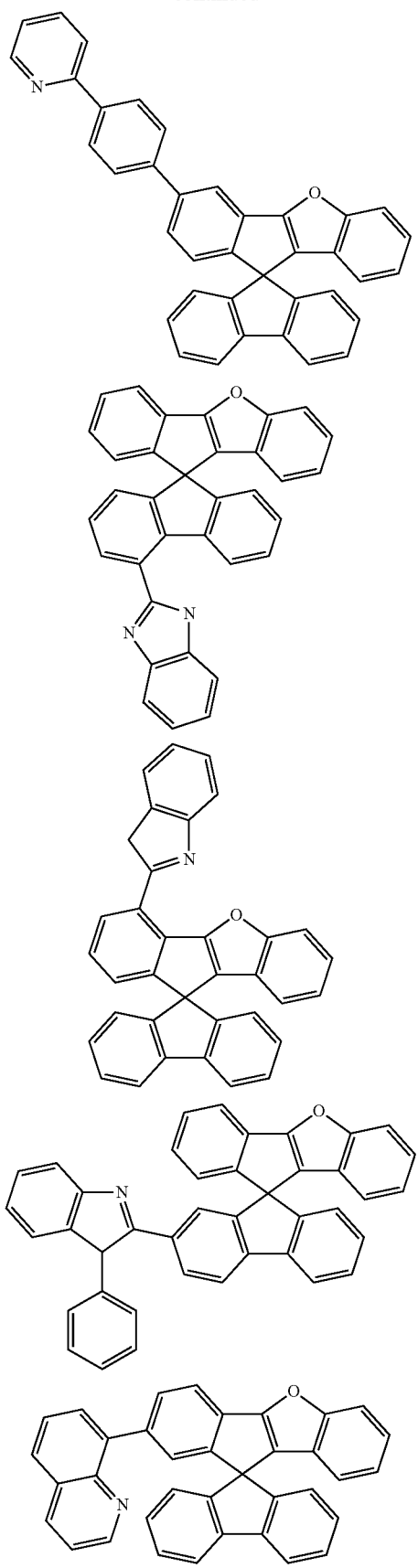
280
-continued
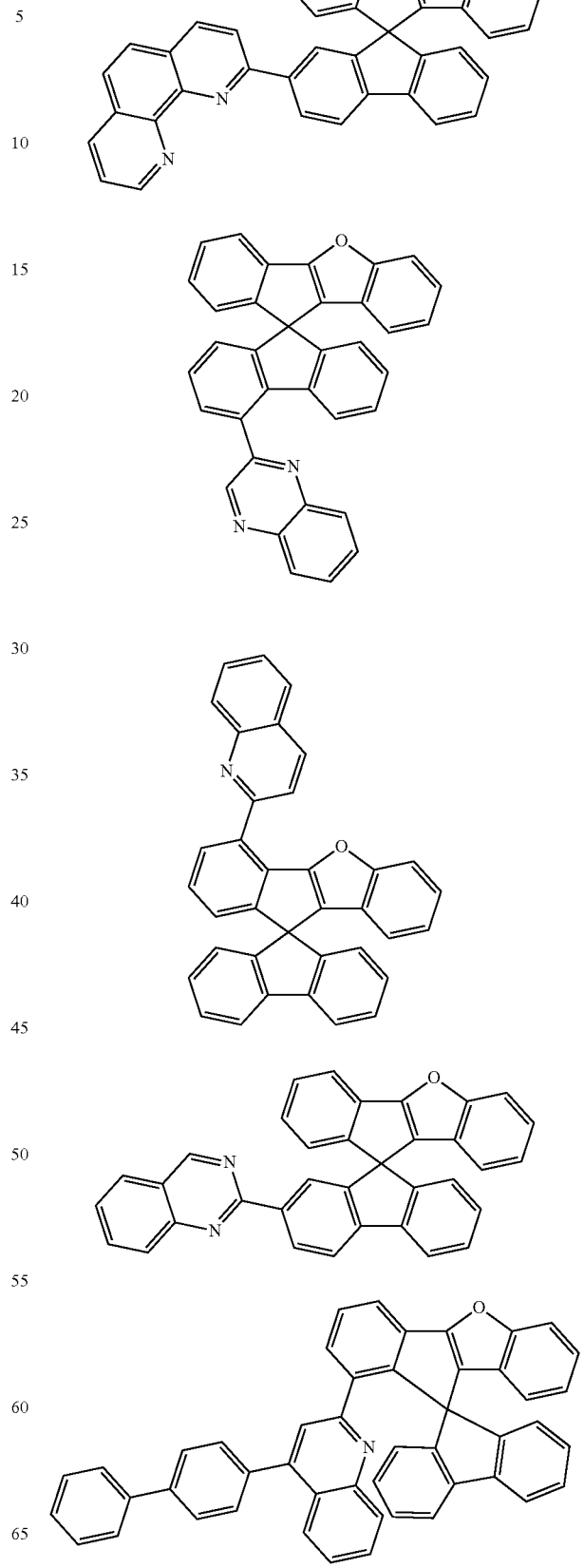

281
-continued
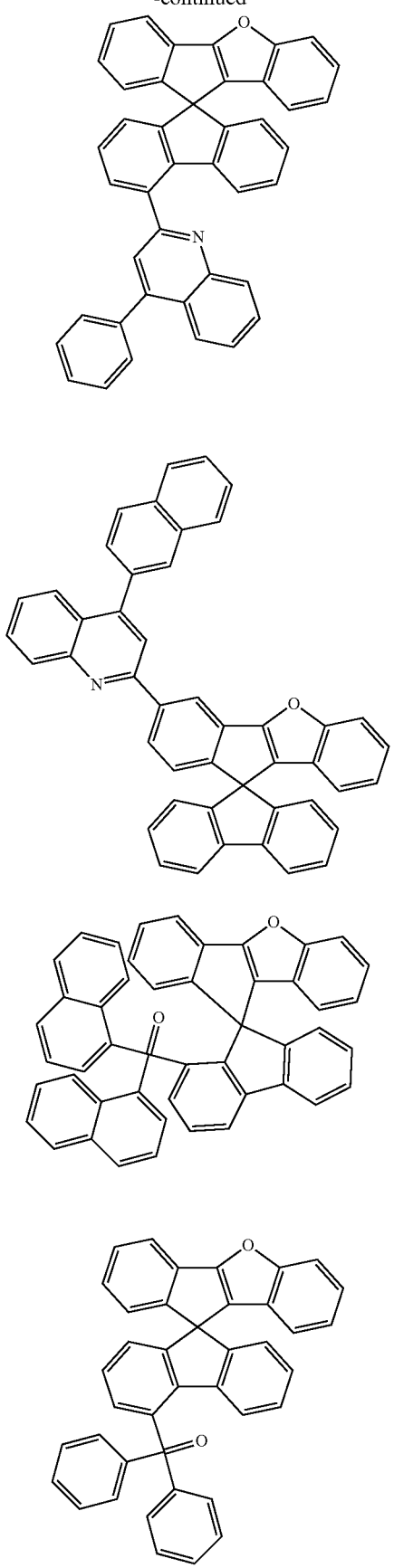
282
-continued
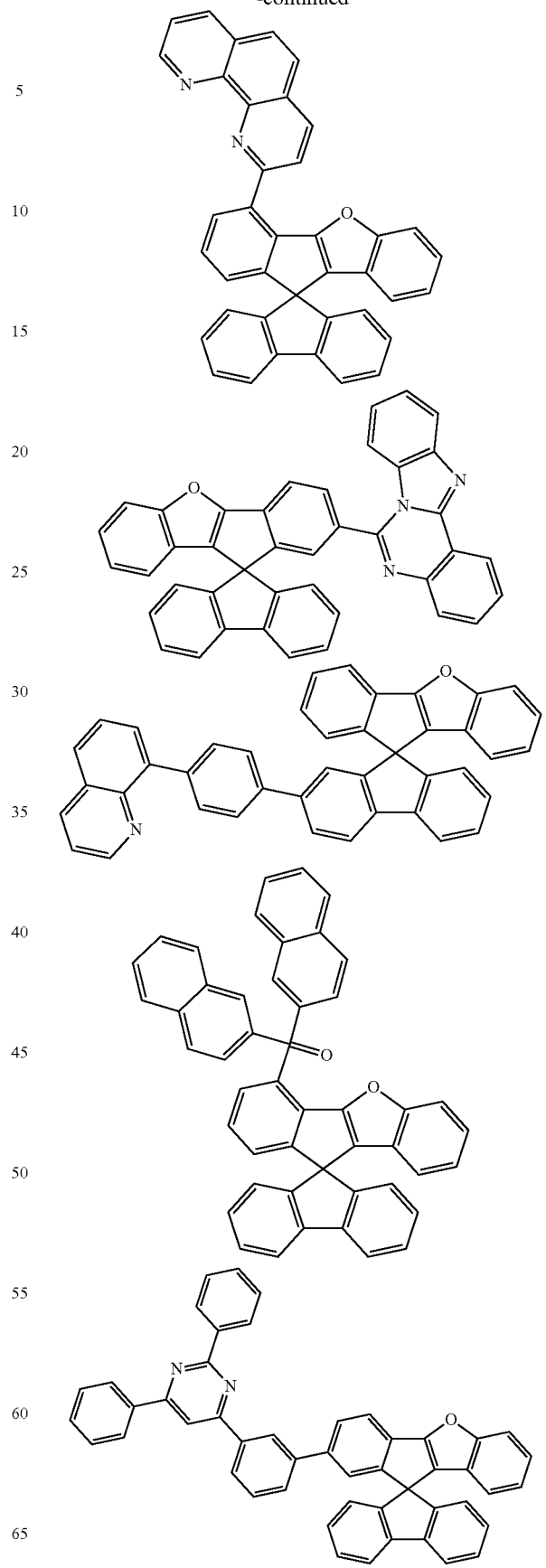

283
-continued
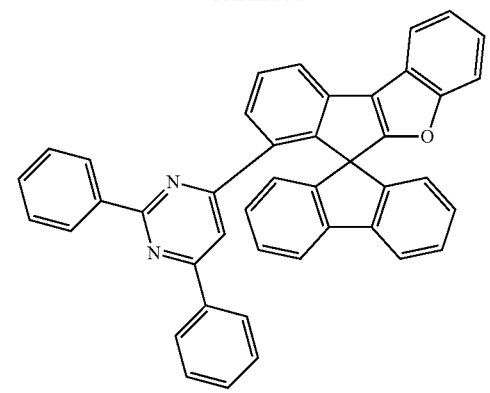
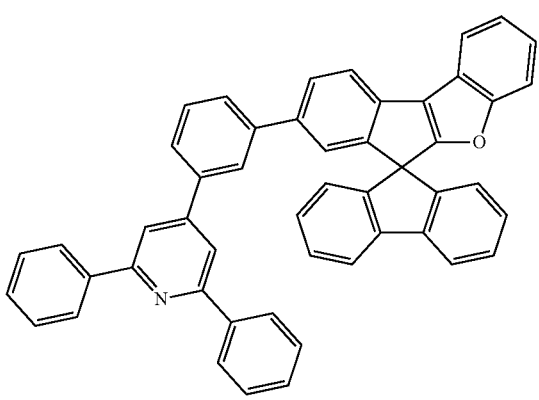
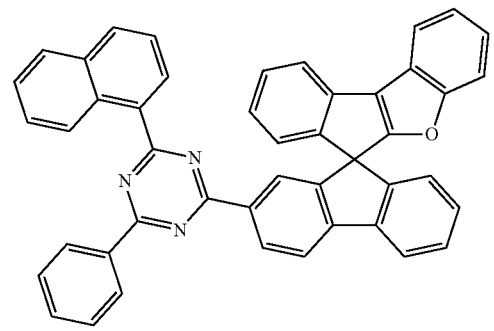
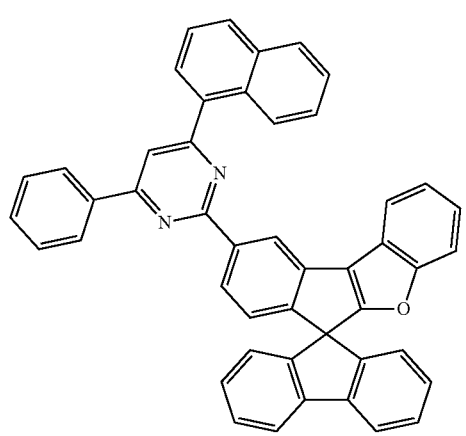
284
-continued
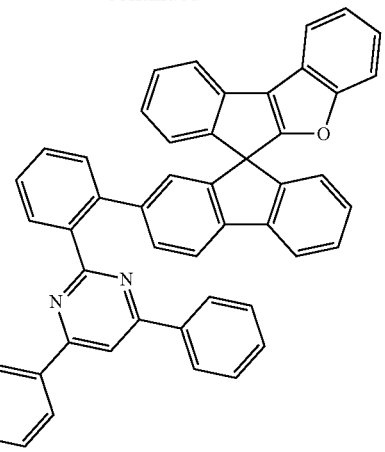
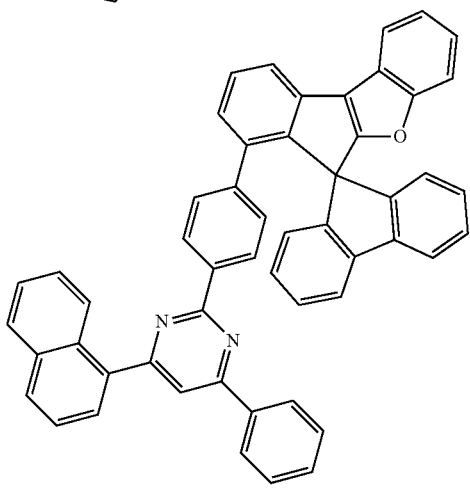
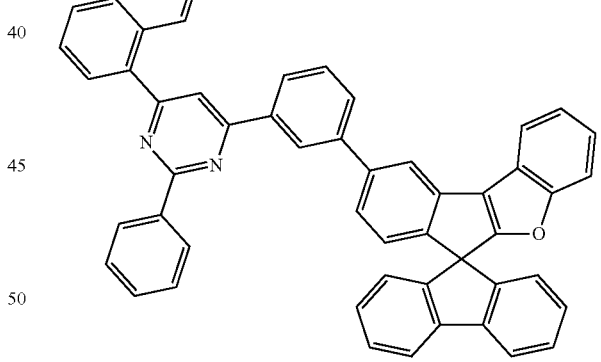
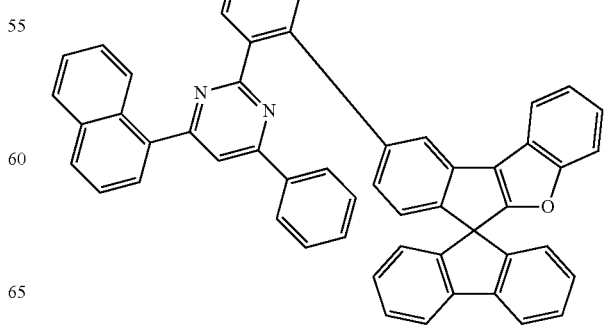

285
-continued
286
-continued
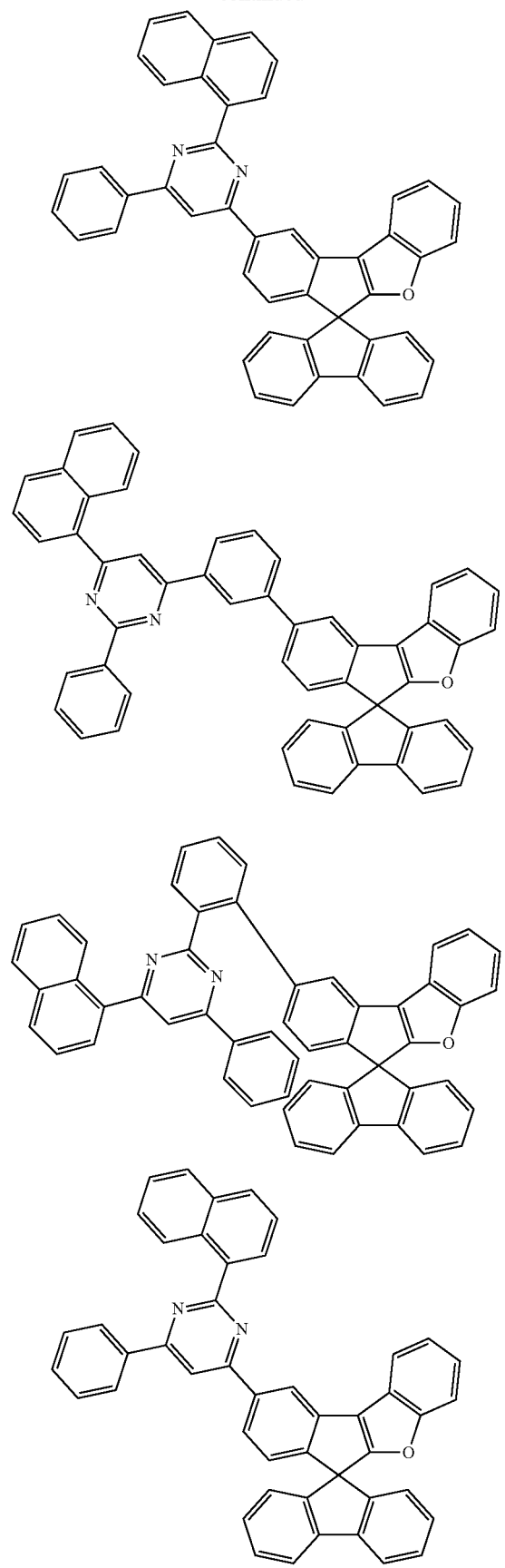
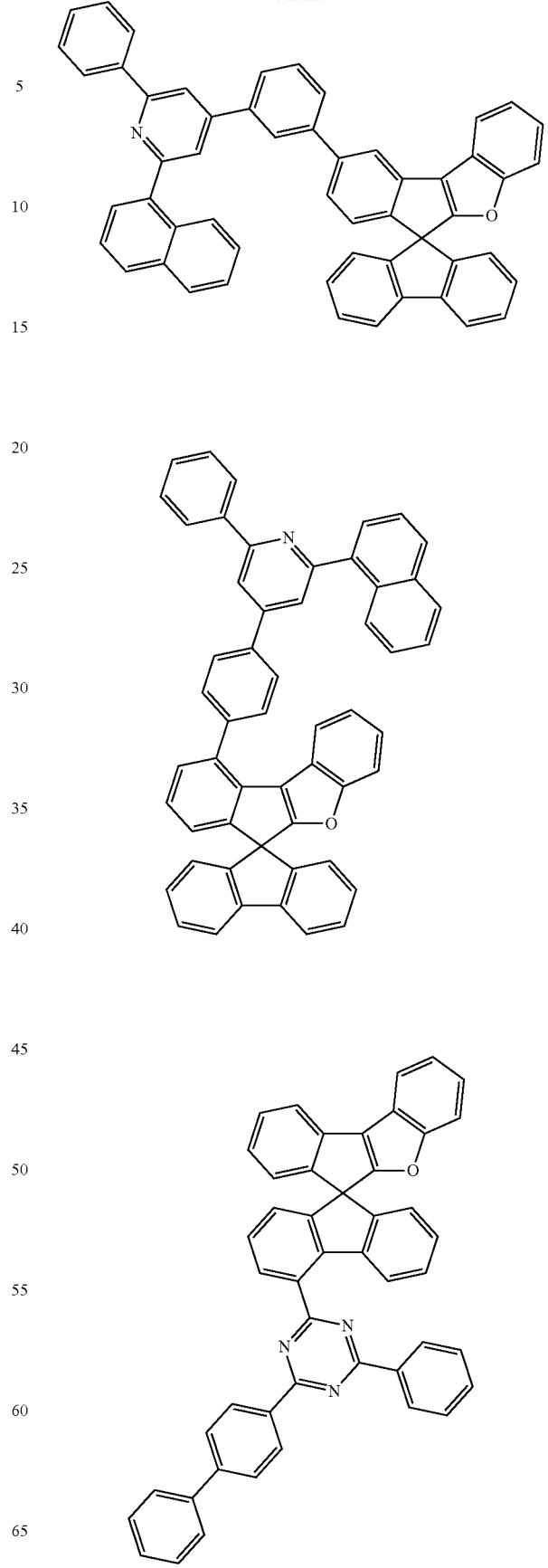

287
-continued
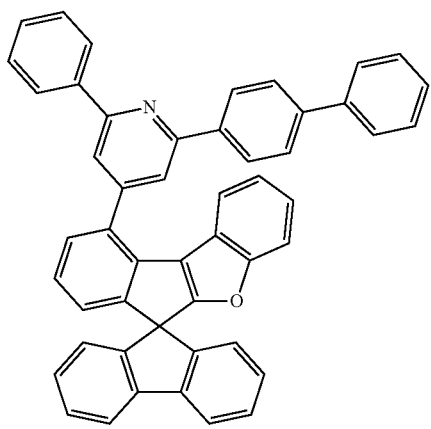
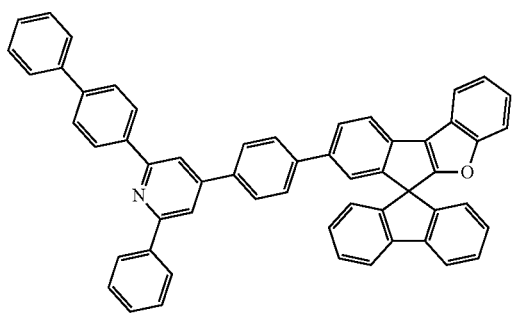
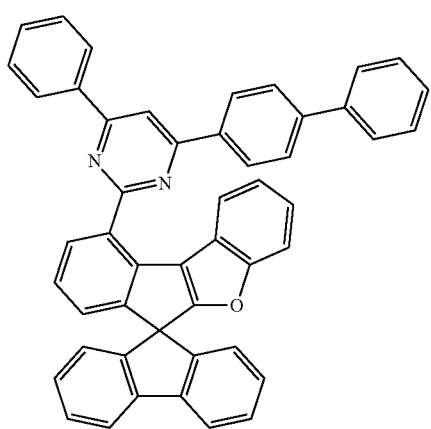
288
-continued
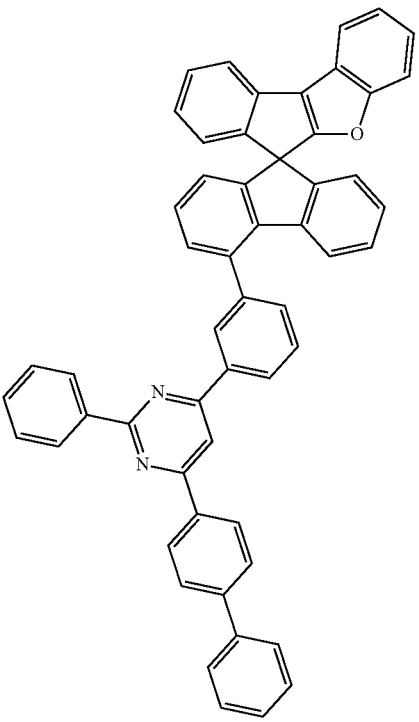
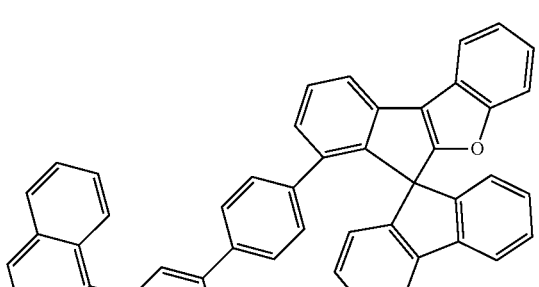
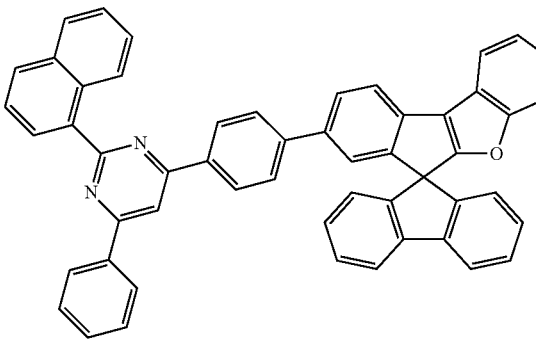

289
-continued
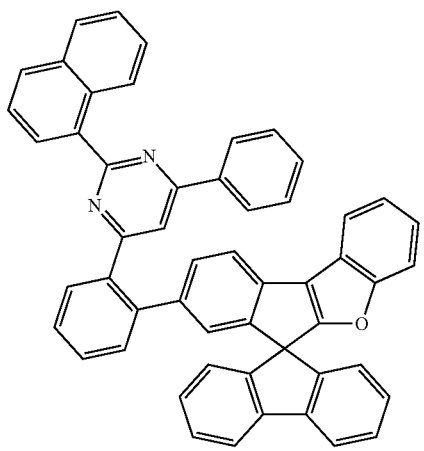
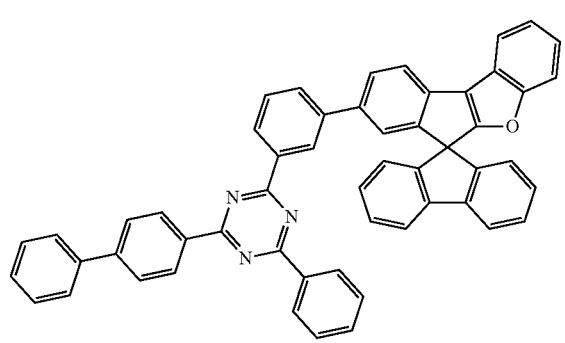
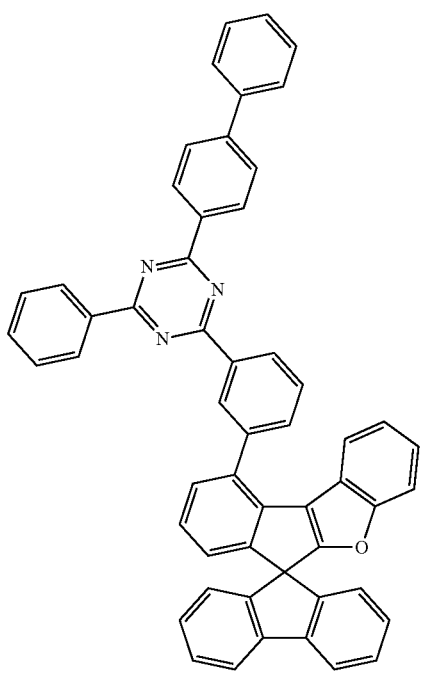
290
-continued
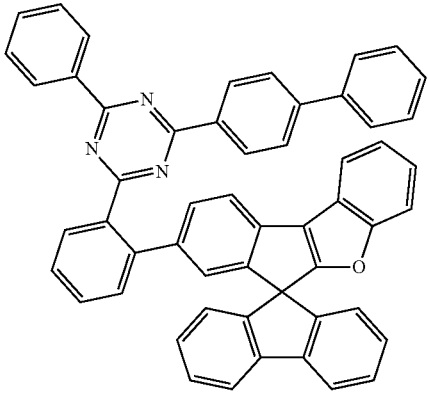
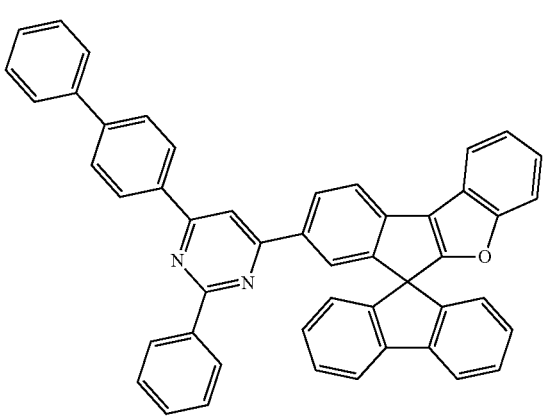
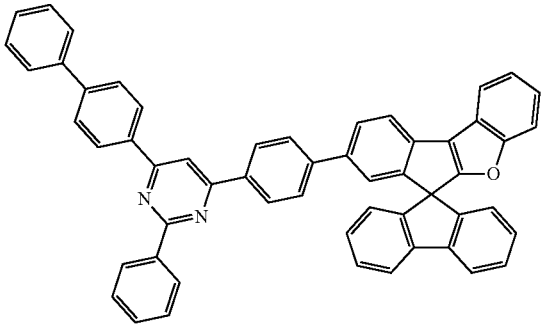
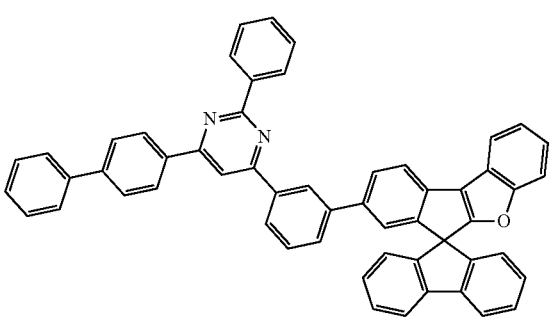

291
-continued
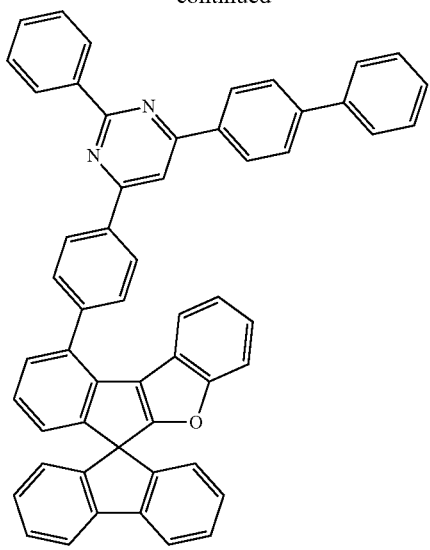
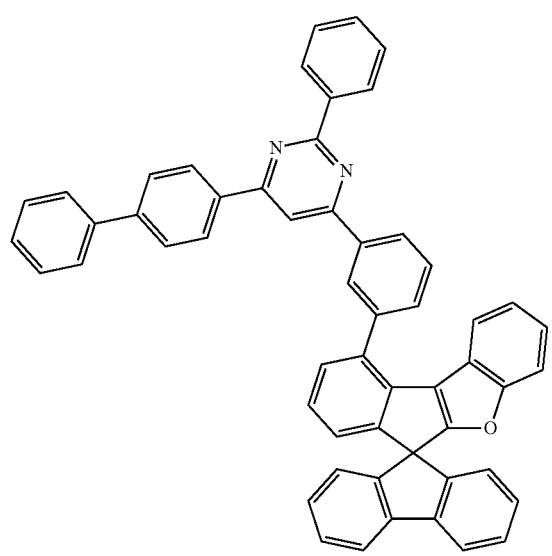
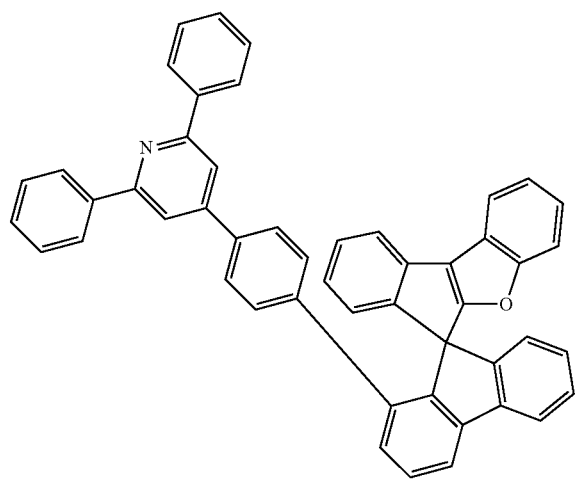
292
-continued
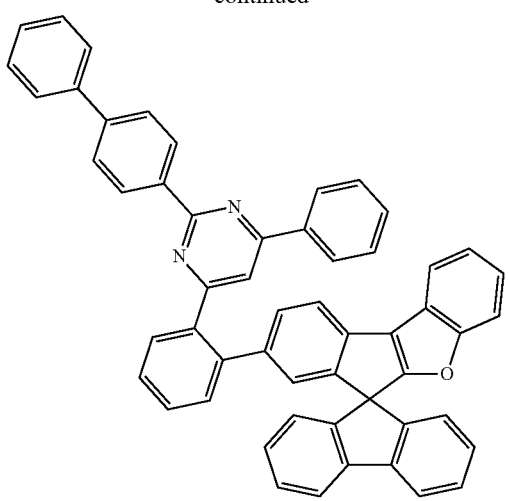
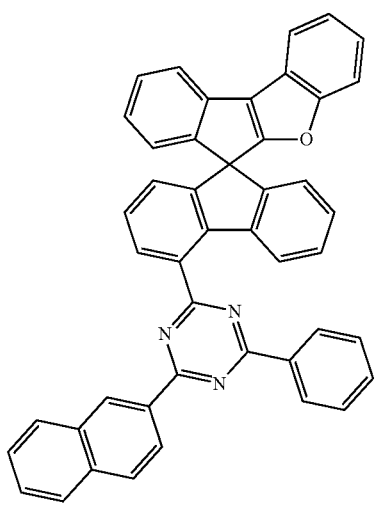
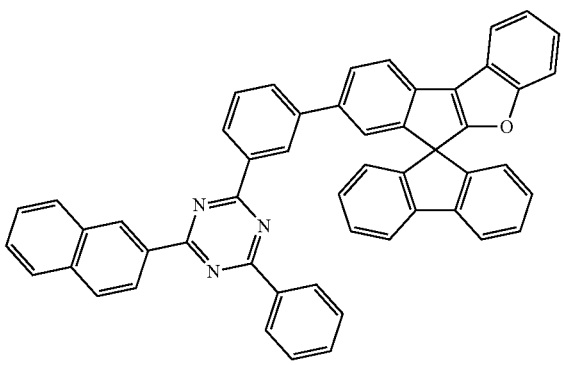

293
-continued
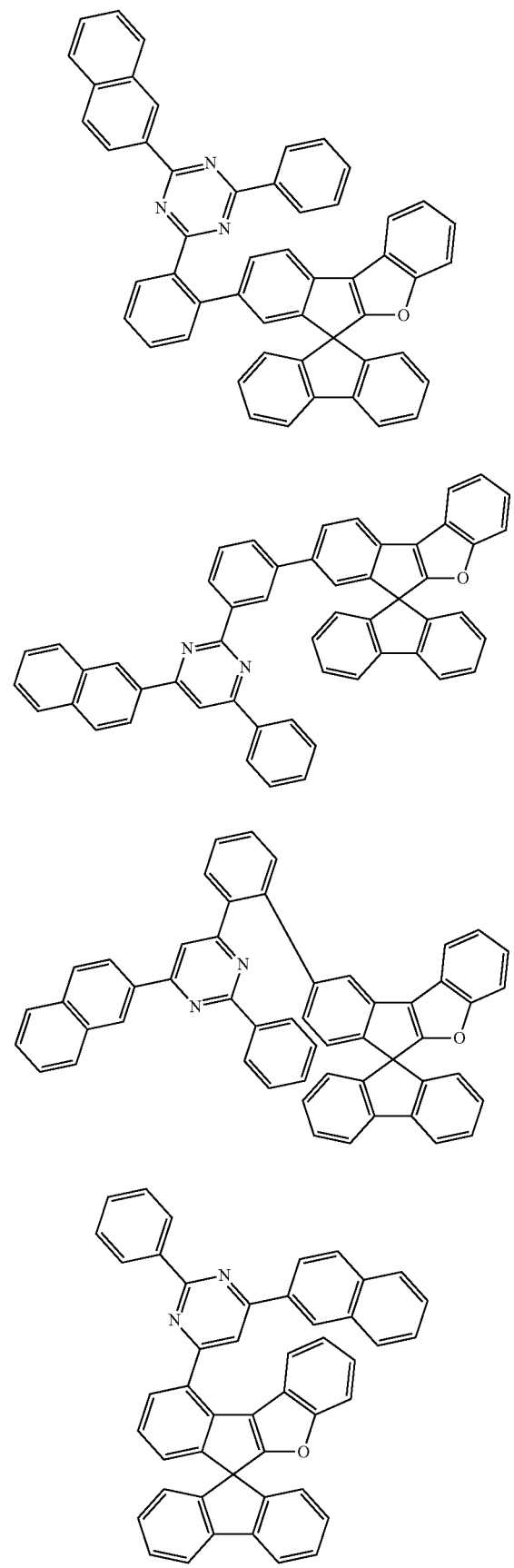
294
-continued
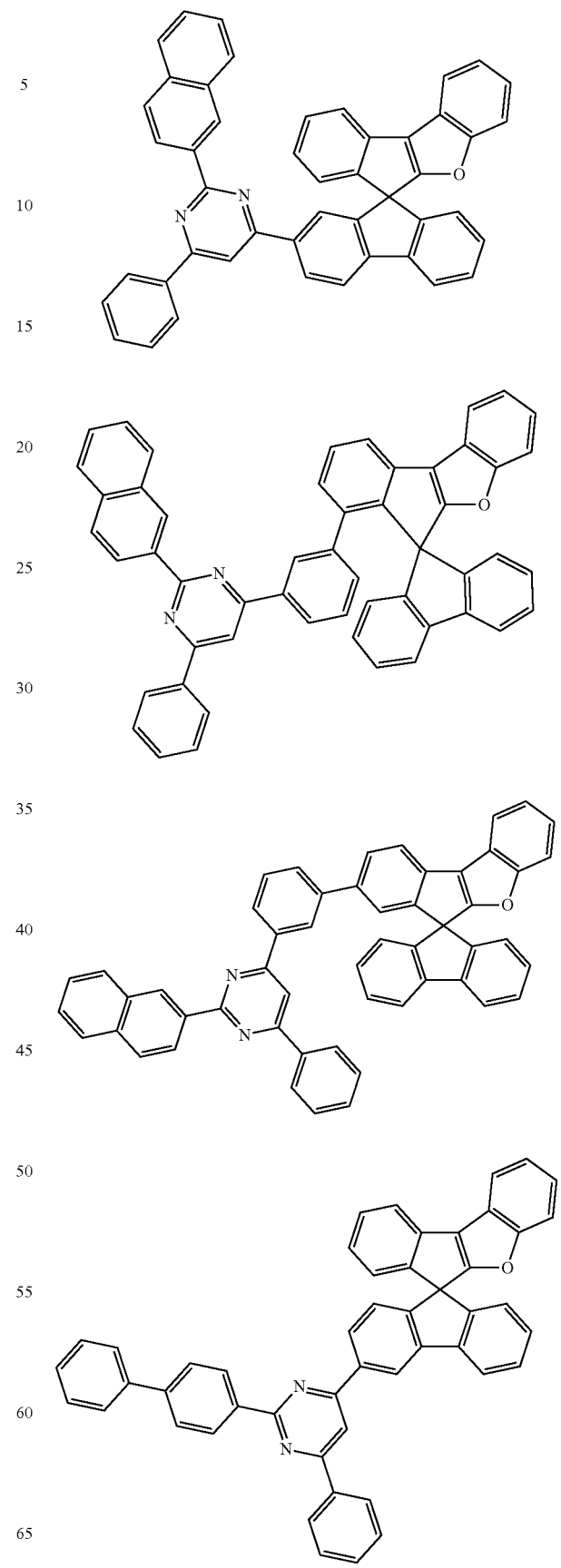

295
-continued
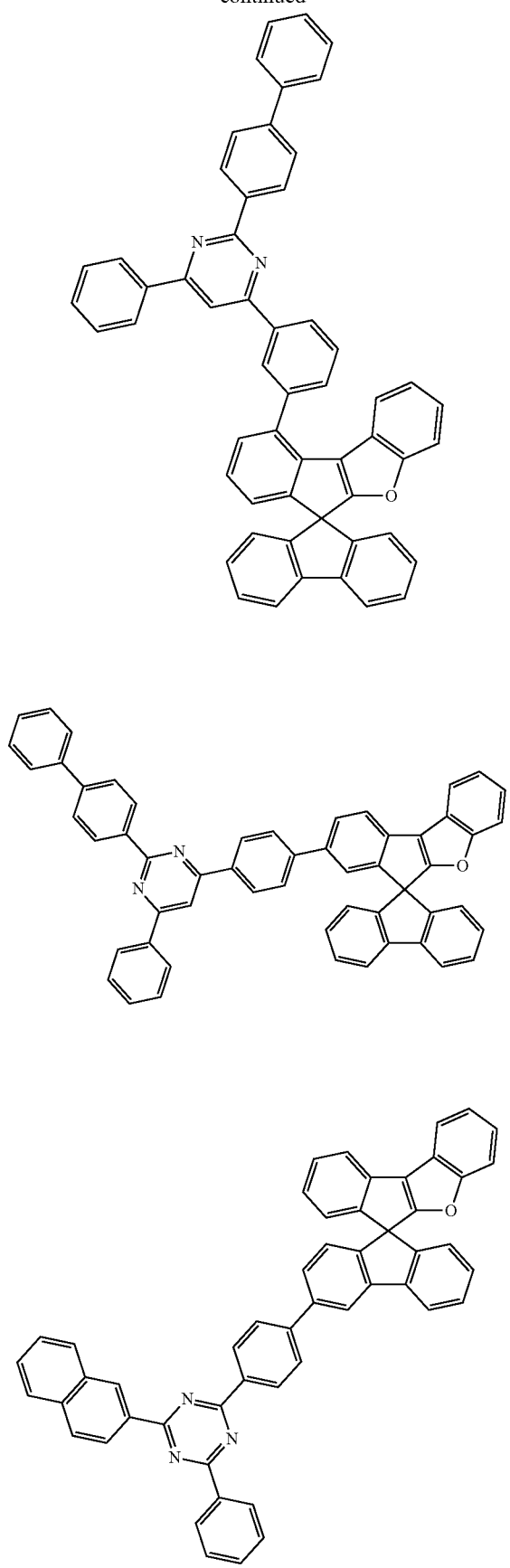
296
-continued
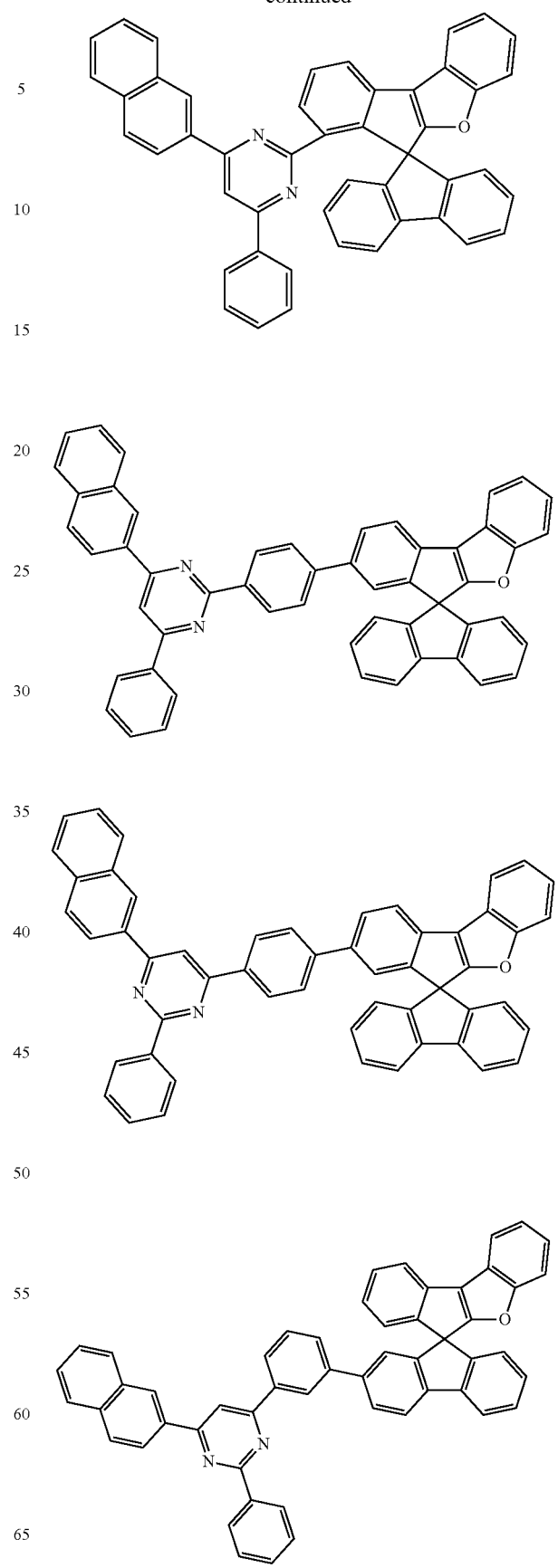

297
-continued
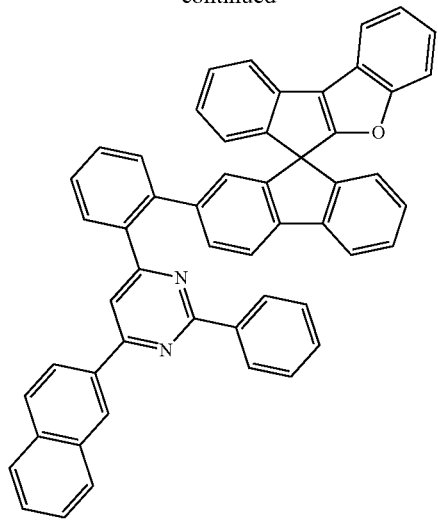
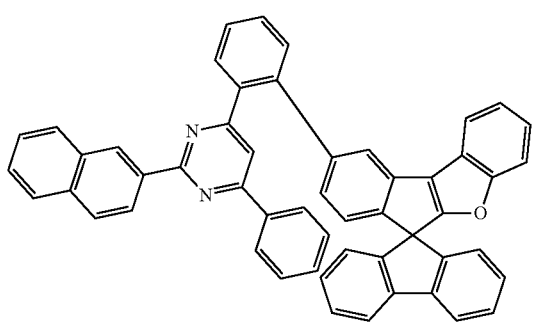
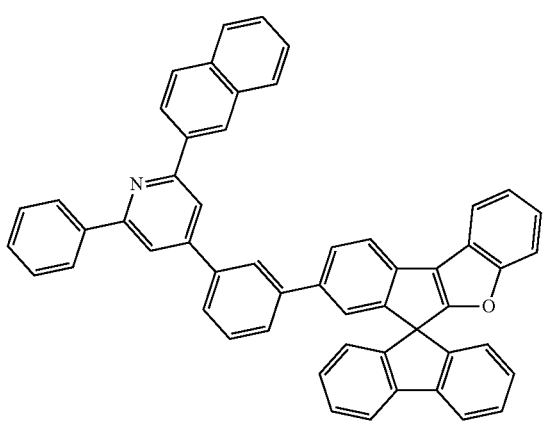
298
-continued
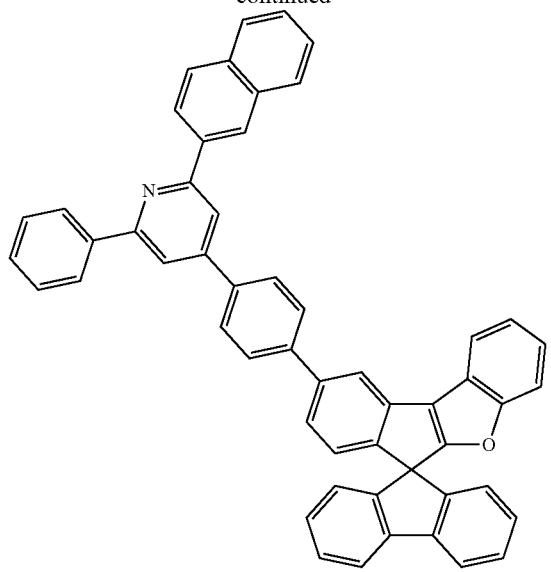
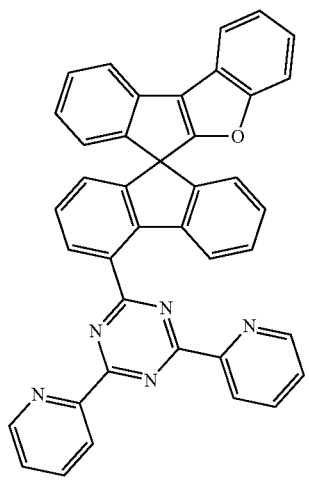
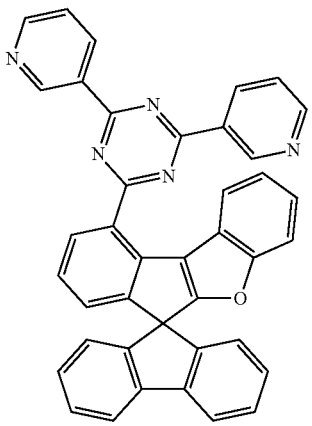

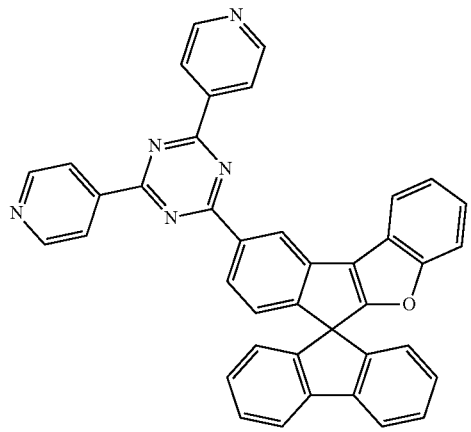
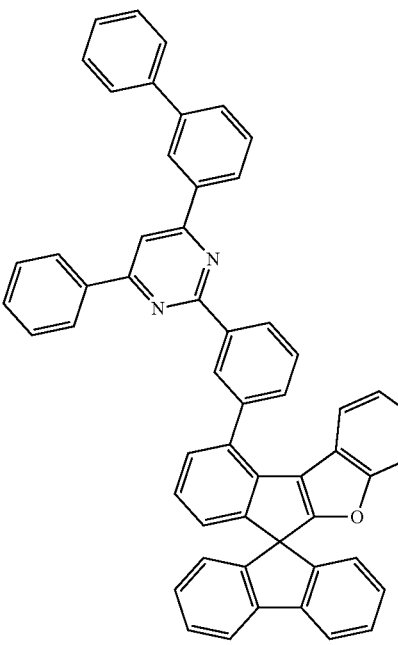
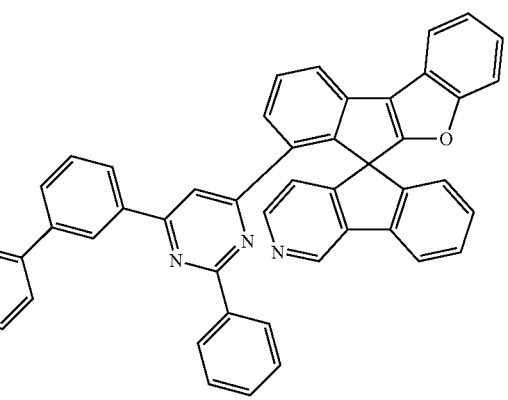
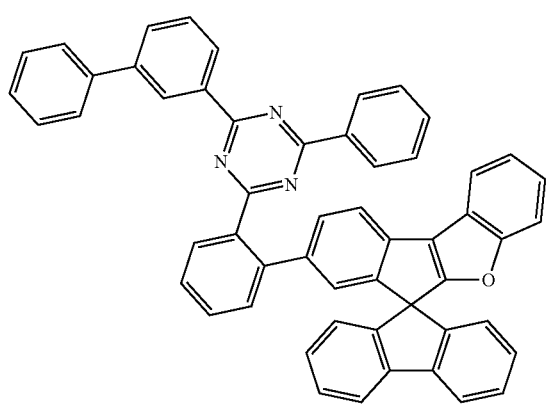
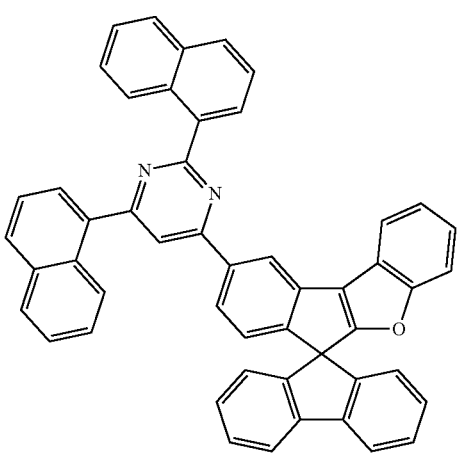

301
-continued
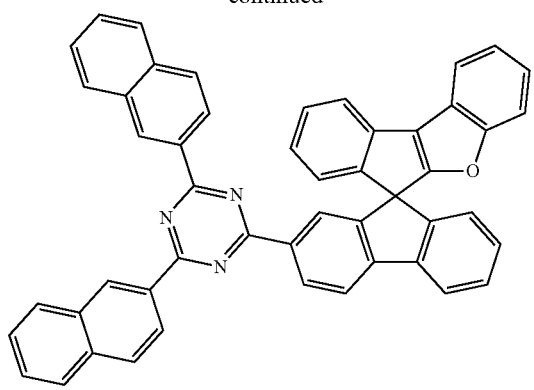
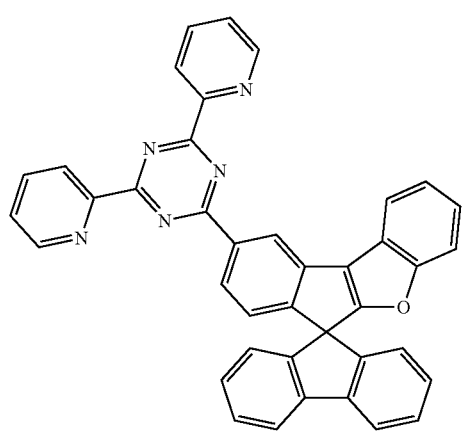
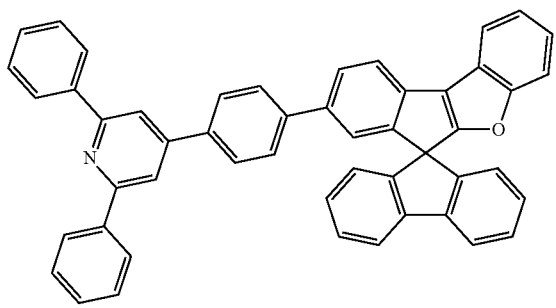
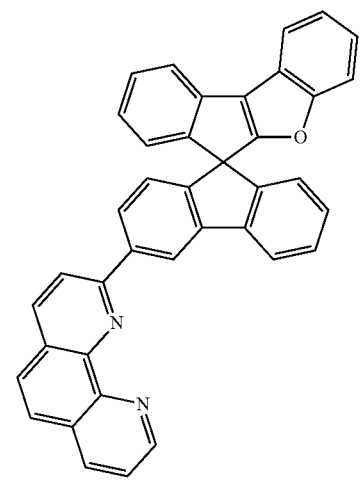
302
-continued
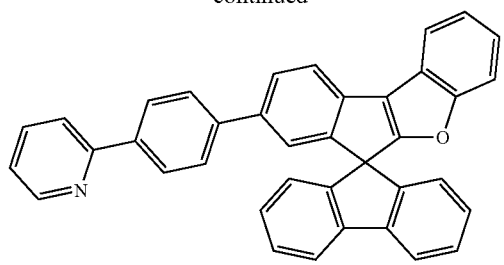
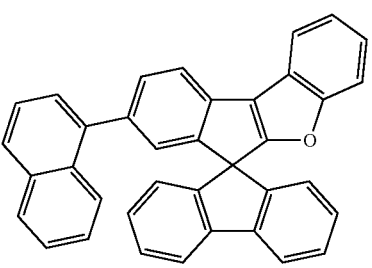
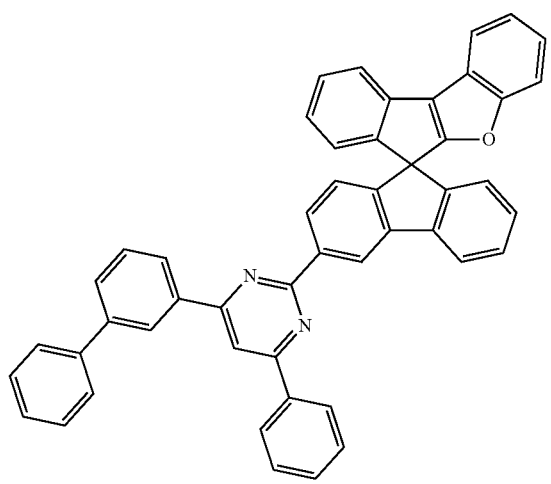
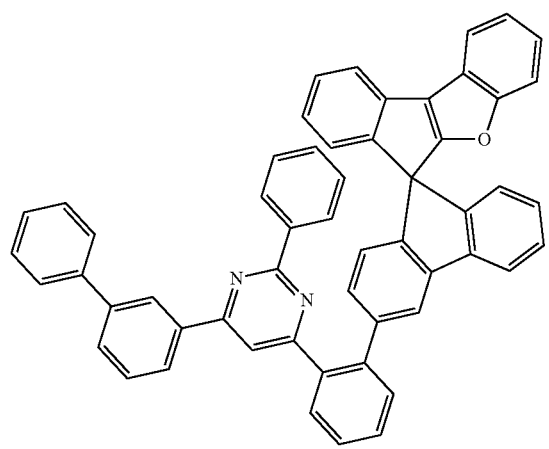

303
-continued
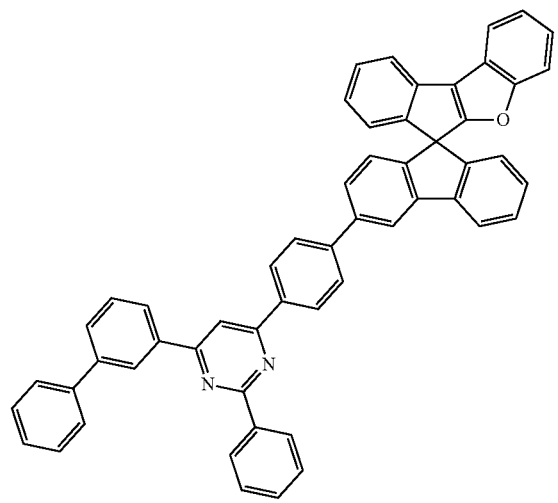
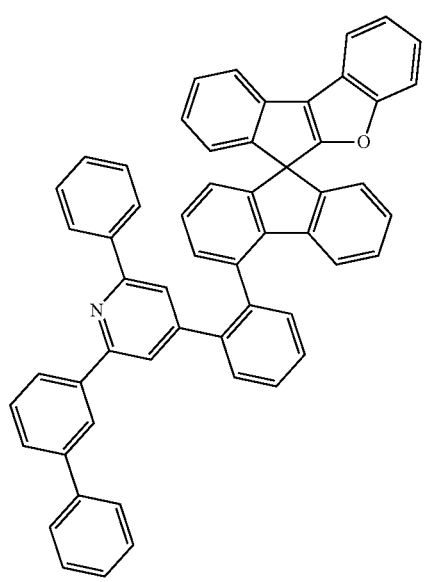
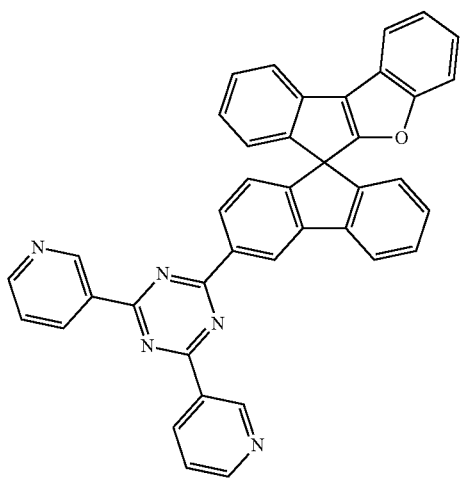
304
-continued
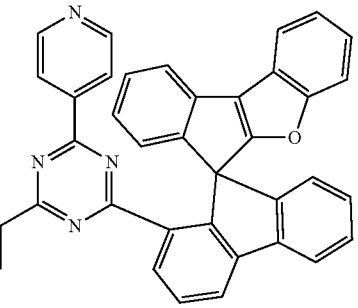
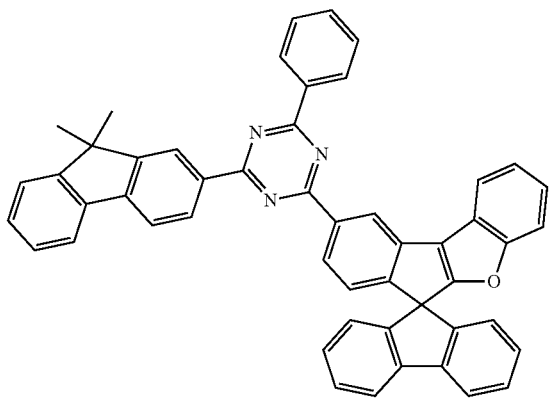
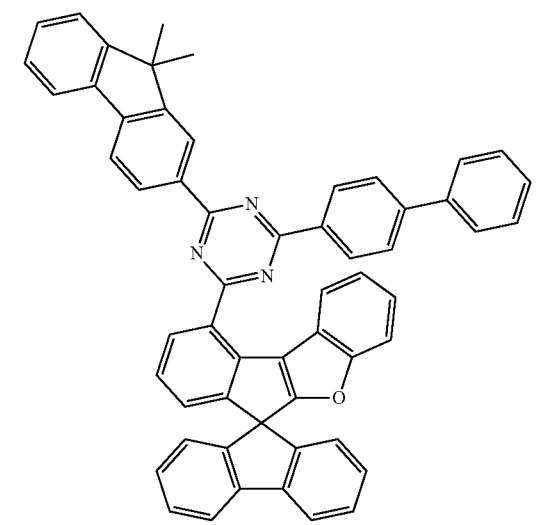
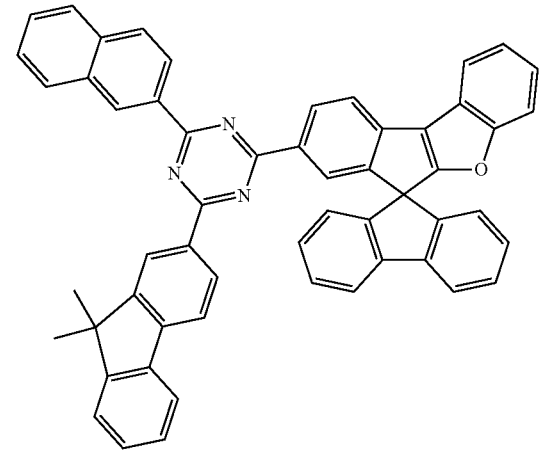

305
-continued
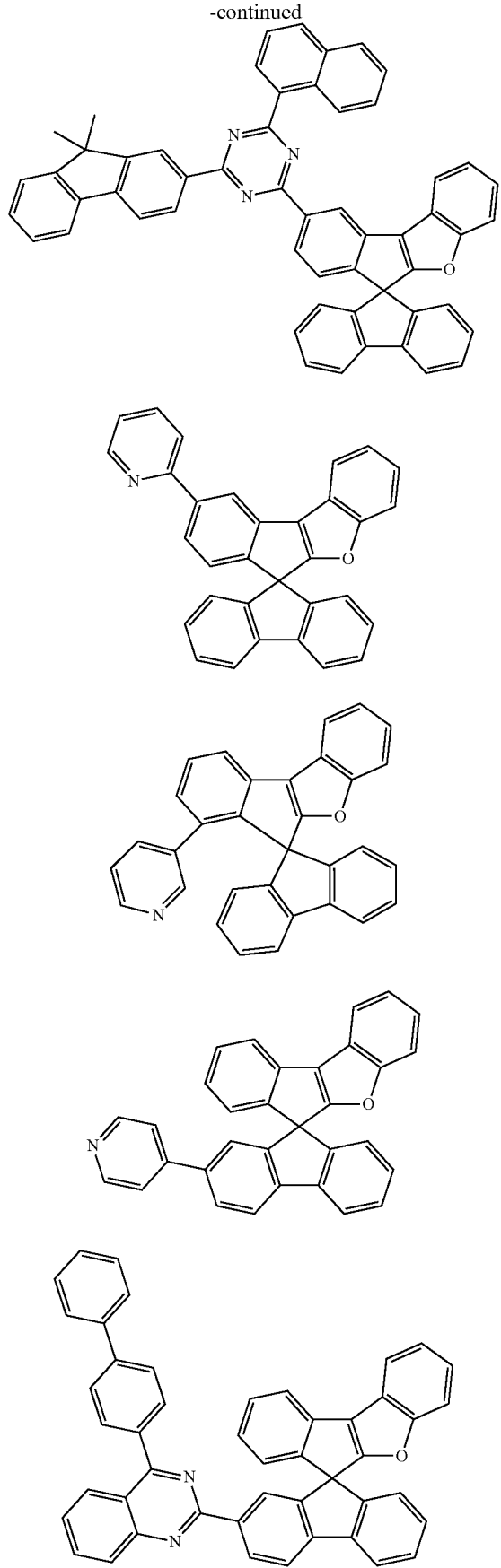
306
-continued
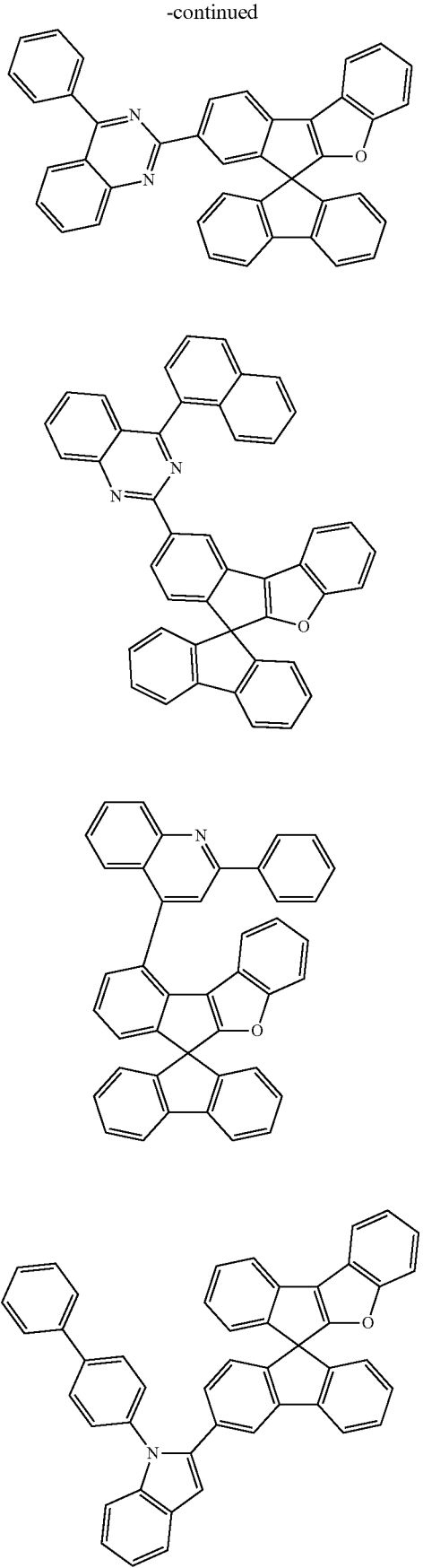

307
-continued
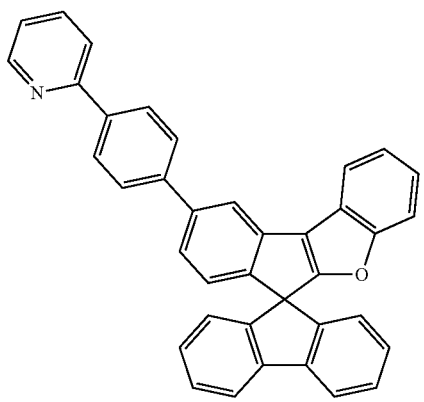
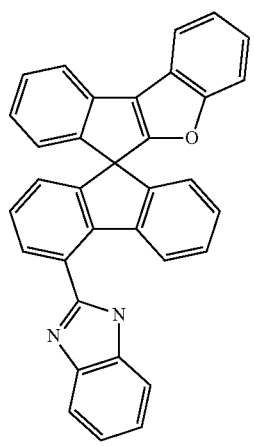
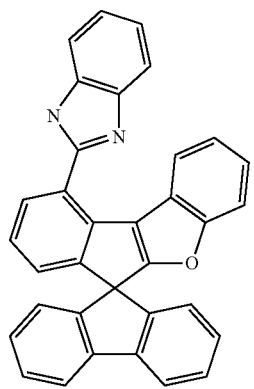
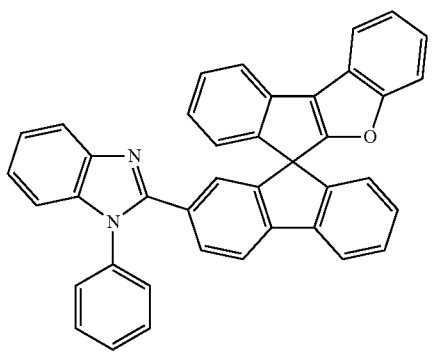
308
-continued
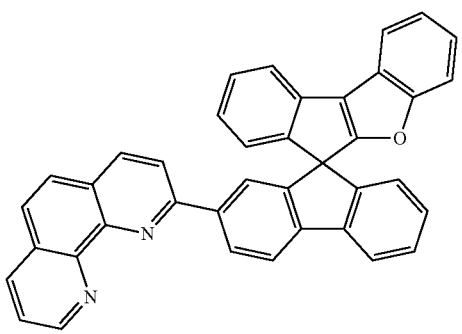
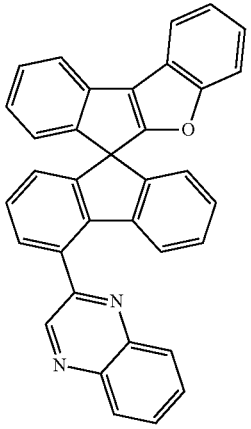
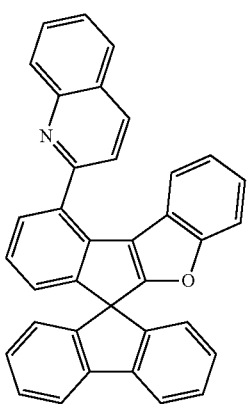
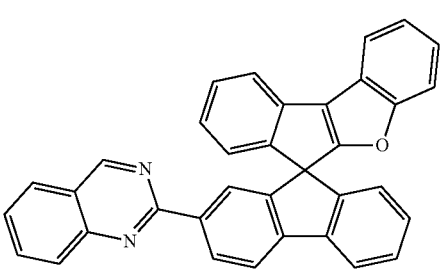

309
-continued
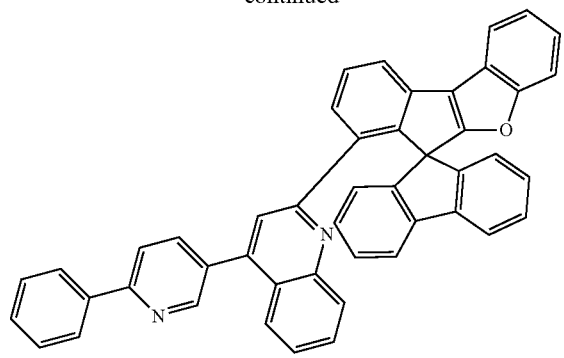
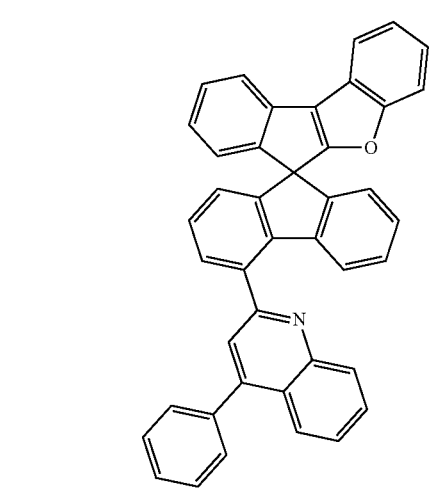
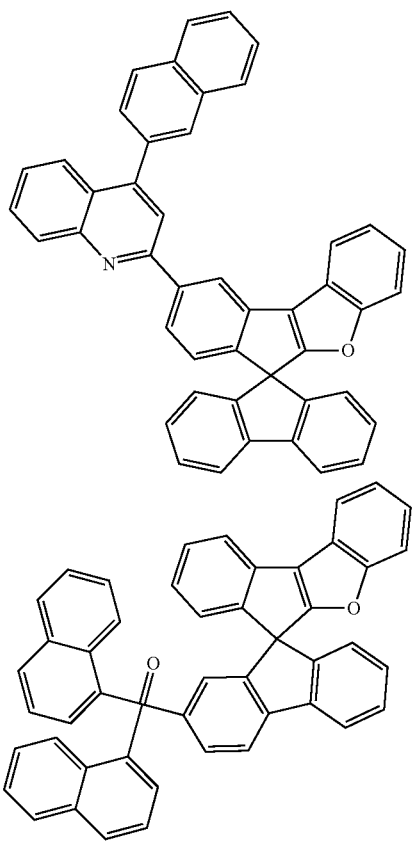
310
-continued
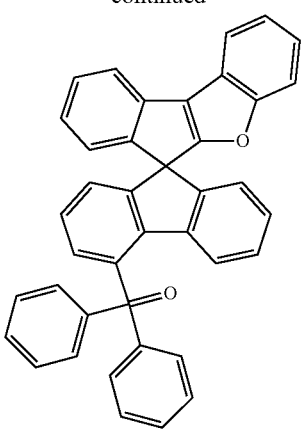
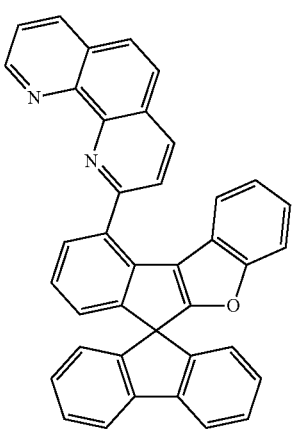
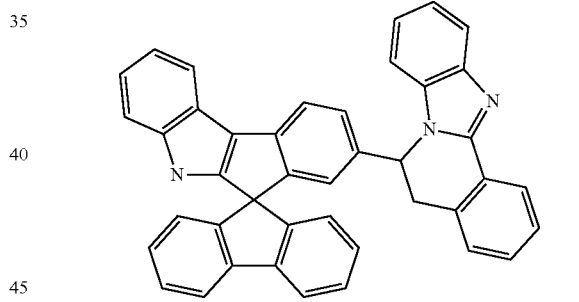
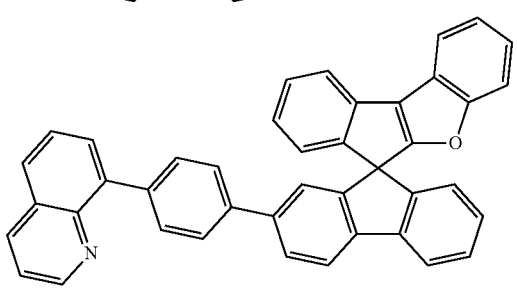
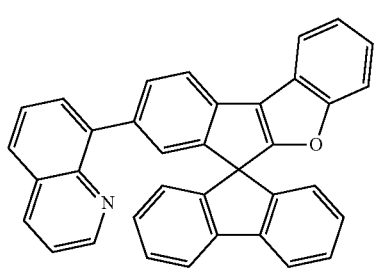

311
-continued
312
-continued
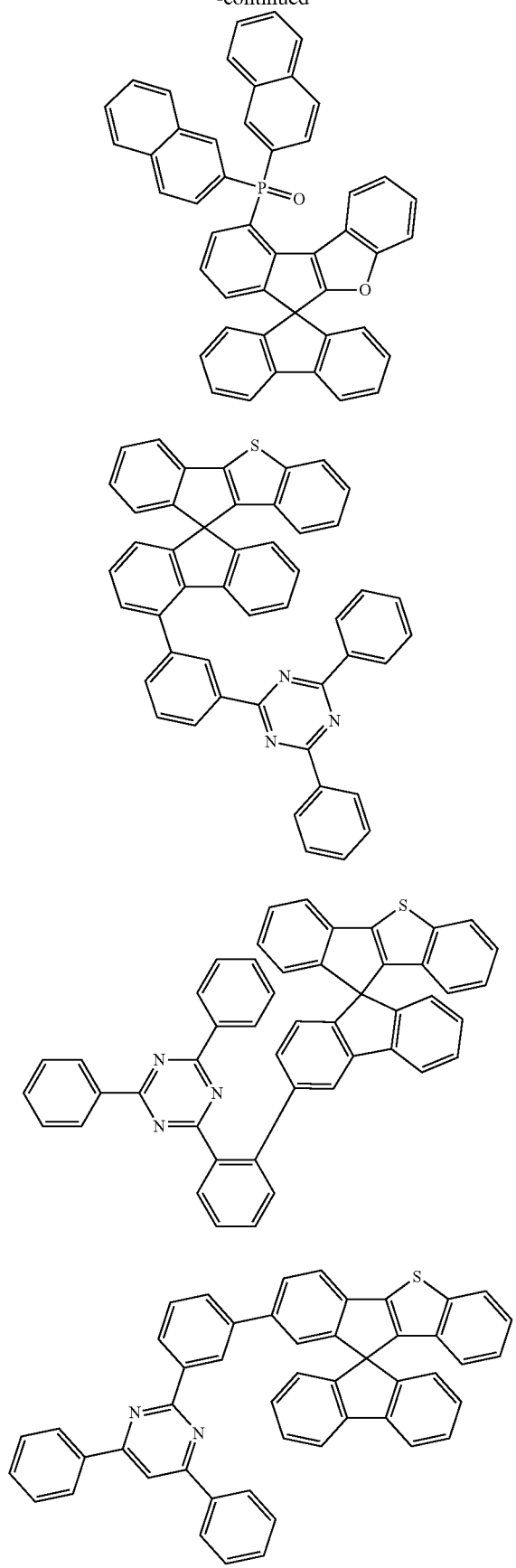
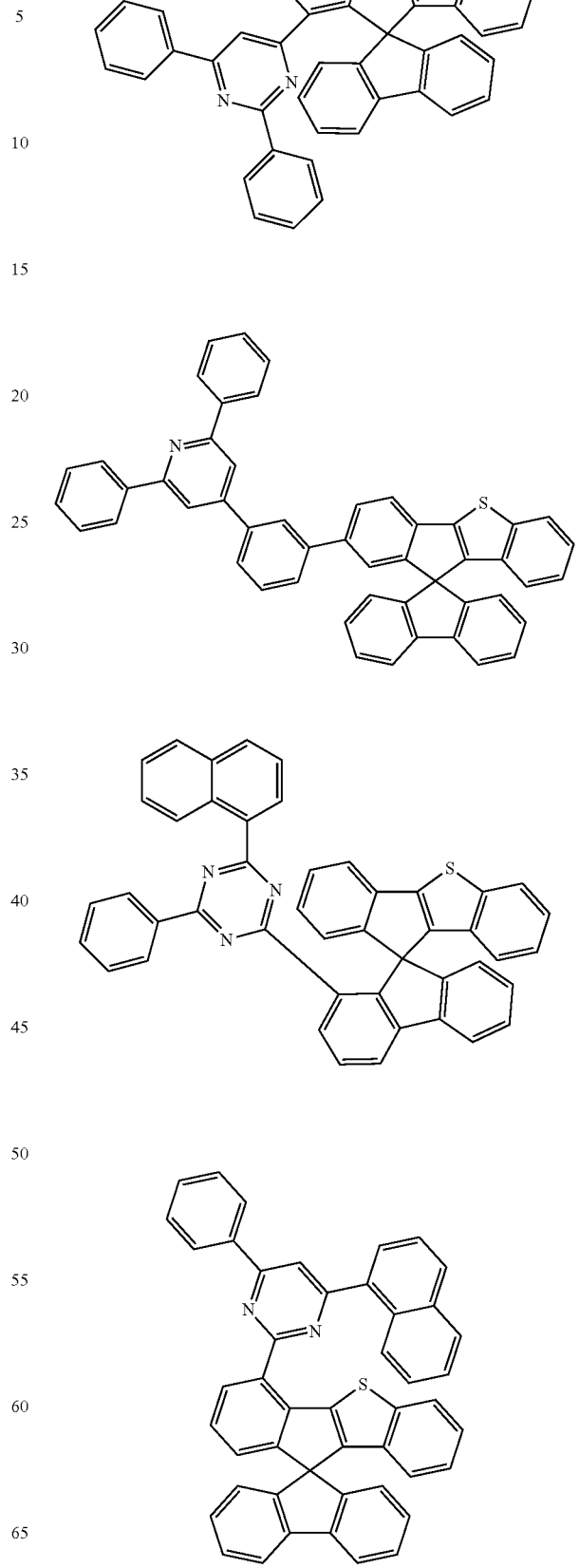

313
-continued
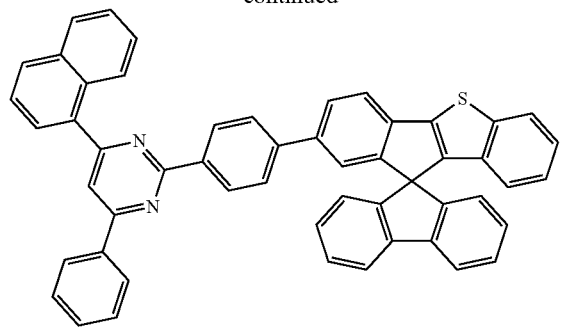
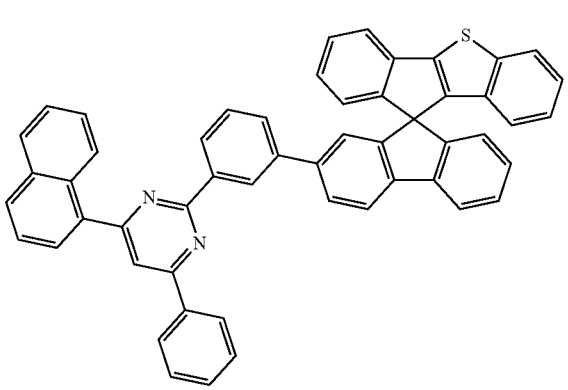
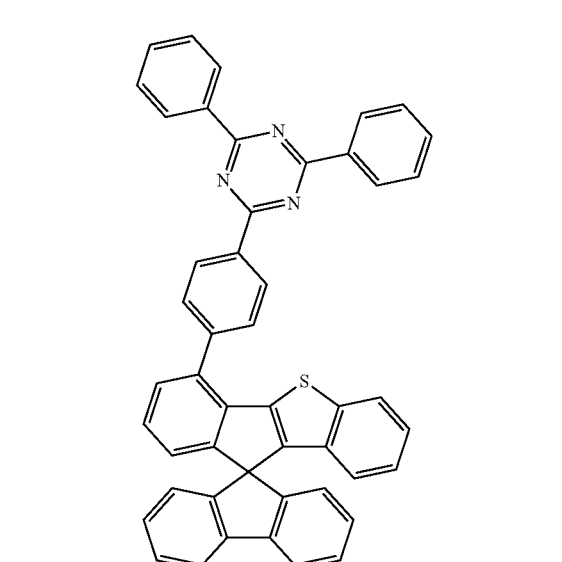
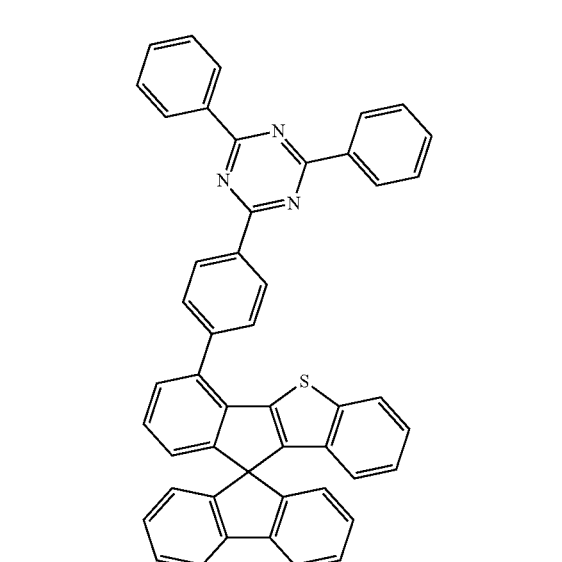
314
-continued
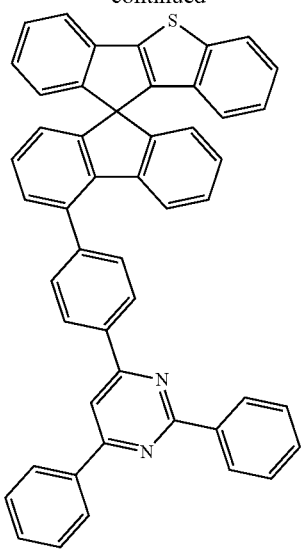
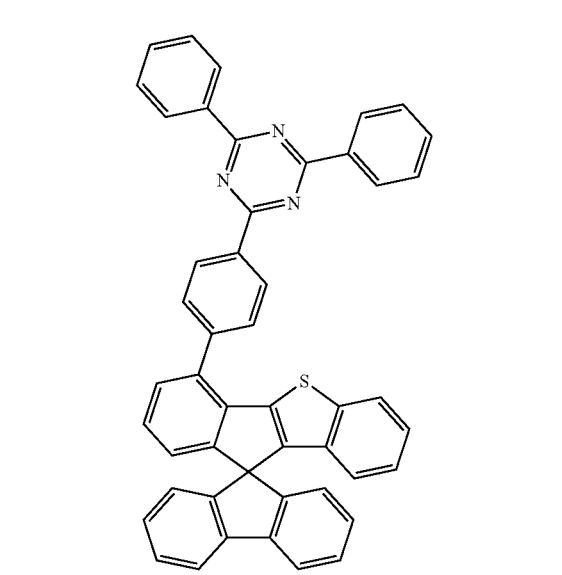
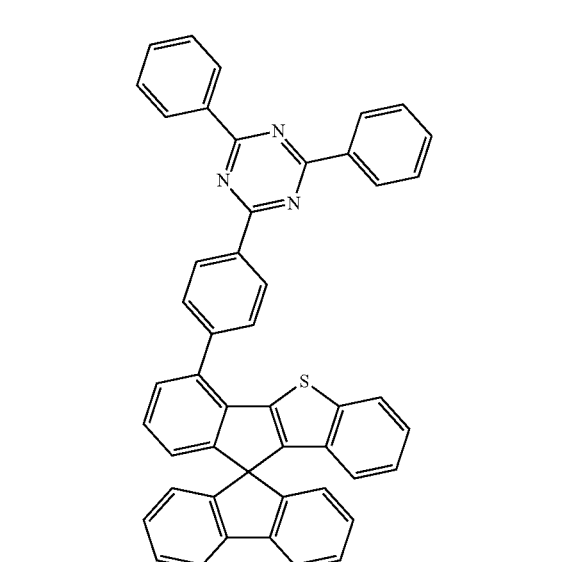

315
-continued
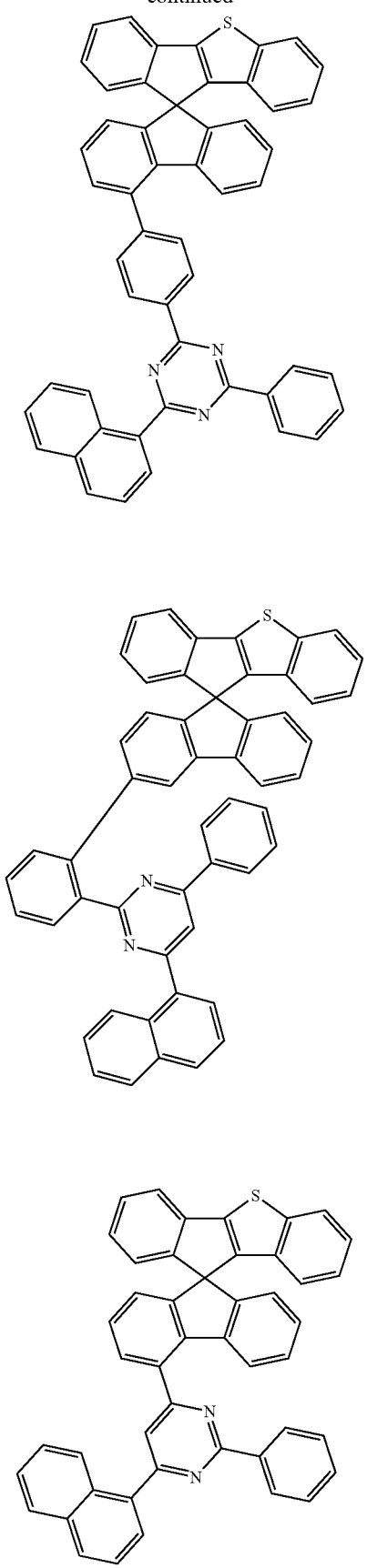
316
-continued
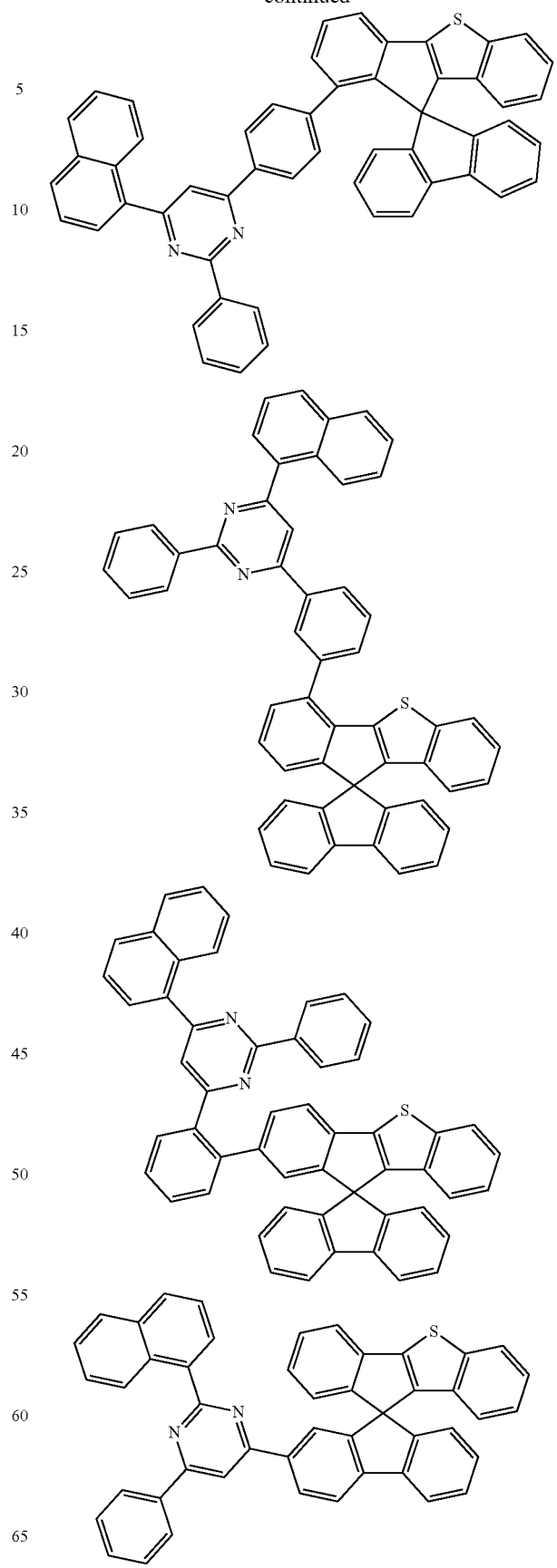

317
-continued
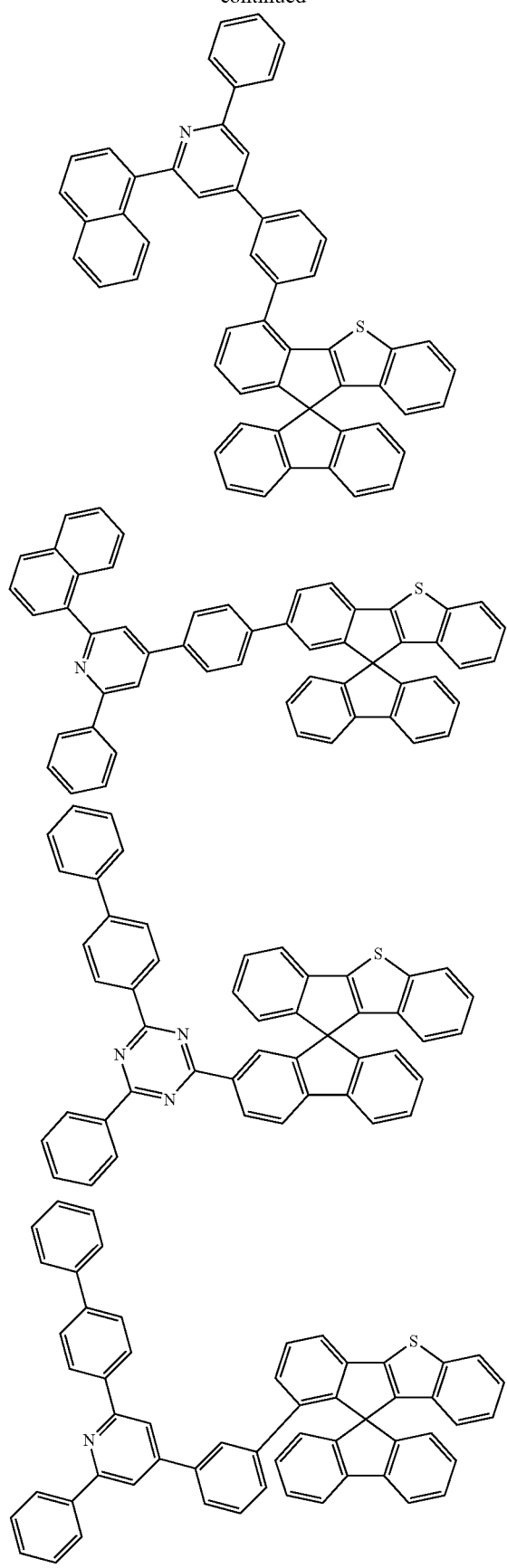
318
-continued
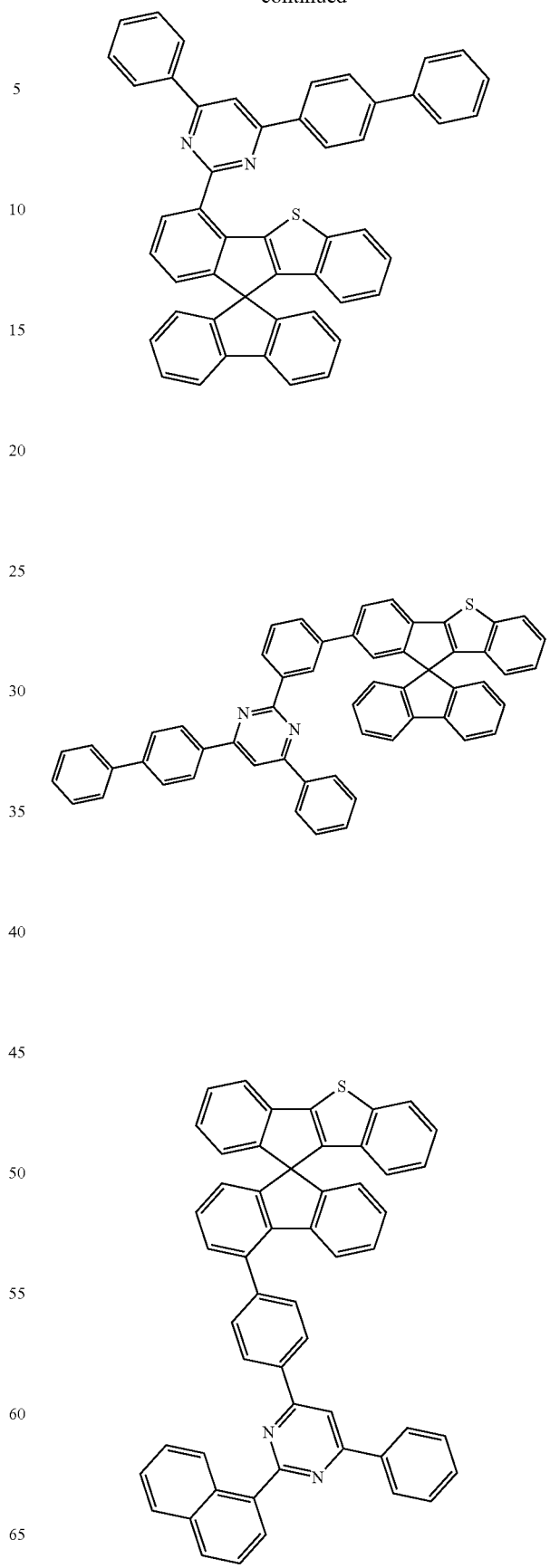

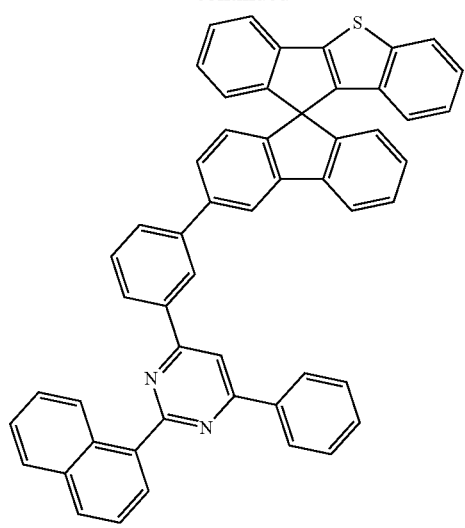
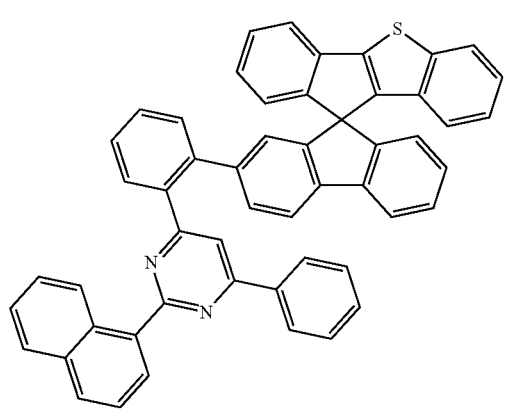
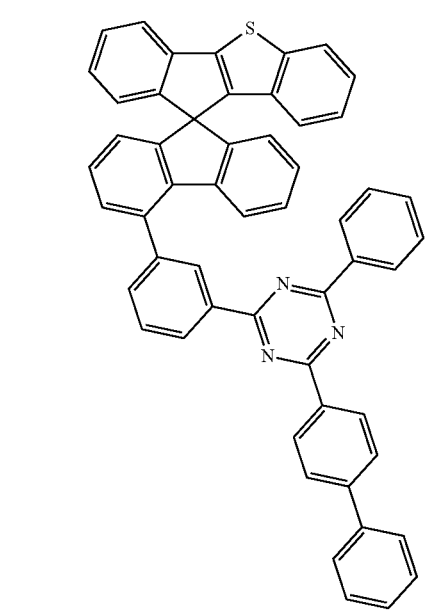
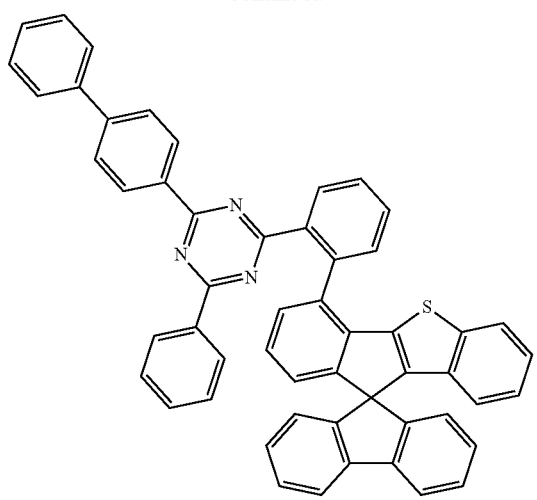
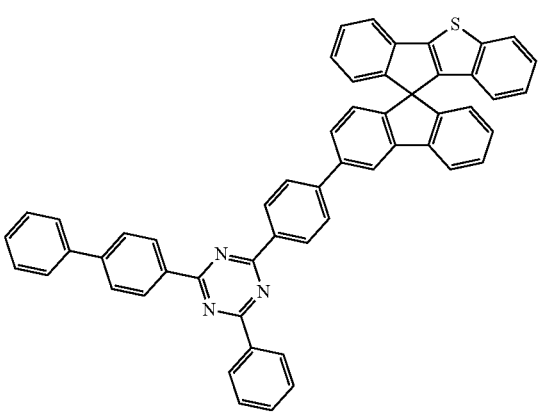
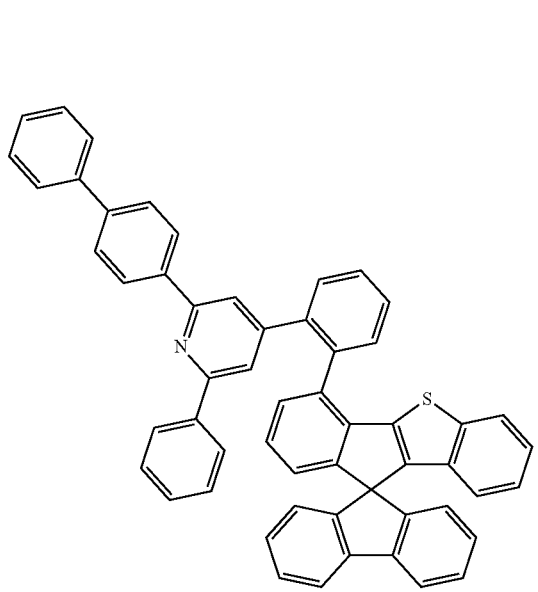

321
-continued
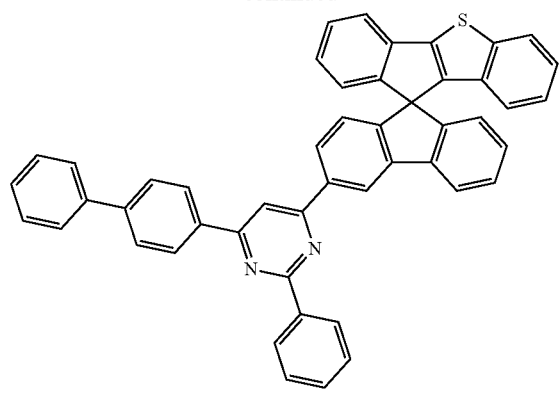
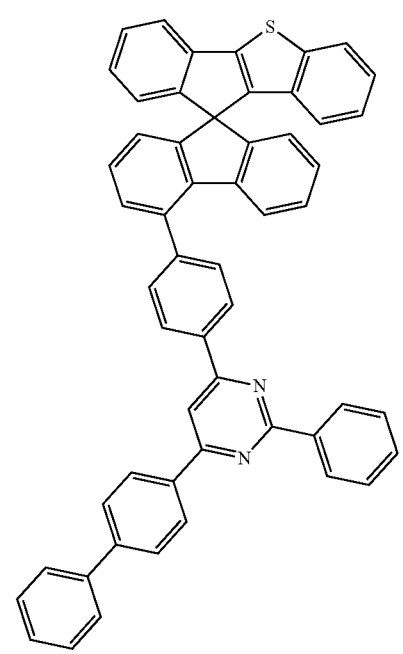
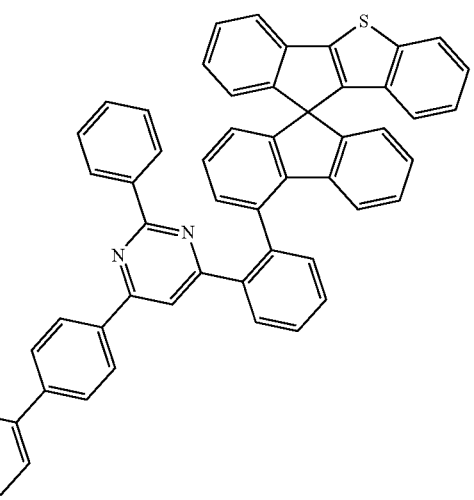
322
-continued
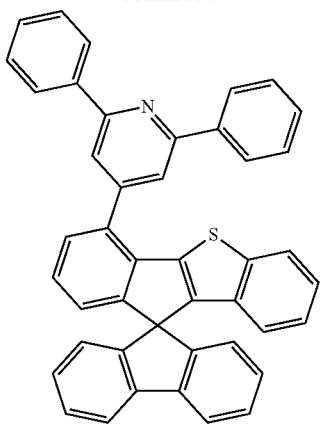
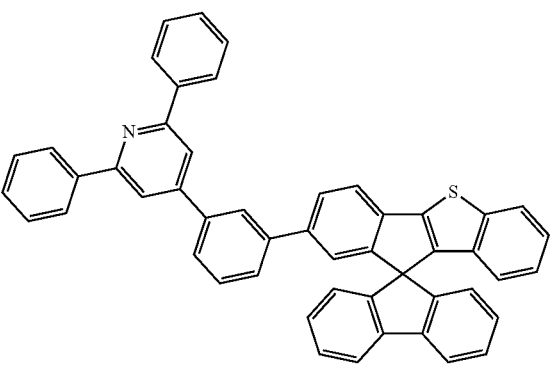
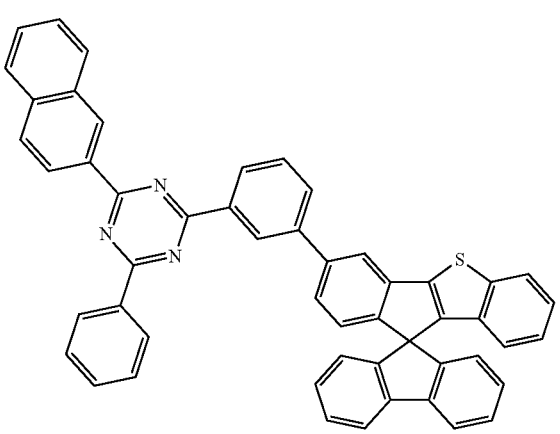

323
-continued
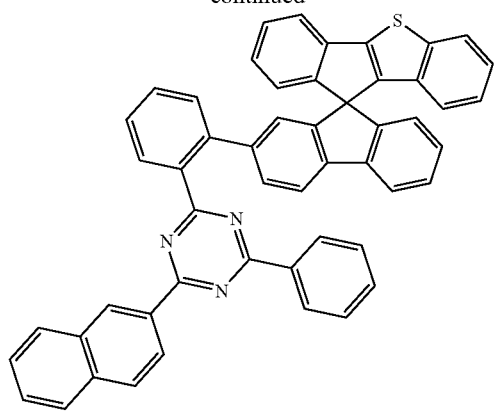
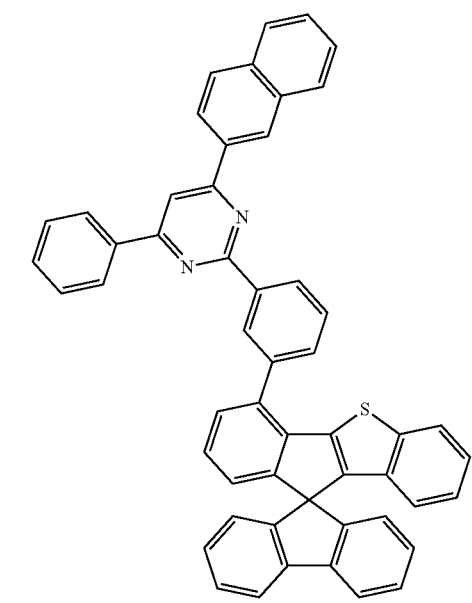
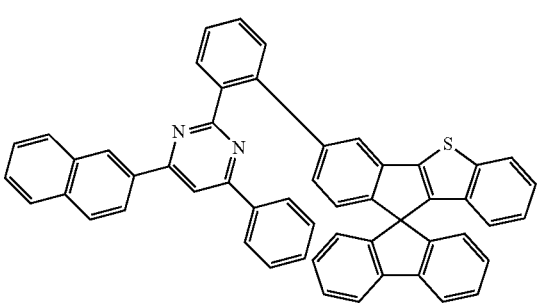
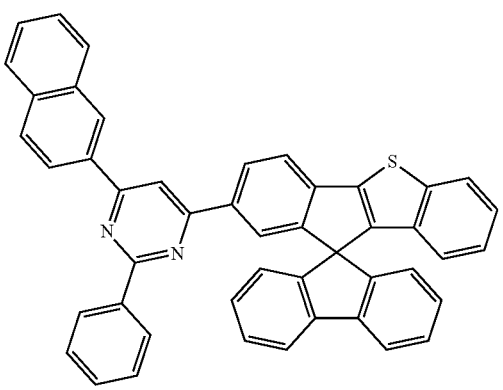
324
-continued
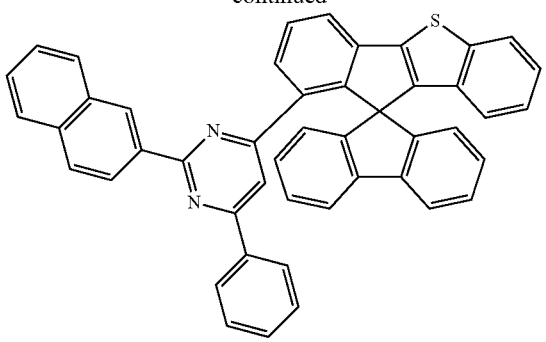
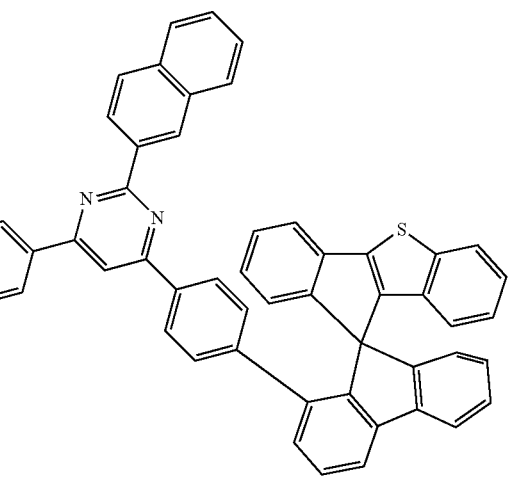
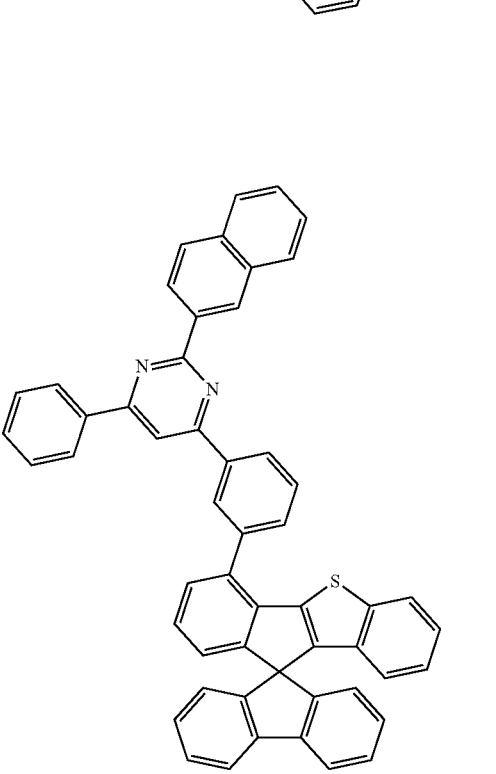

325
-continued
326
-continued
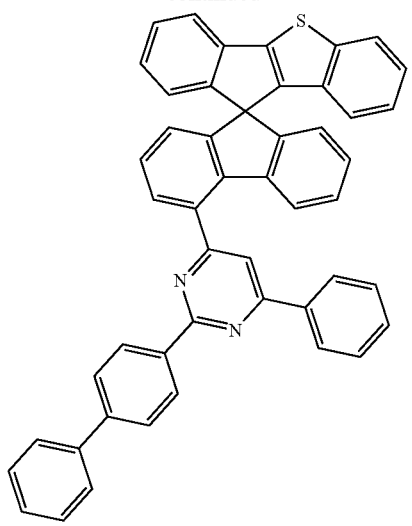
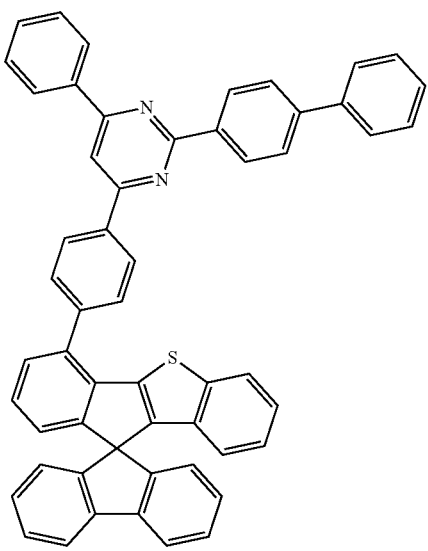
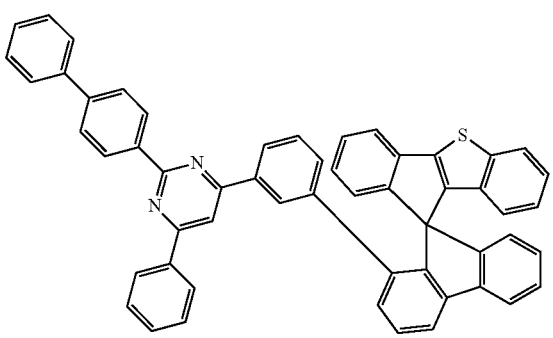
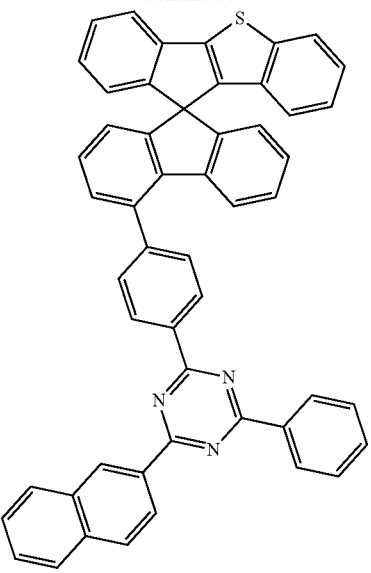
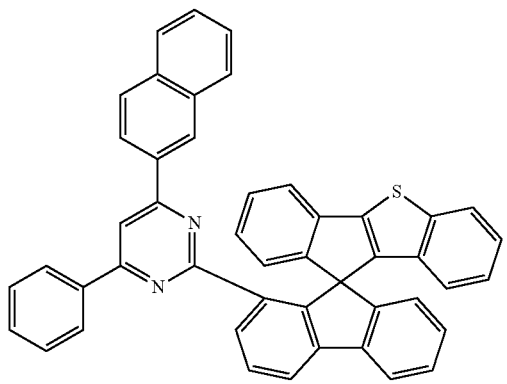
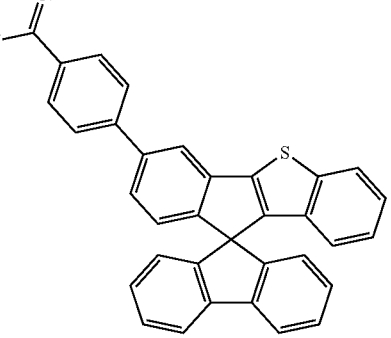

327
-continued
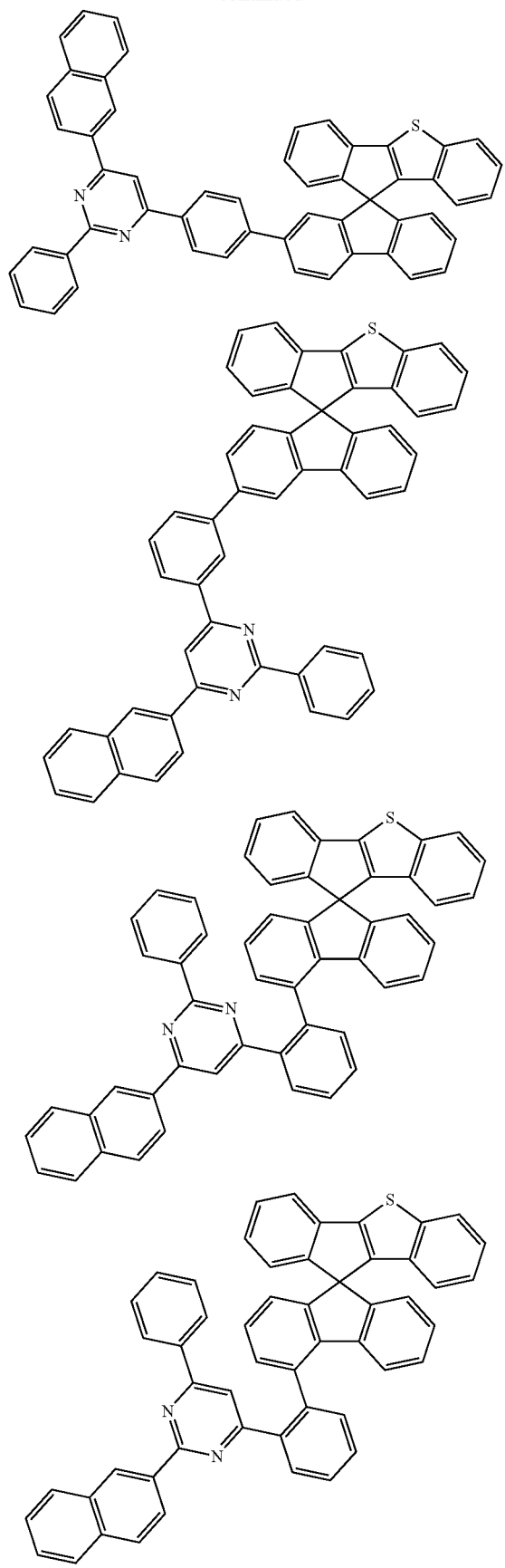
328
-continued
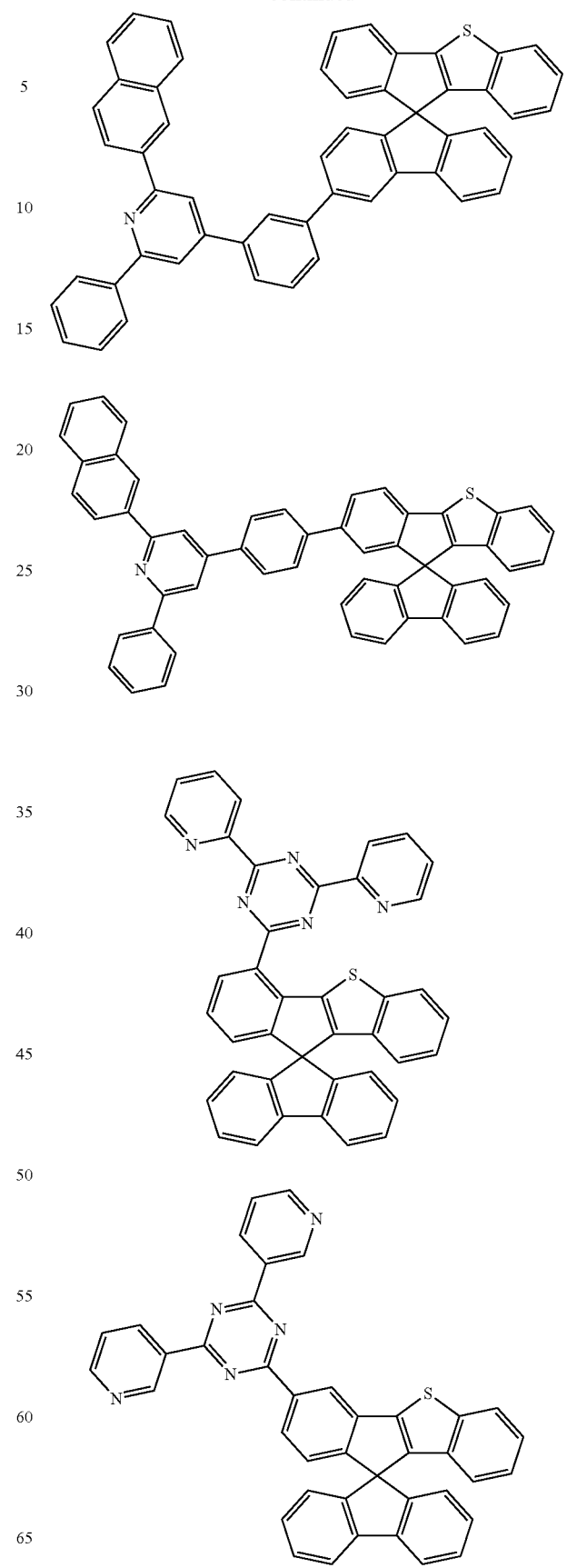

329
-continued
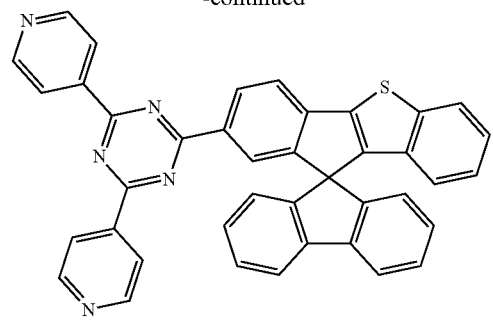
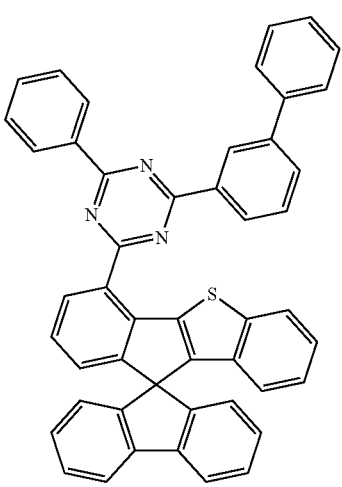
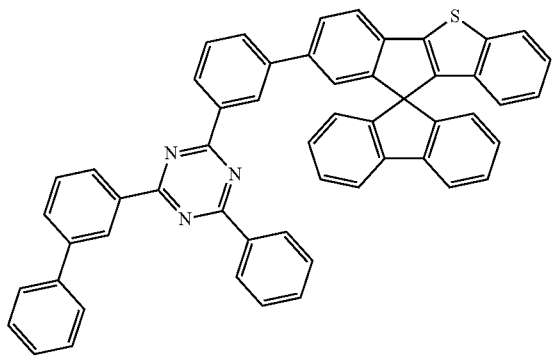
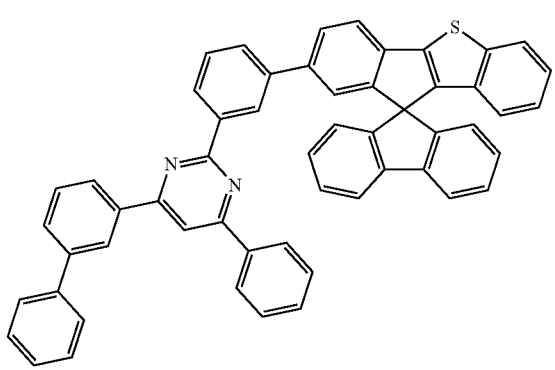
330
-continued
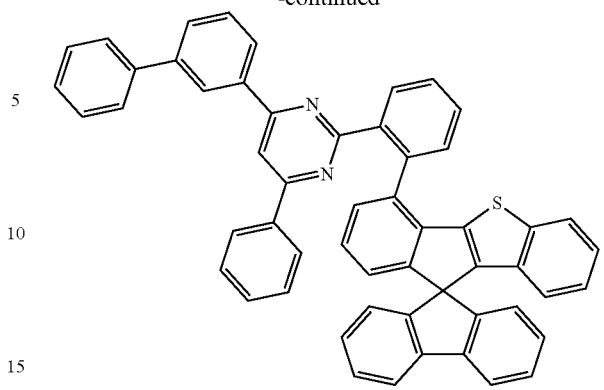
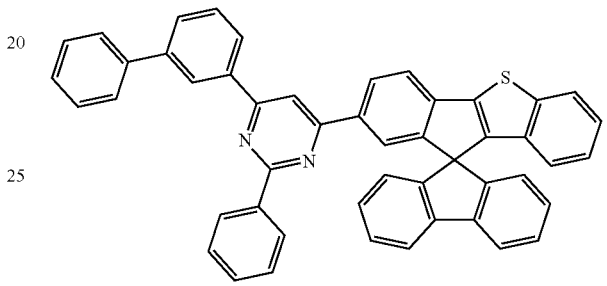
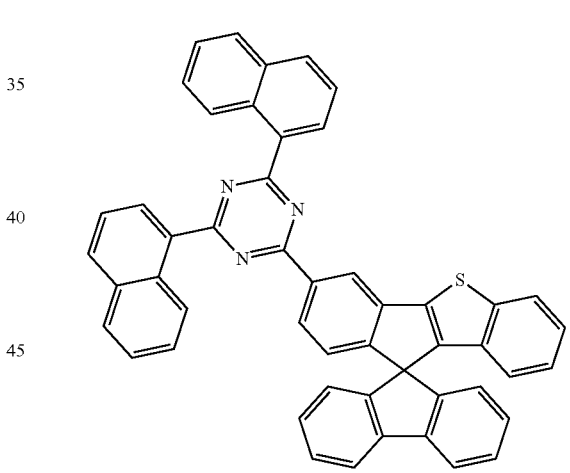
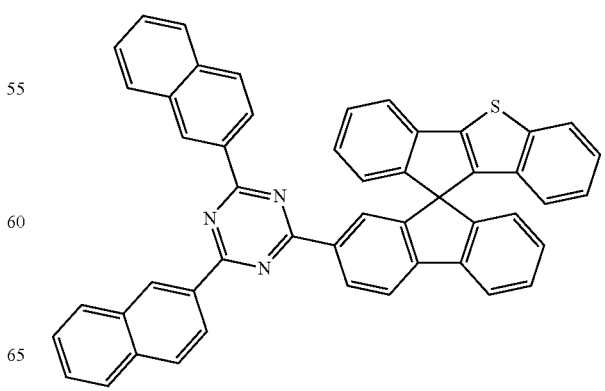

331
-continued
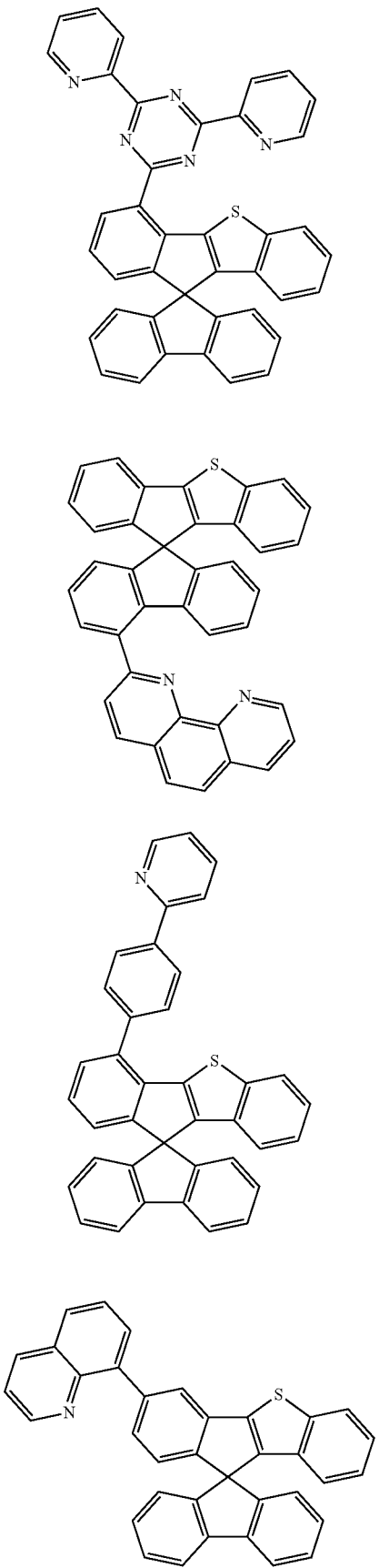
332
-continued
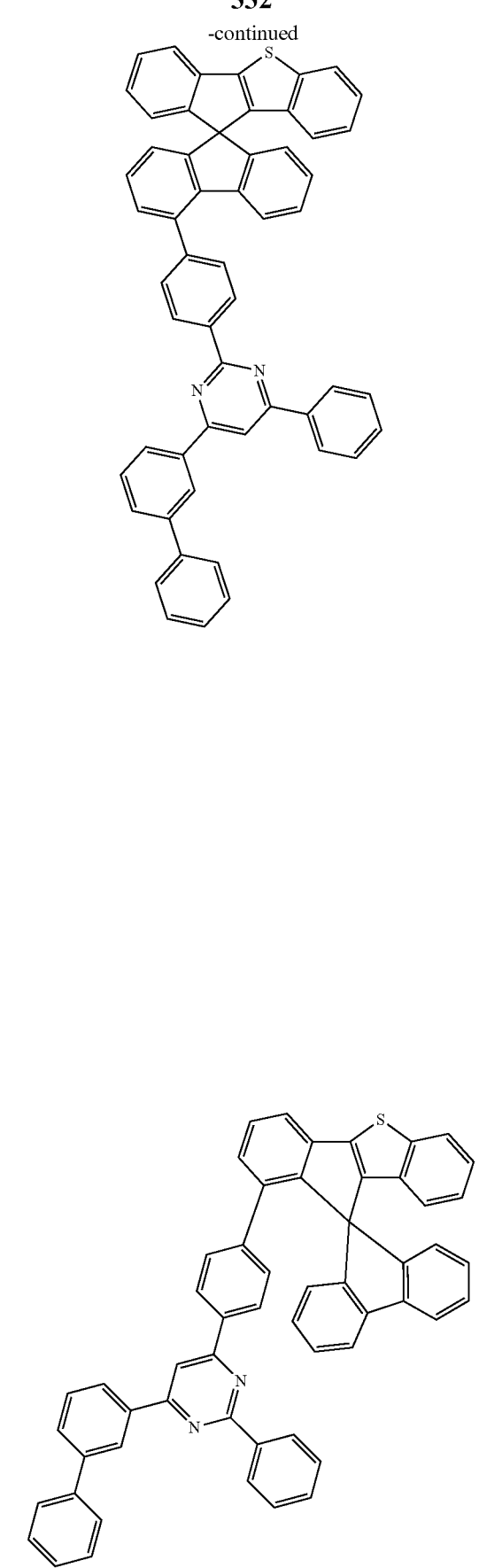

333
-continued
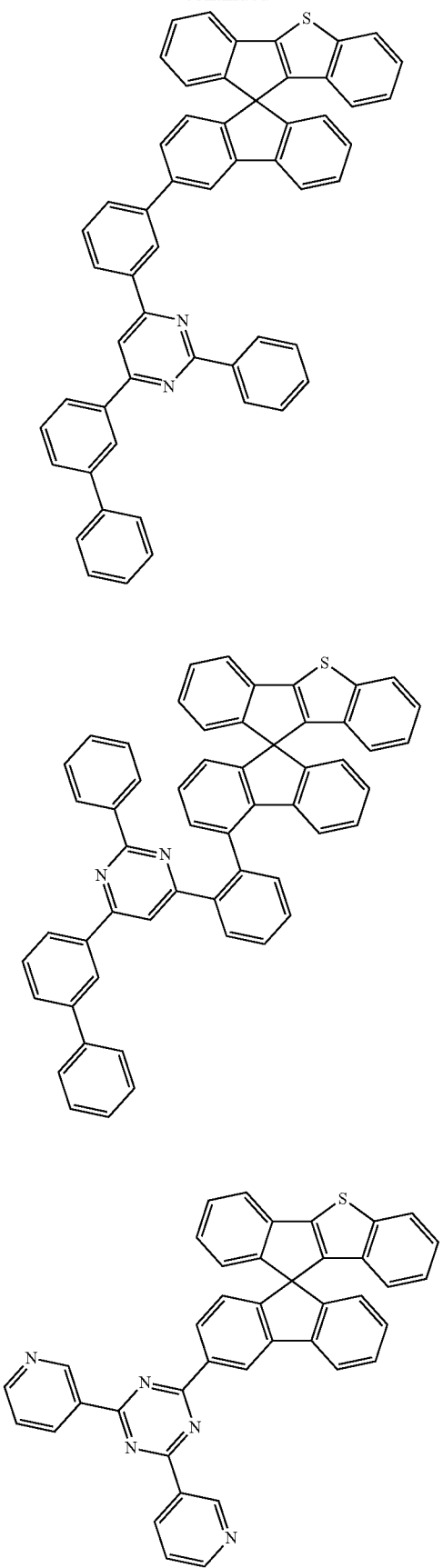
334
-continued
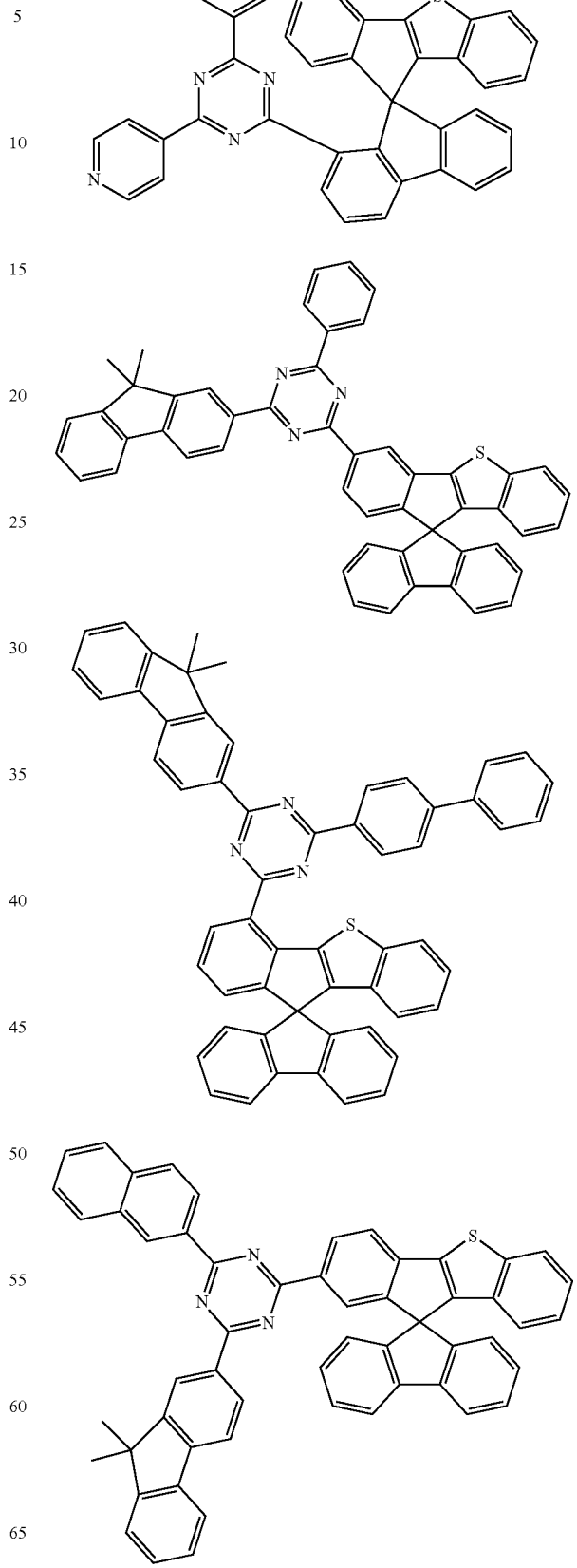

335
-continued
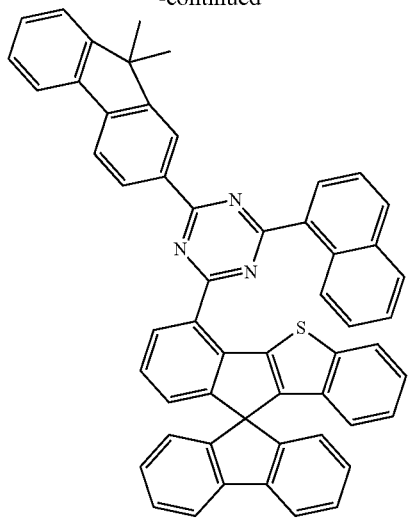
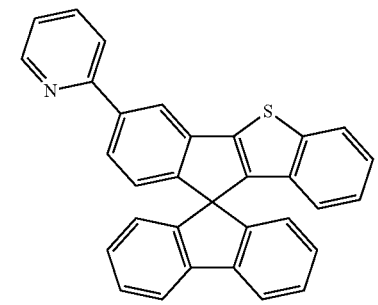
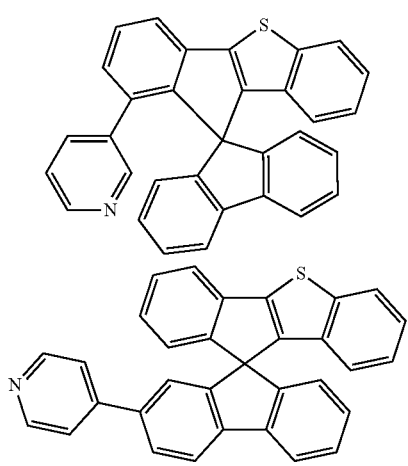
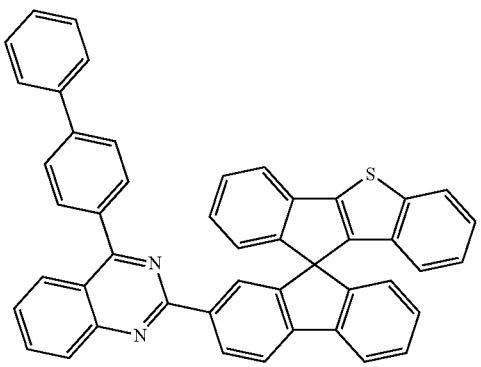
336
-continued
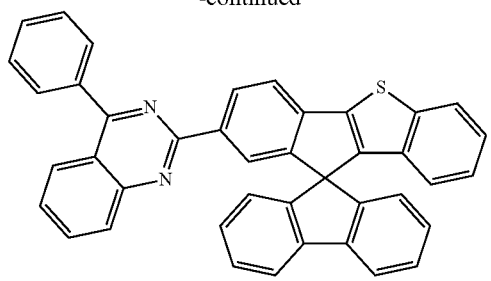
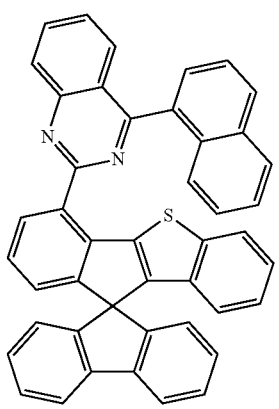
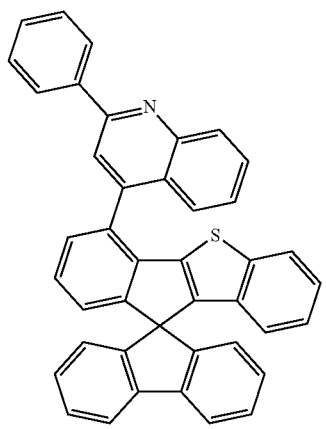
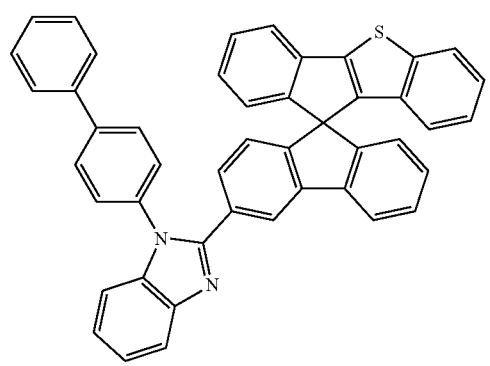

337
-continued
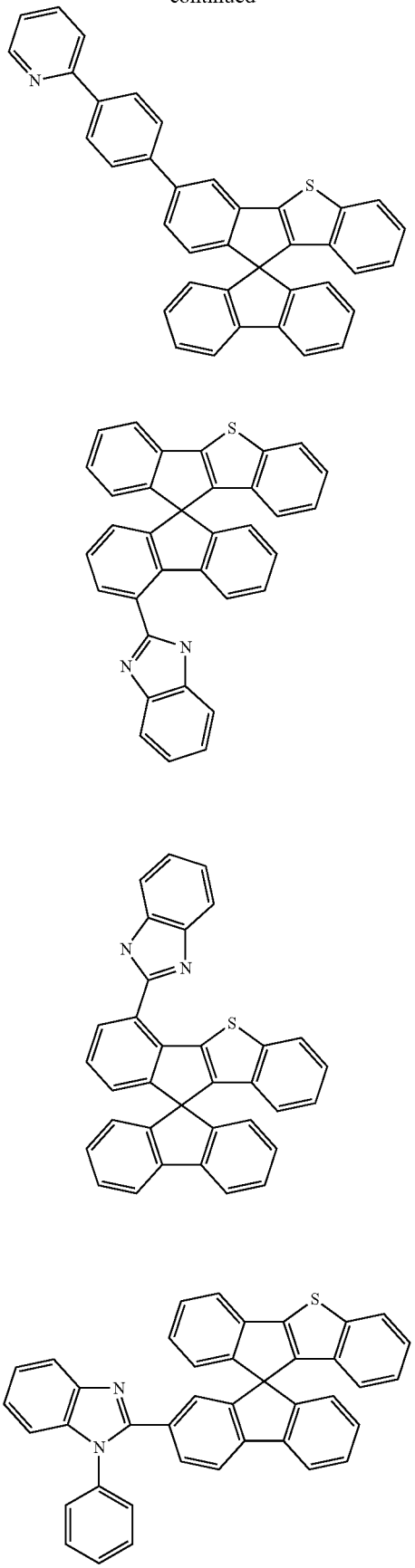
338
-continued
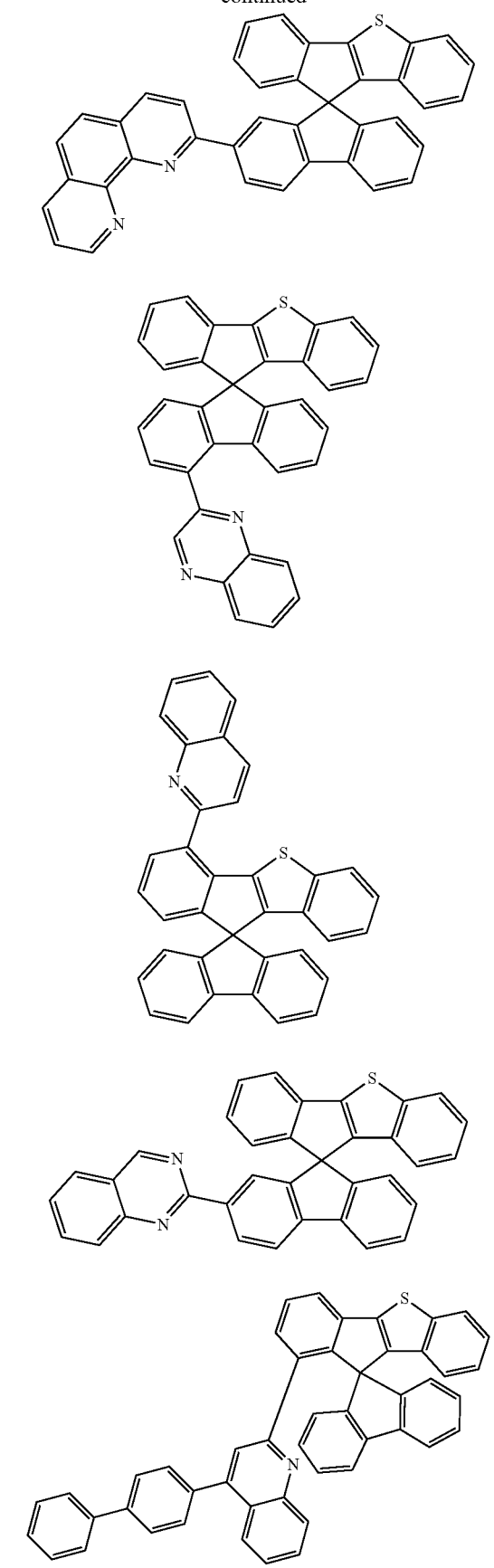

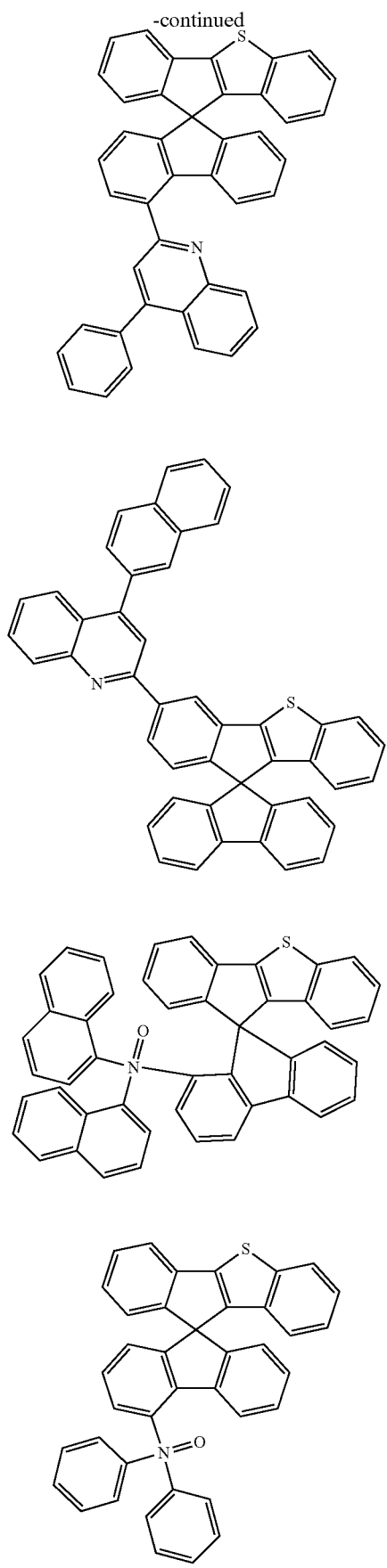

341
-continued
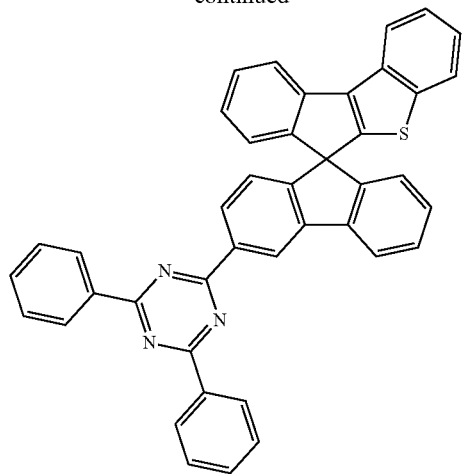
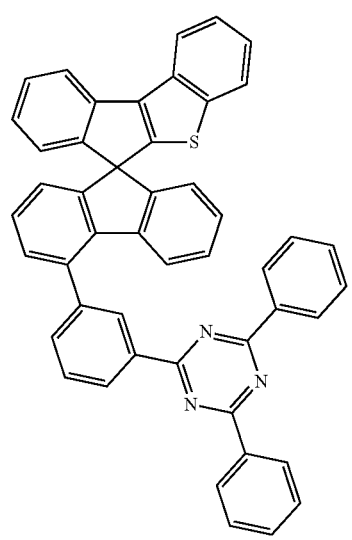
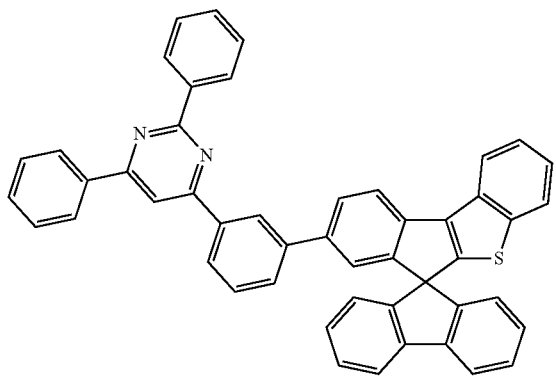
342
-continued
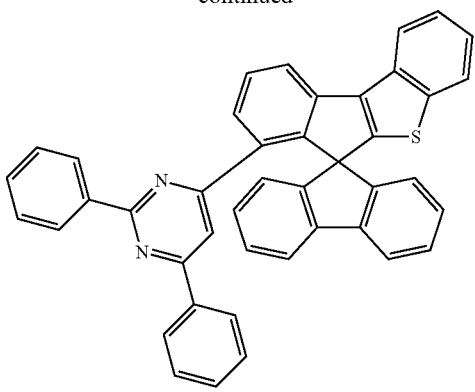
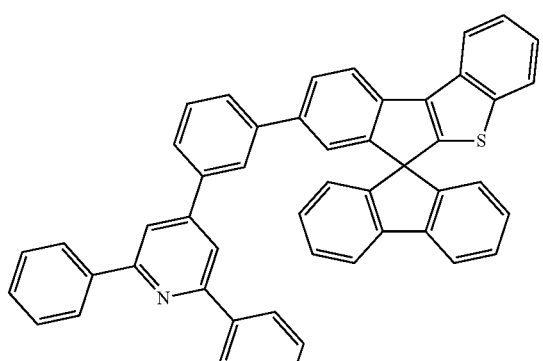
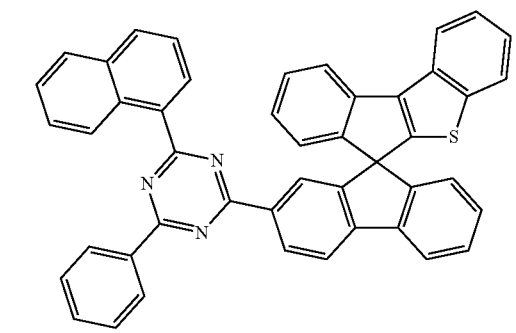
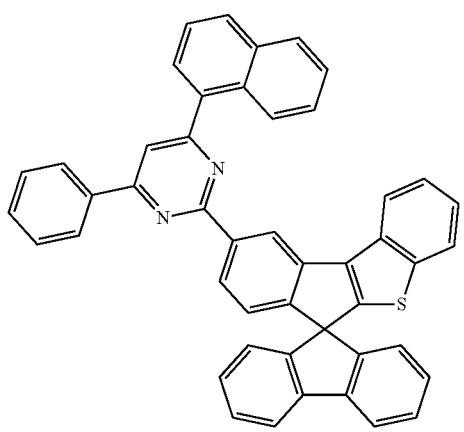

343
-continued
344
-continued
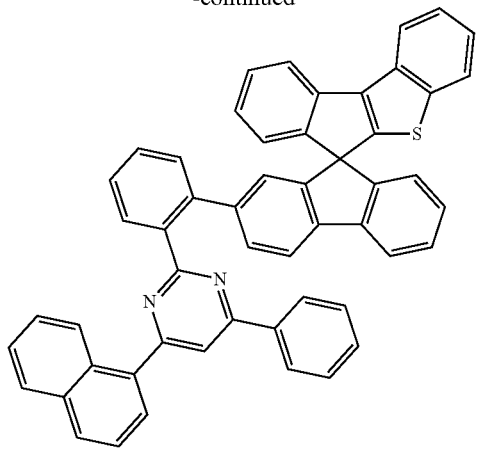
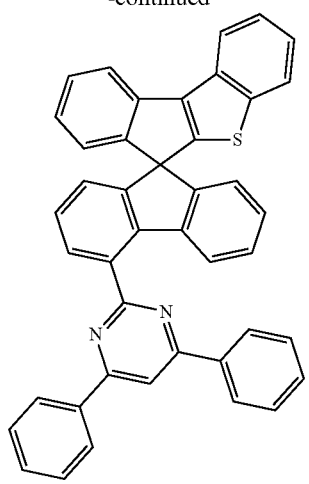
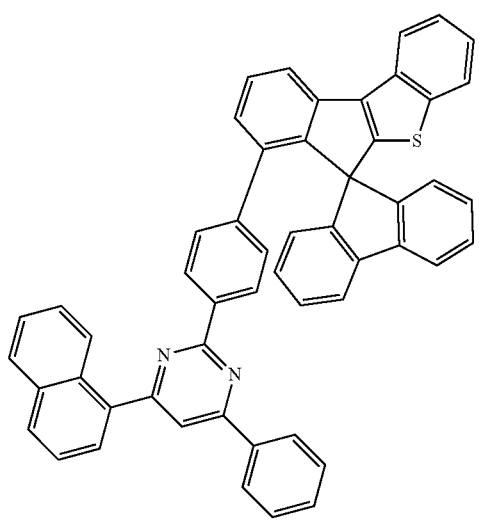
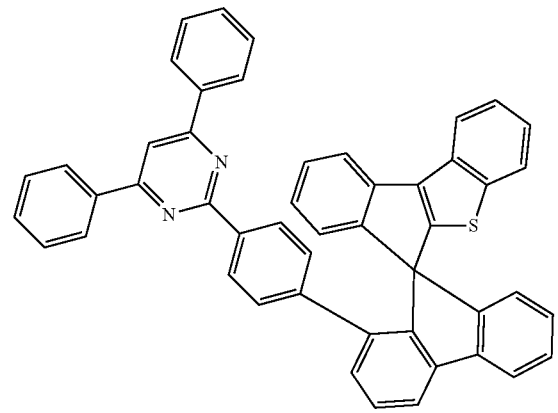
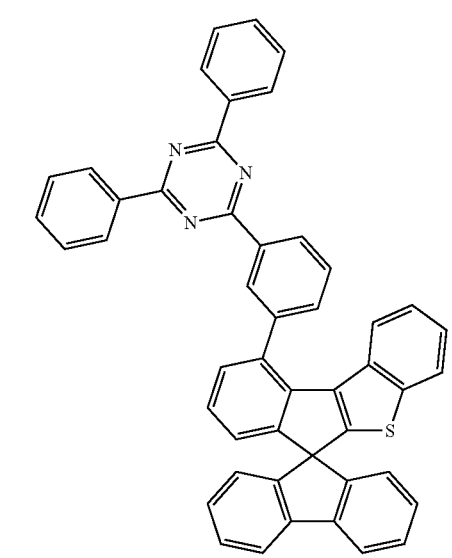
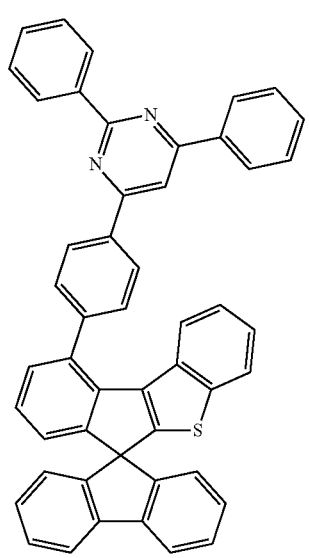

345
-continued
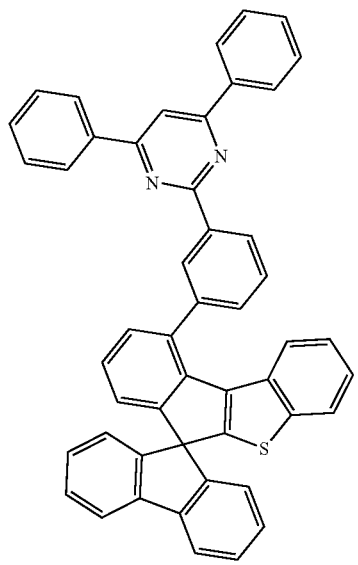
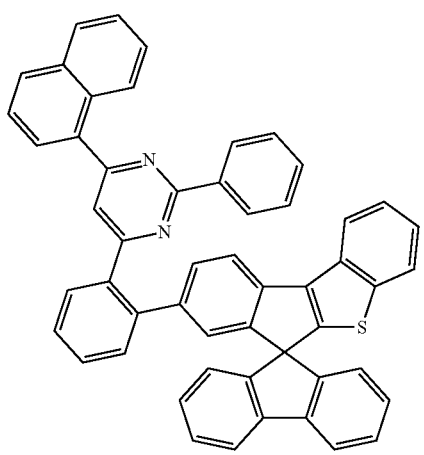
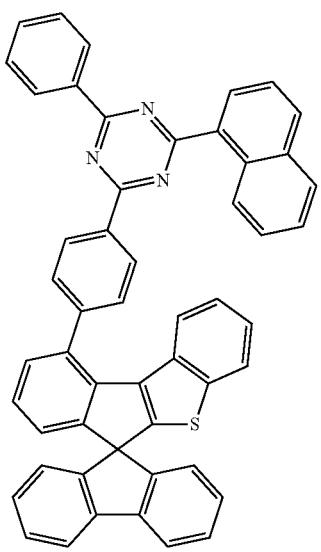
346
-continued
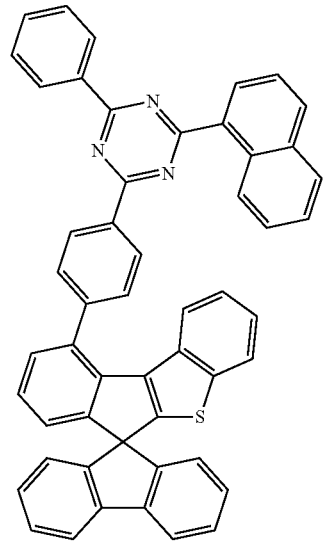
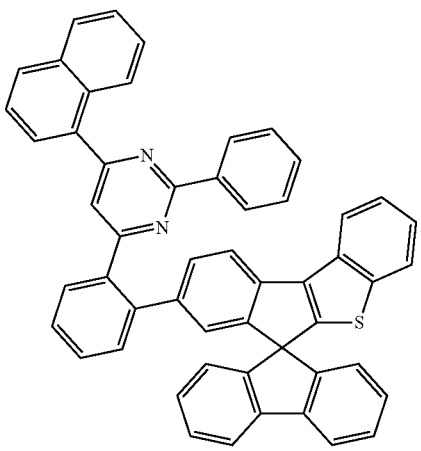
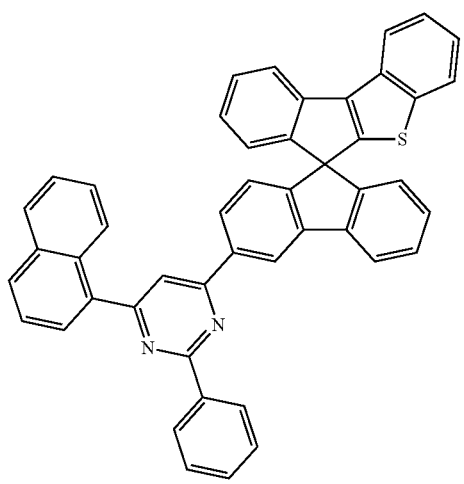

347
-continued
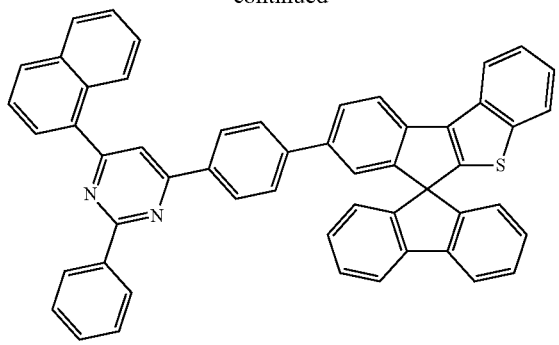
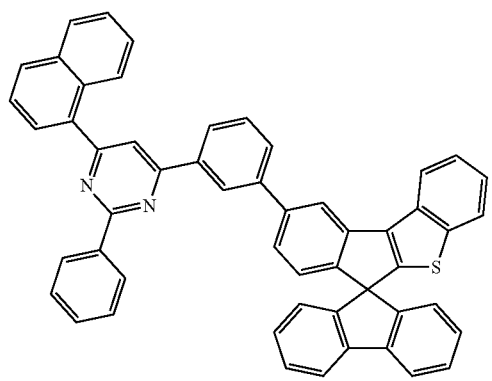
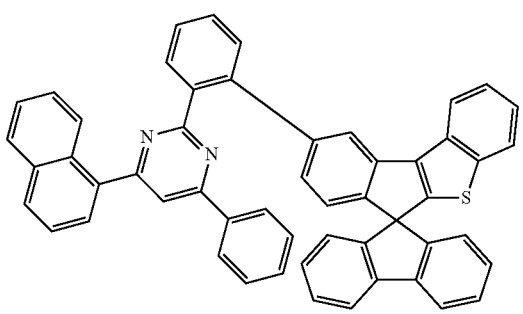
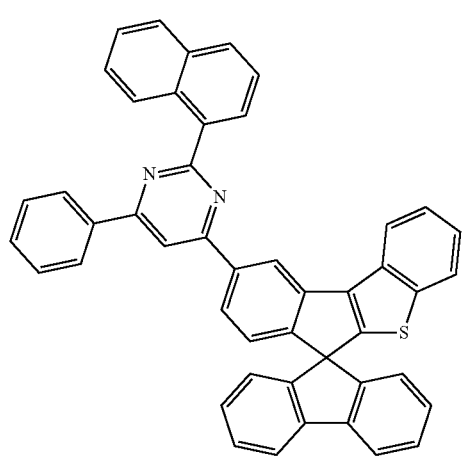
348
-continued
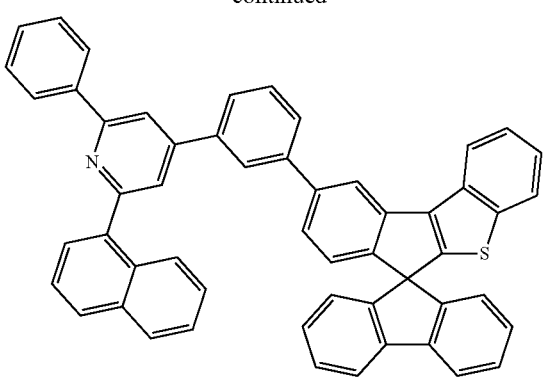
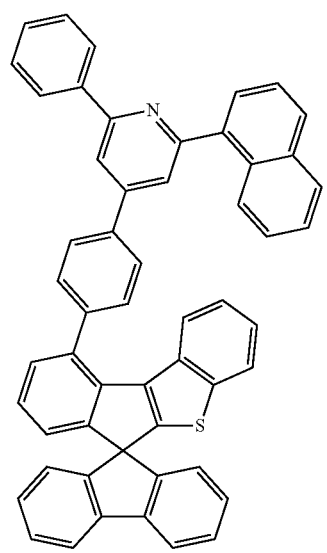
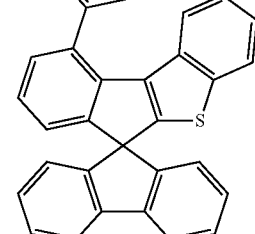
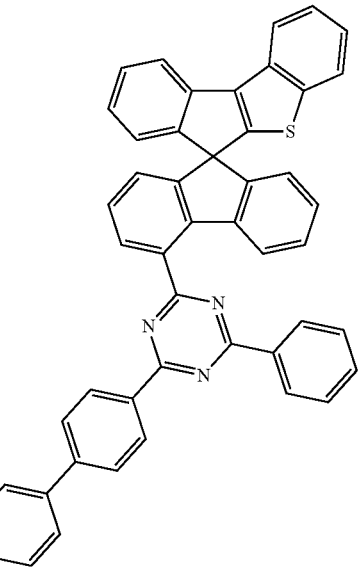

349
-continued
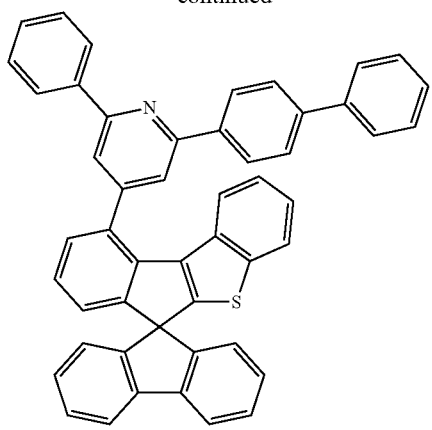
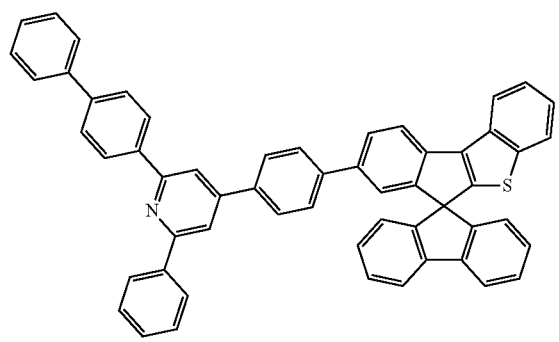
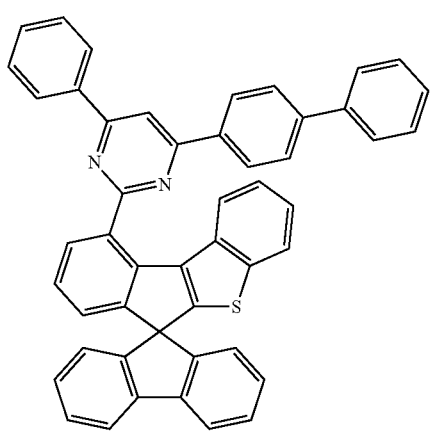
350
-continued
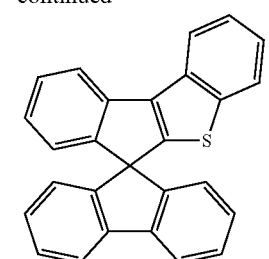
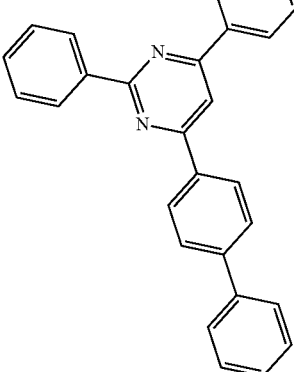
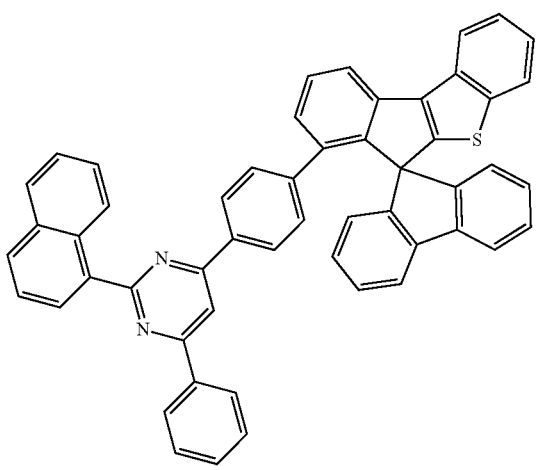
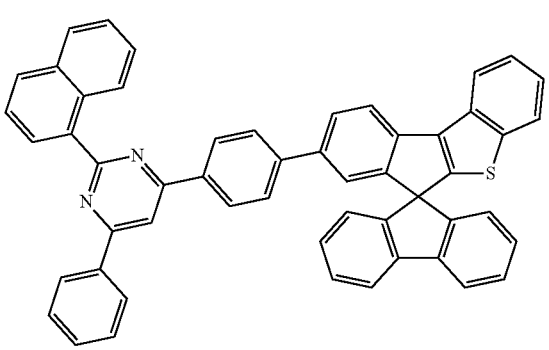

351
-continued
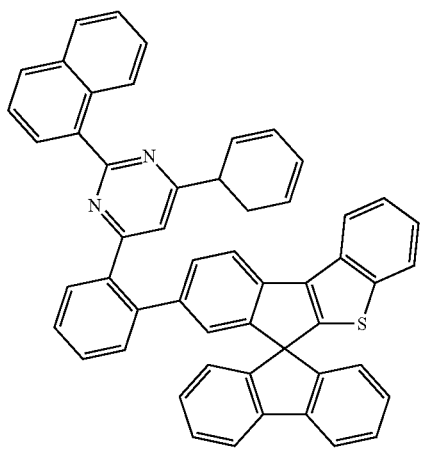
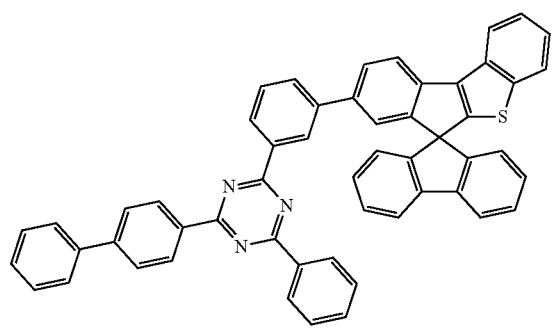
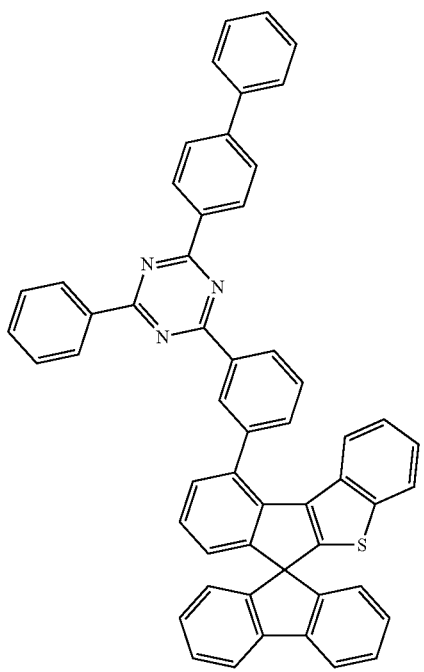
352
-continued
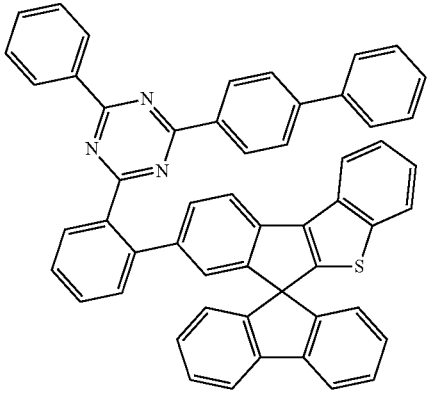
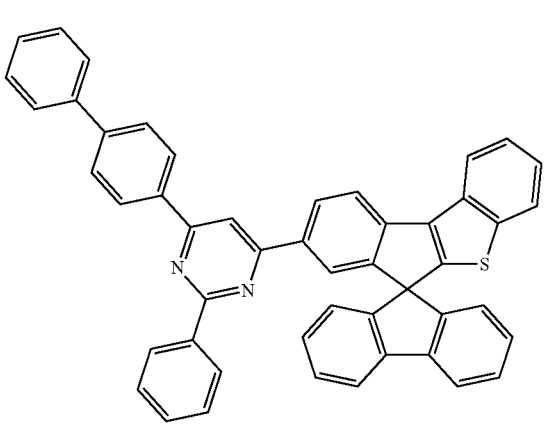
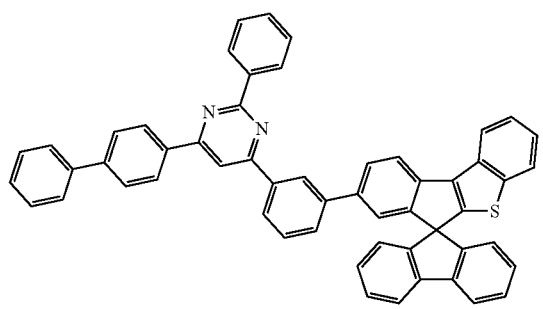

353
-continued
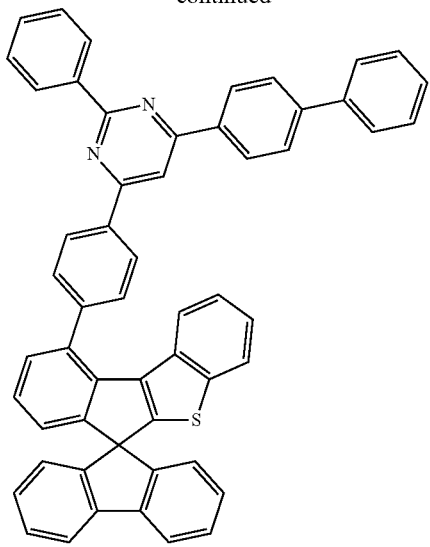
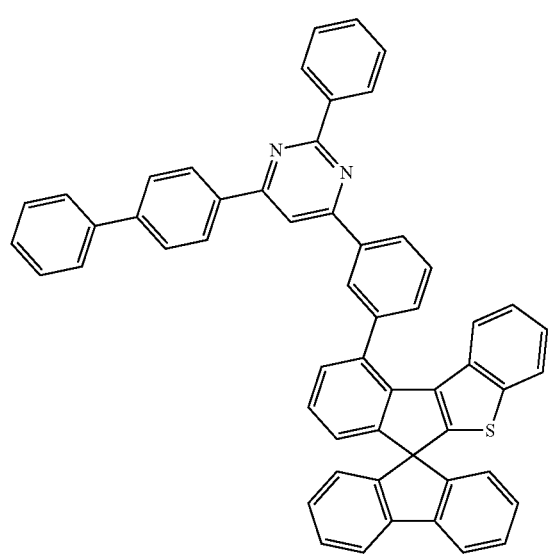
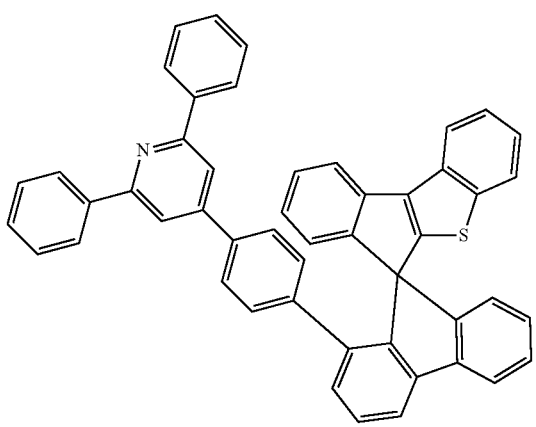
354
-continued
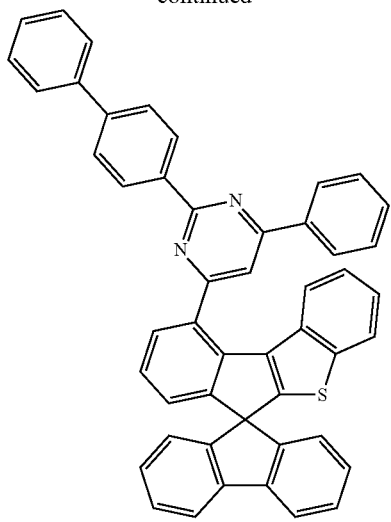
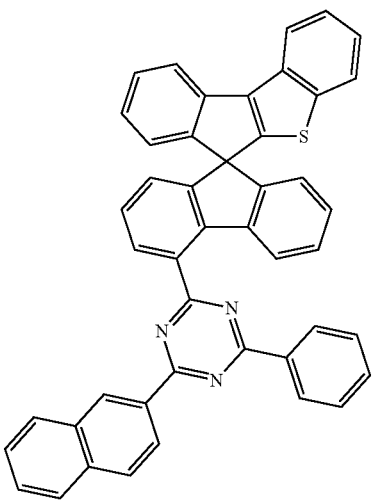
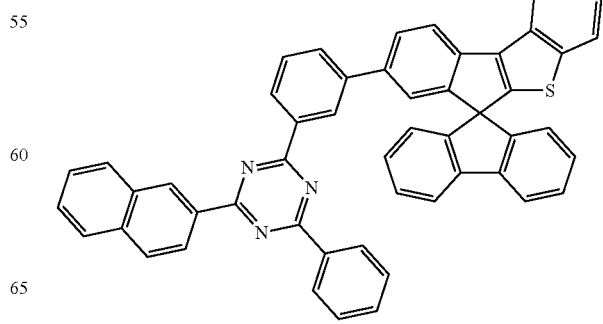

355
-continued
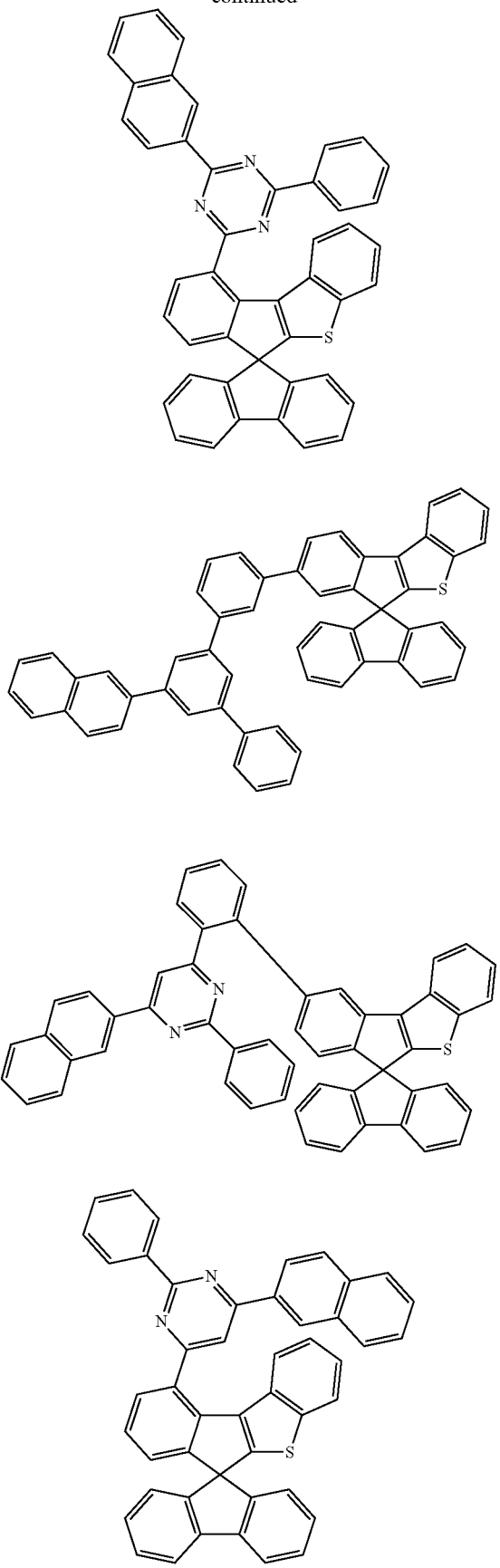
356
-continued
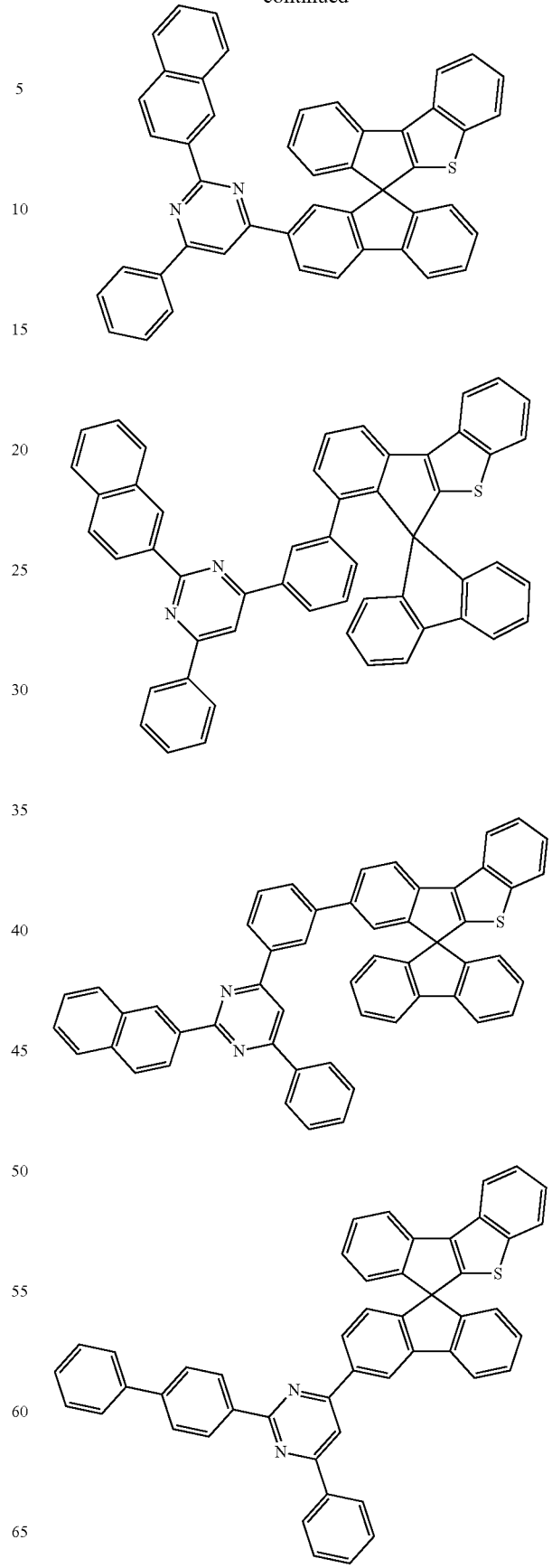

357
-continued
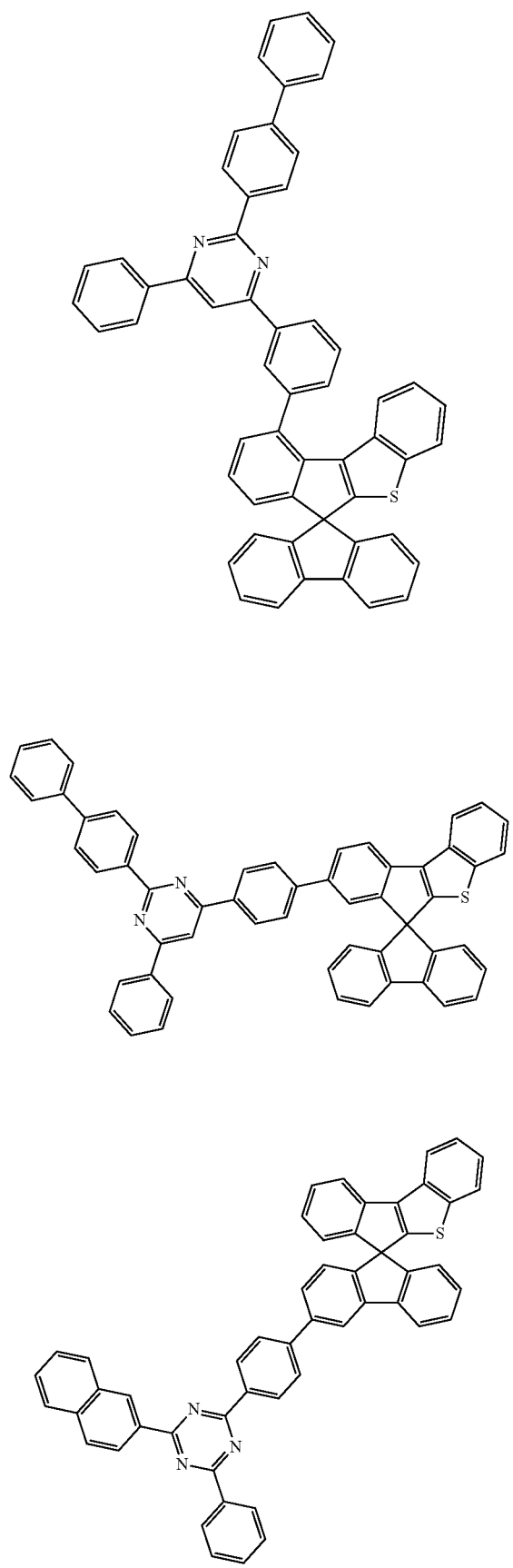
358
-continued
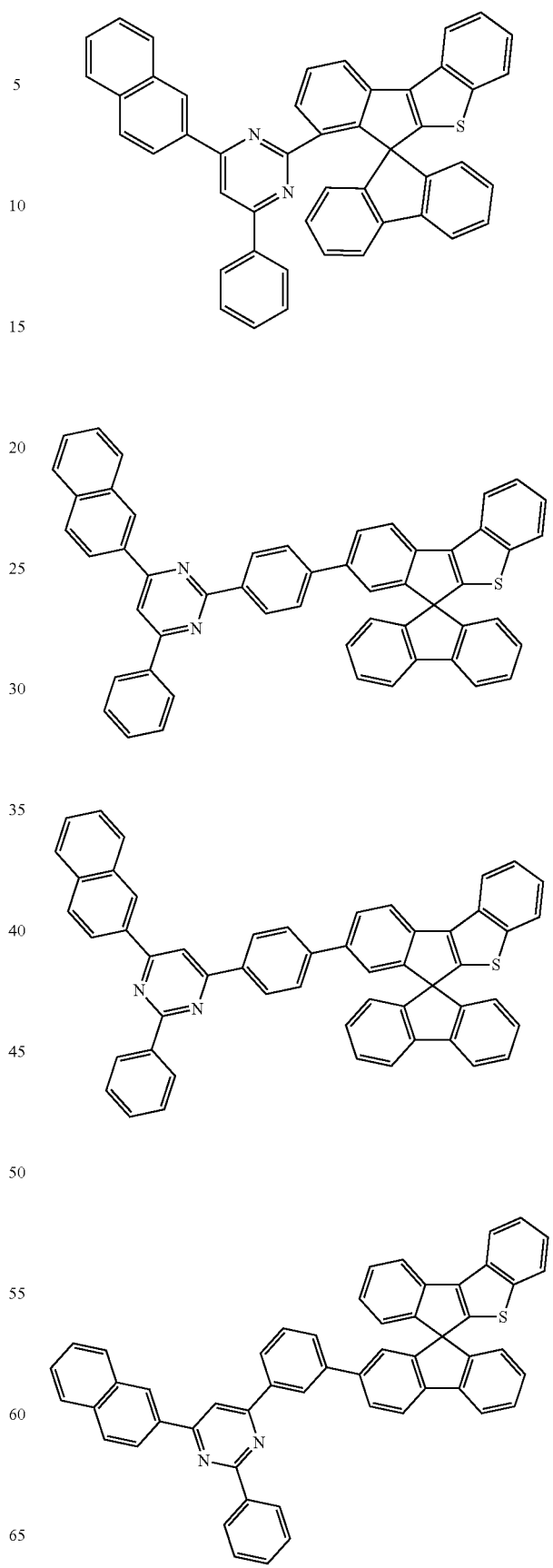

359
-continued
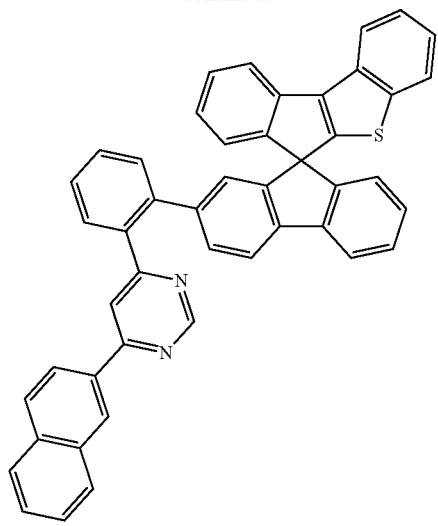
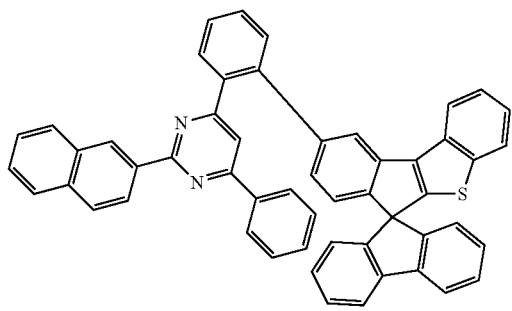
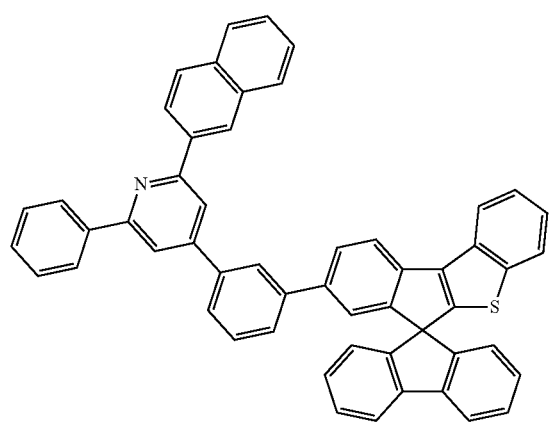
360
-continued
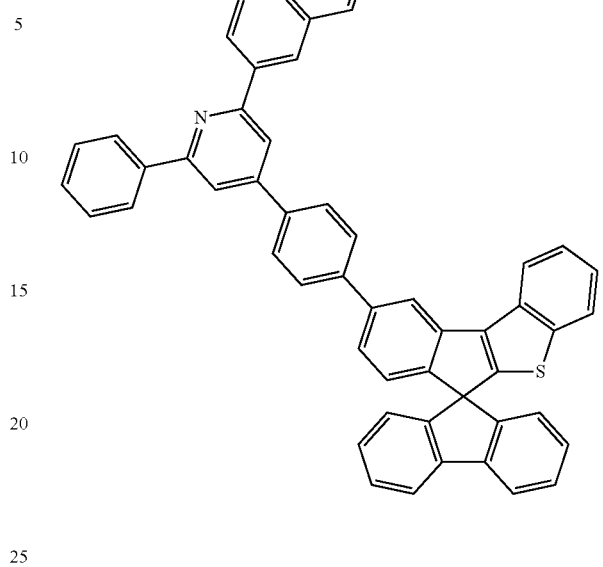
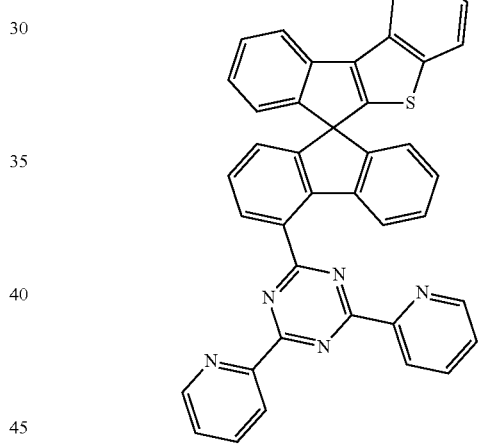
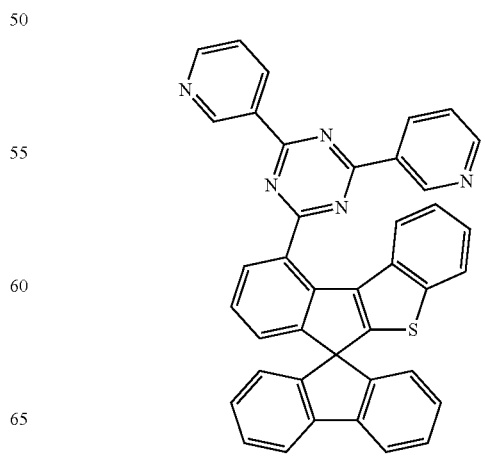

361
-continued
362
-continued
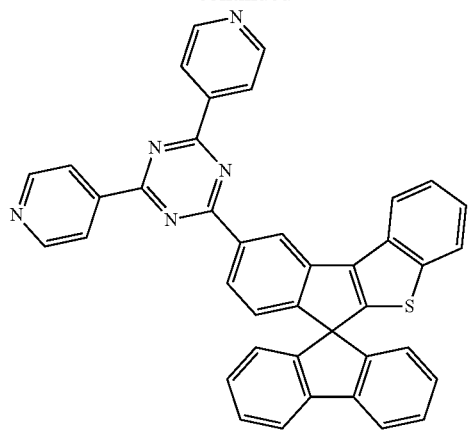
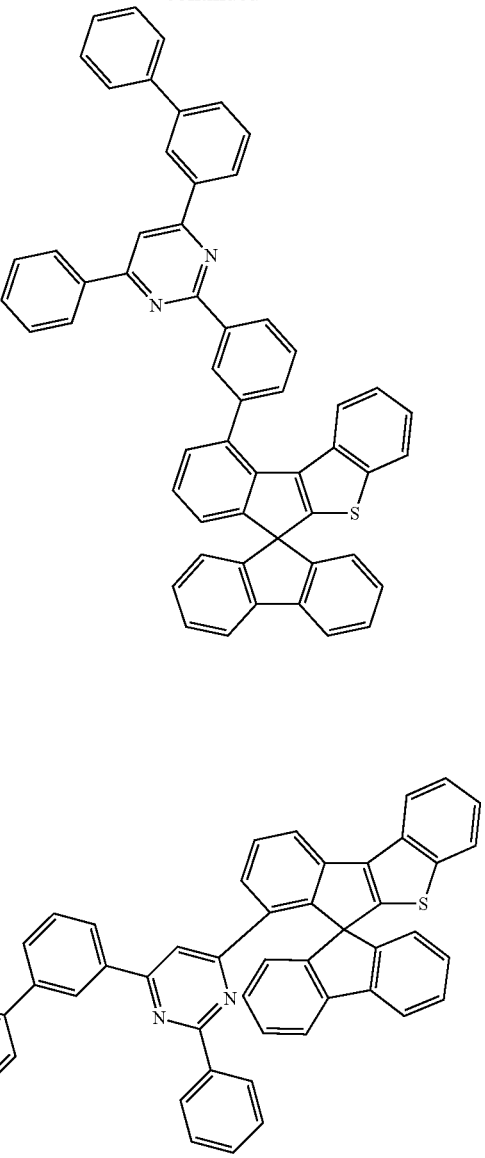
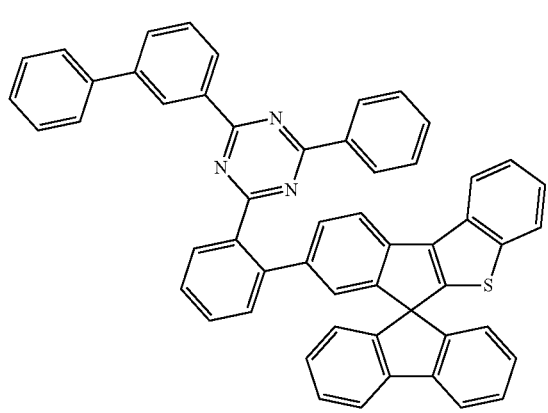
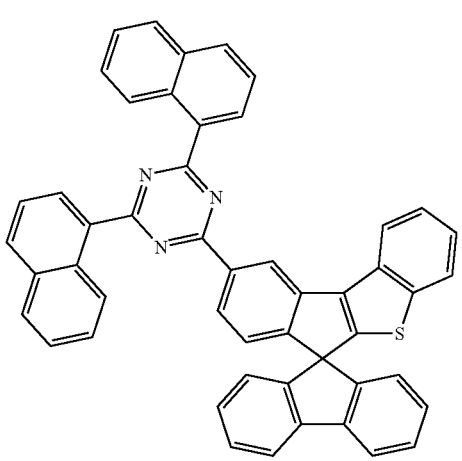

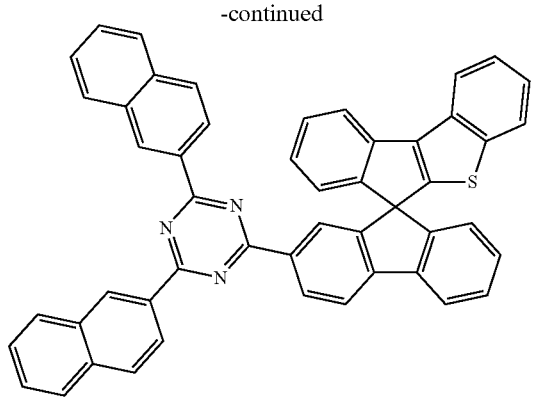
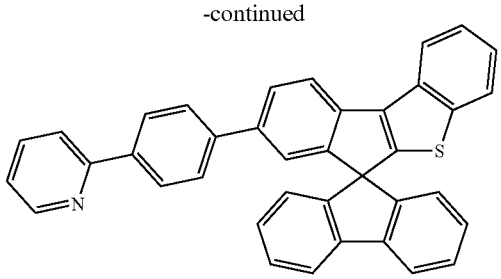
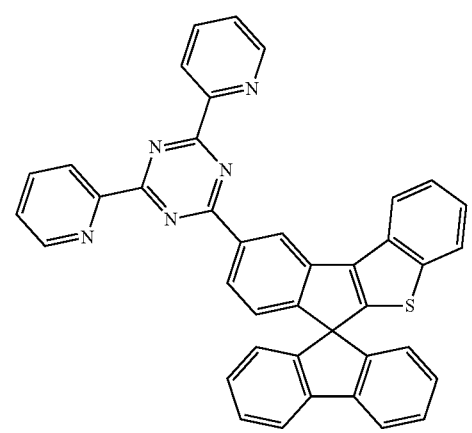
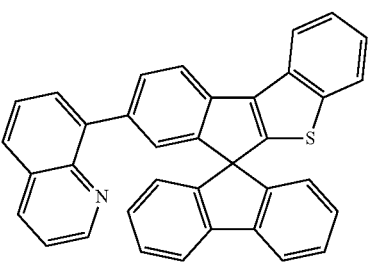
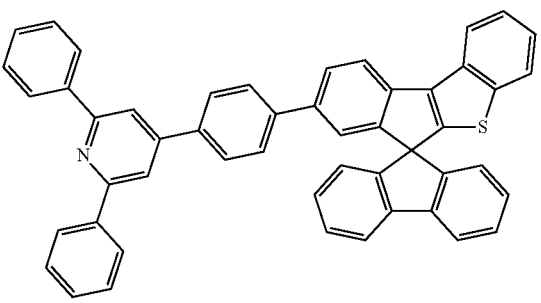
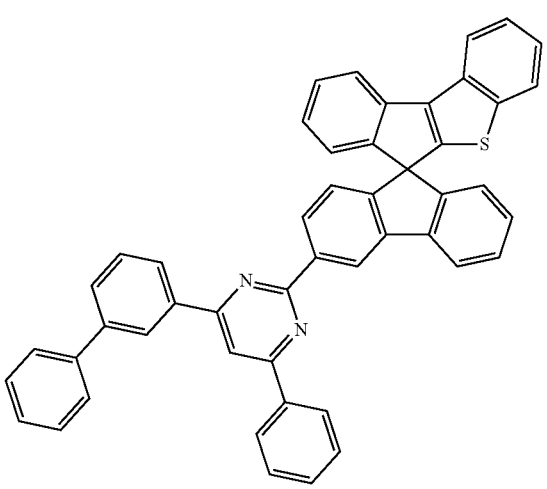
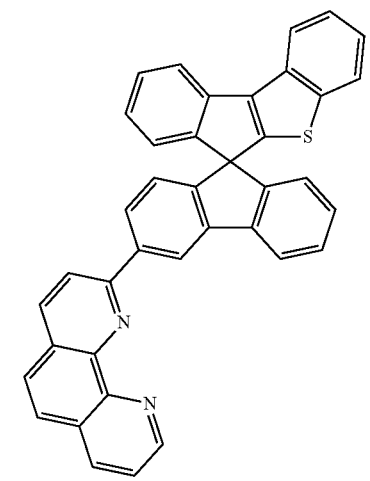
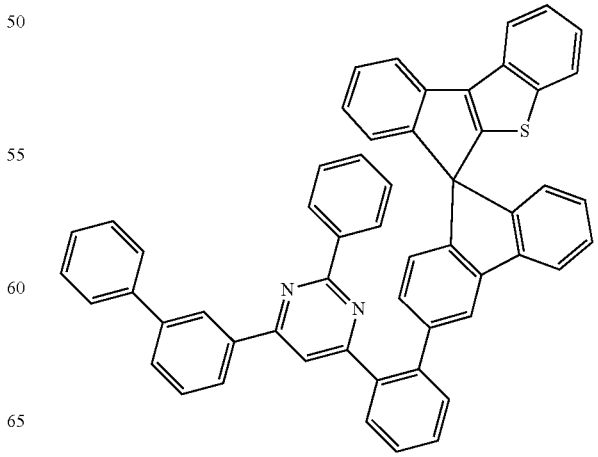

365
-continued
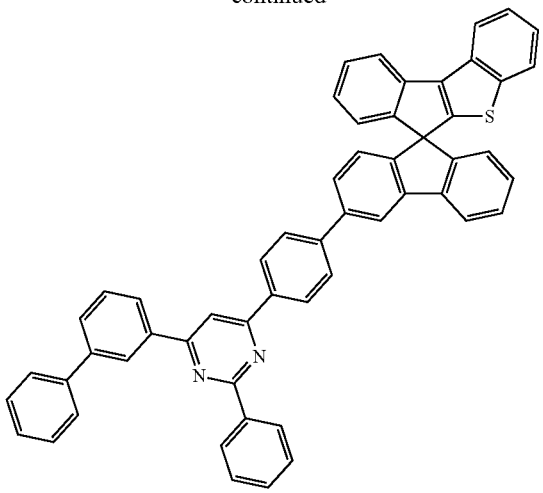
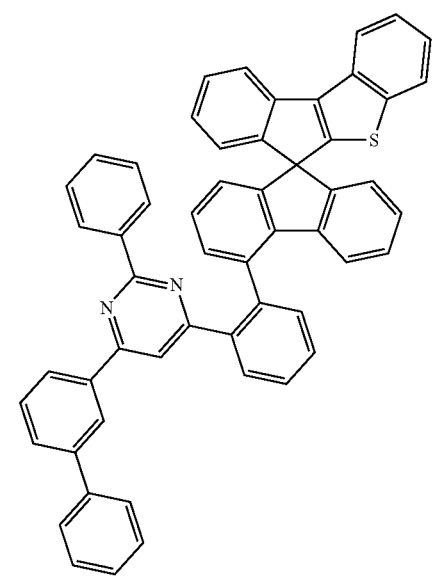
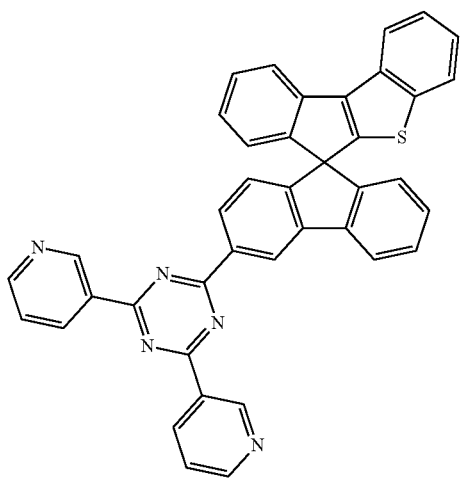
366
-continued
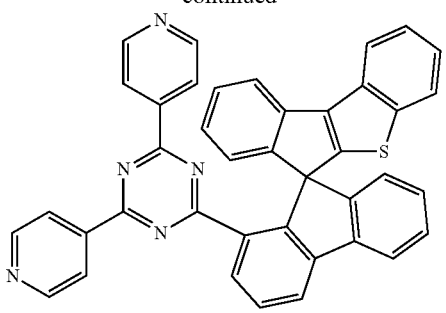
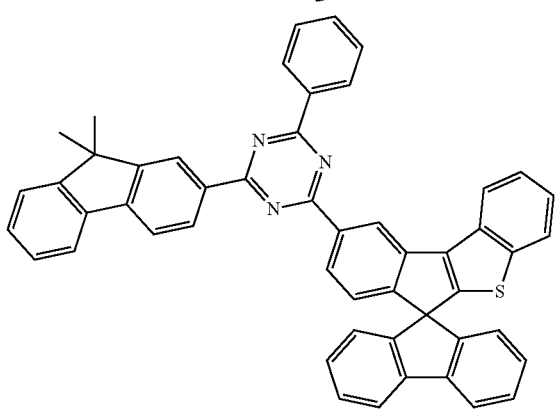
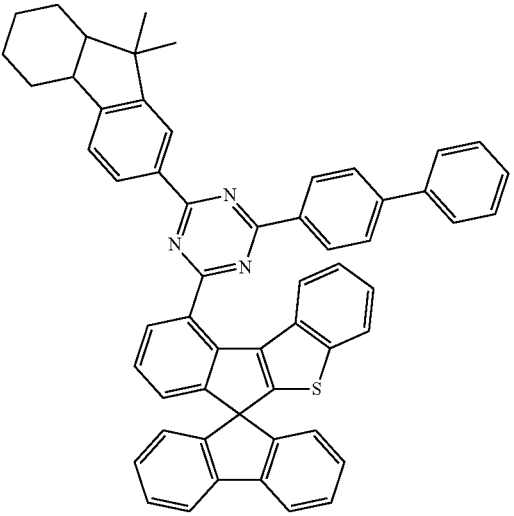
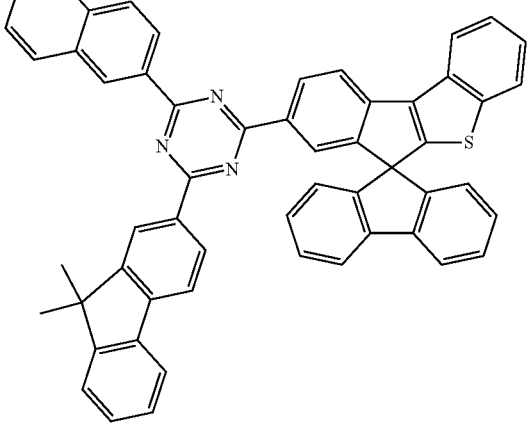

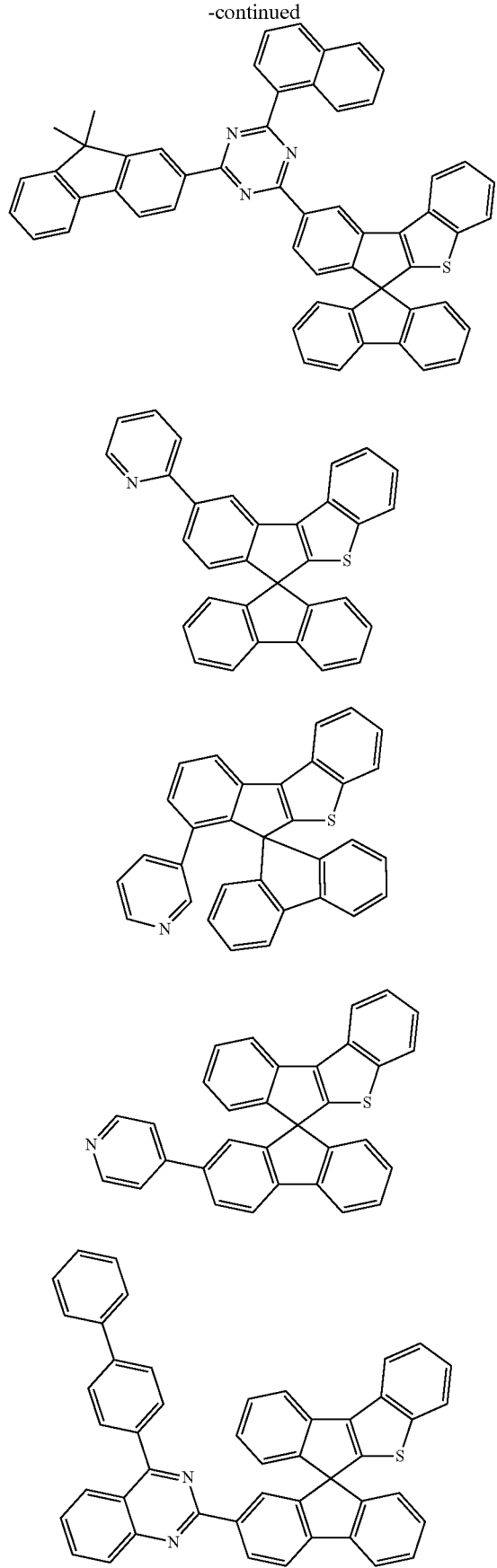
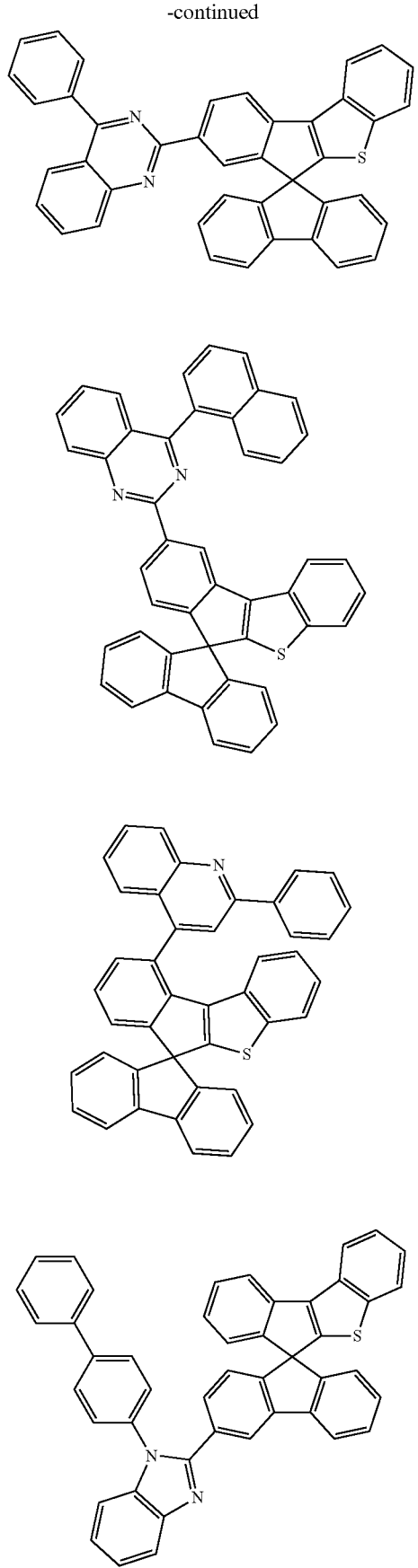

369
-continued
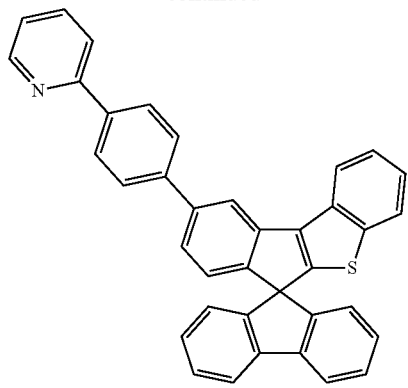
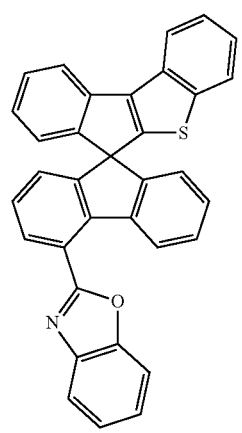
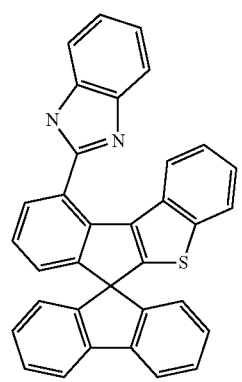
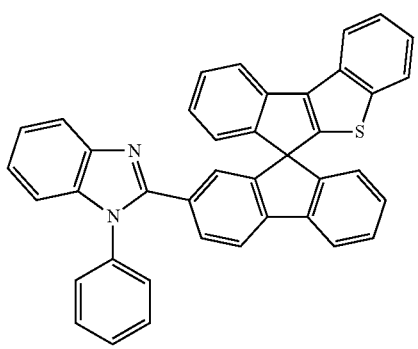
370
-continued
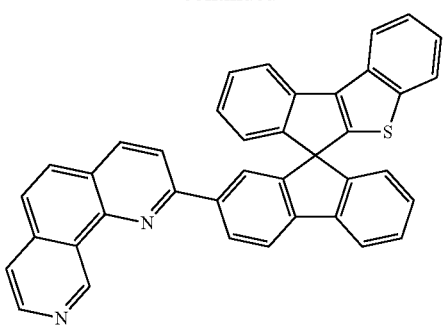
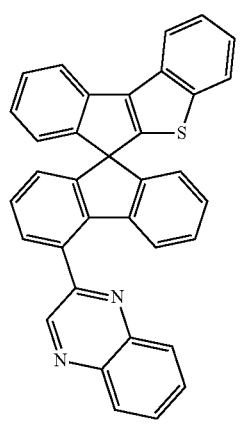
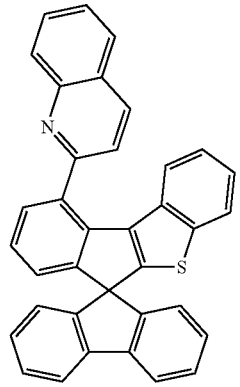
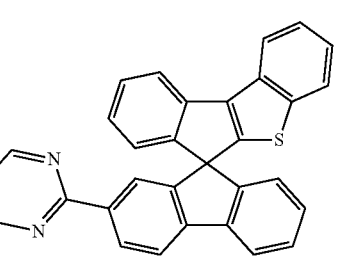

371
-continued
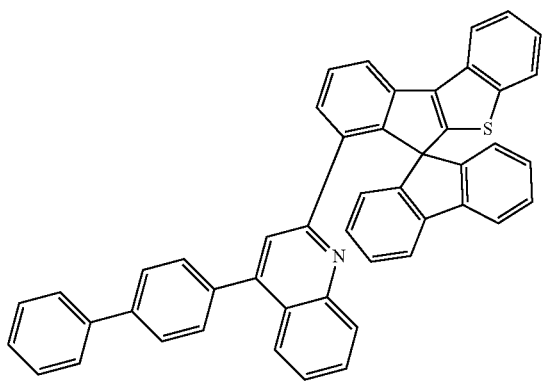
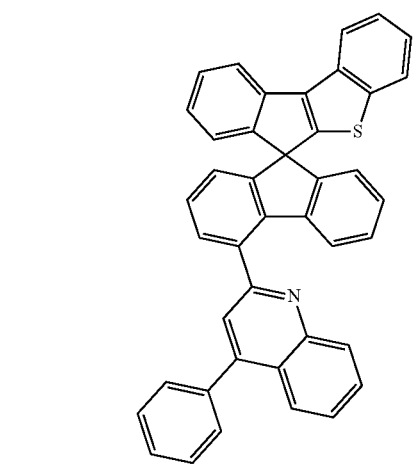
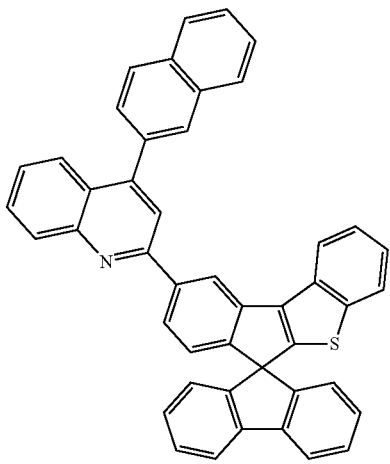
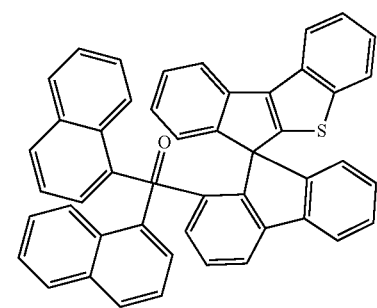
372
-continued
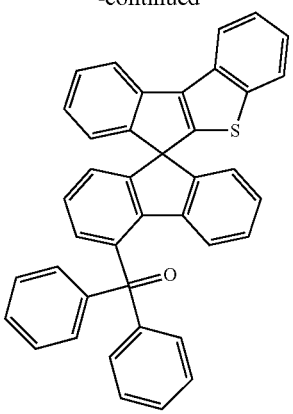
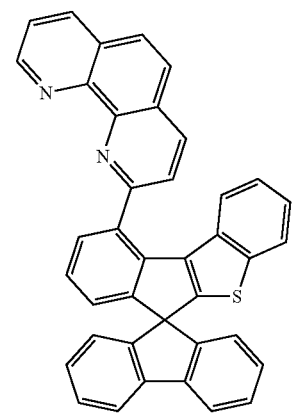
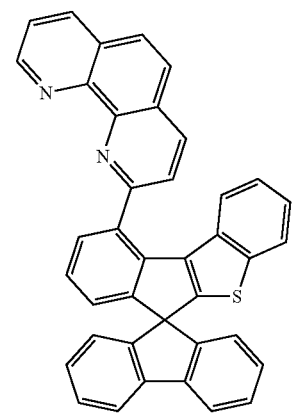
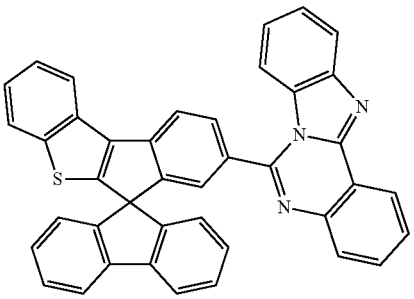
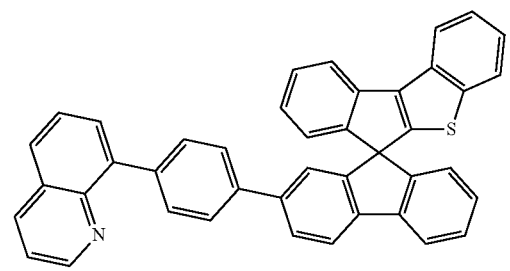
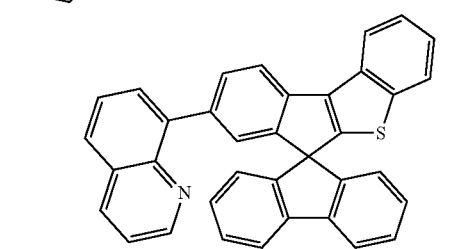

-continued

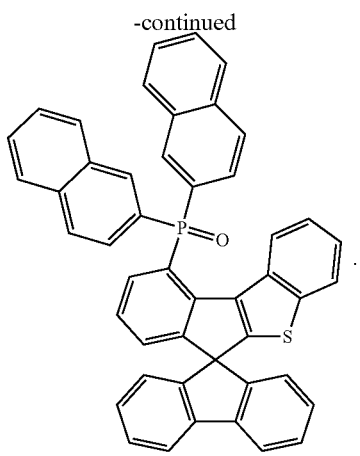

7. An organic light emitting device comprising:
a first electrode;
a second electrode provided to face the first electrode; and
one or more organic material layers provided between the first electrode and the second electrode,
wherein one or more layers of the organic material layers comprise the spiro structure compound of claim 1.

8. The organic light emitting device comprising:
a first electrode;
a second electrode provided to fact the first electrode; and
one or more organic material layers provided between the first electrode and the second electrode,
wherein the one or more organic material layers comprises an electron injection layer, an electron transport layer, or a layer which injects and transports electrons simultaneously, and the electron injection layer, the electron transport layer, or the layer which injects and transports electrons simultaneously comprises the spiro structure compound represented by the following Chemical Formula 1:

[Chemical Formula 1]

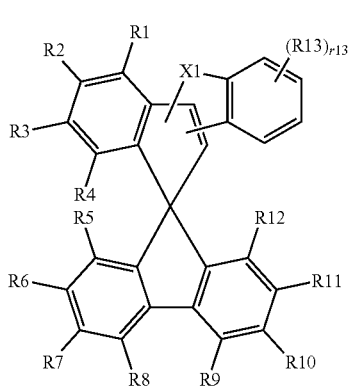

in Chemical Formula 1,
X1 is O or S,
at least one of R1 to R12 is -L1-Ar1, and the others and R13 are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, r13 is an integer of 1 to 4, when r13 is 2 or more, two or more R13's are the same as or different from each other, L1 is a direct bond; a substituted or unsubstituted arylene group; or a substituted or unsubstituted heteroarylene group, Ar1 is a substituted or unsubstituted phosphine oxide group; or is represented by any one of the following Chemical Formulae 2 to 6,

[Chemical Formula 2]

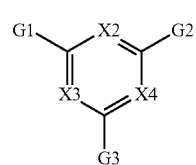

in Chemical Formula 2,
X2 is N or CR14, X3 is N or CR15, and X4 is N or CR16,
at least one of X2 to X4 is N,
any one of G1 to G3 and R14 to R16 is a moiety bonded to L1 of Chemical Formula 1, and the others of G1 to G3 and R14 to R16 are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, wherein when R2, is -L1-Ar1, Ar1 is Chemical Formula 2, the other of G1 to G3 and R14 to R16 are each independently hydrogen, or a substituted or unsubstituted aryl group, and at least one of G1 to G3 or R14 to R16 is a substituted or unsubstituted aryl group, the at least one of G1-G3 or R14-R16 is a substituted or unsubstituted polycyclic aryl group,

[Chemical Formula 3]

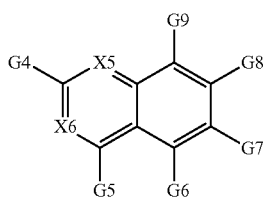

in Chemical Formula 3,

X5 is N or CR17, and X6 is N or CR18, at least one of X5 and X6 is N, any one of G4 to G9, R17, and R18 is a moiety bonded to L1 of Chemical Formula 1, and the others are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, or adjacent groups combine with each other to form a substituted or unsubstituted ring,

[Chemical Formula 4]

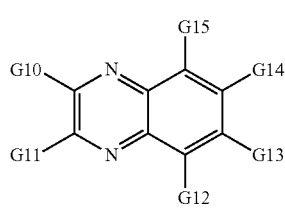

in Chemical Formula 4, any one of G10 to G15 is a moiety bonded to L1 of Chemical Formula 1, and the others are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group,

[Chemical Formula 5]

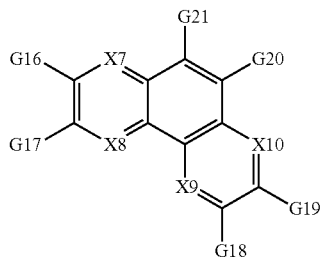

in Chemical Formula 5,

X7 is N or CR19, X8 is N or CR20, X9 is N or CR21, and X10 is N or CR22, at least one of X7 to X10 is N, any one of G16 to G21 and R19 to R22 is a moiety bonded to L1 of Chemical Formula 1, and the others are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group,

[Chemical Formula 6]

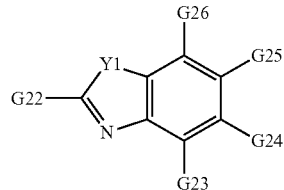

in Chemical Formula 6,

Y1 is O, S, NQ1, or CQ2Q3, and any one of G22 to G26 is a moiety bonded to L1 of Chemical Formula 1, and the others and Q1 to Q3 are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group.

9. An organic light emitting device comprising:
a first electrode;
a second electrode provided to face the first electrode; and
one or more organic material layers provided between the first electrode and the second electrode,
wherein the one or more layers of the organic material layers comprise the spiro structure compound represented by the following Chemical Formula 1:

[Chemical Formula 1]

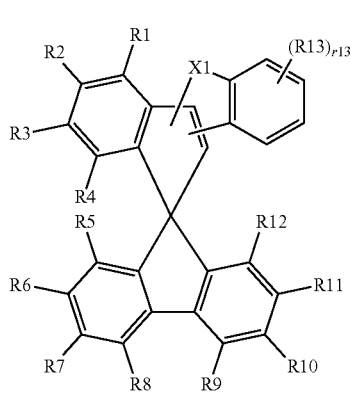

in Chemical Formula 1,
X1 is O or S,
at least one of R1 to R12 is -L1-Ar1, and the others and R13 are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group,
r13 is an integer of 1 to 4,
when r13 is 2 or more, two or more R13's are the same as or different from each other,
L1 is a direct bond; a substituted or unsubstituted arylene group; or a substituted or unsubstituted heteroarylene group,
Ar1 is a substituted or unsubstituted phosphine oxide group; or is represented by any one of the following Chemical Formulae 2 to 6,

[Chemical Formula 2]

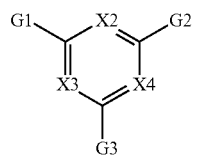

in Chemical Formula 2,
X2 is N or CR14, X3 is N or CR15, and X4 is N or CR16,
at least one of X2 to X4 is N,
any one of G1 to G3 and R14 to R16 is a moiety bonded to L1 of Chemical Formula 1, and the others of G1 to G3 and R14 to R16 are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group,

[Chemical Formula 3]

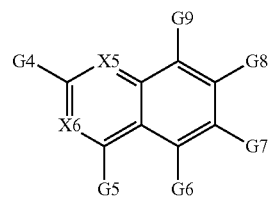

in Chemical Formula 3,
X5 is N or CR17, and X6 is N or CR18,
at least one of X5 and X6 is N,
any one of G4 to G9, R17, and R18 is a moiety bonded to L1 of Chemical Formula 1, and the others are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, or adjacent groups combine with each other to form a substituted or unsubstituted ring,

[Chemical Formula 4]

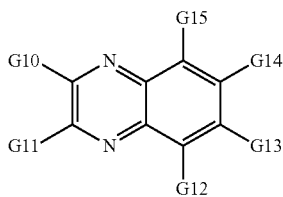

in Chemical Formula 4,
any one of G10 to G15 is a moiety bonded to L1 of Chemical Formula 1, and the others are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group,

[Chemical Formula 5]

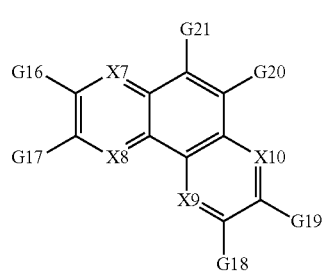

in Chemical Formula 5,
X7 is N or CR19, X8 is N or CR20, X9 is N or CR21, and X10 is N or CR22,
at least one of X7 to X10 is N,
any one of G16 to G21 and R19 to R22 is a moiety bonded to L1 of Chemical Formula 1, and the others are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group,

[Chemical Formula 6]

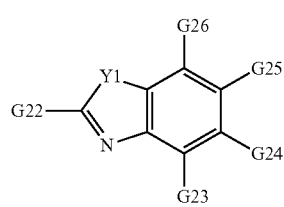

in Chemical Formula 6,
Y1 is O, S, NQ1, or CQ2Q3, and
any one of G22 to G26 is a moiety bonded to L1 of Chemical Formula 1, and the others and Q1 to Q3 are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group,
wherein the one or more organic material layers comprise a light emitting layer, and the light emitting layer comprises a compound represented by the following Chemical Formula 1-A:

[Chemical Formula 1-A]

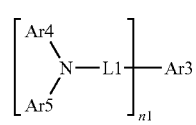

in Chemical Formula 1-A,
n1 is an integer of 1 or more,
Ar3 is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group,
L1 is a direct bond; a substituted or unsubstituted arylene group; or a substituted or unsubstituted heteroarylene group, Ar4 and Ar5 are the same as or different from each other, and are each independently a substituted or unsubstituted aryl group; a substituted or unsubstituted silyl group; a substituted or unsubstituted alkyl group; a substituted or unsubstituted arylalkyl group; or a substituted or unsubstituted heteroaryl group, or optionally combine with each other to form a substituted or unsubstituted ring, and when n1 is 2 or more, two or more structures in the parenthesis are the same as or different from each other.

10. The organic light emitting device of claim 9, wherein L1 is a direct bond, Ar3 is a divalent pyrene group, Ar4 and Ar5 are the same as or different from each other, and are each independently an aryl group which is unsubstituted or substituted with a silyl group which is substituted with an alkyl group, and n1 is 2.

11. An organic light emitting device comprising:
a first electrode;
a second electrode provided to face the first electrode; and
one or more organic material layers provided between the first electrode and the second electrode,
wherein the one or more layers of the organic material layers comprise the spiro structure compound represented by the following Chemical Formula 1:

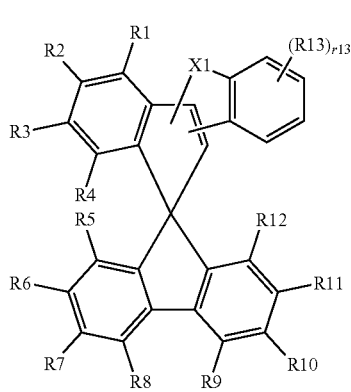

[Chemical Formula 1]

in Chemical Formula 1,
X1 is O or S,
at least one of R1 to R12 is -L1-Ar1, and the others and R13 are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, r13 is an integer of 1 to 4,
when r13 is 2 or more, two or more R13's are the same as or different from each other,
L1 is a direct bond; a substituted or unsubstituted arylene group; or a substituted or unsubstituted heteroarylene group,
Ar1 is a substituted or unsubstituted phosphine oxide group; or is represented by any one of the following Chemical Formulae 2 to 6,

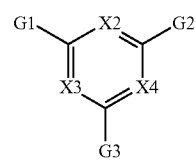

[Chemical Formula 2]

in Chemical Formula 2,
X2 is N or CR14, X3 is N or CR15, and X4 is N or CR16,
at least one of X2 to X4 is N,
any one of G1 to G3 and R14 to R16 is a moiety bonded to L1 of Chemical Formula 1, and the others of G1 to G3 and R14 to R16 are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group,

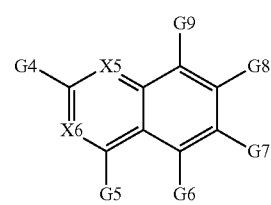

[Chemical Formula 3]

in Chemical Formula 3,
X5 is N or CR17, and X6 is N or CR18,
at least one of X5 and X6 is N,
any one of G4 to G9, R17, and R18 is a moiety bonded to L1 of Chemical Formula 1, and the others are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, or adjacent groups combine with each other to form a substituted or unsubstituted ring,

[Chemical Formula 4]

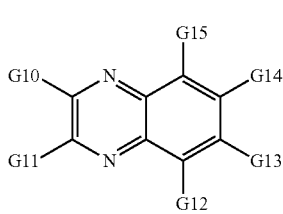

in Chemical Formula 4,
any one of G10 to G15 is a moiety bonded to L1 of Chemical Formula 1, and the others are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group,

[Chemical Formula 5]

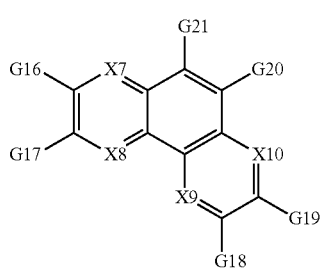

in Chemical Formula 5,
X7 is N or CR19, X8 is N or CR20, X9 is N or CR21, and X10 is N or CR22,
at least one of X7 to X10 is N,
any one of G16 to G21 and R19 to R22 is a moiety bonded to L1 of Chemical Formula 1, and the others are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group,

[Chemical Formula 6]

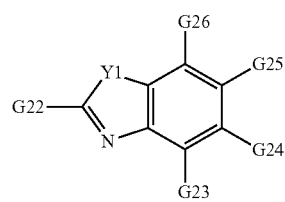

in Chemical Formula 6,
Y1 is O, S, NQ1, or CQ2Q3, and
any one of G22 to G26 is a moiety bonded to L1 of Chemical Formula 1, and the others and Q1 to Q3 are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, and
wherein the one or more organic material layers comprise a light emitting layer, and the light emitting layer comprises a compound represented by the following Chemical Formula 2-A:

[Chemical Formula 2-A]

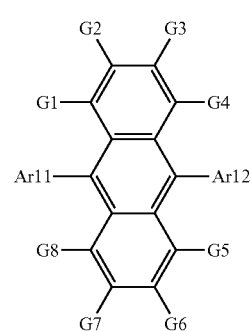

in Chemical Formula 2-A, n1 is an integer of 1 or more,

Ar11 and Ar12 are the same as or different from each other, and are each independently a substituted or unsubstituted monocyclic aryl group; or a substituted or unsubstituted polycyclic aryl group, and G1 to G8 are the same as or different from each other, and are each independently hydrogen; a substituted or unsubstituted monocyclic aryl group; or a substituted or unsubstituted polycyclic aryl group.

12. The organic light emitting device of claim 11, wherein Ar11 and Ar12 are a 1-naphthyl group, and G1 to G8 are hydrogen.

13. The organic light emitting device of claim 9, wherein the light emitting layer comprises a compound represented by the following Chemical Formula 2-A:

[Chemical Formula 2-A]

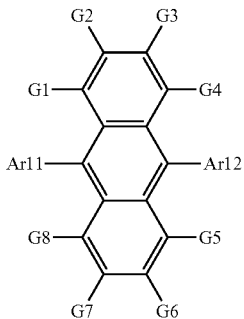

in Chemical Formula 2-A,

Ar11 and Ar12 are the same as or different from each other, and are each independently a substituted or unsubstituted monocyclic aryl group; or a substituted or unsubstituted polycyclic aryl group, and G1 to G8 are the same as or different from each other, and are each independently hydrogen; a substituted or unsubstituted monocyclic aryl group; or a substituted or unsubstituted polycyclic aryl group.

14. The organic light emitting device of claim 9, wherein when R2, R6 or R11 is -L1-Ar1, Ar1 is Chemical Formula 2, the other of G1 to G3 and R14 to R16 are each independently hydrogen, or a substituted or unsubstituted aryl group, and at least one of G1 to G3 or R14 to R16 is a substituted or unsubstituted aryl group, the at lest one of G1-G3 or R14-R16 is a substituted or unsubstituted polycyclic aryl group.

15. The organic light emitting device of claim 11, wherein when R2, R6 or R11 is -L1-Ar1, Ar1 is Chemical Formula 2, the other of G1 to G3 and R14 to R16 are each independently hydrogen, or a substituted or unsubstituted aryl group, and at least one of G1 to G3 or R14 to R16 is a substituted or unsubstituted aryl group, the at lest one of G1-G3 or R14-R16 is a substituted or unsubstituted polycyclic aryl group.

* * * * *